US009533967B2

(12) United States Patent
Short et al.

(10) Patent No.: US 9,533,967 B2
(45) Date of Patent: Jan. 3, 2017

(54) MULTISUBSTITUTED AROMATIC COMPOUNDS AS INHIBITORS OF THROMBIN

(71) Applicant: Verseon Corporation, Fremont, CA (US)

(72) Inventors: Kevin Michael Short, Fremont, CA (US); Son Minh Pham, Fremont, CA (US); David Charles Williams, Fremont, CA (US); Somalee Datta, Sunnyvale, CA (US)

(73) Assignee: VERSEON CORPORATION, Fremont, CA (US)

( * ) Notice: Subject to any disclaimer, the term of this patent is extended or adjusted under 35 U.S.C. 154(b) by 0 days.

(21) Appl. No.: 13/630,201

(22) Filed: Sep. 28, 2012

(65) Prior Publication Data
US 2013/0040950 A1 Feb. 14, 2013

Related U.S. Application Data

(63) Continuation of application No. PCT/US2011/030585, filed on Mar. 30, 2011.

(60) Provisional application No. 61/319,175, filed on Mar. 30, 2010.

(51) Int. Cl.
C07D 231/10 (2006.01)
C07D 231/00 (2006.01)
C07D 231/12 (2006.01)
A61K 31/415 (2006.01)
C07D 401/04 (2006.01)
A61K 31/4427 (2006.01)
A61K 31/4439 (2006.01)
C07D 405/14 (2006.01)
C07D 409/14 (2006.01)

(52) U.S. Cl.
CPC ......... C07D 401/04 (2013.01); A61K 31/4427 (2013.01); A61K 31/4439 (2013.01); C07D 405/14 (2013.01); C07D 409/14 (2013.01)

(58) Field of Classification Search
USPC ......... 548/255, 262.2, 263.2, 356.1, 366.1,5 48/367.4, 373.1, 374.1, 379.4; 514/359, 514/383, 402, 407, 406
See application file for complete search history.

(56) References Cited

U.S. PATENT DOCUMENTS

| 3,250,761 | A | | 5/1966 | Schmidt et al. |
| 3,926,999 | A | * | 12/1975 | Poetsch ........................ 544/392 |
| 4,008,249 | A | * | 2/1977 | Fischer et al. ............ 548/366.1 |
| 4,160,452 | A | | 7/1979 | Theeuwes |
| 4,256,108 | A | | 3/1981 | Theeuwes |
| 4,265,874 | A | | 5/1981 | Bonsen et al. |
| 4,861,760 | A | | 8/1989 | Mazuel et al. |
| 4,911,920 | A | | 3/1990 | Jani et al. |
| 5,212,162 | A | | 5/1993 | Missel et al. |
| 5,403,841 | A | | 4/1995 | Lang et al. |
| 5,466,823 | A | | 11/1995 | Talley et al. |
| 5,739,083 | A | | 4/1998 | Endo et al. |
| 5,753,688 | A | | 5/1998 | Talley et al. |
| 5,792,761 | A | | 8/1998 | Fraley et al. |
| 5,902,852 | A | | 5/1999 | Schulz et al. |
| 6,589,997 | B2 | * | 7/2003 | Pillarisetti et al. ........... 514/685 |
| 7,625,944 | B2 | | 12/2009 | Sinha et al. |
| 2002/0055639 | A1 | | 5/2002 | Nebel et al. |
| 2004/0132726 | A1 | | 7/2004 | Arora et al. |
| 2005/0009827 | A1 | | 1/2005 | Nazare et al. |
| 2005/0065144 | A1 | | 3/2005 | Feng et al. |
| 2005/0203127 | A1 | | 9/2005 | Cezanne et al. |
| 2008/0188527 | A1 | | 8/2008 | Cashman |
| 2008/0269293 | A1 | | 10/2008 | Chi et al. |
| 2008/0275070 | A1 | | 11/2008 | Liu et al. |
| 2009/0105253 | A1 | | 4/2009 | Kubo et al. |
| 2009/0163545 | A1 | | 6/2009 | Goldfarb |
| 2010/0016320 | A1 | | 1/2010 | Dyckman et al. |
| 2010/0210696 | A1 | | 8/2010 | Nishida et al. |
| 2011/0071182 | A1 | | 3/2011 | Seefeld et al. |

FOREIGN PATENT DOCUMENTS

| DE | WO 0009500 A2 * | 2/2000 | ............. A01N 43/56 |
| EP | 0246888 A2 | 11/1987 | |
| EP | 0854723 B1 | 7/1998 | |
| JP | S50-117936 | 9/1975 | |
| JP | H10-509708 | 9/1998 | |
| KR | WO 2010127855 A1 * | 11/2010 | .......... C07D 231/12 |
| WO | 9605309 A2 | 2/1996 | |
| WO | 96/14843 A2 | 5/1996 | |
| WO | WO9614843 A2 * | 5/1996 | .......... A61K 31/415 |
| WO | 9828269 A1 | 7/1998 | |

(Continued)

OTHER PUBLICATIONS

Schepetkin et al., (J. Med. Chem. vol. 50, pp. 4928-4938. Published 2007).*
Cherton et al., (Canadian Journal of Chemistry vol. 63, pp. 2601-2608, published 1985).*
Farghaly et al (ARKIVOC vol. XI pp. 76-90, published 2006).*
Dabau, F-P. et al., Chemische Berichte vol. 108 pp. 2189-2201. Published 1975.*

(Continued)

*Primary Examiner* — Timothy Thomas
*Assistant Examiner* — George W Kosturko
(74) *Attorney, Agent, or Firm* — Davis Wright Tremaine LLP

(57) ABSTRACT

There are provided inter alia multisubstituted aromatic compounds useful for the inhibition of thrombin, which compounds include substituted pyrazolyl or substituted triazolyl. There are additionally provided pharmaceutical compositions. There are additionally provided methods of treating and preventing a disease or disorder, which disease or disorder is amenable to treatment or prevention by the inhibition of thrombin.

22 Claims, No Drawings

(56) References Cited

FOREIGN PATENT DOCUMENTS

| WO | WO0009500 A2 * | 2/2000 | |
|---|---|---|---|
| WO | 0041716 A1 | 7/2000 | |
| WO | WO 0112189 A1 * | 2/2001 | ........... A61K 31/415 |
| WO | 03048155 A1 | 6/2003 | |
| WO | 03061682 A1 | 7/2003 | |
| WO | 03062206 A2 | 7/2003 | |
| WO | 2004/000785 A2 | 12/2003 | |
| WO | 2004035564 A1 | 4/2004 | |
| WO | 2004058721 A2 | 7/2004 | |
| WO | 2004058722 A1 | 7/2004 | |
| WO | 2004/089911 A1 | 10/2004 | |
| WO | 2004098589 A1 | 11/2004 | |
| WO | 2004101555 A1 | 11/2004 | |
| WO | 2008009638 A2 | 1/2008 | |
| WO | 2008016883 A2 | 2/2008 | |
| WO | WO 2009/041447 | 4/2009 | |
| WO | 2010020600 A1 | 2/2010 | |
| WO | 2010020601 A1 | 2/2010 | |
| WO | 2010020602 A1 | 2/2010 | |
| WO | 2012065019 A2 | 5/2012 | |

OTHER PUBLICATIONS

Wardakhan et al., Journal of Chilean Chemistry Society vol. 52, pp. 1145-1149, published 2007.*

Ramalakshmi et al., Rasayan J. Chem. vol. 2 pp. 393-396. Published Apr. 2009.*

Akerblom, E. B. and D. E. Campbell, "Nitrofuryltriazole derivatives as potential urinary tract antibacterial agents", *J. Med. Chem.*, (Apr. 1973), 16(4):312-9.

Chang, K. Y. et al., "Synthesis and Structure-Activity Relationships of Quaternary Ammonium Cephalosporins with 3-Pyrazolylpyridinium Derivatives", *Bioordanic & Medicinal Chemistry Letters*, (Mar. 25, 2000),10:1211-1214.

Katritzky, Alan R. et al., "Selective Reactivity of sp3 and sp2 Carbanions of 1-Substituted 1,2,4-Triazoles. A Comparative Approach", J. Org. Chem., (1998), 63(13):4323-4331.

Montoya, V. , et al., "Regioselective formation of N-alkyl-3,5-pyrazole derived ligands. A synthetic and computational study", *Tetrahedron*, (Oct. 10, 2005) 61:12377-12385.

Observations by third parties under Article 115 EPC for European Application No. 11 766 507.5, dated Aug. 30, 2013, 8 pages.

Chen, Y. et al., "Interaction of Novel Positive Allosteric Modulators of Metabotropic Glutamate Receptor 5 with the Negative Allosteric Antagonist Site Is Required for Potentiation of Receptor Responses", *Molecular Pharmacology*, (Feb. 1, 2007), 61(5):1389-1398.

Cipens, G. et al., "Aminoguanidine derivatives and their transformations. V. Alkyl- and arylamino substituted 1,2,4-triazoles" (1962).

Dzygiel, Anetta et al. "Synthesis, Structure and Properties of N-Acetylated Derivatives of Methyl 5-Amino-1H-[1,2,4] triazole-3-carboxylate", *Chem. Pharm. Bull.*, (Jan. 1, 2004) 52(2):192-198.

Herrera, Rafael et al., "Regio- and Stereoselectivity of Captodative in 1,3-Diploar Cycloadditions. A DFT/HSAB Theory Rationale for the Observed Regiochemistry of Nitrones", *Journal of Organic Chemistry*, (Feb. 1, 2001), 66(4):1252-1263.

Kantlehner, Willi et al., "Orthoamide, XXXIV. Synthesen mit Vinylidendiaminen", *Liebigs Annalen der Chem.*, (Mar. 1, 1980), 1980(3):372-388.

Kumar, Saresh et al., "Efficient Routes to Pyrazolo[3,4- b]indoles and Pyrazolo[I,S-a]benzimidazoles via Palladium- and Copper-Catalyzed Intramolecular C—C and C—N. Bond Formation", *Journal of Organic Chemistry*, (Sep. 2009), 74(18):7046-7051.

Labanauskas, L. et al., "Synthesis of 3-(3,4-dimethoxyphenyl)-1H-1,2,4-triazole-5-thiol and 2-amino-5-(3,4-dimethoxyphenyl)-1,3,4-thiadiazole derivatives exhibiting anti-inflammatory activity", *Die Parmazie*, (Jan. 1, 2001), 56(8):617-619.

Reiter, J., et al., "On Triazoles. VI [1]. The Acylation of 5-Amino-1,2,4-Triazoles", *Journal of Heterocyclic Chemistry*, Wiley-Blackwell Publishing, Inc., (Jan. 187), 24(1): 127-142.

Saalfrank, Rolf W., et al., "4,5-Dihydro-1*H*-tetrazol-5-ylidene aus 3,3-Diazido-2-cyanacrylsaureestern und Hydrazinen, Hydraziden sowie0-substituierten Hydroxylaminen", *Chemische Berichte*, (Mar. 1, 1989), 122(3):519-522.

Simiti, I. et al., "Kondensation von 3-Merkapto-5-phenyl-1,2,4-triazol mit Monochloracetaldehyd", *Arch. Pharm.* (Wcinheim), (Jan. 1, 1987), 320(6):528-534.

Yu, Xiao-yuan et al., "Synthesis and biological activities of 5-substituted benzamide triazole" (2004).

European Search Report for International Application No. 11 766 507.5 dated Aug. 28, 2013, 13 pages.

Abdel-Salam, O. M., et al., "A study of unfractionated and low molecular weight heparins in a model of cholestatic liver injury in the rat", *Pharmacological Research*, (2005), vol. 51, pp. 59-67.

Abe, W., et al., "Low molecular weight heparin prevents hepatic fibrogenesis caused by carbon tetrachloride in the rat", *Journal of Hepatology*, (2007), vol. 46, pp. 286-294.

Akiyama, H., et al., "Thrombin accumulation in brains of patients with Alzheimer's disease", *Neuroscience Letters*, (1992), vol. 146, pp. 152-154.

Akl, E. A., et al., "Parenteral anticoagulation may prolong the survival of patients with limited small cell lung cancer: a Cochane systematic review", *Journal of Experimental & Clinical Cancer Research* (2008), vol. 27, Issue 4, pp. 1-10.

Altinbas, M., et al., "A randomized clinical trial of combination chemotherapy with and without low-molecular-weight heparin in small cell lung cancer", *Journal of Thrombosis and Haemostasis*, (2004), vol. 2, pp. 1266-1271.

Assy, N., et al., "The Beneficial Effect of Aspirin and Enoxaparin on Fibrosis Progression and Regenerative Activity in a Rat Model of Cirrhosis", *Dig Dis Science* (Mar. 20, 2007) vol. 52, pp. 1187-1193.

Avis, Kenneth E., "Parental Preparations", Chapter 84, Remington's Pharmaceutical Sciences, 17th ed., (Mack Pub. Co., Easton, PA), 1985, pp. 1461-1487.

Berge et al., "Pharmaceutical 58 Salts", *Journal of Pharmaceutical Science*, (1977) vol. 66, pp. 1-19.

Bogatkevich, G. S., et al., "Dabigatran, a Direct Thrombin Inhibitor, Demonstrates Antifibrotic Effects on Lung Fibroblasts", *Arthritis and Rheumatism*, (Nov. 2009), vol. 60, Issue 11, pp. 3455-3464.

Calvaruso, V., et al., "Coagulation and fibrosis in chronic liver disease", *Gut*, (2008), vol. 57, pp. 1722-1727.

Chambers, R. C. & Laurent, G. J., "Coagulation cascade proteases and tissue fibrosis", *Biochemical Society Transactions*, (2002). vol. 30, part 2, pp. 194-200.

Chambers, R. C., "Procoagulant signalling mechanisms in lung inflammation and fibrosis: novel opportunitites for pharmacological intervention?", *British Journal Pharmacology*, (2008), vol. 153, Suppl 1, pp. S367-S378.

Chelmicka-Szorc, Ewa and Barry G. W. Arnason, "Partial Suppression of Experimental Allergic Encephalomyelitis With Heparin", *Arch Neurol*, (Aug. 1972), vol. 27, pp. 153-158.

Deardorff, Dwight L., "Isotonic Solutions", Chapter 79, Remington's Pharmaceutical Sciences, 15th ed., (Mack Pub. Co., Easton, PA), 1975 pp. 1405-1412.

Defeo, K., et al., "Use of dabigatran etexilate to reduce breast cancer progression", *Cancer Biology &I Therapy*, (2010), vol. 10, pp. 1001-1008.

Defeo, K.et al., "Dabigatran etexilate blocks breast cancer progression in vitro and in a 4T1 breast cancer tumor model in mice", *Thrombosis Research*, (2010), vol. 125 (Supplement 2): S188-S188.

Deng, J. Z., et al., "Development of an oxazolopyridine series of dual thrombin/factor Xa inhibitors via structure-guided lead optimization", Bioorganic & Medicinal Chemistry Letters, (2005), vol. 15, pp. 4411-4416.

Duplantier, J. G., et al., "A role for thrombin in liver fibrosis", Gut, (2004), vol. 53, pp. 1682-1687.

Eliel, E. L. and S. H. Wilen, 1993, Stereochemistry in Organic Compounds, John Wiley & Sons: New York.

Falanga, A. & Piccioli, A., "Effect of anticoagulant drugs in cancer", *Current Opinion in Pulmonary Medicine*, (2005), vol. 11, pp. 403-407.

(56) References Cited

OTHER PUBLICATIONS

Favreau, F., et al., "Anti-thrombin Therapy During Warm Ischemia and Cold Preservation Prevents Chronic Kidney Graft Fibrosis in a DCD Model", *American Journal of Transplantation*, (2010), vol. 10, pp. 30-39.

Garcia, P. S., et al., "The role of thrombin and protease-activated receptors in pain Mechanisms", *Thrombosis and Haemostasis*, (2010), vol. 103, pp. 1145-1151.

Giardino, E. C., et al., "Cooperative antithrombotic effect from the simultaneous inhibition of thrombin and factor Xa", *Blood Coagulation and Fibrinolysis*, (2010), vol. 21, pp. 128-134.

Goding, James W., *Monoclonal Antibodies: Principles and Practice*, Academic Press, (2nd ed.), 1986, p. 104.

Goodman and Gilman (eds.), The Pharmacological Basis for Therapeutics (7th ed.), 1990. pp. 1-40.

Gross, P. L. & Weitz, J. I., "New Anticoagulants for Treatment of Venous Thromboembolism", *Arteriosclerosis, Thrombosis, and Vascular Biology*, (2008), vol. 28, pp. 380-386.

Han, M. H., et al., "Proteomic analysis of active multiple sclerosis lesions reveals therapeutic targets", *Nature*, vol. 451, pp. 1076-1081.

Hettiarachchi, R. J., et al., "Do Heparins Do More than Just Treat Thrombosis? The Influence of Heparins on Cancer Spread", *Thrombosis and Haemostasis*, (1999), vol. 82, pp. 947-952.

Hirsh, J., et al., "New anticoagulants", *Blood*, vol. 105, No. 2, pp. 453-463.

Howell, D. C., et al., "Direct Thrombin Inhibition Reduces Lung Collagen, Accumulation, and Connective Tissue Growth mRNA Levels in Bleomycin-Induced Pulmonary Fibrosis", *American Journal of Pathology*, (2001), vol. 159, No. 4, pp. 1383-1395.

Hua, Y., et al., "Systemic use of argatroban reduces tumor mass, attenuates neurological deficits and prolongs survival time in rat glioma models" *Acta Neurochir*, (2005), [Suppl] vol. 95, pp. 403-406.

Hua, Y., et al., "The role of thrombin in gliomas", *Journal of Thrombosis and Haemostasis*, (2005), vol. 3, pp. 1917-1923.

Highes, B., "First oral warfarin alternative approved in the US", *Nature Reviews Drug Discovery*, (2010), vol 9, pp. 903-906.

Inaba, Y., et al., "Suppression of Experimental Autoimmune Encephalomyelitis by Dermatan Sulfate", *Cellular Immunology*, (1999), vol. 198, pp. 96-102.

Kakkar, A. K., et al., "Low Molecular Weight Heparin, Therapy With Dalteparin, and Survival in Advanced Cancer: The Fragmin Advanced Malignancy Outcome Study (FAMOUS)", *Journal Of Clinical Oncology*, (2004), vol. 22, No. 10, pp. 1944-1948.

Klerk, C. P.et al., "The Effect of Low Molecular Weight Heparin on Survival in Patients With Advanced Malignancy", *Journal Of Clinical Oncology*, (2005), vol. 23, No. 10, pp. 2130-2135.

Kranjc, A. & Kikelj, D., "Dual Inhibitors of the Blood Coagulation Enzymes" *Current Medicinal Chemistry*, (2004), vol. 11, pp. 2535-2547.

Langer, "New Methods of Drug Delivery", *Science*, vol. 249, No. 4976 (Sep. 28, 1990), pp. 1527-1533.

Lee, A. Y.et al., "Randomized Comparison of Low Molecular Weight Heparin and Coumarin Derivatives on the Survival of Patients With Cancer and Venous Thromboembolism", *Journal Of Clinical Oncology*, (2005), vol. 23, No. 10, pp. 2123-2129.

Lottenberg, R, et al., "The Action of Thrombin on Peptide P-Nitroanilide Substrates Substrate Selectivity and Examination of Hydrolysis Under Different Conditions", *Biochimica et Biophysica Acta*, (1983), vol. 752, pp. 539-557.

Luo, W., et al., Maragoudakis, M. E.; Tsopanoglou, N. E., (Eds). "Chapter 8: The Role of Thrombin and Thrombin Receptors in the Brain", *Thrombin*, 2009; pp. 133-159, Springer Science + Business Media: New York: NY.

Miller-Keane, Encyclopedia & Dictionary of Medicine, Nursing & Allied Health, 5th Ed., (W. B. Saunders Co.), 1992, pp. 1651 and 1708.

Narita, M., et al., "Protease-Activated Receptor-1 and Platelet-Derived Growth Factor in Spinal Cord Neurons Are Implicated in Neuropathic Pain after Nerve Injury", *The Journal of Neuroscience*, (Oct. 26, 2005), vol. 25, No. 43, pp. 10000-10009.

Nieman, M. T., et al., "Oral Thrombostatin FM19 inhibits prostate cancer", *Thrombosis and Haemostasis*, (2010), vol. 104, pp. 1044-1048.

Nieman, M. T., et al., "Thrombostatin FM compounds: direct thrombin inhibitors—mechanism of action in vitro and in vivo"; *Journal of Thrombosis and Haemostasis*, (2008), vol. 6, pp. 837-845.

Prezelj, A., et al., "Recent Advances in Serine Protease Inhibitors as Anticoagulant Agents", *Current Pharmaceutical Design*, (2007), vol. 13, pp. 287-312.

Silver, R. M., et al., "Dabigatran Etexilate, An Oral Direct Thrombin Inhibitor, Represses Fibrotic Changes in a Murine Model of Pulmonary Fibrosis", Am. J. Respir. Crit. Care Med., (2010), vol. 181, pp. A6780.

Smorenburg, S. M., et al., "The Effects of Unfractionated Heparin on Survival in Patients with Matignancy—A Systematic Review", *Thrombosis Haemostasis*, (1999), vol. 82, pp. 1600-1604.

T. Higuchi and V. Stella, "Pro-drugs: An Overview and Definition", in *Pro-drugs as Novel Delivery Systems*, vol. 14, A.C.S. Symposium Series, American Chemical Society (Jun. 1, 1975), pp. 1-115.

The National Formulary XIV, 14th ed. (American Pharmaceutical Association: Washington, DC), (Jul. 1, 1975), pp. 1-5.

The National Formulary XIV, 14th ed. (American Pharmaceutical Association: Washington, DC), (Jul. 1, 1975), pp. 6-19.

Van Noorden, C. J., "Experimental and clinical effects of anticoagulants on cancer progression", *Thrombosis Research*, (2010), vol. 125, Suppl. 2, pp. S77-S79.

Vaughan, P. J., et al., "Protease nexin-1, a potent thrombin inhibitor, is reduced around cerebral blood vessles in Alzheimer's disease", *Brain Research*, (1994), vol. 668, pp. 160-170.

Wiederman, CH. J. & Romisch, J., "The Anti-Inflammatory Actions of Antithrombin—A Review", *Acta Med Austriaca*, (2002), vol. 29, pp. 89-92.

Wieland, H. A., et al., "Approaches in anticoagulation: Rationales for target positioning", *Current Opinion in Investigational Drugs*, (2003), vol. 4, No. 3, pp. 264-271.

Yin, X., et al., "Short Communication", *The American Journal of Pathology*, (2010), No. 4, pp. 1600-1606.

Young, R. J., et al.,"Selective and dual action orally active inhibitors of thrombin and factor Xa", *Bioorganic & Medicinal Chemistry Letter*, (2007), vol 17, pp. 2927-2930.

Zacharski, Leo R. and Agnes Y. Y. Lee, "Heparin as an anticancer therapeutic", *Expert Opinion on Investigational Drugs*, Jul. 2008, vol. 17, No. 7, pp. 1029-1037.

Office Action, mailed in related Chinese Patent Application No. 201180026731.8, dated Aug. 22, 2014.

Brent et al., "Fomepizole for the treatment of ethylene glycol poisoning. Methylpyrazole for Toxic Alcohols Study Group," N. Engl. J. Med., Mar. 18, 1999, pp. 832-838, vol. 340(11).

European Patent Office, "Examination Report," in corresponding European patent application No. 11 766 507.5, mailed on Oct. 31, 2014, 7 pages.

Intellectual Property Office of New Zealand, "Examination Report," in corresponding New Zealand patent application No. 700332, mailed on Oct. 14, 2014, 3 pages.

IP Australia, "Examination Report," in corresponding Australia patent application No. 2011238616, mailed on Oct. 22, 2014, 7 pages.

STN International Registry File [Online], May 14, 2008, CAS Registration No. RN: 1020709-18-5.

Office Action, mailed in related Japanese Patent Application No. 2013-502815, dated Jan. 20, 2015.

Office Action, mailed in related Israeli Patent Application No. 555222, dated Jan. 18, 2015.

STN International Registry File [online], Apr. 30, 3006, CAS Registration No. RN: 882239-05-6.

STN International Registry File [online], Nov. 30, 2007, CAS Registration No. RN: 956375-74-9.

STN International Registry File [online], Dec. 2, 2007, CAS Registration No. RN: 956441-56-8.

(56) References Cited

OTHER PUBLICATIONS

STN International Registry File [online], Dec. 2, 2007, CAS Registration No. RN: 956442-20-9.
STN International Registry File [online], Mar. 9, 2008 CAS Registration No. RN: 1007171-70-1.
STN International Registry File [online], Oct. 25, 2009, CAS Registration No. RN: 1189909-54-3.
Dzvinchuk, I.B. et al., "Synthesis of 3-aryl-1-aroyl-5[2-[(trifluoroacetyl)amino]anilino]pyrazoles from 2-(aroylmethyl)-1H-benzimidazole aroylhydrazones," Zhurnal Organichnoi to Parmatsevtichnoi Khmii, 4(1), 2006, pp. 32-37.
Lloyd, J. et al., "Benzopyran sulfonamides as Kv1.5 potassium channel blockers," Bioorganic & Medicinal Chemistry Letters, 17(12), Jun. 15, 2007, pp. 3271-3275.
Wardakhan, W.W. et al., "Synthesis of novel pyrazole, coumarin and pyridazine derivatives evaluated as potential antimicrobial and antifungal agents," Journal of the Chilean Chemical Society, 52(2), 2007, pp. 1145-1149.
Final Rejection in related Japanese Patent Application No. 2013-502815, dated Oct. 6, 2015.
Office Action, mailed in related Russian Patent Application No. 2013-502815, dated Mar. 18, 2015.
CAS Registry No. 105-20-4.
CAS Registry No. 2458-26-6.
CAS Registry No. 6085-94-5.
CAS Registry No. 6086-22-2.
CAS Registry No. 67-51-6.
CAS Registry No. 7411-16-7.
CAS Registry No. 7554-65-6.
CAS Registry No. 79746-00-2.
CAS registration number RN: 943609-51-6, 943609-60-7.
Calabresi et al., "Section IX Chemotherapy of Neoplastic Diseases Introduction," Goodman & Gilman's The Pharmacological Basis of Therapeutics Tenth Edition: 1381-1388, 2001.
Hallet, "Acude Peripheral Arterial Occulusion," Merck Manual, Professional/Cardiovascular Disorders/Peripheral Arterial Disorders, two pages, May 2014.
Diener et al., "Stroke prevention using the oral direct thrombin inhibitor ximelagatran in patients with non-valvular atrial fibrillation. Pooled analysis from the SPORTIF III and V studies" Cerebrovascular Diseases, 21(4):279-293. Mar. 2006.
Eriksson et al., "Direct thrombin inhibitor melagatran followed by oral ximelagatran in comparison with enoxaparin for prevention of venous thromboembolism after total hip or knee replacement." Thrombosis and Haemostasi, 89(2):288-296. Feb. 2003.
Francis et al., "Ximelagatran versus warfarin for the prevention of venous thromboembolism after total knee arthroplasty. A randomized, double-blind trial." Annals of Internal Medicine, 137(8):648-655. Oct. 15, 2002.
Hankey et al, "Antithrombotic Drugs for Patients with Ischaemic Stroke and Transient Ischaemic Attack to Prevent Recurrent Major Vascular Events," The Lancet Neurology, 9(3):273-284, Mar. 2010.
Heit et al., "Comparison of the Oral Direct Thrombin Inhibitor Ximelagatran With Enoxaparin as Prophylaxis Against Venoug Thromboembolism After Total Knee Replacement: A Phase 2 Dose-Finding Study," Archives of Internal Medicine 161(18):2215-2221, Oct. 8, 2001.
Hu et al., "Role of endogenous thrombin in tumor implantation, seeding, and spontaneous metastasis," Blood, 104(9). pp. 2746-2751. Nov. 1, 2004.
Keel et al., "Pathophysiology of polytrauma," Injury, 36(6). pp. 691-709. Jun. 2005.
Kokolis et al., "Anticoagulation strategies for patients undergoing percutaneous coronary intervention: unfractionated heparin, low-molecular-weight herapins, and direct thrombin inhibitors." Progress in Cardiovascular Disease, 46(6):506-523. May-Jun. 2004.
Lewis et al., "Agratroban anticoagulation during percutaneous coronary intervention in patients with heparin-induced thrombocytopenia." Catherization & Cardiovascular Interventions, 57(2):177-184. Oct. 2002. Published ahead of print Sep. 30, 2002.
Miura "Transactivation of KDR/Flk-1 by the B2 receptor induces tube formation in human coronary endothelial cells," Hypertension, 41(5). pp. 1118-1123. Published ahead of print Mar. 24, 2003.
Olsson et al., "Stroke prevention with the oral direct thrombin inhibitor ximelagatran compared with warfarin in patients with non-valvular atrial fibrillation (SPORTIF III): randomised controlled trial.," Lancet, 362(9397): 1691-1698, Nov. 22, 2003.
Pinto et al., "Discovery of 1-[3-(Aminomethyl)phenyl]-N-[3-fluro-2'-(methylsulfonyl)- [1,1'-biphenyl]-4-yl]-3-(trifuloromethyl)-1H-pyrazole-5-carboxamide (DPC423), a Highly Potent, Selective, and Orally Bioavailable Inhibitor of Blood Coagulation Factor Xa," Journal of Medicinal Chemistry, 44(4). pp. 566-578. Jan. 24, 2001.
Xiong et al., "Discovery and Structure-Activity Relationship of 3-Methoxy-N-(3-(1-methyl-1 H pyrazol -5-y-l)-4(2-morpholinoethoxy)phenyl)benzamide (APD791): A Highly Selective 5-Hydroxytryptamine 2A Receptor Inverse Agonist for the Treament of Arterial Thrombosis," Journal of Medicinal Chemistry 53(11):4412-4421, Jun. 10, 2010, ISSN: 0022-2623, DOI: 10.1021/jm100044a.

\* cited by examiner

MULTISUBSTITUTED AROMATIC COMPOUNDS AS INHIBITORS OF THROMBIN

CROSS-REFERENCES TO RELATED APPLICATIONS

This application is a continuation of PCT application PCT/US2011/30585, filed Mar. 30, 2011, which claims the benefit of U.S. Provisional Application No. 61/319,175, filed Mar. 30, 2010, the entire contents of each of which is hereby incorporated by reference herein and for all purposes.

BACKGROUND OF THE INVENTION

The present disclosure relates to compounds, e.g., multisubstituted aromatic compounds, which exhibit biological activity, e.g., inhibitory action, against thrombin (activated blood-coagulation factor II; EC 3.4.21.5).

In mammalian systems, blood vessel injuries result in bleeding events, which are dealt with by the blood coagulation cascade. The cascade includes the Extrinsic and Intrinsic pathways, involving the activation of at least 13 interconnected factors and a variety of co-factors and other regulatory proteins. Upon vascular injury, plasma factor VII interacts with exposed Tissue Factor (TF), and the resultant TF-fVIIa complex initiates a complex series of events. Factor fXa is produced directly 'downstream' from the TF-fVIIa complex, and amplified manifold via the Intrinsic Pathway. FXa then serves as the catalyst for formation of thrombin (fIIa), which in turn is the direct precursor to fibrinolysis. The outcome is a fibrinolytic clot, which stops the bleeding. Fibrinolysis of the polymeric clot into fibrin monomers leads to dissolution and a return of the system to the pre-clot state. The cascade is a complex balance of factors and co-factors and is tightly regulated.

In disease states, undesired up- or down-regulation of any factor leads to conditions such as bleeding or thrombosis. Historically, anticoagulants have been used in patients at risk of suffering from thrombotic complications, such as angina, stroke and heart attack. Warfarin has enjoyed dominance as a first-in-line anticoagulant therapeutic. Developed in the 1940s, it is a Vitamin K antagonist and inhibits factors II, VII, IX and X, amongst others. It is administered orally, but its ease of use is tempered by other effects: it has a very long half life (>2 days) and has serious drug-drug interactions. Importantly, since Vitamin K is a ubiquitous cofactor within the coagulation cascade, antagonism results in the simultaneous inhibition of many clotting factors and thus can lead to significant bleeding complications.

Much attention has been focused on heparin, the naturally-occurring polysaccharide that activates AT III, the endogenous inhibitor of many of the factors in the coagulation cascade. The need for parenteral administration for the heparin-derived therapeutics, and the inconvenient requirements for close supervision for the orally available warfarin, has resulted in a drive to discover and develop orally available drugs with wide therapeutic windows for safety and efficacy.

Indeed, the position of thrombin in the coagulation cascade has made it a popular target for drug discovery. Without wishing to be bound by any theory, it is believed that the ultimate development of direct thrombin inhibitors (DTIs) is usefully based upon the classical D-Phe-Pro-Arg motif, a sequence that mimics fibrinogen, which is a natural substrate of thrombin. Without further wishing to be bound by any theory, it is believed that the use of DTIs is very well precedented, such as with the hirudin-based anticoagulants, and thus there is strong interest in the discovery and development of novel DTIs.

A thorough discussion of thrombin and its roles in the coagulation process can be found in a variety of references, including the following which are incorporated herein by reference in their entireties and for all purposes: Wieland, H. A., et al., 2003, *Curr Opin Investig Drugs*, 4:264-71; Gross, P. L. & Weitz, J. I., 2008, *Arterioscler Thromb Vasc Biol*, 28:380-6; Hirsh, J., et al., 2005, *Blood*, 105:453-63; Prezelj, A., et al., 2007, *Curr Pharm Des*, 13:287-312.

BRIEF SUMMARY OF THE INVENTION

In a first aspect, there is provided a compound with structure of Formula (Ia)

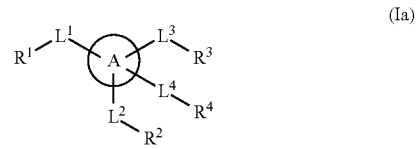

(Ia)

or pharmaceutically acceptable salt, ester, solvate, or prodrug thereof. Ring A is substituted or unsubstituted pyrazolyl, or substituted or unsubstituted triazolyl. $L^1$, $L^2$ and $L^3$ are independently a bond, substituted or unsubstituted alkylene, substituted or unsubstituted heteroalkylene, —S—, —SO—, —$SO_2$—, —O—, —$NHSO_2$—, or —$NR^5$—. $L^4$ is absent, a bond, substituted or unsubstituted alkylene, substituted or unsubstituted heteroalkylene, —S—, —SO—, —$SO_2$—, —O—, —$NHSO_2$—, or —$NR^5$—. $R^1$, $R^2$ and $R^3$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is absent, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, provided that when $L^4$ is absent, then $R^4$ is absent. $R^5$ is independently hydrogen, or substituted or unsubstituted alkyl. It has been discovered that compounds described herein are useful for the inhibition of thrombin.

In another aspect, there is provided a pharmaceutical composition comprising a compound disclosed herein and a pharmaceutically acceptable excipient. The compound is a compound of any of Formulae (Ia), (Ib), (IIa), (IIb), (IIIa), (IIIb), (IV) or (V) as disclosed herein, or a compound as set forth in any of Tables A, B or C herein, or pharmaceutically acceptable salt, ester, solvate, or prodrug thereof.

In yet another aspect, there is provided a method for treating a disease or disorder in a subject. The method includes administering a compound of any of Formulae (Ia), (Ib), (IIa), (IIb), (IIIa), (IIIb), (IV) or (V) as disclosed herein, compound as set forth in any of Tables A, B or C herein, pharmaceutically acceptable salt, ester, solvate, or prodrug thereof, or pharmaceutical composition thereof, to a subject in need thereof in an amount effective to treat the disease or disorder.

In still another aspect, there is provided a method for preventing a disease or disorder in a subject. The method includes administering a compound of any of Formulae (Ia), (Ib), (IIa), (IIb), (IIIa), (IIIb), (IV) or (V) as disclosed herein, compound as set forth in any of Tables A, B or C herein, pharmaceutically acceptable salt, ester, solvate, or prodrug thereof, or pharmaceutical composition thereof, to a subject in need thereof in an amount effective to prevent the disease or disorder.

BRIEF DESCRIPTION OF THE DRAWINGS

Not applicable.

DETAILED DESCRIPTION OF THE INVENTION

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Accordingly, the term "alkyl" can refer to $C_1$-$C_{16}$ straight chain saturated, $C_1$-$C_{16}$ branched saturated, $C_3$-$C_8$ cyclic saturated and $C_1$-$C_{16}$ straight chain or branched saturated aliphatic hydrocarbon groups substituted with $C_3$-$C_8$ cyclic saturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, octyl, nonyl, decyl, undecyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopropylmethyl, and the like.

The term "alkylene," by itself or as part of another substituent, means, unless otherwise stated, a divalent radical derived from an alkyl, as exemplified, but not limited by, —$CH_2CH_2$ $CH_2CH_2$—. Typically, an alkyl (or alkylene) group will have from 1 to 24 carbon atoms, with those groups having 10 or fewer carbon atoms being preferred in the compounds disclosed herein. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "alkenyl" includes $C_2$-$C_{16}$ straight chain unsaturated, $C_2$-$C_{11}$ branched unsaturated, $C_5$-$C_8$ unsaturated cyclic, and $C_2$-$C_{16}$ straight chain or branched unsaturated aliphatic hydrocarbon groups substituted with $C_3$-$C_8$ cyclic saturated and unsaturated aliphatic hydrocarbon groups having the specified number of carbon atoms. Double bonds may occur in any stable point along the chain and the carbon-carbon double bonds may have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds.

The term "alkynyl" refers in the customary sense to alkyl additionally having one or more triple bonds. The term "cycloalkenyl" refers to cycloalkyl additionally having one or more double bonds. The term "heterocycloalkenyl" refers to heterocycloalkyl additionally having one or more double bonds.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Each of the above terms (e.g., "alkyl," "heteroalkyl," "aryl," and "heteroaryl") includes both substituted and unsubstituted forms of the indicated radical. Preferred substituents for each type of radical are provided herein.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

The term "alkyloxy" (e.g. methoxy, ethoxy, propyloxy, allyloxy, cyclohexyloxy) represents an alkyl group as defined above having the indicated number of carbon atoms attached through an oxygen bridge (—O—).

The term "alkylthio" (e.g. methylthio, ethylthio, propylthio, cyclohexylthio and the like) represents an alkyl group as defined above having the indicated number of carbon atoms attached through a sulfur bridge (—S—).

The term "alkylamino" represents one or two alkyl groups as defined above having the indicated number of carbon atoms attached through an amine bridge. The two alkyl groups maybe taken together with the nitrogen to which they are attached forming a cyclic system containing 3 to 8 carbon atoms with or without one $C_1$-$C_{16}$ alkyl, aryl$C_0$-$C_{16}$ alkyl, or $C_0$-$C_{16}$alkylaryl substituent.

The term "alkylaminoalkyl" represents an alkylamino group attached through an alkyl group as defined above having the indicated number of carbon atoms.

The term "alkyloxy(alkyl)amino" (e.g. methoxy(methyl)amine, ethoxy(propyl)amine) represents an alkyloxy group as defined above attached through an amino group, the amino group itself having an alkyl substituent.

The term "alkylcarbonyl" (e.g. cyclooctylcarbonyl, pentylcarbonyl, 3-hexylcarbonyl) represents an alkyl group as defined above having the indicated number of carbon atoms attached through a carbonyl group.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen.

The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonylaminomethyl, methylcarbonylaminophenyl) represents an alkylcarbonyl group as defined above wherein the carbonyl is in turn attached through the nitrogen atom of an amino group.

The nitrogen group may itself be substituted with an alkyl or aryl group.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g. 3-indolyl, 4-imidazolyl). The aryl substituents are independently selected from the group consisting of halo, nitro, cyano, trihalomethyl, $C_{1-16}$alkyl, aryl$C_{1-16}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$ alkylamino$C_{0-16}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl $C_{0-16}$alkyl, $C_{1-16}$alkylcarboxy$C_{0-16}$alkyl, aryl$C_{1-16}$alkylcarboxy$C_{0-16}$alkyl, $C_{1-16}$alkylcarbonylamino$C_{0-16}$alkyl, aryl$C_{1-16}$alkylcarbonylamino$C_{0-16}$alkyl,-$C_{0-16}$alkylCOOR$_4$, —$C_{0-16}$alkylCONR$_5$R$_6$ wherein R$_4$, R$_5$ and R$_6$ are independently selected from hydrogen, $C_1$-$C_{11}$alkyl, aryl$C_0$-$C_{11}$alkyl, or R$_5$ and R$_6$ are taken together with the nitrogen to which they are attached forming a cyclic system containing 3 to 8 carbon atoms with or without one $C_{1-16}$ alkyl, aryl$C_0$-$C_{16}$ alkyl, or $C_0$-$Cl_{16}$ alkylaryl substituent. Aryl includes but is not limited to pyrazolyl and triazolyl.

For brevity, the term "aryl" when used in combination with other terms (e.g., aryloxy, arylthioxy, arylalkyl) includes both aryl and heteroaryl rings as defined above. Thus, the terms "arylalkyl," "aralkyl" and the like are meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom. Accordingly, the terms "arylalkyl" and the like (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "$C_1$-$C_4$ alkylsulfonyl").

The term "carbonyloxy" represents a carbonyl group attached through an oxygen bridge.

In the above definitions, the terms "alkyl" and "alkenyl" may be used interchangeably in so far as a stable chemical entity is formed, as would be apparent to those skilled in the art.

The term "linker" refers to attachment groups interposed between substituents, e.g., R$^1$, R$^2$, R$^3$ or R$^4$ described herein, e.g., Formula (Ia) and generically referred to as R", and the group which is substituted, e.g., "ring A" group of e.g., Formula (Ia). In some embodiments, the linker includes amido (—CONH—R" or —NHCO—R"), thioamido (—CSNH—R" or —NHCS—R"), carboxyl (—CO$_2$—R" or —OCOR"), carbonyl (—CO—R"), urea (—NHCONH—R"), thiourea (—NHCSNH—R), sulfonamido (—NHSO$_2$—R" or —SO$_2$NH—R"), ether (—O—R"), sulfonyl (—SO$_2$—R), sulfoxyl (—SO—R), carbamoyl (—NHCO$_2$—R" or —OCONH—R), or amino (—NHR") linking moieties.

A "substituent group," as used herein, means a group selected from the following moieties:

(A) —OH, —NH$_2$, —SH, —CN, —CF$_3$, —NO$_2$, oxo, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —$NH_2$, —SH, —CN, —$CF_3$, —$NO_2$, halogen, —COOH, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "about" used in the context of a numeric value indicates a range of +/−10% of the numeric value, unless expressly indicated otherwise.

II. COMPOUNDS

In one aspect, there is provided a compound with structure of Formula (Ia):

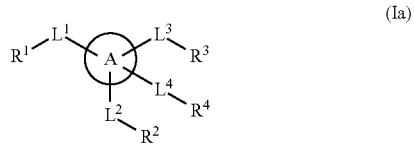

(Ia)

or pharmaceutically acceptable salt, ester, solvate, or prodrug thereof. Ring A is substituted or unsubstituted pyrazolyl, or substituted or unsubstituted triazolyl. $L^1$, $L^2$ and $L^3$ are independently a bond, substituted or unsubstituted alkylene, substituted or unsubstituted heteroalkylene, —S—, —SO—, —$SO_2$—, —O—, —$NHSO_2$—, or —$NR^5$—. $L^4$ is absent, a bond, substituted or unsubstituted alkylene, substituted or unsubstituted heteroalkylene, —S—, —SO—, —$SO_2$—, —O—, —$NHSO_2$—, or —$NR^5$—. $R^1$, $R^2$ and $R^3$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is absent, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, provided that when $L^4$ is absent, then $R^4$ is absent. $R^5$ is independently hydrogen, or substituted or unsubstituted alkyl.

In some embodiments, the compound is a pharmaceutically acceptable salt, ester, solvate, or prodrug of a compound of Formula (Ia). In some embodiments, the compound is not an ester, not a solvate, and not a prodrug.

In some embodiments, $L^4$ and $R^4$ are absent, providing a compound with structure of Formula (Ib) following.

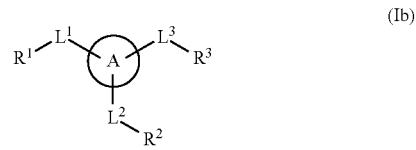

(Ib)

In some embodiments, there is provided a compound according to Formula (Ib) with structures of either of Formulae (IIa) or (IIb) following.

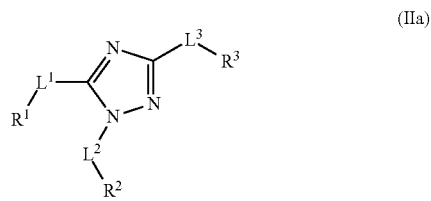

(IIa)

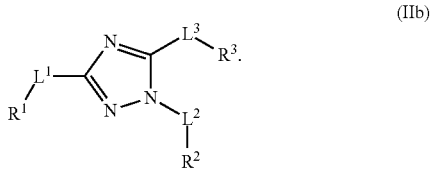

(IIb)

In some embodiments, the compound has the structure of Formula (IIa), wherein $L^3$ is a bond, and $R^3$ is substituted or unsubstituted aryl, or substituted or unsubstituted heteroaryl. In some embodiments, the pendant heteroaryl $R^3$ is substituted or unsubstituted pyridyl, thienyl, or furyl. In some embodiments, the $R^3$ is unsubstituted pyridyl, thienyl, or furyl. In some embodiments, $R^3$ is unsubstituted aryl, preferably phenyl. In some embodiments, $R^3$ is substituted aryl, preferably halogen-substituted phenyl.

In some embodiments, a compound is provided with structure of Formula (IIa), wherein $L^3$ is a bond, substituted or unsubstituted alkylene, and $R^3$ is substituted or unsubstituted aryl, or substituted or unsubstituted heterocycloalkyl.

In some embodiments, the compound has the structure of Formula (IIa), wherein $L^3$ is —C(O)O—, and $R^3$ is substituted or unsubstituted alkyl, preferably unsubstituted alkyl, more preferably unsubstituted lower alkyl.

In some embodiments, the compound has the structure of Formula (IIa), wherein $L^3$ is —C(O)NR$^5$—, $R^5$ is hydrogen or alkyl, and $R^3$ is substituted or unsubstituted alkyl, or substituted or unsubstituted aryl.

Further to any embodiment above, in some embodiments $L^1$ is —S—, —NR$^5$—, substituted or unsubstituted alkylene, or substituted or unsubstituted heteroalkylene, and $R^1$ is hydrogen, substituted or unsubstituted alkyl, substituted or unsubstituted aryl, substituted or unsubstituted heteroaryl, or substituted or unsubstituted heterocycloalkyl. In some embodiments, $L^1$ is —NC(O)—. In some embodiments, $R^3$ is substituted or unsubstituted aryl. In some embodiments, $R^3$ is unsubstituted aryl. In some embodiments, $L^2$ is a bond. In some embodiments, $L^2$ is a bond and $R^2$ is hydrogen.

Further to any embodiment above, in some embodiments $L^2$ is substituted or unsubstituted alkylene or —C(O)—, and $R^2$ is hydrogen, substituted or unsubstituted alkyl, substituted or unsubstituted aryl, substituted or unsubstituted heteroaryl, or substituted or unsubstituted heterocycloalkyl.

In some embodiments, the compound of Formula (IIa) has the structure of Formula (IIc) following, wherein $L^1$ is —NH—(CH$_2$)$_n$—, n is 0 to 6, preferably 1, and $R^1$ is hydrogen, substituted or unsubstituted alkyl, substituted or unsubstituted aryl, substituted or unsubstituted heteroaryl, or substituted or unsubstituted heterocycloalkyl.

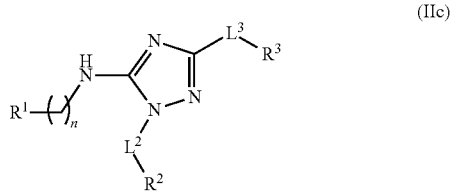

(IIc)

In some embodiments of the compound of Formula (IIc), $L^1$ is —NHCH$_2$— or —NH(CH$_2$)$_2$—, and $R^1$ is substituted or unsubstituted aryl. In some embodiments, $R^1$ is unsubstituted aryl. In some embodiments, $R^1$ is aryl, preferably phenyl, substituted with halogen, —CN or alkyloxy, preferably methoxy. In some embodiments, $R^1$ is unsubstituted alkyl, preferably lower alkyl, more preferably methyl or ethyl. In some embodiments, n is 0, and $R^1$ is hydrogen.

In some embodiments, the compound of Formula (IIa) has the structure of Formula (IId) following, wherein $L^1$ is a bond, and $R^1$ is unsubstituted alkyl, or substituted or unsubstituted aryl. In some embodiments, $R^1$ is unsubstituted alkyl, preferably lower alkyl. In some embodiments, $R^1$ is substituted aryl, preferably halogen-substituted phenyl.

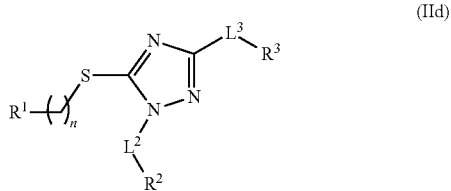

(IId)

In some embodiments, there is provided a compound with structure of Formula (IIb). In some embodiments, $L^2$ is a bond, or substituted or unsubstituted alkylene. In some embodiments, $L^2$ is a bond, and $R^2$ is alkyl, preferably lower alkyl. In some embodiments, $L^2$ is a substituted alkylene. In some embodiments, $L^2$ is an unsubstituted alkylene, preferably methylene or ethylene. In some embodiments, $L^2$ is an unsubstituted alkylene, and $R^2$ is unsubstituted aryl, preferably phenyl. In some embodiments, $R^2$ is substituted or unsubstituted alkyl, or substituted or unsubstituted aryl.

In some embodiments, there is provided a compound according to Formula (Ib) with structure of either of Formulae (IIIa) or (IIIb) following.

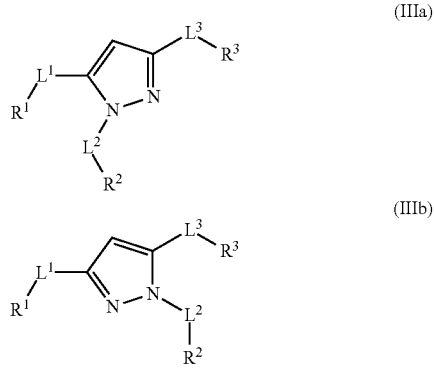

In some embodiments, the compound has the structure of Formula (IIIa). In some embodiments, $L^3$ is a bond, or substituted or unsubstituted alkylene, and $R^3$ is substituted or unsubstituted aryl, or substituted or unsubstituted heterocycloalkyl. In some embodiments, $R^3$ is substituted or unsubstituted phenyl, or substituted or unsubstituted pyridyl. In some embodiments, $R^3$ is unsubstituted phenyl. In some embodiments, $R^3$ is unsubstituted pyridyl.

In some embodiments, the compound has the structure of Formula (IIIa) wherein $L^3$ is —C(O)O—, and $R^3$ is substituted or unsubstituted alkyl.

In some embodiments, the compound has the structure of Formula (IIIa) wherein $L^3$ is —C(O)NR$^6$, $R^6$ is hydrogen or alkyl, and $R^3$ is substituted or unsubstituted alkyl, or substituted or unsubstituted aryl.

Further to any embodiment above wherein the compound has the structure of Formula (IIIa), in some embodiments, $L^1$ is —S—, —NR$^4$—, substituted or unsubstituted alkylene, or substituted or unsubstituted heteroalkylene, and $R^1$ is hydrogen, substituted or unsubstituted alkyl, substituted or unsubstituted aryl, substituted or unsubstituted heteroaryl, or substituted or unsubstituted heterocycloalkyl. In some embodiments, $L^2$ is a bond. In some embodiments, $R^2$ is hydrogen. In some embodiments, $L^2$ is substituted or unsubstituted alkylene or —C(O)—, and $R^2$ is hydrogen, substituted or unsubstituted alkyl, substituted or unsubstituted aryl, substituted or unsubstituted heteroaryl, or substituted or unsubstituted heterocycloalkyl.

In some embodiments, the compound has the structure of Formula (IIIb). In some embodiments, $L^2$ is a bond or substituted or unsubstituted alkylene. In some embodiments, $L^2$ is a bond. In some embodiments, $L^2$ is unsubstituted alkylene. In some embodiments, $L^2$ is substituted alkylene. In some embodiments, $R^2$ is substituted or unsubstituted alkyl, or substituted or unsubstituted aryl. Further to any particular $L^2$, in some embodiments $R^2$ is substituted or unsubstituted alkyl, or substituted or unsubstituted aryl. In some embodiments, $R^2$ is unsubstituted alkyl. In some embodiments, $R^2$ is unsubstituted aryl. In some embodiments, $R^2$ is substituted alkyl. In some embodiments, $R^2$ is substituted aryl.

In some embodiments, there is provided a compound according to Formula (Ib) with structure of Formulae (IV) following.

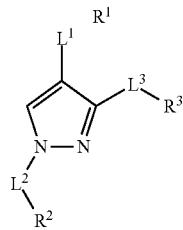

(IV)

In some embodiments, there is provided a compound according with Formula (IV) wherein $L^3$ is a bond, substituted or unsubstituted alkylene, or substituted or unsubstituted heteroalkylene, and $R^3$ is substituted or unsubstituted aryl, or substituted or unsubstituted heteroaryl. In some embodiments, $L^3$ is a bond, —NH—, —NHCH$_2$— or —NH(CH$_2$)$_2$—.

Further to any embodiment of a compound with structure of Formula (IV), in some embodiments, $L^1$ is a bond, substituted or unsubstituted alkylene, substituted or unsubstituted heteroalkylene, —C(O)—, —C(O)—NR$^6$—. In some embodiments, $R^1$ is hydrogen, —COOH, substituted or unsubstituted alkyl, substituted or unsubstituted aryl, substituted or unsubstituted heteroaryl; substituted or unsubstituted heterocycloalkyl. In some embodiments, $R^6$ is hydrogen, or substituted or unsubstituted alkyl.

In some embodiments, there is provided a compound according to Formula (Ia) with structure of Formulae (V) following.

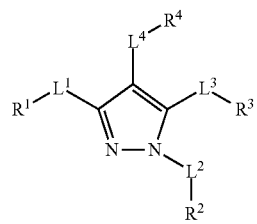

(V)

In some embodiments, there is provided a compound according with Formula (V) wherein $L^4$ is a bond; and $R^4$ is hydrogen, substituted or unsubstituted alkyl, or substituted or unsubstituted heteroalkyl. In some embodiments, $R^4$ is unsubstituted alkyl.

Exemplary compounds, e.g., multisubstituted aromatic compounds, in accordance with the present disclosure are provided herein. In Table A following, compound (Cmpd) number, chemical name (i.e., International Union of Pure and Applied Chemistry [IUPAC] name), molecular weight ($MW_{calc}$ calculated mass and $MW_{meas}$ measured mass) and biological activity (i.e., inhibition activity in a thrombin assay) are disclosed.

Regarding experimental molecular weights obtained by mass spectrometric analysis as described herein including Table A, unless indicated otherwise it is understood that the measured chemical species can be the protonated compound, e.g., [M+H]$^+$, whereby the measured mass is 1 atomic unit greater than the calculated mass of the compound, as well known in the art.

For Table A following, the disclosed compounds were assayed for inhibition of the protease activity of thrombin as described herein. In Table A, the level of inhibition in the thrombin assay is indicated as follows: a: IC$_{50}$≤0.1 μM; b: 0.1 μM<IC$_{50}$<1 μM; c: IC$_{50}$≥1 μM. Accordingly, in some embodiments, there is provided a compound as expressly set forth in Table A following.

TABLE A

| Cmpd No. | IUPAC name | $MW_{calc}$ | $MW_{meas}$ | Thrombin Activity |
|---|---|---|---|---|
| 4 | N-[(4-fluorophenyl)methyl]-3-(pyridin-3-yl)-1H-1,2,4-triazol-5-amine | 269 | 270 | c |
| 5 | N-benzyl-3-(pyridin-2-yl)-1H-1,2,4-triazol-5-amine | 251 | 252 | c |
| 6 | N-[(4-fluorophenyl)methyl]-3-(pyridin-2-yl)-1H-1,2,4-triazol-5-amine | 269 | 270 | c |
| 7 | 1-(5-[(4-fluorophenyl)methyl]amino-3-(pyridin-3-yl)-1H-1,2,4-triazol-1-yl)propan-1-one | 325 | 326 | a |
| 9 | 1-(5-[(2-fluorophenyl)methyl]amino-3-(pyridin-3-yl)-1H-1,2,4-triazol-1-yl)propan-1-one | 325 | 326 | b |
| 10 | 4-([1-propanoyl-3-(pyridin-3-yl)-1H-1,2,4-triazol-5-yl]aminomethyl)benzonitrile | 332 | 333 | c |
| 11 | N-benzyl-1-[(furan-2-yl)carbonyl]-3-(pyridin-2-yl)-1H-1,2,4-triazol-5-amine | 345 | 346 | a |
| 12 | 1-[5-(benzylamino)-3-(pyridin-2-yl)-1H-1,2,4-triazol-1-yl]-3-phenylpropan-1-one | 383 | 384 | a |
| 13 | N-[(4-fluorophenyl)methyl]-3-(pyridin-2-yl)-1-[(thiophen-2-yl)carbonyl]-1H-1,2,4-triazol-5-amine | 379 | 380 | a |
| 14 | 1-benzoyl-N-[(4-fluorophenyl)methyl]-3-(pyridin-4-yl)-1H-1,2,4-triazol-5-amine | 373 | 374 | a |
| 15 | N-[(4-fluorophenyl)methyl]-3-(pyridin-4-yl)-1-[(thiophen-3-yl)carbonyl]-1H-1,2,4-triazol-5-amine | 379 | 380 | a |
| 16 | 1-(5-[(4-methoxyphenyl)methyl]amino-3-(pyridin-4-yl)-1H-1,2,4-triazol-1-yl)-2,2-dimethylpropan-1-one | 365 | 366 | a |
| 17 | N-[(4-fluorophenyl)methyl]-1-[(morpholin-4-yl)carbonyl]-3-(pyridin-3-yl)-1H-1,2,4-triazol-5-amine | 382 | 383 | c |
| 18 | N-(2-fluorophenyl)-5-[(4-fluorophenyl)methyl]amino-3-(pyridin-3-yl)-1H-1,2,4-triazole-1-carboxamide | 406 | 407 | c |

TABLE A-continued

| Cmpd No. | IUPAC name | MW$_{calc}$ | MW$_{meas}$ | Thrombin Activity |
|---|---|---|---|---|
| 19 | 5-[(4-fluorophenyl)methyl]amino-N-methyl-3-(pyridin-3-yl)-1H-1,2,4-triazole-1-carboxamide | 326 | 327 | c |
| 20 | methyl 5-[(4-fluorophenyl)methyl]amino-3-(pyridin-3-yl)-1H-1,2,4-triazole-1-carboxylate | 327 | 328 | b |
| 21 | 2-(5-[(4-fluorophenyl)methyl]amino-3-(pyridin-3-yl)-1H-1,2,4-triazol-1-yl)-1-phenylethan-1-one | 387 | 388 | c |
| 22 | 1-5-[(2-phenylethyl)amino]-3-(pyridin-3-yl)-1H-1,2,4-triazol-1-ylpropan-1-one | 321 | 322 | c |
| 23 | 1-(5-[2-(morpholin-4-yl)ethyl]amino-3-(pyridin-3-yl)-1H-1,2,4-triazol-1-yl)propan-1-one | 330 | 331 | c |
| 24 | 1-[5-(dimethylamino)-3-(pyridin-3-yl)-1H-1,2,4-triazol-1-yl]propan-1-one | 245 | 246 | c |
| 26 | N-[(4-fluorophenyl)methyl]-3-(furan-2-yl)-1-[(2-methoxyphenyl)carbonyl]-1H-1,2,4-triazol-5-amine | 392 | 393 | a |
| 27 | N-[(4-fluorophenyl)methyl]-1-[(2-methoxyphenyl)carbonyl]-3-(thiophen-2-yl)-1H-1,2,4-triazol-5-amine | 408 | 409 | b |
| 28 | 3-(5-[(4-fluorophenyl)methyl]sulfanyl-1-[(2-methoxyphenyl)carbonyl]-1H-1,2,4-triazol-3-yl)pyridine | 420 | 421 | a |
| 29 | 1-[(2-methoxyphenyl)carbonyl]-5-(methylsulfanyl)-3-(thiophen-2-yl)-1H-1,2,4-triazole | 331 | 332 | a |
| 30 | methyl 5-(benzylamino)-1-[(4-chlorophenyl)carbonyl]-1H-1,2,4-triazole-3-carboxylate | 371 | 371, 373 | a |
| 32 | methyl 5-amino-1-[(2-chlorophenyl)carbonyl]-1H-1,2,4-triazole-3-carboxylate | 281 | 281, 283 | a |
| 33 | N-benzyl-1-[(2-methoxyphenyl)carbonyl]-3-(pyrimidin-4-yl)-1H-1,2,4-triazol-5-amine | 386 | 387 | a |
| 34 | N-benzyl-1-[(2-methoxyphenyl)carbonyl]-3-(pyrimidin-5-yl)-1H-,2,4-triazol-5-amine | 386 | 387 | a |
| 35 | N-benzyl-1-[(2-methoxyphenyl)carbonyl]-3-(pyrimidin-2-yl)-1H-1,2,4-triazol-5-amine | 386 | 387 | a |
| 36 | 1-(5-[(4-fluorophenyl)methyl]amino-3-phenyl-1H-pyrazol-1-yl)-2,2-dimethylpropan-1-one | 351 | 352 | c |
| 37 | 1-(5-[(4-fluorophenyl)methyl]amino-3-(pyridin-3-yl)-1H-pyrazol-1-yl)-2,2-dimethylpropan-1-one | 352 | 353 | c |
| 38 | 1-(5-[(4-fluorophenyl)methyl]amino-4-methyl-3-phenyl-1H-pyrazol-1-yl)-2,2-dimethylpropan-1-one | 365 | 366 | c |
| 39 | 1-(5-[(4-fluorophenyl)methyl]amino-3-(pyridin-2-yl)-1H-pyrazol-1-yl)-2,2-dimethylpropan-1-one | 352 | 353 | a |
| 40 | 1-(5-[(4-fluorophenyl)methyl]amino-3-(pyridin-2-yl)-1H-pyrazol-1-yl)propan-1-one | 324 | 325 | b |
| 41 | 1-[(2-chlorophenyl)carbonyl]-N-[(4-fluorophenyl)methyl]-3-(pyridin-2-yl)-1H-pyrazol-5-amine | 407 | 407, 409 | b |
| 42 | 1-(2-chlorophenyl)-3-(pyridin-2-yl)-1H-pyrazol-5-amine | 271 | 271, 273 | c |
| 43 | N-[1-(2-chlorophenyl)-3-(pyridin-2-yl)-1H-pyrazol-5-yl]-4-fluorobenzamide | 393 | 393, 395 | c |
| 44 | 1-(2-chlorophenyl)-N,N-bis[(4-fluorophenyl)methyl]-3-(pyridin-2-yl)-1H-pyrazol-5-amine | 487 | 487, 489 | c |
| 45 | 1-(2-chlorophenyl)-N-[(4-fluorophenyl)methyl]-3-(pyridin-2-yl)-1H-pyrazol-5-amine | 379 | 379, 381 | c |
| 46 | ethyl 3-[(4-fluorophenyl)methyl]amino-1-(pyridin-2-yl)-1H-pyrazole-4-carboxylate | 340 | 341 | c |
| 47 | 3-[(4-fluorophenyl)methyl]amino-1-(pyridin-2-yl)-1H-pyrazole-4-carboxylic acid | 312 | 313 | c |
| 48 | 3-[(4-fluorophenyl)methyl]amino-N-methoxy-N-methyl-1-(pyridin-2-yl)-1H-pyrazole-4-carboxamide | 355 | 356 | c |
| 49 | 3-[(4-fluorophenyl)methyl]amino-N,N-dimethyl-1-(pyridin-2-yl)-1H-pyrazole-4-carboxamide | 339 | 340 | c |
| 50 | 1-(3-[(4-fluorophenyl)methyl]amino-1-(pyridin-2-yl)-1H-pyrazol-4-yl)propan-1-one | 324 | 325 | c |
| 51 | ethyl 1-[2-(4-fluorophenyl)ethyl]-3-(pyridin-2-yl)-1H-pyrazole-5-carboxylate | 339 | 340 | c |
| 52 | 1-[2-(4-fluorophenyl)ethyl]-3-(pyridin-2-yl)-1H-pyrazole-5-carboxylic acid | 311 | 312 | c |
| 53 | 1-[2-(4-fluorophenyl)ethyl]-N-methoxy-N-methyl-3-(pyridin-2-yl)-1H-pyrazole-5-carboxamide | 354 | 355 | c |
| 54 | 2-1-[2-(4-fluorophenyl)ethyl]-5-[(piperidin-1-yl)carbonyl]-1H-pyrazol-3-ylpyridine | 378 | 379 | c |
| 55 | 1-1-[2-(4-fluorophenyl)ethyl]-3-(pyridin-2-yl)-1H-pyrazol-5-ylpropan-1-ol | 325 | 326 | c |
| 56 | 1-1-[2-(4-fluorophenyl)ethyl]-3-(pyridin-2-yl)-1H-pyrazol-5-ylpropan-1-one | 323 | 324 | c |
| 57 | ethyl 1-[2-(4-fluorophenyl)ethyl]-5-(pyridin-2-yl)-1H-pyrazole-3-carboxylate | 339 | 340 | c |

TABLE A-continued

| Cmpd No. | IUPAC name | MW$_{calc}$ | MW$_{meas}$ | Thrombin Activity |
|---|---|---|---|---|
| 58 | 1-[2-(4-fluorophenyl)ethyl]-5-(pyridin-2-yl)-1H-pyrazole-3-carboxylic acid | 311 | 312 | c |
| 59 | 2-1-[2-(4-fluorophenyl)ethyl]-3-[(piperidin-1-yl)carbonyl]-1H-pyrazol-5-ylpyridine | 378 | 379 | c |
| 60 | 1-(3-[(4-fluorophenyl)methyl]amino-1-(pyridin-2-yl)-1H-pyrazol-4-yl)ethan-1-one | 310 | 311 | c |
| 61 | 1-(3-[(4-fluorophenyl)methyl]amino-1-phenyl-1H-pyrazol-4-yl)ethan-1-one | 309 | 310 | c |
| 62 | 1-(3-[(4-fluorophenyl)methyl]amino-1-phenyl-1H-pyrazol-4-yl)propan-1-one | 323 | 324 | c |
| 63 | 1-(5-[(4-fluorophenyl)methyl]amino-3-(furan-2-yl)-1H-1,2,4-triazol-1-yl)propan-1-one | 314 | 315 | a |
| 64 | 1-(5-[(4-fluorophenyl)methyl]amino-3-(pyridin-2-yl)-1H-1,2,4-triazol-1-yl)-2,2-dimethylpropan-1-one | 353 | 354 | a |
| 65 | 1-(5-[(4-fluorophenyl)methyl]amino-3-(pyridin-2-yl)-1H-1,2,4-triazol-1-yl)-2-methylpropan-1-one | 339 | 340 | a |
| 66 | 1-(5-[(4-fluorophenyl)methyl]amino-3-(pyridin-2-yl)-1H-1,2,4-triazol-1-yl)-2-phenylethan-1-one | 387 | 388 | a |
| 67 | 1-(5-[(4-fluorophenyl)methyl]amino-3-(pyridin-2-yl)-1H-1,2,4-triazol-1-yl)-3-methylbutan-1-one | 353 | 354 | a |
| 68 | 1-(5-[(4-fluorophenyl)methyl]amino-3-(pyridin-2-yl)-1H-1,2,4-triazol-1-yl)-3-phenylpropan-1-one | 401 | 402 | a |
| 69 | 1-(5-[(4-fluorophenyl)methyl]amino-3-(pyridin-2-yl)-1H-1,2,4-triazol-1-yl)butan-1-one | 339 | 340 | a |
| 70 | 1-(5-[(4-fluorophenyl)methyl]amino-3-(pyridin-2-yl)-1H-1,2,4-triazol-1-yl)propan-1-one | 325 | 326 | a |
| 71 | 1-(5-[(4-fluorophenyl)methyl]amino-3-(pyridin-3-yl)-1H-1,2,4-triazol-1-yl)-2,2-dimethylpropan-1-one | 353 | 354 | a |
| 72 | 1-(5-[(4-fluorophenyl)methyl]amino-3-(pyridin-3-yl)-1H-1,2,4-triazol-1-yl)-3,3-dimethylbutan-2-one | 367 | 368 | c |
| 73 | 1-(5-[(4-fluorophenyl)methyl]amino-3-(pyridin-3-yl)-1H-1,2,4-triazol-1-yl)propan-2-one | 325 | 326 | c |
| 74 | 1-(5-[(4-fluorophenyl)methyl]amino-3-(pyridin-3-yl)-1H-pyrazol-1-yl)propan-1-one | 324 | 325 | c |
| 75 | 1-(5-[(4-fluorophenyl)methyl]amino-3-(pyridin-4-yl)-1H-1,2,4-triazol-1-yl)-2,2-dimethylpropan-1-one | 353 | 354 | a |
| 76 | 1-(5-[(4-fluorophenyl)methyl]amino-3-(pyridin-4-yl)-1H-1,2,4-triazol-1-yl)-2-methylpropan-1-one | 339 | 340 | a |
| 77 | 1-(5-[(4-fluorophenyl)methyl]amino-3-(pyridin-4-yl)-1H-1,2,4-triazol-1-yl)-2-phenylethan-1-one | 387 | 388 | a |
| 78 | 1-(5-[(4-fluorophenyl)methyl]amino-3-(pyridin-4-yl)-1H-1,2,4-triazol-1-yl)-3-methylbutan-1-one | 353 | 354 | a |
| 79 | 1-(5-[(4-fluorophenyl)methyl]amino-3-(pyridin-4-yl)-1H-1,2,4-triazol-1-yl)-3-phenylpropan-1-one | 401 | 402 | a |
| 80 | 1-(5-[(4-fluorophenyl)methyl]amino-3-(pyridin-4-yl)-1H-1,2,4-triazol-1-yl)butan-1-one | 339 | 340 | a |
| 81 | 1-(5-[(4-fluorophenyl)methyl]amino-3-(pyridin-4-yl)-1H-1,2,4-triazol-1-yl)propan-1-one | 325 | 326 | a |
| 82 | 1-(5-[(4-fluorophenyl)methyl]amino-3-(thiophen-2-yl)-1H-1,2,4-triazol-1-yl)-2,2-dimethylpropan-1-one | 358 | 359 | a |
| 83 | 1-(5-[(4-fluorophenyl)methyl]amino-3-(thiophen-2-yl)-1H-1,2,4-triazol-1-yl)propan-1-one | 330 | 331 | b |
| 84 | 1-(5-[(4-fluorophenyl)methyl]amino-3-phenyl-1H-pyrazol-1-yl)propan-1-one | 323 | 324 | c |
| 85 | 1-(5-[(4-fluorophenyl)methyl]amino-4-methyl-3-phenyl-1H-pyrazol-1-yl)propan-1-one | 337 | 338 | c |
| 86 | 1-(5-[(4-fluorophenyl)methyl]sulfanyl-3-(pyridin-3-yl)-1H-1,2,4-triazol-1-yl)propan-1-one | 342 | 343 | a |
| 87 | 1-(5-[(4-methoxyphenyl)methyl]amino-3-(pyridin-2-yl)-1H-1,2,4-triazol-1-yl)-2,2-dimethylpropan-1-one | 365 | 366 | a |
| 88 | 1-(5-[(4-methoxyphenyl)methyl]amino-3-(pyridin-2-yl)-1H-1,2,4-triazol-1-yl)-2-methylpropan-1-one | 351 | 352 | a |
| 89 | 1-(5-[(4-methoxyphenyl)methyl]amino-3-(pyridin-2-yl)-1H-1,2,4-triazol-1-yl)-2-phenylethan-1-one | 399 | 400 | a |
| 90 | 1-(5-[(4-methoxyphenyl)methyl]amino-3-(pyridin-2-yl)-1H-1,2,4-triazol-1-yl)-3-methylbutan-1-one | 365 | 366 | a |
| 91 | 1-(5-[(4-methoxyphenyl)methyl]amino-3-(pyridin-2-yl)-1H-1,2,4-triazol-1-yl)-3-phenylpropan-1-one | 413 | 414 | b |
| 92 | 1-(5-[(4-methoxyphenyl)methyl]amino-3-(pyridin-2-yl)-1H-1,2,4-triazol-1-yl)butan-1-one | 351 | 352 | a |
| 93 | 1-(5-[(4-methoxyphenyl)methyl]amino-3-(pyridin-2-yl)-1H-1,2,4-triazol-1-yl)propan-1-one | 337 | 338 | a |
| 94 | 1-(5-[(4-methoxyphenyl)methyl]amino-3-(pyridin-3-yl)-1H-1,2,4-triazol-1-yl)-2,2-dimethylpropan-1-one | 365 | 366 | a |
| 95 | 1-(5-[(4-methoxyphenyl)methyl]amino-3-(pyridin-4-yl)-1H-1,2,4-triazol-1-yl)-2-methylpropan-1-one | 351 | 352 | a |

TABLE A-continued

| Cmpd No. | IUPAC name | MW$_{calc}$ | MW$_{meas}$ | Thrombin Activity |
|---|---|---|---|---|
| 96 | 1-(5-[(4-methoxyphenyl)methyl]amino-3-(pyridin-4-yl)-1H-1,2,4-triazol-1-yl)-2-phenylethan-1-one | 399 | 400 | a |
| 97 | 1-(5-[(4-methoxyphenyl)methyl]amino-3-(pyridin-4-yl)-1H-1,2,4-triazol-1-yl)-3-methylbutan-1-one | 365 | 366 | a |
| 98 | 1-(5-[(4-methoxyphenyl)methyl]amino-3-(pyridin-4-yl)-1H-1,2,4-triazol-1-yl)-3-phenylpropan-1-one | 413 | 414 | c |
| 99 | 1-(5-[(4-methoxyphenyl)methyl]amino-3-(pyridin-4-yl)-1H-1,2,4-triazol-1-yl)butan-1-one | 351 | 352 | a |
| 100 | 1-(5-[(4-methoxyphenyl)methyl]amino-3-(pyridin-4-yl)-1H-1,2,4-triazol-1-yl)propan-1-one | 337 | 338 | b |
| 101 | 1-[(2,2-difluoro-2H-1,3-benzodioxol-4-yl)carbonyl]-N-[(4-fluorophenyl)methyl]-3-phenyl-1H-1,2,4-triazol-5-amine | 452 | 453 | c |
| 102 | 1-[(2,3-dihydro-1,4-benzodioxin-5-yl)carbonyl]-N-[(4-fluorophenyl)methyl]-3-phenyl-1H-1,2,4-triazol-5-amine | 430 | 431 | a |
| 103 | 1-[(2-amino-4-methoxyphenyl)carbonyl]-N-benzyl-3-(2-fluorophenyl)-1H-pyrazol-5-amine | 416 | 417 | c |
| 104 | 1-[(2-amino-4-methoxyphenyl)carbonyl]-N-benzyl-3-(pyridin-2-yl)-1H-1,2,4-triazol-5-amine | 400 | 401 | a |
| 105 | 1-[(2-amino-4-methoxyphenyl)carbonyl]-N-benzyl-3-(pyridin-2-yl)-1H-pyrazol-5-amine | 399 | 400 | b |
| 106 | 1-[(2-amino-4-methylphenyl)carbonyl]-N-benzyl-3-(2-fluorophenyl)-1H-pyrazol-5-amine | 400 | 401 | c |
| 107 | 1-[(2-amino-4-methylphenyl)carbonyl]-N-benzyl-3-(pyridin-2-yl)-1H-1,2,4-triazol-5-amine | 384 | 385 | a |
| 108 | 1-[(2-amino-4-methylphenyl)carbonyl]-N-benzyl-3-(pyridin-2-yl)-1H-pyrazol-5-amine | 383 | 384 | b |
| 109 | 1-[(2-aminophenyl)carbonyl]-N-benzyl-3-(pyridin-2-yl)-1H-1,2,4-triazol-5-amine | 370 | 371 | a |
| 110 | 1-[(2-chlorophenyl)carbonyl]-5-(methylsulfanyl)-3-(thiophen-2-yl)-1H-1,2,4-triazole | 336 | 336, 338 | a |
| 111 | 1-[(2-chlorophenyl)carbonyl]-N-[(4-fluorophenyl)methyl]-3-(pyridin-2-yl)-1H-1,2,4-triazol-5-amine | 408 | 408, 410 | a |
| 112 | 1-[(2-chlorophenyl)carbonyl]-N-[(4-fluorophenyl)methyl]-3-(pyridin-4-yl)-1H-1,2,4-triazol-5-amine | 408 | 408, 410 | a |
| 113 | 1-[(2-chlorophenyl)carbonyl]-N-[(4-fluorophenyl)methyl]-3-(thiophen-2-yl)-1H-1,2,4-triazol-5-amine | 413 | 413, 415 | a |
| 114 | 1-[(2-chlorophenyl)carbonyl]-N-[(4-fluorophenyl)methyl]-3-phenyl-1H-pyrazol-5-amine | 406 | 406, 408 | c |
| 115 | 1-[(2-methoxyphenyl)carbonyl]-3-(pyridin-2-yl)-N-(thiophen-2-ylmethyl)-1H-1,2,4-triazol-5-amine | 391 | 392 | a |
| 116 | 1-[(2-methoxyphenyl)carbonyl]-3-(pyridin-2-yl)-N-(thiophen-2-ylmethyl)-1H-pyrazol-5-amine | 390 | 391 | b |
| 117 | 1-[(2-methoxyphenyl)carbonyl]-3-(pyridin-2-yl)-N-(thiophen-3-ylmethyl)-1H-1,2,4-triazol-5-amine | 391 | 392 | a |
| 118 | 1-[(2-methoxyphenyl)carbonyl]-3-(pyridin-2-yl)-N-(thiophen-3-ylmethyl)-1H-pyrazol-5-amine | 390 | 391 | b |
| 119 | 1-[(2-methoxyphenyl)carbonyl]-N-(naphthalen-1-ylmethyl)-3-(pyridin-2-yl)-1H-1,2,4-triazol-5-amine | 435 | 436 | c |
| 120 | 1-[(2-methoxyphenyl)carbonyl]-N-(naphthalen-2-ylmethyl)-3-(pyridin-2-yl)-1H-1,2,4-triazol-5-amine | 435 | 436 | c |
| 121 | 1-[(4-chlorophenyl)carbonyl]-N-[(4-fluorophenyl)methyl]-3-(pyridin-2-yl)-1H-1,2,4-triazol-5-amine | 408 | 408, 410 | a |
| 122 | 1-[(4-chlorophenyl)carbonyl]-N-[(4-fluorophenyl)methyl]-3-(pyridin-4-yl)-1H-1,2,4-triazol-5-amine | 408 | 408, 410 | b |
| 123 | 1-[(furan-2-yl)carbonyl]-N-[(4-methoxyphenyl)methyl]-3-(pyridin-2-yl)-1H-1,2,4-triazol-5-amine | 375 | 376 | b |
| 124 | 1-[(furan-2-yl)carbonyl]-N-[(4-methoxyphenyl)methyl]-3-(pyridin-4-yl)-1H-1,2,4-triazol-5-amine | 375 | 376 | b |
| 125 | 1-[(furan-3-yl)carbonyl]-N-[(4-methoxyphenyl)methyl]-3-(pyridin-2-yl)-1H-1,2,4-triazol-5-amine | 375 | 376 | b |
| 126 | 1-[(furan-3-yl)carbonyl]-N-[(4-methoxyphenyl)methyl]-3-(pyridin-3-yl)-1H-1,2,4-triazol-5-amine | 375 | 376 | b |
| 127 | 1-[(furan-3-yl)carbonyl]-N-[(4-methoxyphenyl)methyl]-3-(pyridin-4-yl)-1H-1,2,4-triazol-5-amine | 375 | 376 | c |
| 128 | 1-[2-(4-fluorophenyl)ethyl]-N,N-dimethyl-3-(pyridin-2-yl)-1H-pyrazole-5-carboxamide | 338 | 339 | c |
| 129 | 1-[2-(4-fluorophenyl)ethyl]-N,N-dimethyl-5-(pyridin-2-yl)-1H-pyrazole-3-carboxamide | 338 | 339 | c |
| 130 | 1-[2-(4-fluorophenyl)ethyl]-N-methyl-N-phenyl-3-(pyridin-2-yl)-1H-pyrazole-5-carboxamide | 400 | 401 | c |
| 131 | 1-[2-(4-fluorophenyl)ethyl]-N-methyl-N-phenyl-5-(pyridin-2-yl)-1H-pyrazole-3-carboxamide | 400 | 401 | c |
| 132 | 1-[5-(benzylamino)-3-(2-fluorophenyl)-1H-1,2,4-triazol-1-yl]propan-1-one | 324 | 325 | a |

TABLE A-continued

| Cmpd No. | IUPAC name | MW$_{calc}$ | MW$_{meas}$ | Thrombin Activity |
|---|---|---|---|---|
| 133 | 1-[5-(benzylamino)-3-(2-fluorophenyl)-1H-pyrazol-1-yl]-2,2-dimethylpropan-1-one | 351 | 352 | b |
| 134 | 1-[5-(benzylamino)-3-(2-fluorophenyl)-1H-pyrazol-1-yl]-3-methylbutan-1-one | 351 | 352 | c |
| 135 | 1-[5-(benzylamino)-3-(3-fluorophenyl)-1H-1,2,4-triazol-1-yl]propan-1-one | 324 | 325 | b |
| 136 | 1-[5-(benzylamino)-3-(furan-2-yl)-1H-1,2,4-triazol-1-yl]-2,2-dimethylpropan-1-one | 324 | 325 | a |
| 137 | 1-[5-(benzylamino)-3-(pyridin-2-yl)-1H-1,2,4-triazol-1-yl]-2,2-dimethylpropan-1-one | 335 | 336 | a |
| 138 | 1-[5-(benzylamino)-3-(pyridin-2-yl)-1H-1,2,4-triazol-1-yl]-2-methylpropan-1-one | 321 | 322 | a |
| 139 | 1-[5-(benzylamino)-3-(pyridin-2-yl)-1H-1,2,4-triazol-1-yl]-2-phenylethan-1-one | 369 | 370 | a |
| 140 | 1-[5-(benzylamino)-3-(pyridin-2-yl)-1H-1,2,4-triazol-1-yl]-3-methylbutan-1-one | 335 | 336 | a |
| 141 | 1-[5-(benzylamino)-3-(pyridin-2-yl)-1H-1,2,4-triazol-1-yl]butan-1-one | 321 | 322 | a |
| 142 | 1-[5-(benzylamino)-3-(pyridin-2-yl)-1H-1,2,4-triazol-1-yl]propan-1-one | 307 | 308 | a |
| 143 | 1-[5-(benzylamino)-3-(pyridin-2-yl)-1H-pyrazol-1-yl]-2,2-dimethylpropan-1-one | 334 | 335 | a |
| 144 | 1-[5-(benzylamino)-3-(pyridin-2-yl)-1H-pyrazol-1-yl]-3-methylbutan-1-one | 334 | 335 | b |
| 145 | 1-[5-(benzylamino)-3-(pyridin-4-yl)-1H-1,2,4-triazol-1-yl]-2,2-dimethylpropan-1-one | 335 | 336 | a |
| 146 | 1-[5-(benzylamino)-3-(pyridin-4-yl)-1H-1,2,4-triazol-1-yl]-2-methylpropan-1-one | 321 | 322 | a |
| 147 | 1-[5-(benzylamino)-3-(pyridin-4-yl)-1H-1,2,4-triazol-1-yl]-2-phenylethan-1-one | 369 | 370 | a |
| 148 | 1-[5-(benzylamino)-3-(pyridin-4-yl)-1H-1,2,4-triazol-1-yl]-3-methylbutan-1-one | 335 | 336 | a |
| 149 | 1-[5-(benzylamino)-3-(pyridin-4-yl)-1H-1,2,4-triazol-1-yl]-3-phenylpropan-1-one | 383 | 384 | b |
| 150 | 1-[5-(benzylamino)-3-(pyridin-4-yl)-1H-1,2,4-triazol-1-yl]butan-1-one | 321 | 322 | a |
| 151 | 1-[5-(benzylamino)-3-(pyridin-4-yl)-1H-1,2,4-triazol-1-yl]propan-1-one | 307 | 308 | a |
| 152 | 1-[5-(benzylamino)-3-(thiophen-2-yl)-1H-1,2,4-triazol-1-yl]-2,2-dimethylpropan-1-one | 340 | 341 | a |
| 153 | 1-[5-(methylsulfanyl)-3-(pyridin-3-yl)-1H-1,2,4-triazol-1-yl]propan-1-one | 248 | 249 | c |
| 154 | 1-[5-(methylsulfanyl)-3-(thiophen-2-yl)-1H-1,2,4-triazol-1-yl]propan-1-one | 253 | 254 | c |
| 155 | 1-[5-amino-3-(pyridin-3-yl)-1H-1,2,4-triazol-1-yl]propan-1-one | 217 | 218 | c |
| 156 | 1-benzoyl-N-[(4-fluorophenyl)methyl]-3-(pyridin-2-yl)-1H-1,2,4-triazol-5-amine | 373 | 374 | a |
| 157 | 1-benzoyl-N-[(4-methoxyphenyl)methyl]-3-(pyridin-2-yl)-1H-1,2,4-triazol-5-amine | 385 | 386 | b |
| 158 | 1-benzoyl-N-[(4-methoxyphenyl)methyl]-3-(pyridin-4-yl)-1H-1,2,4-triazol-5-amine | 385 | 386 | c |
| 159 | 1-benzoyl-N-benzyl-3-(pyridin-2-yl)-1H-1,2,4-triazol-5-amine | 355 | 356 | a |
| 160 | 1-benzoyl-N-benzyl-3-(pyridin-4-yl)-1H-1,2,4-triazol-5-amine | 355 | 356 | a |
| 161 | 1-benzyl-N-[(4-fluorophenyl)methyl]-3-(pyridin-2-yl)-1H-1,2,4-triazol-5-amine | 359 | 360 | c |
| 162 | 1-benzyl-N-[(4-fluorophenyl)methyl]-5-(pyridin-2-yl)-1H-1,2,4-triazol-3-amine | 359 | 360 | c |
| 163 | 1-1-[2-(4-fluorophenyl)ethyl]-3-(pyridin-2-yl)-1H-pyrazol-5-ylethan-1-ol | 311 | 312 | c |
| 164 | 1-1-[2-(4-fluorophenyl)ethyl]-3-(pyridin-2-yl)-1H-pyrazol-5-ylethan-1-one | 309 | 310 | c |
| 165 | 1-5-[(furan-2-ylmethyl)amino]-3-(pyridin-2-yl)-1H-pyrazol-1-yl-2,2-dimethylpropan-1-one | 324 | 325 | b |
| 166 | 1-5-[(furan-3-ylmethyl)amino]-3-(pyridin-2-yl)-1H-pyrazol-1-yl-2,2-dimethylpropan-1-one | 324 | 325 | b |
| 167 | 2,2-dimethyl-1-[3-(pyridin-2-yl)-5-[(thiophen-2-ylmethyl)amino]-1H-pyrazol-1-yl]propan-1-one | 340 | 341 | a |
| 168 | 2,2-dimethyl-1-[3-(pyridin-2-yl)-5-[(thiophen-3-ylmethyl)amino]-1H-pyrazol-1-yl]propan-1-one | 340 | 341 | b |
| 169 | 2,2-dimethyl-N-3-[(morpholin-4-yl)carbonyl]-1H-1,2,4-triazol-5-ylpropanamide | 281 | 282 | c |
| 170 | 2-chloro-N-3-[(morpholin-4-yl)carbonyl]-1H-1,2,4-triazol-5-ylbenzamide | 336 | 336, 338 | c |

TABLE A-continued

| Cmpd No. | IUPAC name | MW$_{calc}$ | MW$_{meas}$ | Thrombin Activity |
|---|---|---|---|---|
| 171 | 2-chloro-N-3-[(pyrrolidin-1-yl)carbonyl]-1H-1,2,4-triazol-5-ylbenzamide | 320 | 320, 322 | c |
| 172 | 2-chlorophenyl 5-[(4-fluorophenyl)methyl]amino-3-(pyridin-3-yl)-1H-1,2,4-triazole-1-carboxylate | 424 | 424, 426 | c |
| 173 | 2-fluorophenyl 5-[(4-fluorophenyl)methyl]amino-3-(pyridin-3-yl)-1H-1,2,4-triazole-1-carboxylate | 407 | 408 | c |
| 174 | 2-methoxyphenyl 5-[(4-fluorophenyl)methyl]amino-3-(pyridin-3-yl)-1H-1,2,4-triazole-1-carboxylate | 419 | 420 | c |
| 175 | 2-1-[2-(4-fluorophenyl)ethyl]-5-[(2-methoxyphenyl)carbonyl]-1H-pyrazol-3-ylpyridine | 401 | 402 | c |
| 176 | 2-[5-(benzylamino)-3-(pyridin-2-yl)-1H-1,2,4-triazol-1-yl]carbonylbenzonitrile | 380 | 381 | b |
| 177 | 2-[5-(benzylamino)-3-(pyridin-2-yl)-1H-1,2,4-triazol-1-yl]carbonylphenyl acetate | 413 | 414 | a |
| 178 | 3-(pyridin-3-yl)-N-(thiophen-2-ylmethyl)-1H-1,2,4-triazol-5-amine | 257 | 258 | c |
| 179 | 3-([1-propanoyl-3-(pyridin-3-yl)-1H-1,2,4-triazol-5-yl]aminomethyl)benzonitrile | 332 | 333 | c |
| 180 | 3-1-[(2-chlorophenyl)carbonyl]-5-(methylsulfanyl)-1H-1,2,4-triazol-3-ylpyridine | 331 | 331, 333 | a |
| 181 | 3-1-[(2-chlorophenyl)carbonyl]-5-[(4-fluorophenyl)methyl]sulfanyl-1H-1,2,4-triazol-3-ylpyridine | 425 | 425, 427 | b |
| 182 | 3-1-[(2-methoxyphenyl)carbonyl]-5-(methylsulfanyl)-1H-1,2,4-triazol-3-ylpyridine | 326 | 327 | a |
| 183 | 3-[(4-fluorophenyl)methyl]amino-N-phenyl-1-(pyridin-2-yl)-1H-pyrazole-4-carboxamide | 387 | 388 | c |
| 184 | 4-chloro-N-3-[(morpholin-4-yl)carbonyl]-1H-1,2,4-triazol-5-ylbenzamide | 336 | 336, 338 | c |
| 185 | 4-methyl-N-3-[(morpholin-4-yl)carbonyl]-1H-1,2,4-triazol-5-ylbenzamide | 315 | 316 | c |
| 186 | 5-C-(2-chlorobenzene)-3-N,3-N-dimethyl-1H-1,2,4-triazole-3,5-dicarboxamide | 294 | 294, 296 | c |
| 187 | 5-C-(2-chlorobenzene)-3-N-methyl-1H-1,2,4-triazole-3,5-dicarboxamide | 280 | 280, 282 | c |
| 188 | 5-[(4-fluorophenyl)methyl]amino-N,N-dimethyl-3-(pyridin-3-yl)-1H-1,2,4-triazole-1-carboxamide | 340 | 341 | c |
| 189 | 5-[(4-fluorophenyl)methyl]amino-N-(2-methoxyphenyl)-3-(pyridin-3-yl)-1H-1,2,4-triazole-1-carboxamide | 418 | 419 | c |
| 190 | 5-[(4-fluorophenyl)methyl]amino-N-(propan-2-yl)-3-(pyridin-3-yl)-1H-1,2,4-triazole-1-carboxamide | 354 | 355 | c |
| 191 | 5-[(4-fluorophenyl)methyl]amino-N-phenyl-3-(pyridin-3-yl)-1H-1,2,4-triazole-1-carboxamide | 388 | 389 | c |
| 192 | ethyl 5-[(4-fluorophenyl)methyl]amino-3-(pyridin-3-yl)-1H-1,2,4-triazole-1-carboxylate | 341 | 342 | b |
| 193 | methyl 5-[(2-fluorobenzene)amido]-1H-1,2,4-triazole-3-carboxylate | 264 | 265 | c |
| 194 | methyl 5-[(2-methoxybenzene)amido]-1H-1,2,4-triazole-3-carboxylate | 276 | 277 | c |
| 195 | methyl 5-[(3-chlorobenzene)amido]-1H-1,2,4-triazole-3-carboxylate | 281 | 281, 283 | c |
| 196 | methyl 5-[(4-methylbenzene)amido]-1H-1,2,4-triazole-3-carboxylate | 260 | 261 | c |
| 197 | methyl 5-amino-1-[(4-chlorophenyl)carbonyl]-1H-1,2,4-triazole-3-carboxylate | 281 | 281, 283 | a |
| 198 | N-(1-benzothiophen-2-ylmethyl)-1-[(2-methoxyphenyl)carbonyl]-3-(pyridin-2-yl)-1H-1,2,4-triazol-5-amine | 442 | 442 | c |
| 199 | N-(1-benzothiophen-3-ylmethyl)-1-[(2-methoxyphenyl)carbonyl]-3-(pyridin-2-yl)-1H-1,2,4-triazol-5-amine | 442 | 442 | c |
| 200 | N-(2-chlorophenyl)-5-[(4-fluorophenyl)methyl]amino-3-(pyridin-3-yl)-1H-1,2,4-triazole-1-carboxamide | 423 | 423, 425 | c |
| 201 | N-(furan-2-ylmethyl)-1-[(2-methoxyphenyl)carbonyl]-3-(pyridin-2-yl)-1H-pyrazol-5-amine | 374 | 375 | b |
| 202 | N-(furan-3-ylmethyl)-1-[(2-methoxyphenyl)carbonyl]-3-(pyridin-2-yl)-1H-pyrazol-5-amine | 374 | 375 | b |
| 203 | N-[(4-fluorophenyl)methyl]-1-(2-phenylethyl)-3-(pyridin-2-yl)-1H-1,2,4-triazol-5-amine | 373 | 374 | c |
| 204 | N-[(4-fluorophenyl)methyl]-1-(2-phenylethyl)-5-(pyridin-2-yl)-1H-1,2,4-triazol-3-amine | 373 | 374 | c |
| 205 | N-[(4-fluorophenyl)methyl]-1-[(2-methoxy-4-methylphenyl)carbonyl]-3-phenyl-1H-1,2,4-triazol-5-amine | 416 | 417 | b |

TABLE A-continued

| Cmpd No. | IUPAC name | MW$_{calc}$ | MW$_{meas}$ | Thrombin Activity |
|---|---|---|---|---|
| 206 | N-[(4-fluorophenyl)methyl]-1-[(2-methoxyphenyl)carbonyl]-3-(pyridin-2-yl)-1H-1,2,4-triazol-5-amine | 403 | 404 | a |
| 207 | N-[(4-fluorophenyl)methyl]-1-[(2-methoxyphenyl)carbonyl]-3-(pyridin-4-yl)-1H-1,2,4-triazol-5-amine | 403 | 404 | a |
| 208 | N-[(4-fluorophenyl)methyl]-1-[(2-methoxyphenyl)carbonyl]-3-phenyl-1H-pyrazol-5-amine | 401 | 402 | c |
| 209 | N-[(4-fluorophenyl)methyl]-1-[(2-methylphenyl)carbonyl]-3-phenyl-1H-1,2,4-triazol-5-amine | 386 | 387 | b |
| 210 | N-[(4-fluorophenyl)methyl]-1-[(furan-2-yl)carbonyl]-3-(pyridin-2-yl)-1H-1,2,4-triazol-5-amine | 363 | 364 | a |
| 211 | N-[(4-fluorophenyl)methyl]-1-[(furan-2-yl)carbonyl]-3-(pyridin-4-yl)-1H-1,2,4-triazol-5-amine | 363 | 364 | a |
| 212 | N-[(4-fluorophenyl)methyl]-1-[(furan-3-yl)carbonyl]-3-(pyridin-2-yl)-1H-1,2,4-triazol-5-amine | 363 | 364 | a |
| 213 | N-[(4-fluorophenyl)methyl]-1-[(furan-3-yl)carbonyl]-3-(pyridin-3-yl)-1H-1,2,4-triazol-5-amine | 363 | 364 | a |
| 214 | N-[(4-fluorophenyl)methyl]-1-[(furan-3-yl)carbonyl]-3-(pyridin-4-yl)-1H-1,2,4-triazol-5-amine | 363 | 364 | a |
| 215 | N-[(4-fluorophenyl)methyl]-1-[(piperidin-1-yl)carbonyl]-3-(pyridin-3-yl)-1H-1,2,4-triazol-5-amine | 380 | 381 | c |
| 216 | N-[(4-fluorophenyl)methyl]-1-propyl-3-(pyridin-2-yl)-1H-1,2,4-triazol-5-amine | 311 | 312 | c |
| 217 | N-[(4-fluorophenyl)methyl]-1-propyl-5-(pyridin-2-yl)-1H-1,2,4-triazol-3-amine | 311 | 312 | c |
| 218 | N-[(4-fluorophenyl)methyl]-2,2-dimethyl-N-(4-methyl-3-phenyl-1H-pyrazol-5-yl)propanamide | 365 | 366 | c |
| 219 | N-[(4-fluorophenyl)methyl]-3-(pyridin-2-yl)-1-[(thiophen-3-yl)carbonyl]-1H-1,2,4-triazol-5-amine | 379 | 380 | a |
| 220 | N-[(4-fluorophenyl)methyl]-3-(pyridin-3-yl)-1-[(thiophen-3-yl)carbonyl]-1H-1,2,4-triazol-5-amine | 379 | 380 | a |
| 221 | N-[(4-fluorophenyl)methyl]-3-(pyridin-4-yl)-1-[(thiophen-2-yl)carbonyl]-1H-1,2,4-triazol-5-amine | 379 | 380 | b |
| 222 | N-[(4-fluorophenyl)methyl]-3-phenyl-1-[(thiophen-3-yl)carbonyl]-1H-1,2,4-triazol-5-amine | 378 | 379 | a |
| 223 | N-[(4-fluorophenyl)methyl]-4-[(2-methoxyphenyl)carbonyl]-1-(pyridin-2-yl)-1H-pyrazol-3-amine | 402 | 403 | c |
| 224 | N-[(4-fluorophenyl)methyl]-4-[(2-methoxyphenyl)carbonyl]-1-phenyl-1H-pyrazol-3-amine | 401 | 402 | c |
| 225 | N-[(4-fluorophenyl)methyl]-4-[(piperidin-1-yl)carbonyl]-1-(pyridin-2-yl)-1H-pyrazol-3-amine | 379 | 380 | c |
| 226 | N-[(4-methoxyphenyl)methyl]-3-(pyridin-2-yl)-1-[(thiophen-2-yl)carbonyl]-1H-1,2,4-triazol-5-amine | 391 | 392 | c |
| 227 | N-[(4-methoxyphenyl)methyl]-3-(pyridin-2-yl)-1-[(thiophen-3-yl)carbonyl]-1H-1,2,4-triazol-5-amine | 391 | 392 | b |
| 228 | N-[(4-methoxyphenyl)methyl]-3-(pyridin-3-yl)-1-[(thiophen-3-yl)carbonyl]-1H-1,2,4-triazol-5-amine | 391 | 392 | c |
| 229 | N-[(4-methoxyphenyl)methyl]-3-(pyridin-4-yl)-1-[(thiophen-2-yl)carbonyl]-1H-1,2,4-triazol-5-amine | 391 | 392 | c |
| 230 | N-[(4-methoxyphenyl)methyl]-3-(pyridin-4-yl)-1-[(thiophen-3-yl)carbonyl]-1H-1,2,4-triazol-5-amine | 391 | 392 | b |
| 231 | N-benzyl-1-[(2,2-difluoro-2H-1,3-benzodioxol-4-yl)carbonyl]-3-(pyridin-2-yl)-1H-1,2,4-triazol-5-amine | 435 | 436 | c |
| 232 | N-benzyl-1-[(2,3-dihydro-1,4-benzodioxin-5-yl)carbonyl]-3-(pyridin-2-yl)-1H-1,2,4-triazol-5-amine | 413 | 414 | a |
| 233 | N-benzyl-1-[(2,3-dimethoxyphenyl)carbonyl]-3-(pyridin-2-yl)-1H-1,2,4-triazol-5-amine | 415 | 416 | a |
| 234 | N-benzyl-1-[(2,4-dimethoxyphenyl)carbonyl]-3-(2-fluorophenyl)-1H-pyrazol-5-amine | 431 | 432 | c |
| 235 | N-benzyl-1-[(2,4-dimethoxyphenyl)carbonyl]-3-(pyridin-2-yl)-1H-1,2,4-triazol-5-amine | 415 | 416 | a |
| 236 | N-benzyl-1-[(2,4-dimethoxyphenyl)carbonyl]-3-(pyridin-2-yl)-1H-pyrazol-5-amine | 414 | 415 | b |
| 237 | N-benzyl-1-[(2,4-dimethylphenyl)carbonyl]-3-(pyridin-2-yl)-1H-1,2,4-triazol-5-amine | 383 | 384 | b |
| 238 | N-benzyl-1-[(2,6-dichlorophenyl)carbonyl]-3-(pyridin-2-yl)-1H-1,2,4-triazol-5-amine | 424 | 424, 426, 428 | c |
| 239 | N-benzyl-1-[(2,6-difluorophenyl)carbonyl]-3-(pyridin-2-yl)-1H-1,2,4-triazol-5-amine | 391 | 392 | b |
| 240 | N-benzyl-1-[(2-bromophenyl)carbonyl]-3-(pyridin-2-yl)-1H-1,2,4-triazol-5-amine | 434 | 434, 436 | a |
| 241 | N-benzyl-1-[(2-bromophenyl)carbonyl]-3-(pyridin-2-yl)-1H-pyrazol-5-amine | 433 | 433, 435 | b |

TABLE A-continued

| Cmpd No. | IUPAC name | MW$_{calc}$ | MW$_{meas}$ | Thrombin Activity |
|---|---|---|---|---|
| 242 | N-benzyl-1-[(2-chlorophenyl)carbonyl]-3-(2-fluorophenyl)-1H-pyrazol-5-amine | 406 | 406, 408 | b |
| 243 | N-benzyl-1-[(2-chlorophenyl)carbonyl]-3-(pyridin-2-yl)-1H-1,2,4-triazol-5-amine | 390 | 390, 392 | a |
| 244 | N-benzyl-1-[(2-chlorophenyl)carbonyl]-3-(pyridin-2-yl)-1H-pyrazol-5-amine | 389 | 389, 391 | b |
| 245 | N-benzyl-1-[(2-chlorophenyl)carbonyl]-3-(pyridin-4-yl)-1H-1,2,4-triazol-5-amine | 390 | 390, 392 | a |
| 246 | N-benzyl-1-[(2-ethylphenyl)carbonyl]-3-(pyridin-2-yl)-1H-1,2,4-triazol-5-amine | 383 | 384 | b |
| 247 | N-benzyl-1-[(2-ethylphenyl)carbonyl]-3-(pyridin-2-yl)-1H-pyrazol-5-amine | 382 | 383 | c |
| 248 | N-benzyl-1-[(2-fluoro-4-methoxyphenyl)carbonyl]-3-(pyridin-2-yl)-1H-1,2,4-triazol-5-amine | 403 | 404 | a |
| 249 | N-benzyl-1-[(2-fluoro-4-methylphenyl)carbonyl]-3-(pyridin-2-yl)-1H-1,2,4-triazol-5-amine | 387 | 388 | a |
| 250 | N-benzyl-1-[(2-fluorophenyl)carbonyl]-3-(pyridin-2-yl)-1H-1,2,4-triazol-5-amine | 373 | 374 | a |
| 251 | N-benzyl-1-[(2-fluorophenyl)carbonyl]-3-(pyridin-2-yl)-1H-pyrazol-5-amine | 372 | 373 | a |
| 252 | N-benzyl-1-[(2-fluorophenyl)carbonyl]-N-methyl-3-(pyridin-2-yl)-1H-1,2,4-triazol-5-amine | 387 | 388 | b |
| 253 | N-benzyl-1-[(2-methoxy-4-methylphenyl)carbonyl]-3-(pyridin-2-yl)-1H-1,2,4-triazol-5-amine | 399 | 400 | a |
| 254 | N-benzyl-1-[(2-methoxyphenyl)carbonyl]-3-(pyridazin-3-yl)-1H-1,2,4-triazol-5-amine | 386 | 387 | a |
| 255 | N-benzyl-1-[(2-methoxyphenyl)carbonyl]-3-(pyridin-2-yl)-1H-1,2,4-triazol-5-amine | 385 | 386 | a |
| 256 | N-benzyl-1-[(2-methoxyphenyl)carbonyl]-3-(pyridin-2-yl)-1H-pyrazol-5-amine | 384 | 385 | b |
| 257 | N-benzyl-1-[(2-methoxyphenyl)carbonyl]-3-(pyridin-4-yl)-1H-1,2,4-triazol-5-amine | 385 | 386 | a |
| 258 | N-benzyl-1-[(2-methoxyphenyl)carbonyl]-3-(thiophen-2-yl)-1H-1,2,4-triazol-5-amine | 390 | 391 | a |
| 259 | N-benzyl-1-[(2-methylphenyl)carbonyl]-3-(pyridin-2-yl)-1H-1,2,4-triazol-5-amine | 369 | 370 | a |
| 260 | N-benzyl-1-[(2-methylphenyl)carbonyl]-3-(pyridin-2-yl)-1H-pyrazol-5-amine | 368 | 369 | c |
| 261 | N-benzyl-1-[(3-methoxyphenyl)carbonyl]-3-(pyridin-2-yl)-1H-1,2,4-triazol-5-amine | 385 | 386 | a |
| 262 | N-benzyl-1-[(4-chlorophenyl)carbonyl]-3-(pyridin-2-yl)-1H-1,2,4-triazol-5-amine | 390 | 390, 392 | a |
| 263 | N-benzyl-1-[(4-chlorophenyl)carbonyl]-3-(pyridin-4-yl)-1H-1,2,4-triazol-5-amine | 390 | 390, 392 | a |
| 264 | N-benzyl-1-[(4-methoxy-2-methylphenyl)carbonyl]-3-(pyridin-2-yl)-1H-1,2,4-triazol-5-amine | 399 | 400 | a |
| 265 | N-benzyl-1-[(4-methoxyphenyl)carbonyl]-3-(pyridin-2-yl)-1H-1,2,4-triazol-5-amine | 385 | 386 | a |
| 266 | N-benzyl-1-[(furan-2-yl)carbonyl]-3-(pyridin-4-yl)-1H-1,2,4-triazol-5-amine | 345 | 346 | a |
| 267 | N-benzyl-1-[(furan-3-yl)carbonyl]-3-(pyridin-2-yl)-1H-1,2,4-triazol-5-amine | 345 | 346 | a |
| 268 | N-benzyl-1-[(furan-3-yl)carbonyl]-3-(pyridin-4-yl)-1H-1,2,4-triazol-5-amine | 345 | 346 | a |
| 269 | N-benzyl-1-[(naphthalen-1-yl)carbonyl]-3-(pyridin-2-yl)-1H-1,2,4-triazol-5-amine | 405 | 406 | a |
| 270 | N-benzyl-1-[(naphthalen-1-yl)carbonyl]-3-(pyridin-2-yl)-1H-pyrazol-5-amine | 404 | 405 | c |
| 271 | N-benzyl-1-[(naphthalen-2-yl)carbonyl]-3-(pyridin-2-yl)-1H-1,2,4-triazol-5-amine | 405 | 406 | b |
| 272 | N-benzyl-1-[(naphthalen-2-yl)carbonyl]-3-(pyridin-2-yl)-1H-pyrazol-5-amine | 404 | 405 | c |
| 273 | N-benzyl-1-[2-(dimethylamino)phenyl]carbonyl-3-(pyridin-2-yl)-1H-1,2,4-triazol-5-amine | 398 | 399 | c |
| 274 | N-benzyl-1-[2-(methylamino)phenyl]carbonyl-3-(pyridin-2-yl)-1H-1,2,4-triazol-5-amine | 384 | 385 | N/A |
| 275 | N-benzyl-1-[2-(propan-2-yl)phenyl]carbonyl-3-(pyridin-2-yl)-1H-1,2,4-triazol-5-amine | 397 | 398 | c |
| 276 | N-benzyl-1-[2-(propan-2-yl)phenyl]carbonyl-3-(pyridin-2-yl)-1H-pyrazol-5-amine | 396 | 397 | c |
| 277 | N-benzyl-3-(2-fluorophenyl)-1-[(2-fluorophenyl)carbonyl]-1H-pyrazol-5-amine | 389 | 390 | b |
| 278 | N-benzyl-3-(2-fluorophenyl)-1-[(2-methoxyphenyl)carbonyl]-1H-pyrazol-5-amine | 401 | 402 | c |
| 279 | N-benzyl-3-(2-fluorophenyl)-1-[(thiophen-3-yl)carbonyl]-1H-pyrazol-5-amine | 377 | 378 | c |

TABLE A-continued

| Cmpd No. | IUPAC name | MW$_{calc}$ | MW$_{meas}$ | Thrombin Activity |
|---|---|---|---|---|
| 280 | N-benzyl-3-(furan-2-yl)-1-[(2-methoxyphenyl)carbonyl]-1H-1,2,4-triazol-5-amine | 374 | 375 | a |
| 281 | N-benzyl-3-(furan-2-yl)-1H-1,2,4-triazol-5-amine | 240 | 241 | c |
| 282 | N-benzyl-3-(pyridin-2-yl)-1-[(thiophen-2-yl)carbonyl]-1H-1,2,4-triazol-5-amine | 361 | 362 | a |
| 283 | N-benzyl-3-(pyridin-2-yl)-1-[(thiophen-3-yl)carbonyl]-1H-1,2,4-triazol-5-amine | 361 | 362 | a |
| 284 | N-benzyl-3-(pyridin-2-yl)-1-[(thiophen-3-yl)carbonyl]-1H-pyrazol-5-amine | 360 | 361 | a |
| 285 | N-benzyl-3-(pyridin-2-yl)-1-[2-(trifluoromethoxy)phenyl]carbonyl-1H-1,2,4-triazol-5-amine | 439 | 440 | a |
| 286 | N-benzyl-3-(pyridin-2-yl)-1-[2-(trifluoromethyl)phenyl]carbonyl-1H-1,2,4-triazol-5-amine | 423 | 424 | c |
| 287 | N-benzyl-3-(pyridin-3-yl)-1H-1,2,4-triazol-5-amine | 251 | 252 | c |
| 288 | N-benzyl-3-(pyridin-4-yl)-1-[(thiophen-2-yl)carbonyl]-1H-1,2,4-triazol-5-amine | 361 | 362 | a |
| 289 | N-benzyl-3-(pyridin-4-yl)-1-[(thiophen-3-yl)carbonyl]-1H-1,2,4-triazol-5-amine | 361 | 362 | a |
| 290 | N-benzyl-3-(pyridin-4-yl)-1H-1,2,4-triazol-5-amine | 251 | 252 | c |
| 291 | N-benzyl-3-(thiophen-2-yl)-1-[(thiophen-3-yl)carbonyl]-1H-1,2,4-triazol-5-amine | 366 | 367 | b |
| 292 | N-benzyl-N-[3-(2-fluorophenyl)-1H-pyrazol-5-yl]-2-methoxybenzamide | 401 | 402 | c |
| 293 | N-ethyl-1-[2-(4-fluorophenyl)ethyl]-N-methyl-3-(pyridin-2-yl)-1H-pyrazole-5-carboxamide | 352 | 353 | c |
| 294 | N-ethyl-1-[2-(4-fluorophenyl)ethyl]-N-methyl-5-(pyridin-2-yl)-1H-pyrazole-3-carboxamide | 352 | 353 | c |
| 295 | N-ethyl-3-[(4-fluorophenyl)methyl]amino-1-(pyridin-2-yl)-1H-pyrazole-4-carboxamide | 339 | 340 | c |
| 296 | N-ethyl-5-[(4-fluorophenyl)methyl]amino-3-(pyridin-3-yl)-1H-1,2,4-triazole-1-carboxamide | 340 | 341 | c |
| 297 | N-ethyl-5-[(4-fluorophenyl)methyl]amino-N-methyl-3-(pyridin-3-yl)-1H-1,2,4-triazole-1-carboxamide | 354 | 355 | c |
| 298 | phenyl 5-[(4-fluorophenyl)methyl]amino-3-(pyridin-3-yl)-1H-1,2,4-triazole-1-carboxylate | 389 | 390 | a |
| 299 | propan-2-yl 5-[(4-fluorophenyl)methyl]amino-3-(pyridin-3-yl)-1H-1,2,4-triazole-1-carboxylate | 355 | 356 | c |
| 300 | tert-butyl 5-[(4-fluorophenyl)methyl]amino-3-(pyridin-3-yl)-1H-1,2,4-triazole-1-carboxylate | 369 | 370 | c |
| 301 | tert-butyl N-(2-[5-(benzylamino)-3-(pyridin-2-yl)-1H-1,2,4-triazol-1-yl]carbonylphenyl)carbamate | 471 | 471 | c |
| 302 | tert-butyl N-(4-acetyl-1-phenyl-1H-pyrazol-3-yl)-N-[(4-fluorophenyl)methyl]carbamate | 409 | 410 | c |
| 303 | tert-butyl N-[(4-fluorophenyl)methyl]-N-4-[(2-methoxyphenyl)carbonyl]-1-phenyl-1H-pyrazol-3-ylcarbamate | 502 | 502 | c |
| 304 | 1-[2-(4-fluorophenyl)ethyl]-3-(pyridin-2-yl)-1H-pyrazol-5-yl(2-methoxyphenyl)methanol | 403 | 404 | c |

In some embodiments, there is provided a compound as expressly set forth in Table B following.

TABLE B

| Cmpd No | IUPAC name |
|---|---|
| 413 | 1-[3-(4-chlorophenyl)-5-[(4-fluorophenyl)methyl]amino-1H-1,2,4-triazol-1-yl]-2-methoxyethan-1-one |
| 414 | 1-[5-(benzylamino)-3-(furan-2-yl)-1H-1,2,4-triazol-1-yl]-3-methylbutan-1-one |
| 415 | 1-[5-(benzylamino)-3-(furan-2-yl)-1H-1,2,4-triazol-1-yl]ethan-1-one |
| 416 | 1-[5-(benzylamino)-3-(pyridin-2-yl)-1H-1,2,4-triazol-1-yl]ethan-1-one |
| 417 | 1-[5-(benzylamino)-3-(pyridin-3-yl)-1H-1,2,4-triazol-1-yl]ethan-1-one |
| 418 | 1-[5-(benzylamino)-3-(pyridin-3-yl)-1H-pyrazol-1-yl]-2-methylpropan-1-one |
| 419 | 1-[5-(benzylamino)-3-(pyridin-3-yl)-1H-pyrazol-1-yl]-2-phenylethan-1-one |
| 420 | 1-[5-(benzylamino)-3-(pyridin-3-yl)-1H-pyrazol-1-yl]-3-methylbutan-1-one |
| 421 | 1-[5-(benzylamino)-3-(pyridin-3-yl)-1H-pyrazol-1-yl]-3-phenylpropan-1-one |
| 422 | 1-[5-(benzylamino)-3-(pyridin-3-yl)-1H-pyrazol-1-yl]butan-1-one |
| 423 | 1-[5-(benzylamino)-3-(pyridin-3-yl)-1H-pyrazol-1-yl]ethan-1-one |
| 424 | 1-[5-(benzylamino)-3-(pyridin-3-yl)-1H-pyrazol-1-yl]propan-1-one |
| 425 | 1-[5-(benzylamino)-3-(pyridin-4-yl)-1H-1,2,4-triazol-1-yl]ethan-1-one |
| 426 | 1-[5-(benzylamino)-3-(thiophen-2-yl)-1H-1,2,4-triazol-1-yl]-2-methylpropan-1-one |
| 427 | 1-[5-(benzylamino)-3-(thiophen-2-yl)-1H-1,2,4-triazol-1-yl]-2-phenylethan-1-one |
| 428 | 1-[5-(benzylamino)-3-(thiophen-2-yl)-1H-1,2,4-triazol-1-yl]-3-methylbutan-1-one |
| 429 | 1-[5-(benzylamino)-3-(thiophen-2-yl)-1H-1,2,4-triazol-1-yl]-3-phenylpropan-1-one |

TABLE B-continued

| Cmpd No | IUPAC name |
|---|---|
| 430 | 1-[5-(benzylamino)-3-(thiophen-2-yl)-1H-1,2,4-triazol-1-yl]butan-1-one |
| 431 | 1-[5-(benzylamino)-3-(thiophen-2-yl)-1H-1,2,4-triazol-1-yl]ethan-1-one |
| 432 | 1-[5-(benzylamino)-3-phenyl-1H-1,2,4-triazol-1-yl]-2-methylpropan-1-one |
| 433 | 1-[5-(benzylamino)-3-phenyl-1H-1,2,4-triazol-1-yl]-3-methylbutan-1-one |
| 434 | 1-[5-(benzylamino)-3-phenyl-1H-1,2,4-triazol-1-yl]butan-1-one |
| 435 | 1-[5-(benzylamino)-3-phenyl-1H-1,2,4-triazol-1-yl]ethan-1-one |
| 436 | 1-[5-(benzylamino)-3-phenyl-1H-pyrazol-1-yl]-2-methylpropan-1-one |
| 437 | 1-[5-(benzylamino)-3-phenyl-1H-pyrazol-1-yl]-2-phenylethan-1-one |
| 438 | 1-[5-(benzylamino)-3-phenyl-1H-pyrazol-1-yl]-3-methylbutan-1-one |
| 439 | 1-[5-(benzylamino)-3-phenyl-1H-pyrazol-1-yl]-3-phenylpropan-1-one |
| 440 | 1-[5-(benzylamino)-3-phenyl-1H-pyrazol-1-yl]butan-1-one |
| 441 | 1-[5-(benzylamino)-3-phenyl-1H-pyrazol-1-yl]ethan-1-one |
| 442 | 1-[5-(benzylamino)-3-phenyl-1H-pyrazol-1-yl]propan-1-one |
| 443 | 1-benzoyl-3-(furan-2-yl)-1H-1,2,4-triazol-5-amine |
| 444 | 1-benzoyl-3-(furan-2-yl)-N-(pyridin-2-ylmethyl)-1H-1,2,4-triazol-5-amine |
| 445 | 1-benzoyl-3-(furan-2-yl)-N-(pyridin-2-ylmethyl)-1H-1,2,4-triazol-5-amine |
| 446 | 1-benzoyl-3-(furan-2-yl)-N-(pyridin-3-ylmethyl)-1H-1,2,4-triazol-5-amine |
| 447 | 1-benzoyl-3-(furan-2-yl)-N-(pyridin-3-ylmethyl)-1H-1,2,4-triazol-5-amine |
| 448 | 1-benzoyl-3-(furan-2-yl)-N-(pyridin-4-ylmethyl)-1H-1,2,4-triazol-5-amine |
| 449 | 1-benzoyl-3-(furan-2-yl)-N-(pyridin-4-ylmethyl)-1H-1,2,4-triazol-5-amine |
| 450 | 1-benzoyl-3-(furan-2-yl)-N-[(2-methylphenyl)methyl]-1H-1,2,4-triazol-5-amine |
| 451 | 1-benzoyl-3-(furan-2-yl)-N-[(3-methoxyphenyl)methyl]-1H-1,2,4-triazol-5-amine |
| 452 | 1-benzoyl-3-(furan-2-yl)-N-[(3-methylphenyl)methyl]-1H-1,2,4-triazol-5-amine |
| 453 | 1-benzoyl-3-(pyridin-2-yl)-1H-1,2,4-triazol-5-amine |
| 454 | 1-benzoyl-3-(pyridin-2-yl)-N-(pyridin-2-ylmethyl)-1H-1,2,4-triazol-5-amine |
| 455 | 1-benzoyl-3-(pyridin-2-yl)-N-(pyridin-3-ylmethyl)-1H-1,2,4-triazol-5-amine |
| 456 | 1-benzoyl-3-(pyridin-2-yl)-N-(pyridin-4-ylmethyl)-1H-1,2,4-triazol-5-amine |
| 457 | 1-benzoyl-3-(pyridin-3-yl)-1H-1,2,4-triazol-5-amine |
| 458 | 1-benzoyl-3-(pyridin-3-yl)-1H-pyrazol-5-amine |
| 459 | 1-benzoyl-3-(pyridin-3-yl)-N-(pyridin-3-ylmethyl)-1H-1,2,4-triazol-5-amine |
| 460 | 1-benzoyl-3-(pyridin-3-yl)-N-(pyridin-3-ylmethyl)-1H-pyrazol-5-amine |
| 461 | 1-benzoyl-3-(pyridin-3-yl)-N-(pyridin-3-ylmethyl)-1H-pyrazol-5-amine |
| 462 | 1-benzoyl-3-(pyridin-3-yl)-N-(pyridin-4-ylmethyl)-1H-1,2,4-triazol-5-amine |
| 463 | 1-benzoyl-3-(pyridin-3-yl)-N-(pyridin-4-ylmethyl)-1H-pyrazol-5-amine |
| 464 | 1-benzoyl-3-(pyridin-3-yl)-N-(pyridin-4-ylmethyl)-1H-pyrazol-5-amine |
| 465 | 1-benzoyl-3-(pyridin-4-yl)-1H-1,2,4-triazol-5-amine |
| 466 | 1-benzoyl-3-(pyridin-4-yl)-N-(pyridin-4-ylmethyl)-1H-1,2,4-triazol-5-amine |
| 467 | 1-benzoyl-3-(thiophen-2-yl)-1H-1,2,4-triazol-5-amine |
| 468 | 1-benzoyl-3-phenyl-1H-1,2,4-triazol-5-amine |
| 469 | 1-benzoyl-3-phenyl-1H-pyrazol-5-amine |
| 470 | 1-benzoyl-3-phenyl-N-(pyridin-2-ylmethyl)-1H-pyrazol-5-amine |
| 471 | 1-benzoyl-3-phenyl-N-(pyridin-2-ylmethyl)-1H-pyrazol-5-amine |
| 472 | 1-benzoyl-3-phenyl-N-(pyridin-3-ylmethyl)-1H-1,2,4-triazol-5-amine |
| 473 | 1-benzoyl-3-phenyl-N-(pyridin-3-ylmethyl)-1H-1,2,4-triazol-5-amine |
| 474 | 1-benzoyl-3-phenyl-N-(pyridin-3-ylmethyl)-1H-pyrazol-5-amine |
| 475 | 1-benzoyl-3-phenyl-N-(pyridin-3-ylmethyl)-1H-pyrazol-5-amine |
| 476 | 1-benzoyl-3-phenyl-N-(pyridin-4-ylmethyl)-1H-pyrazol-5-amine |
| 477 | 1-benzoyl-3-phenyl-N-(pyridin-4-ylmethyl)-1H-pyrazol-5-amine |
| 478 | 1-benzoyl-N-(pyridin-2-ylmethyl)-3-(pyridin-3-yl)-1H-1,2,4-triazol-5-amine |
| 479 | 1-benzoyl-N-(pyridin-2-ylmethyl)-3-(pyridin-3-yl)-1H-pyrazol-5-amine |
| 480 | 1-benzoyl-N-(pyridin-2-ylmethyl)-3-(pyridin-3-yl)-1H-pyrazol-5-amine |
| 481 | 1-benzoyl-N-(pyridin-2-ylmethyl)-3-(pyridin-4-yl)-1H-1,2,4-triazol-5-amine |
| 482 | 1-benzoyl-N-(pyridin-2-ylmethyl)-3-(thiophen-2-yl)-1H-1,2,4-triazol-5-amine |
| 483 | 1-benzoyl-N-(pyridin-2-ylmethyl)-3-(thiophen-2-yl)-1H-1,2,4-triazol-5-amine |
| 484 | 1-benzoyl-N-(pyridin-3-ylmethyl)-3-(pyridin-4-yl)-1H-1,2,4-triazol-5-amine |
| 485 | 1-benzoyl-N-(pyridin-3-ylmethyl)-3-(thiophen-2-yl)-1H-1,2,4-triazol-5-amine |
| 486 | 1-benzoyl-N-(pyridin-3-ylmethyl)-3-(thiophen-2-yl)-1H-1,2,4-triazol-5-amine |
| 487 | 1-benzoyl-N-(pyridin-4-ylmethyl)-3-(thiophen-2-yl)-1H-1,2,4-triazol-5-amine |
| 488 | 1-benzoyl-N-(pyridin-4-ylmethyl)-3-(thiophen-2-yl)-1H-1,2,4-triazol-5-amine |
| 489 | 1-benzoyl-N-[(2-chlorophenyl)methyl]-3-(pyridin-2-yl)-1H-1,2,4-triazol-5-amine |
| 490 | 1-benzoyl-N-[(2-chlorophenyl)methyl]-3-(pyridin-3-yl)-1H-1,2,4-triazol-5-amine |
| 491 | 1-benzoyl-N-[(2-chlorophenyl)methyl]-3-(pyridin-3-yl)-1H-pyrazol-5-amine |
| 492 | 1-benzoyl-N-[(2-chlorophenyl)methyl]-3-(pyridin-4-yl)-1H-1,2,4-triazol-5-amine |
| 493 | 1-benzoyl-N-[(2-chlorophenyl)methyl]-3-(thiophen-2-yl)-1H-1,2,4-triazol-5-amine |
| 494 | 1-benzoyl-N-[(2-chlorophenyl)methyl]-3-phenyl-1H-1,2,4-triazol-5-amine |
| 495 | 1-benzoyl-N-[(2-chlorophenyl)methyl]-3-phenyl-1H-pyrazol-5-amine |
| 496 | 1-benzoyl-N-[(2-fluorophenyl)methyl]-3-(furan-2-yl)-1H-1,2,4-triazol-5-amine |
| 497 | 1-benzoyl-N-[(2-fluorophenyl)methyl]-3-(pyridin-3-yl)-1H-pyrazol-5-amine |
| 498 | 1-benzoyl-N-[(2-fluorophenyl)methyl]-3-(thiophen-2-yl)-1H-1,2,4-triazol-5-amine |
| 499 | 1-benzoyl-N-[(2-fluorophenyl)methyl]-3-phenyl-1H-1,2,4-triazol-5-amine |
| 500 | 1-benzoyl-N-[(2-fluorophenyl)methyl]-3-phenyl-1H-pyrazol-5-amine |
| 501 | 1-benzoyl-N-[(2-methoxyphenyl)methyl]-3-(pyridin-2-yl)-1H-1,2,4-triazol-5-amine |
| 502 | 1-benzoyl-N-[(2-methoxyphenyl)methyl]-3-(pyridin-3-yl)-1H-pyrazol-5-amine |
| 503 | 1-benzoyl-N-[(2-methoxyphenyl)methyl]-3-(pyridin-4-yl)-1H-1,2,4-triazol-5-amine |
| 504 | 1-benzoyl-N-[(2-methoxyphenyl)methyl]-3-(thiophen-2-yl)-1H-1,2,4-triazol-5-amine |
| 505 | 1-benzoyl-N-[(2-methoxyphenyl)methyl]-3-phenyl-1H-1,2,4-triazol-5-amine |
| 506 | 1-benzoyl-N-[(2-methoxyphenyl)methyl]-3-phenyl-1H-pyrazol-5-amine |
| 507 | 1-benzoyl-N-[(2-methylphenyl)methyl]-3-(pyridin-3-yl)-1H-1,2,4-triazol-5-amine |

TABLE B-continued

| Cmpd No | IUPAC name |
|---|---|
| 508 | 1-benzoyl-N-[(2-methylphenyl)methyl]-3-(pyridin-3-yl)-1H-pyrazol-5-amine |
| 509 | 1-benzoyl-N-[(2-methylphenyl)methyl]-3-(pyridin-4-yl)-1H-1,2,4-triazol-5-amine |
| 510 | 1-benzoyl-N-[(2-methylphenyl)methyl]-3-(thiophen-2-yl)-1H-1,2,4-triazol-5-amine |
| 511 | 1-benzoyl-N-[(2-methylphenyl)methyl]-3-phenyl-1H-1,2,4-triazol-5-amine |
| 512 | 1-benzoyl-N-[(2-methylphenyl)methyl]-3-phenyl-1H-pyrazol-5-amine |
| 513 | 1-benzoyl-N-[(3-chlorophenyl)methyl]-3-(pyridin-2-yl)-1H-1,2,4-triazol-5-amine |
| 514 | 1-benzoyl-N-[(3-chlorophenyl)methyl]-3-(pyridin-3-yl)-1H-pyrazol-5-amine |
| 515 | 1-benzoyl-N-[(3-chlorophenyl)methyl]-3-(pyridin-4-yl)-1H-1,2,4-triazol-5-amine |
| 516 | 1-benzoyl-N-[(3-chlorophenyl)methyl]-3-(thiophen-2-yl)-1H-1,2,4-triazol-5-amine |
| 517 | 1-benzoyl-N-[(3-chlorophenyl)methyl]-3-phenyl-1H-1,2,4-triazol-5-amine |
| 518 | 1-benzoyl-N-[(3-chlorophenyl)methyl]-3-phenyl-1H-pyrazol-5-amine |
| 519 | 1-benzoyl-N-[(3-fluorophenyl)methyl]-3-(furan-2-yl)-1H-1,2,4-triazol-5-amine |
| 520 | 1-benzoyl-N-[(3-fluorophenyl)methyl]-3-(pyridin-3-yl)-1H-pyrazol-5-amine |
| 521 | 1-benzoyl-N-[(3-fluorophenyl)methyl]-3-(thiophen-2-yl)-1H-1,2,4-triazol-5-amine |
| 522 | 1-benzoyl-N-[(3-fluorophenyl)methyl]-3-phenyl-1H-1,2,4-triazol-5-amine |
| 523 | 1-benzoyl-N-[(3-fluorophenyl)methyl]-3-phenyl-1H-pyrazol-5-amine |
| 524 | 1-benzoyl-N-[(3-methoxyphenyl)methyl]-3-(pyridin-2-yl)-1H-1,2,4-triazol-5-amine |
| 525 | 1-benzoyl-N-[(3-methoxyphenyl)methyl]-3-(pyridin-3-yl)-1H-1,2,4-triazol-5-amine |
| 526 | 1-benzoyl-N-[(3-methoxyphenyl)methyl]-3-(pyridin-3-yl)-1H-pyrazol-5-amine |
| 527 | 1-benzoyl-N-[(3-methoxyphenyl)methyl]-3-(pyridin-4-yl)-1H-1,2,4-triazol-5-amine |
| 528 | 1-benzoyl-N-[(3-methoxyphenyl)methyl]-3-(thiophen-2-yl)-1H-1,2,4-triazol-5-amine |
| 529 | 1-benzoyl-N-[(3-methoxyphenyl)methyl]-3-phenyl-1H-1,2,4-triazol-5-amine |
| 530 | 1-benzoyl-N-[(3-methoxyphenyl)methyl]-3-phenyl-1H-pyrazol-5-amine |
| 531 | 1-benzoyl-N-[(3-methylphenyl)methyl]-3-(pyridin-2-yl)-1H-1,2,4-triazol-5-amine |
| 532 | 1-benzoyl-N-[(3-methylphenyl)methyl]-3-(pyridin-3-yl)-1H-1,2,4-triazol-5-amine |
| 533 | 1-benzoyl-N-[(3-methylphenyl)methyl]-3-(pyridin-3-yl)-1H-pyrazol-5-amine |
| 534 | 1-benzoyl-N-[(3-methylphenyl)methyl]-3-(pyridin-4-yl)-1H-1,2,4-triazol-5-amine |
| 535 | 1-benzoyl-N-[(3-methylphenyl)methyl]-3-(thiophen-2-yl)-1H-1,2,4-triazol-5-amine |
| 536 | 1-benzoyl-N-[(3-methylphenyl)methyl]-3-phenyl-1H-1,2,4-triazol-5-amine |
| 537 | 1-benzoyl-N-[(3-methylphenyl)methyl]-3-phenyl-1H-pyrazol-5-amine |
| 538 | 1-benzoyl-N-[(4-chlorophenyl)methyl]-3-(pyridin-3-yl)-1H-pyrazol-5-amine |
| 539 | 1-benzoyl-N-[(4-chlorophenyl)methyl]-3-(thiophen-2-yl)-1H-1,2,4-triazol-5-amine |
| 540 | 1-benzoyl-N-[(4-chlorophenyl)methyl]-3-phenyl-1H-1,2,4-triazol-5-amine |
| 541 | 1-benzoyl-N-[(4-chlorophenyl)methyl]-3-phenyl-1H-pyrazol-5-amine |
| 542 | 1-benzoyl-N-[(4-fluorophenyl)methyl]-3-(pyridin-3-yl)-1H-pyrazol-5-amine |
| 543 | 1-benzoyl-N-[(4-fluorophenyl)methyl]-3-(thiophen-2-yl)-1H-1,2,4-triazol-5-amine |
| 544 | 1-benzoyl-N-[(4-fluorophenyl)methyl]-3-phenyl-1H-pyrazol-5-amine |
| 545 | 1-benzoyl-N-[(4-methoxyphenyl)methyl]-3-(pyridin-3-yl)-1H-pyrazol-5-amine |
| 546 | 1-benzoyl-N-[(4-methoxyphenyl)methyl]-3-(thiophen-2-yl)-1H-1,2,4-triazol-5-amine |
| 547 | 1-benzoyl-N-[(4-methoxyphenyl)methyl]-3-phenyl-1H-pyrazol-5-amine |
| 548 | 1-benzoyl-N-[(4-methylphenyl)methyl]-3-(pyridin-2-yl)-1H-1,2,4-triazol-5-amine |
| 549 | 1-benzoyl-N-[(4-methylphenyl)methyl]-3-(pyridin-3-yl)-1H-pyrazol-5-amine |
| 550 | 1-benzoyl-N-[(4-methylphenyl)methyl]-3-(pyridin-4-yl)-1H-1,2,4-triazol-5-amine |
| 551 | 1-benzoyl-N-[(4-methylphenyl)methyl]-3-(thiophen-2-yl)-1H-1,2,4-triazol-5-amine |
| 552 | 1-benzoyl-N-[(4-methylphenyl)methyl]-3-phenyl-1H-1,2,4-triazol-5-amine |
| 553 | 1-benzoyl-N-[(4-methylphenyl)methyl]-3-phenyl-1H-pyrazol-5-amine |
| 554 | 1-benzoyl-N-benzyl-3-(2-fluorophenyl)-1H-1,2,4-triazol-5-amine |
| 555 | 1-benzoyl-N-benzyl-3-(2-methylphenyl)-1H-1,2,4-triazol-5-amine |
| 556 | 1-benzoyl-N-benzyl-3-(3-fluorophenyl)-1H-1,2,4-triazol-5-amine |
| 557 | 1-benzoyl-N-benzyl-3-(3-methylphenyl)-1H-1,2,4-triazol-5-amine |
| 558 | 1-benzoyl-N-benzyl-3-(4-fluorophenyl)-1H-1,2,4-triazol-5-amine |
| 559 | 1-benzoyl-N-benzyl-3-(4-methylphenyl)-1H-1,2,4-triazol-5-amine |
| 560 | 1-benzoyl-N-benzyl-3-(pyridin-3-yl)-1H-pyrazol-5-amine |
| 561 | 1-benzoyl-N-benzyl-3-(pyridin-3-yl)-1H-pyrazol-5-amine |
| 562 | 1-benzoyl-N-benzyl-3-(pyridin-3-yl)-1H-pyrazol-5-amine |
| 563 | 1-benzoyl-N-benzyl-3-(pyridin-3-yl)-1H-pyrazol-5-amine |
| 564 | 1-benzoyl-N-benzyl-3-(pyridin-3-yl)-1H-pyrazol-5-amine |
| 565 | 1-benzoyl-N-benzyl-3-(pyridin-3-yl)-1H-pyrazol-5-amine |
| 566 | 1-benzoyl-N-benzyl-3-(thiophen-2-yl)-1H-1,2,4-triazol-5-amine |
| 567 | 1-benzoyl-N-benzyl-3-(thiophen-2-yl)-1H-1,2,4-triazol-5-amine |
| 568 | 1-benzoyl-N-benzyl-3-(thiophen-2-yl)-1H-1,2,4-triazol-5-amine |
| 569 | 1-benzoyl-N-benzyl-3-(thiophen-2-yl)-1H-1,2,4-triazol-5-amine |
| 570 | 1-benzoyl-N-benzyl-3-(thiophen-2-yl)-1H-1,2,4-triazol-5-amine |
| 571 | 1-benzoyl-N-benzyl-3-(thiophen-2-yl)-1H-1,2,4-triazol-5-amine |
| 572 | 1-benzoyl-N-benzyl-3-phenyl-1H-pyrazol-5-amine |
| 573 | 1-benzoyl-N-benzyl-3-phenyl-1H-pyrazol-5-amine |
| 574 | 1-benzoyl-N-benzyl-3-phenyl-1H-pyrazol-5-amine |
| 575 | 1-benzoyl-N-benzyl-3-phenyl-1H-pyrazol-5-amine |
| 576 | 1-benzoyl-N-benzyl-3-phenyl-1H-pyrazol-5-amine |
| 577 | 1-benzoyl-N-benzyl-3-phenyl-1H-pyrazol-5-amine |
| 578 | 1-benzoyl-N-[2-(dimethylamino)phenyl]methyl-3-(furan-2-yl)-1H-1,2,4-triazol-5-amine |
| 579 | 1-benzoyl-N-[2-(dimethylamino)phenyl]methyl-3-(pyridin-2-yl)-1H-1,2,4-triazol-5-amine |
| 580 | 1-benzoyl-N-[2-(dimethylamino)phenyl]methyl-3-(pyridin-3-yl)-1H-1,2,4-triazol-5-amine |
| 581 | 1-benzoyl-N-[2-(dimethylamino)phenyl]methyl-3-(pyridin-3-yl)-1H-pyrazol-5-amine |
| 582 | 1-benzoyl-N-[2-(dimethylamino)phenyl]methyl-3-(pyridin-4-yl)-1H-1,2,4-triazol-5-amine |
| 583 | 1-benzoyl-N-[2-(dimethylamino)phenyl]methyl-3-(thiophen-2-yl)-1H-1,2,4-triazol-5-amine |
| 584 | 1-benzoyl-N-[2-(dimethylamino)phenyl]methyl-3-phenyl-1H-1,2,4-triazol-5-amine |
| 585 | 1-benzoyl-N-[2-(dimethylamino)phenyl]methyl-3-phenyl-1H-pyrazol-5-amine |

TABLE B-continued

| Cmpd No | IUPAC name |
|---|---|
| 586 | 1-benzoyl-N-[3-(dimethylamino)phenyl]methyl-3-(furan-2-yl)-1H-1,2,4-triazol-5-amine |
| 587 | 1-benzoyl-N-[3-(dimethylamino)phenyl]methyl-3-(pyridin-2-yl)-1H-1,2,4-triazol-5-amine |
| 588 | 1-benzoyl-N-[3-(dimethylamino)phenyl]methyl-3-(pyridin-3-yl)-1H-1,2,4-triazol-5-amine |
| 589 | 1-benzoyl-N-[3-(dimethylamino)phenyl]methyl-3-(pyridin-3-yl)-1H-pyrazol-5-amine |
| 590 | 1-benzoyl-N-[3-(dimethylamino)phenyl]methyl-3-(pyridin-4-yl)-1H-1,2,4-triazol-5-amine |
| 591 | 1-benzoyl-N-[3-(dimethylamino)phenyl]methyl-3-(thiophen-2-yl)-1H-1,2,4-triazol-5-amine |
| 592 | 1-benzoyl-N-[3-(dimethylamino)phenyl]methyl-3-phenyl-1H-1,2,4-triazol-5-amine |
| 593 | 1-benzoyl-N-[3-(dimethylamino)phenyl]methyl-3-phenyl-1H-pyrazol-5-amine |
| 594 | 1-benzoyl-N-[4-(dimethylamino)phenyl]methyl-3-(pyridin-2-yl)-1H-1,2,4-triazol-5-amine |
| 595 | 1-benzoyl-N-[4-(dimethylamino)phenyl]methyl-3-(pyridin-3-yl)-1H-1,2,4-triazol-5-amine |
| 596 | 1-benzoyl-N-[4-(dimethylamino)phenyl]methyl-3-(pyridin-3-yl)-1H-pyrazol-5-amine |
| 597 | 1-benzoyl-N-[4-(dimethylamino)phenyl]methyl-3-(pyridin-4-yl)-1H-1,2,4-triazol-5-amine |
| 598 | 1-benzoyl-N-[4-(dimethylamino)phenyl]methyl-3-(thiophen-2-yl)-1H-1,2,4-triazol-5-amine |
| 599 | 1-benzoyl-N-[4-(dimethylamino)phenyl]methyl-3-phenyl-1H-pyrazol-5-amine |
| 600 | 2-([1-benzoyl-3-(furan-2-yl)-1H-1,2,4-triazol-5-yl]aminomethyl)benzonitrile |
| 601 | 2-([1-benzoyl-3-(pyridin-3-yl)-1H-1,2,4-triazol-5-yl]aminomethyl)benzonitrile |
| 602 | 2-([1-benzoyl-3-(pyridin-3-yl)-1H-pyrazol-5-yl]aminomethyl)benzonitrile |
| 603 | 2-([1-benzoyl-3-(pyridin-4-yl)-1H-1,2,4-triazol-5-yl]aminomethyl)benzonitrile |
| 604 | 2-([1-benzoyl-3-(thiophen-2-yl)-1H-1,2,4-triazol-5-yl]aminomethyl)benzonitrile |
| 605 | 2-[(1-benzoyl-3-phenyl-1H-1,2,4-triazol-5-yl)amino]methylbenzonitrile |
| 606 | 2-[(1-benzoyl-3-phenyl-1H-pyrazol-5-yl)amino]methylbenzonitrile |
| 607 | 2-[5-(benzylamino)-3-(furan-2-yl)-1H-1,2,4-triazol-1-yl]carbonylbenzonitrile |
| 608 | 2-[5-(benzylamino)-3-(pyridin-3-yl)-1H-1,2,4-triazol-1-yl]carbonylbenzonitrile |
| 609 | 2-[5-(benzylamino)-3-(pyridin-3-yl)-1H-pyrazol-1-yl]carbonylbenzonitrile |
| 610 | 2-[5-(benzylamino)-3-(pyridin-4-yl)-1H-1,2,4-triazol-1-yl]carbonylbenzonitrile |
| 611 | 2-[5-(benzylamino)-3-(thiophen-2-yl)-1H-1,2,4-triazol-1-yl]carbonylbenzonitrile |
| 612 | 2-[5-(benzylamino)-3-phenyl-1H-1,2,4-triazol-1-yl]carbonylbenzonitrile |
| 613 | 2-[5-(benzylamino)-3-phenyl-1H-pyrazol-1-yl]carbonylbenzonitrile |
| 614 | 3-([1-benzoyl-3-(furan-2-yl)-1H-1,2,4-triazol-5-yl]aminomethyl)benzonitrile |
| 615 | 3-([1-benzoyl-3-(pyridin-2-yl)-1H-1,2,4-triazol-5-yl]aminomethyl)benzonitrile |
| 616 | 3-([1-benzoyl-3-(pyridin-3-yl)-1H-1,2,4-triazol-5-yl]aminomethyl)benzonitrile |
| 617 | 3-([1-benzoyl-3-(pyridin-3-yl)-1H-pyrazol-5-yl]aminomethyl)benzonitrile |
| 618 | 3-([1-benzoyl-3-(pyridin-4-yl)-1H-1,2,4-triazol-5-yl]aminomethyl)benzonitrile |
| 619 | 3-([1-benzoyl-3-(thiophen-2-yl)-1H-1,2,4-triazol-5-yl]aminomethyl)benzonitrile |
| 620 | 3-[(1-benzoyl-3-phenyl-1H-1,2,4-triazol-5-yl)amino]methylbenzonitrile |
| 621 | 3-[(1-benzoyl-3-phenyl-1H-pyrazol-5-yl)amino]methylbenzonitrile |
| 622 | 3-[5-(benzylamino)-3-(furan-2-yl)-1H-1,2,4-triazol-1-yl]carbonylbenzonitrile |
| 623 | 3-[5-(benzylamino)-3-(pyridin-2-yl)-1H-1,2,4-triazol-1-yl]carbonylbenzonitrile |
| 624 | 3-[5-(benzylamino)-3-(pyridin-3-yl)-1H-1,2,4-triazol-1-yl]carbonylbenzonitrile |
| 625 | 3-[5-(benzylamino)-3-(pyridin-3-yl)-1H-pyrazol-1-yl]carbonylbenzonitrile |
| 626 | 3-[5-(benzylamino)-3-(pyridin-4-yl)-1H-1,2,4-triazol-1-yl]carbonylbenzonitrile |
| 627 | 3-[5-(benzylamino)-3-(thiophen-2-yl)-1H-1,2,4-triazol-1-yl]carbonylbenzonitrile |
| 628 | 3-[5-(benzylamino)-3-phenyl-1H-1,2,4-triazol-1-yl]carbonylbenzonitrile |
| 629 | 3-[5-(benzylamino)-3-phenyl-1H-pyrazol-1-yl]carbonylbenzonitrile |
| 630 | 4-([1-benzoyl-3-(furan-2-yl)-1H-1,2,4-triazol-5-yl]aminomethyl)benzonitrile |
| 631 | 4-([1-benzoyl-3-(pyridin-2-yl)-1H-1,2,4-triazol-5-yl]aminomethyl)benzonitrile |
| 632 | 4-([1-benzoyl-3-(pyridin-3-yl)-1H-1,2,4-triazol-5-yl]aminomethyl)benzonitrile |
| 633 | 4-([1-benzoyl-3-(pyridin-3-yl)-1H-pyrazol-5-yl]aminomethyl)benzonitrile |
| 634 | 4-([1-benzoyl-3-(pyridin-4-yl)-1H-1,2,4-triazol-5-yl]aminomethyl)benzonitrile |
| 635 | 4-([1-benzoyl-3-(thiophen-2-yl)-1H-1,2,4-triazol-5-yl]aminomethyl)benzonitrile |
| 636 | 4-[(1-benzoyl-3-phenyl-1H-1,2,4-triazol-5-yl)amino]methylbenzonitrile |
| 637 | 4-[(1-benzoyl-3-phenyl-1H-pyrazol-5-yl)amino]methylbenzonitrile |
| 638 | 4-[5-(benzylamino)-3-(furan-2-yl)-1H-1,2,4-triazol-1-yl]carbonylbenzonitrile |
| 639 | 4-[5-(benzylamino)-3-(pyridin-2-yl)-1H-1,2,4-triazol-1-yl]carbonylbenzonitrile |
| 640 | 4-[5-(benzylamino)-3-(pyridin-3-yl)-1H-1,2,4-triazol-1-yl]carbonylbenzonitrile |
| 641 | 4-[5-(benzylamino)-3-(pyridin-3-yl)-1H-pyrazol-1-yl]carbonylbenzonitrile |
| 642 | 4-[5-(benzylamino)-3-(pyridin-4-yl)-1H-1,2,4-triazol-1-yl]carbonylbenzonitrile |
| 643 | 4-[5-(benzylamino)-3-(thiophen-2-yl)-1H-1,2,4-triazol-1-yl]carbonylbenzonitrile |
| 644 | 4-[5-(benzylamino)-3-phenyl-1H-1,2,4-triazol-1-yl]carbonylbenzonitrile |
| 645 | 4-[5-(benzylamino)-3-phenyl-1H-pyrazol-1-yl]carbonylbenzonitrile |
| 646 | ethyl 5-[(E)-(pyridin-3-ylmethylidene)amino]-1H-1,2,4-triazole-3-carboxylate |
| 647 | N-(2,4-dichlorophenyl)-5-(1H-1,2,4-triazol-1-ylmethyl)-1H-1,2,4-triazole-3-carboxamide |
| 648 | N-benzyl-1-[(2-chlorophenyl)carbonyl]-3-(pyridin-3-yl)-1H-pyrazol-5-amine |
| 649 | N-benzyl-1-[(2-chlorophenyl)carbonyl]-3-phenyl-1H-1,2,4-triazol-5-amine |
| 650 | N-benzyl-1-[(2-chlorophenyl)carbonyl]-3-phenyl-1H-pyrazol-5-amine |
| 651 | N-benzyl-1-[(2-fluorophenyl)carbonyl]-3-(furan-2-yl)-1H-1,2,4-triazol-5-amine |
| 652 | N-benzyl-1-[(2-fluorophenyl)carbonyl]-3-(pyridin-3-yl)-1H-pyrazol-5-amine |
| 653 | N-benzyl-1-[(2-fluorophenyl)carbonyl]-3-(thiophen-2-yl)-1H-1,2,4-triazol-5-amine |
| 654 | N-benzyl-1-[(2-fluorophenyl)carbonyl]-3-phenyl-1H-1,2,4-triazol-5-amine |
| 655 | N-benzyl-1-[(2-fluorophenyl)carbonyl]-3-phenyl-1H-pyrazol-5-amine |
| 656 | N-benzyl-1-[(2-methoxyphenyl)carbonyl]-3-(pyridin-3-yl)-1H-pyrazol-5-amine |
| 657 | N-benzyl-1-[(2-methoxyphenyl)carbonyl]-3-phenyl-1H-pyrazol-5-amine |
| 658 | N-benzyl-1-[(2-methylphenyl)carbonyl]-3-(pyridin-3-yl)-1H-pyrazol-5-amine |
| 659 | N-benzyl-1-[(2-methylphenyl)carbonyl]-3-(pyridin-4-yl)-1H-1,2,4-triazol-5-amine |
| 660 | N-benzyl-1-[(2-methylphenyl)carbonyl]-3-(thiophen-2-yl)-1H-1,2,4-triazol-5-amine |
| 661 | N-benzyl-1-[(2-methylphenyl)carbonyl]-3-phenyl-1H-1,2,4-triazol-5-amine |
| 662 | N-benzyl-1-[(2-methylphenyl)carbonyl]-3-phenyl-1H-pyrazol-5-amine |
| 663 | N-benzyl-1-[(3-chlorophenyl)carbonyl]-3-(pyridin-2-yl)-1H-1,2,4-triazol-5-amine |

TABLE B-continued

| Cmpd No | IUPAC name |
|---|---|
| 664 | N-benzyl-1-[(3-chlorophenyl)carbonyl]-3-(pyridin-3-yl)-1H-pyrazol-5-amine |
| 665 | N-benzyl-1-[(3-chlorophenyl)carbonyl]-3-(pyridin-4-yl)-1H-1,2,4-triazol-5-amine |
| 666 | N-benzyl-1-[(3-chlorophenyl)carbonyl]-3-(thiophen-2-yl)-1H-1,2,4-triazol-5-amine |
| 667 | N-benzyl-1-[(3-chlorophenyl)carbonyl]-3-phenyl-1H-1,2,4-triazol-5-amine |
| 668 | N-benzyl-1-[(3-chlorophenyl)carbonyl]-3-phenyl-1H-pyrazol-5-amine |
| 669 | N-benzyl-1-[(3-fluorophenyl)carbonyl]-3-(furan-2-yl)-1H-1,2,4-triazol-5-amine |
| 670 | N-benzyl-1-[(3-fluorophenyl)carbonyl]-3-(pyridin-3-yl)-1H-pyrazol-5-amine |
| 671 | N-benzyl-1-[(3-fluorophenyl)carbonyl]-3-(thiophen-2-yl)-1H-1,2,4-triazol-5-amine |
| 672 | N-benzyl-1-[(3-fluorophenyl)carbonyl]-3-phenyl-1H-1,2,4-triazol-5-amine |
| 673 | N-benzyl-1-[(3-fluorophenyl)carbonyl]-3-phenyl-1H-pyrazol-5-amine |
| 674 | N-benzyl-1-[(3-methoxyphenyl)carbonyl]-3-(pyridin-3-yl)-1H-pyrazol-5-amine |
| 675 | N-benzyl-1-[(3-methoxyphenyl)carbonyl]-3-(pyridin-4-yl)-1H-1,2,4-triazol-5-amine |
| 676 | N-benzyl-1-[(3-methoxyphenyl)carbonyl]-3-(thiophen-2-yl)-1H-1,2,4-triazol-5-amine |
| 677 | N-benzyl-1-[(3-methoxyphenyl)carbonyl]-3-phenyl-1H-1,2,4-triazol-5-amine |
| 678 | N-benzyl-1-[(3-methoxyphenyl)carbonyl]-3-phenyl-1H-pyrazol-5-amine |
| 679 | N-benzyl-1-[(3-methylphenyl)carbonyl]-3-(pyridin-2-yl)-1H-1,2,4-triazol-5-amine |
| 680 | N-benzyl-1-[(3-methylphenyl)carbonyl]-3-(pyridin-3-yl)-1H-pyrazol-5-amine |
| 681 | N-benzyl-1-[(3-methylphenyl)carbonyl]-3-(pyridin-4-yl)-1H-1,2,4-triazol-5-amine |
| 682 | N-benzyl-1-[(3-methylphenyl)carbonyl]-3-(thiophen-2-yl)-1H-1,2,4-triazol-5-amine |
| 683 | N-benzyl-1-[(3-methylphenyl)carbonyl]-3-phenyl-1H-1,2,4-triazol-5-amine |
| 684 | N-benzyl-1-[(3-methylphenyl)carbonyl]-3-phenyl-1H-pyrazol-5-amine |
| 685 | N-benzyl-1-[(4-chlorophenyl)carbonyl]-3-(furan-2-yl)-1H-1,2,4-triazol-5-amine |
| 686 | N-benzyl-1-[(4-chlorophenyl)carbonyl]-3-(pyridin-3-yl)-1H-pyrazol-5-amine |
| 687 | N-benzyl-1-[(4-chlorophenyl)carbonyl]-3-(thiophen-2-yl)-1H-1,2,4-triazol-5-amine |
| 688 | N-benzyl-1-[(4-chlorophenyl)carbonyl]-3-phenyl-1H-1,2,4-triazol-5-amine |
| 689 | N-benzyl-1-[(4-chlorophenyl)carbonyl]-3-phenyl-1H-pyrazol-5-amine |
| 690 | N-benzyl-1-[(4-fluorophenyl)carbonyl]-3-(pyridin-3-yl)-1H-pyrazol-5-amine |
| 691 | N-benzyl-1-[(4-fluorophenyl)carbonyl]-3-(thiophen-2-yl)-1H-1,2,4-triazol-5-amine |
| 692 | N-benzyl-1-[(4-fluorophenyl)carbonyl]-3-phenyl-1H-pyrazol-5-amine |
| 693 | N-benzyl-1-[(4-methoxyphenyl)carbonyl]-3-(pyridin-3-yl)-1H-pyrazol-5-amine |
| 694 | N-benzyl-1-[(4-methoxyphenyl)carbonyl]-3-(pyridin-4-yl)-1H-1,2,4-triazol-5-amine |
| 695 | N-benzyl-1-[(4-methoxyphenyl)carbonyl]-3-(thiophen-2-yl)-1H-1,2,4-triazol-5-amine |
| 696 | N-benzyl-1-[(4-methoxyphenyl)carbonyl]-3-phenyl-1H-1,2,4-triazol-5-amine |
| 697 | N-benzyl-1-[(4-methoxyphenyl)carbonyl]-3-phenyl-1H-pyrazol-5-amine |
| 698 | N-benzyl-1-[(4-methylphenyl)carbonyl]-3-(pyridin-2-yl)-1H-1,2,4-triazol-5-amine |
| 699 | N-benzyl-1-[(4-methylphenyl)carbonyl]-3-(pyridin-3-yl)-1H-pyrazol-5-amine |
| 700 | N-benzyl-1-[(4-methylphenyl)carbonyl]-3-(pyridin-4-yl)-1H-1,2,4-triazol-5-amine |
| 701 | N-benzyl-1-[(4-methylphenyl)carbonyl]-3-(thiophen-2-yl)-1H-1,2,4-triazol-5-amine |
| 702 | N-benzyl-1-[(4-methylphenyl)carbonyl]-3-phenyl-1H-pyrazol-5-amine |
| 703 | N-benzyl-1-[(furan-2-yl)carbonyl]-3-(pyridin-3-yl)-1H-pyrazol-5-amine |
| 704 | N-benzyl-1-[(furan-2-yl)carbonyl]-3-phenyl-1H-pyrazol-5-amine |
| 705 | N-benzyl-1-[(pyridin-2-yl)carbonyl]-3-(pyridin-3-yl)-1H-1,2,4-triazol-5-amine |
| 706 | N-benzyl-1-[(pyridin-2-yl)carbonyl]-3-(pyridin-3-yl)-1H-pyrazol-5-amine |
| 707 | N-benzyl-1-[(pyridin-2-yl)carbonyl]-3-(pyridin-4-yl)-1H-1,2,4-triazol-5-amine |
| 708 | N-benzyl-1-[(pyridin-2-yl)carbonyl]-3-(thiophen-2-yl)-1H-1,2,4-triazol-5-amine |
| 709 | N-benzyl-1-[(pyridin-3-yl)carbonyl]-3-(pyridin-4-yl)-1H-1,2,4-triazol-5-amine |
| 710 | N-benzyl-1-[(pyridin-3-yl)carbonyl]-3-(thiophen-2-yl)-1H-1,2,4-triazol-5-amine |
| 711 | N-benzyl-1-[(pyridin-4-yl)carbonyl]-3-(thiophen-2-yl)-1H-1,2,4-triazol-5-amine |
| 712 | N-benzyl-1-[2-(dimethylamino)phenyl]carbonyl-3-(furan-2-yl)-1H-1,2,4-triazol-5-amine |
| 713 | N-benzyl-1-[2-(dimethylamino)phenyl]carbonyl-3-(pyridin-3-yl)-1H-1,2,4-triazol-5-amine |
| 714 | N-benzyl-1-[2-(dimethylamino)phenyl]carbonyl-3-(pyridin-3-yl)-1H-pyrazol-5-amine |
| 715 | N-benzyl-1-[2-(dimethylamino)phenyl]carbonyl-3-(pyridin-4-yl)-1H-1,2,4-triazol-5-amine |
| 716 | N-benzyl-1-[2-(dimethylamino)phenyl]carbonyl-3-(thiophen-2-yl)-1H-1,2,4-triazol-5-amine |
| 717 | N-benzyl-1-[2-(dimethylamino)phenyl]carbonyl-3-phenyl-1H-1,2,4-triazol-5-amine |
| 718 | N-benzyl-1-[2-(dimethylamino)phenyl]carbonyl-3-phenyl-1H-pyrazol-5-amine |
| 719 | N-benzyl-1-[3-(dimethylamino)phenyl]carbonyl-3-(furan-2-yl)-1H-1,2,4-triazol-5-amine |
| 720 | N-benzyl-1-[3-(dimethylamino)phenyl]carbonyl-3-(pyridin-2-yl)-1H-1,2,4-triazol-5-amine |
| 721 | N-benzyl-1-[3-(dimethylamino)phenyl]carbonyl-3-(pyridin-3-yl)-1H-1,2,4-triazol-5-amine |
| 722 | N-benzyl-1-[3-(dimethylamino)phenyl]carbonyl-3-(pyridin-3-yl)-1H-pyrazol-5-amine |
| 723 | N-benzyl-1-[3-(dimethylamino)phenyl]carbonyl-3-(pyridin-4-yl)-1H-1,2,4-triazol-5-amine |
| 724 | N-benzyl-1-[3-(dimethylamino)phenyl]carbonyl-3-(thiophen-2-yl)-1H-1,2,4-triazol-5-amine |
| 725 | N-benzyl-1-[3-(dimethylamino)phenyl]carbonyl-3-phenyl-1H-1,2,4-triazol-5-amine |
| 726 | N-benzyl-1-[3-(dimethylamino)phenyl]carbonyl-3-phenyl-1H-pyrazol-5-amine |
| 727 | N-benzyl-1-[4-(dimethylamino)phenyl]carbonyl-3-(furan-2-yl)-1H-1,2,4-triazol-5-amine |
| 728 | N-benzyl-1-[4-(dimethylamino)phenyl]carbonyl-3-(pyridin-2-yl)-1H-1,2,4-triazol-5-amine |
| 729 | N-benzyl-1-[4-(dimethylamino)phenyl]carbonyl-3-(pyridin-3-yl)-1H-1,2,4-triazol-5-amine |
| 730 | N-benzyl-1-[4-(dimethylamino)phenyl]carbonyl-3-(pyridin-3-yl)-1H-pyrazol-5-amine |
| 731 | N-benzyl-1-[4-(dimethylamino)phenyl]carbonyl-3-(pyridin-4-yl)-1H-1,2,4-triazol-5-amine |
| 732 | N-benzyl-1-[4-(dimethylamino)phenyl]carbonyl-3-(thiophen-2-yl)-1H-1,2,4-triazol-5-amine |
| 733 | N-benzyl-1-[4-(dimethylamino)phenyl]carbonyl-3-phenyl-1H-1,2,4-triazol-5-amine |
| 734 | N-benzyl-1-[4-(dimethylamino)phenyl]carbonyl-3-phenyl-1H-pyrazol-5-amine |
| 735 | N-benzyl-3-(furan-2-yl)-1-[(3-methoxyphenyl)carbonyl]-1H-1,2,4-triazol-5-amine |
| 736 | N-benzyl-3-(furan-2-yl)-1-[(4-methoxyphenyl)carbonyl]-1H-1,2,4-triazol-5-amine |
| 737 | N-benzyl-3-(furan-2-yl)-1-[(pyridin-2-yl)carbonyl]-1H-1,2,4-triazol-5-amine |
| 738 | N-benzyl-3-(furan-2-yl)-1-[(pyridin-3-yl)carbonyl]-1H-1,2,4-triazol-5-amine |
| 739 | N-benzyl-3-(furan-2-yl)-1-[(pyridin-4-yl)carbonyl]-1H-1,2,4-triazol-5-amine |
| 740 | N-benzyl-3-(pyridin-2-yl)-1-[(pyridin-2-yl)carbonyl]-1H-1,2,4-triazol-5-amine |
| 741 | N-benzyl-3-(pyridin-2-yl)-1-[(pyridin-3-yl)carbonyl]-1H-1,2,4-triazol-5-amine |

TABLE B-continued

| Cmpd No | IUPAC name |
|---|---|
| 742 | N-benzyl-3-(pyridin-2-yl)-1-[(pyridin-4-yl)carbonyl]-1H-1,2,4-triazol-5-amine |
| 743 | N-benzyl-3-(pyridin-3-yl)-1-[(pyridin-3-yl)carbonyl]-1H-1,2,4-triazol-5-amine |
| 744 | N-benzyl-3-(pyridin-3-yl)-1-[(pyridin-3-yl)carbonyl]-1H-pyrazol-5-amine |
| 745 | N-benzyl-3-(pyridin-3-yl)-1-[(pyridin-4-yl)carbonyl]-1H-1,2,4-triazol-5-amine |
| 746 | N-benzyl-3-(pyridin-3-yl)-1-[(pyridin-4-yl)carbonyl]-1H-pyrazol-5-amine |
| 747 | N-benzyl-3-(pyridin-3-yl)-1-[(thiophen-2-yl)carbonyl]-1H-pyrazol-5-amine |
| 748 | N-benzyl-3-(pyridin-4-yl)-1-[(pyridin-4-yl)carbonyl]-1H-1,2,4-triazol-5-amine |
| 749 | N-benzyl-3-phenyl-1-[(pyridin-2-yl)carbonyl]-1H-1,2,4-triazol-5-amine |
| 750 | N-benzyl-3-phenyl-1-[(pyridin-2-yl)carbonyl]-1H-pyrazol-5-amine |
| 751 | N-benzyl-3-phenyl-1-[(pyridin-3-yl)carbonyl]-1H-1,2,4-triazol-5-amine |
| 752 | N-benzyl-3-phenyl-1-[(pyridin-3-yl)carbonyl]-1H-pyrazol-5-amine |
| 753 | N-benzyl-3-phenyl-1-[(pyridin-4-yl)carbonyl]-1H-1,2,4-triazol-5-amine |
| 754 | N-benzyl-3-phenyl-1-[(pyridin-4-yl)carbonyl]-1H-pyrazol-5-amine |
| 755 | N-benzyl-3-phenyl-1-[(thiophen-2-yl)carbonyl]-1H-pyrazol-5-amine |

Compounds disclosed herein also include racemic mixtures, stereoisomers and mixtures of the compounds, including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography, and the like. See e.g., Eliel, E. L. & Wilen S. H., 1993, STEREOCHEMISTRY IN ORGANIC COMPOUNDS; John Wiley & Sons, New York.

In some embodiments, compounds disclosed herein have asymmetric centers and may occur as racemates, racemic mixtures, and as individual enantiomers or diastereoisomers, with all isomeric forms as well as mixtures thereof being contemplated for use in the compounds and methods described herein. The compounds contemplated for use in the compounds and methods described herein do not include those that are known in the art to be too unstable to synthesize and/or isolate.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds disclosed herein, whether radioactive or not, are encompassed within the contemplated scope.

In some embodiments, metabolites of the compounds disclosed herein are useful for the methods disclosed herein.

In some embodiments, compounds contemplated herein are provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhanced bioavailable in oral administration, and the like. The prodrug may also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water-solubility is beneficial. Conventional procedures for the selection and preparation of suitable prodrug derivatives are described, for example, in DESIGN OF PRODRUGS, (ed. H. Bundgaard, Elsevier, 1985), which is hereby incorporated herein by reference for the limited purpose describing procedures and preparation of suitable prodrug derivatives.

Accordingly, in some embodiments, compounds contemplated herein are provided in the form of a prodrug ester. The term "prodrug ester" refers to derivatives of the compounds disclosed herein formed by the addition of any of a variety of ester-forming groups, e.g., groups known in the art, that are hydrolyzed under physiological conditions. Examples of prodrug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Pro-drugs as Novel Delivery Systems", Vol. 14, A.C.S. Symposium Series, American Chemical Society (1975); and BIOREVERSIBLE CARRIERS IN DRUG DESIGN: THEORY AND APPLICATION, edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

In some embodiments, prodrugs can be slowly converted to the compounds described herein useful for the methods described herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present invention may exist in multiple crystalline or amorphous forms. In general, all physical forms are equivalent for the compounds and methods contemplated herein and are intended to be within the scope disclosed herein.

III. BIOLOGICAL ACTIVITIES

In some embodiments, compounds described herein exhibit inhibitory activity against thrombin with activities ≥1 µM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100 µM, or even greater. In some embodiments, the compounds exhibit inhibitory activity against thrombin with activities between 0.1 µM and 1 µM, e.g., about 0.1, 0.2, 0.3, 0.4, 0.5, 0.6, 0.7, 0.8, 0.9 or 1.0 µM. In some embodiments, compounds described herein exhibit inhibitory activity against thrombin with activities <0.1 µM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 0.1-1 μM, 1-10 μM, 10-100 μM, 100-200 μM, 200-500 μM, or even 500-1000 μM. In some embodiments, the inhibitory activity is in the range of about 1-10 nM, 10-100 nM, 0.1-1 μM, 1-10 μM, 10-100 μM, 100-200 μM, 200-500 μM, or even 500-1000 μM. It is understood that for purposes of quantification, the terms "activity," "inhibitory activity," "biological activity," "thrombin activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against thrombin in turn inhibits the blood coagulation process. Accordingly, compounds disclosed herein are indicated in the treatment or management of thrombotic disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 μM, 1-10 μM, 10-100 μM, 100-200 μM, 200-500 μM, or even 500-1000 μM, preferably about 1-10 nM, 10-100 nM, or 0.1-1 μM. Without wishing to be bound by any theory, it is believe that such compounds are indicated in the treatment or management of thrombotic disorders.

IV. METHODS OF TREATING AND PREVENTING DISEASE

Thrombosis. Thrombotic diseases are the primary indications for thrombin inhibition, because of thrombin's location in the coagulation cascade and, in turn, the importance of the coagulation cascade in the progression of blood clotting processes. However, without wishing to be bound by any theory, it is believed the coagulation cascade in general, and thrombin in particular, is important in a variety other disease states.

It has been discovered that compounds described herein, e.g., multisubstituted aromatic compounds, exhibit inhibitory action against thrombin (activated blood-coagulation factor II; EC 3.4.21.5). This, in turn inhibits the blood coagulation process.

This inhibitory action is useful in the treatment of a variety of thrombotic disorders, such as, but not limited to, acute vascular diseases such as acute coronary syndromes; venous-, arterial- and cardiogenic thromboembolisms; the prevention of other states such as disseminated intravascular coagulation, or other conditions that involve the presence or the potential formation of a blood clot thrombus. Other indications for methods described herein include the following.

Cancer. It has long been recognized that cancer progression is accompanied by venous thrombosis, but it has not been understood how each disease is related. From several clinical trials studying the treatment of VTE, metaanalyses have shown that low molecular weight heparins (LMWHs) improve overall survival in subgroups of cancer patients. See e.g., Zacharski, L. R. & Lee, A. Y., 2008, *Expert Opin Investig Drugs*, 17:1029-1037; Falanga, A. & Piccioli, A., 2005, *Current Opinion in Pulmonary Medicine*, 11:403-407; Smorenburg, S. M., et al., 1999, *Thromb Haemost*, 82:1600-1604; Hettiarachchi, R. J., et al., 1999, *Thromb Haemost*, 82:947-952. This finding was substantiated in later clinical trials that measured specifically the survival of cancer patients. See e.g., Lee, A. Y. et al., 2005, *J Clin Oncol*, 23:2123-2129; Klerk, C. P. et al., *J Clin Oncol* 2005, 23:2130-2135; Kakkar, A. K., et al., 2004, *J Clin Oncol*, 22:1944-1948; Altinbas, M., et al., 2004, *J Thromb Haemost*, 2:1266-1271.

More recently, researchers have focused on the specific anticancer effect of DTIs. For example, it was shown that heparin significantly prolonged the survival of patients with limited small cell lung cancer. See e.g., Akl, E. A., et al., 2008, *J Exp Clin Cancer Res*, 27:4. Other investigators found that systemic use of argatroban reduced tumor mass and prolonged survival time in rat glioma models leading to the conclusion that argatroban should be considered as a novel therapeutic for glioma, a notoriously difficult to treat cancer type. See e.g., Hua, Y., et al., 2005, *Acta Neurochir, Suppl* 2005, 95:403-406; Hua, Y., et al., 2005, *J Thromb Haemost*, 3:1917-1923. Very recently, it was demonstrated that dabigatran etexilate, a DTI recently FDA-approved (see e.g., Hughes, B., 2010, *Nat Rev Drug Discov*, 9:903-906) for DVT indications, inhibited both the invasion and metastasis of malignant breast tumors. See e.g., DeFeo, K. et al., 2010, *Thrombosis Research*, 125 (Supplement 2): S188-S188; Defeo, K., et al., 2010, *Cancer Biol Ther*, 10:1001-1008. Thus, dabigatran etexilate treatment led to a 50% reduction in tumor volume at 4 weeks with no weight loss in treated mice. Dabigatran etexilate also reduced tumor cells in the blood and liver micrometastases by 50-60%. These investigators concluded that dabigatran etexilate may be beneficial in not only preventing thrombotic events in cancer patients, but also as adjunct therapy to treat malignant tumors.

Further, hirudin and the LMWH nadroparin dramatically reduced the number of lung metastases when administered prior to cancer cell inoculation. See e.g., Hu, L., et al., 2004, *Blood*, 104:2746-51.

The de novo thrombin inhibitor d-Arg-Oic-Pro-d-Ala-Phe (p-Me) has been found to block thrombin-stimulated invasion of prostate cancer cell line PC-3 in a concentration dependent manner. See e.g., Nieman, M. T., et al., 2008, *J Thromb Haemost*, 6:837-845. A reduced rate of tumor growth was observed in mice dosed with the pentapeptide through their drinking water. The mice also showed reduced fold rate in tumor size and reduced overall tumor weight compared to untreated mice. Microscopic examination of treated tumors showed reduced number of large blood vessels thus concluding that the pentapeptide interfered with tumor angiogenesis. Nieman, M. T., et al., *Thromb Haemost*, 104:1044-8.

In view of these and related studies, it is suggested that anticoagulants affect tumor metastasis; that is, angiogenesis, cancer cell adhesion, migration and invasion processes. See e.g., Van Noorden, C. J., et al., 2010, *Thromb Res*, 125 Suppl 2:S77-79.

Fibrosis. Several studies have shown the utility of anticoagulant therapy in fibrotic disorders. For example, in a rat model of $CCl_4$-induced chronic liver injury, the DTI SSR182289 decreased liver fibrogenesis significantly after 7 weeks of administration (ref 24). Similar observations were made in other studies using the LMWHs nadroparin (ref 25), tinzaparin (ref 25), enoxaparin (ref 26), and dalteparin sodium (ref 27). See e.g., Duplantier, J. G., et al., 2004, *Gut*, 53:1682-1687; Abdel-Salam, O. M., et al., 2005, *Pharmacol Res*, 51:59-67; Assy, N., et al., 2007, *Dig Dis Sci*, 52:1187-1193; Abe, W., et al., 2007, *J Hepatol*, 46:286-294.

In another example, the DTI melagatran greatly reduced ischemia reperfusion injury in a kidney transplant model in the large white pig. This led to a drastically improved kidney graft survival at 3 months. See e.g., Favreau, F., et al., 2010, *Am J Transplant*, 10:30-39.

Recent studies have shown that in a bleomycin-induced mouse model of pulmonary fibrosis, dabigatran etexilate treatment reduced important profibrotic events in lung fibroblasts, including the production of collagen and connective tissue growth factor. See e.g., Silver, R. M., et al., 2010, *Am. J. Respir. Crit. Care Med.*, 181:A6780; Bogalkevich, G. S., et al., 2009, *Arthritis Rheum*, 60:3455-3464.

The above experimental evidence points to a close relationship between thrombin and fibrosis (ref 31) and suggests novel therapeutic opportunities for fibrosis using thrombin inhibitors (refs 32-34). See e.g., Calvaruso, V., et al., 2008, *Gut*, 57:1722-1727; Chambers, R. C., 2008, *Br J Pharmacol*, 153 Suppl 1:S367-378; Chambers, R. C. & Laurent, G. J., 2002, *Biochem Soc Trans*, 30:194-200; Howell, D. C., et al., 2001, *Am J Pathol*, 159:1383-1395.

Alzheimer's Disease. Very recent experiments confirm higher thrombin levels in brain endothelial cells of patients with Alzheimer's disease. While 'normal' thrombin levels are connected to regulatory CNS functions, thrombin accumulation in the brain is toxic. It has also been found that the neural thrombin inhibitor Protease Nexin 1 (PN-1) is significantly reduced in the Alzheimer's disease brain, despite the fact that PN-1 mRNA levels are unchanged. These observations have led some investigators to suggest that reduction of CNS-resident thrombin will prove useful in Alzheimer's Disease (AD) treatment. See e.g., Vaughan, P. J., et al., 1994, *Brain Res*, 668:160-170; Yin, X., et al., 2010, *Am J Pathol*, 176:1600-1606; Akiyama, H., et al., 1992, *Neurosci Lett*, 146:152-154.

Multiple Sclerosis. Investigators found that hirudin treatment in an animal model of Multiple Sclerosis (MS) showed a dramatic improvement in disease severity (ref 38). See e.g., Han, M. H., et al., 2008, *Nature*, 451:1076-1081. Similar results were obtained following treatment with heparin (ref 39) (a DTI) and dermatan sulfate (ref 40) another coagulation inhibitor. See e.g., Chelmicka-Szorc, E. & Arnason, B. G., 1972, *Arch Neurol*, 27:153-158; Inaba, Y., et al., 1999, *Cell Immunol*, 198:96-102. Other evidence shows that naturally occurring antithrombin III has anti-inflammatory effects in diseases such as endotoxemia and other sepsis-related conditions. See e.g., Wiedermann, C. J. & Romisch, J., 2002, *Acta Med Austriaca*, 29:89-92. Naturally occurring thrombin inhibitors are presumably synthesized in situ and have protective roles in CNS inflammation. Therefore, therapeutic thrombin inhibition has been proposed as a potential MS treatment. See e.g., Luo, W., et al., 2009, In: THROMBIN, Maragoudakis, M. E.; Tsopanoglou, N. E., Eds. Springer New York: 2009; pp 133-159.

Pain. In a rat pain model with partial lesion of the sciatic nerve, intrathecal hirudin prevented the development of neuropathic pain and curbed pain responses for 7 days. The investigators found that following injury, neuropathic pain was mediated by thrombin generation, which in turn activated PAR-1 receptor in the spinal cord. Hirudin inhibited thrombin generation and ultimately led to pain relief (refs 43, 44). See e.g., Garcia, P. S., et al., 2010, *Thromb Haemost*, 103:1145-1151; Narita, M., et al., 2005, *J Neurosci*, 25:10000-10009. Researchers hypothesize that thrombin and the PARs are involved not just as part of the coagulation cascade, but in inflammation, nociception and neurodevelopment. Development of a DTI to intersect an unexploited pharmacology will lead to pain therapeutics distinct from opioids and NSAIDs, whose shortcomings are well documented. See e.g., Garcia 2010, Id.

Accordingly, in a further aspect, there is provided a method for treating a disease or disorder in a subject in need thereof. The method includes administering a compound of any of Formulae (Ia), (Ib), (IIa), (IIb), (IIIa), (IIIb), (IV) or (V) as disclosed herein, a compound as set forth in any of Tables A, B or C, pharmaceutically acceptable salt, ester, solvate, or prodrug thereof, or pharmaceutical composition thereof, to a subject in need thereof in an amount effective to treat the disease or disorder. The terms "therapeutically effective amount," "amount effective to treat," "amount effective to prevent" and the like refer to that amount of drug or pharmaceutical agent (e.g., compound or pharmaceutical composition disclosed herein) that will elicit the biological or medical response of a tissue, system, animal, or human that is being sought by a researcher, veterinarian, medical doctor or other clinician.

Compounds useful for methods disclosed herein include the compounds set forth for Formulae (Ia), (Ib), (IIa), (IIb), (IIIa), (IIIb), (IV) and (V), and for the compounds set forth in Tables A and B above. Additionally, compounds useful for methods disclosed herein include the compounds set forth in Table C following. For Table C, the compounds were assayed for inhibition of the protease activity of thrombin as described for Table A.

TABLE C

| Cmpd No | IUPAC name | Thrombin Activity |
|---|---|---|
| 1 | 3-(pyridin-3-yl)-1H-1,2,4-triazol-5-amine | c |
| 2 | 3-(pyridin-2-yl)-1H-1,2,4-triazol-5-amine | c |
| 3 | 3-(pyridin-4-yl)-1H-1,2,4-triazol-5-amine | c |
| 8 | 1-(5-[(3-fluorophenyl)methyl]amino-3-(pyridin-3-yl)-1H-1,2,4-triazol-1-yl)propan-1-one | b |
| 25 | 3-(furan-2-yl)-1H-1,2,4-triazol-5-amine | c |
| 31 | methyl 5-[(2-chlorobenzene)amido]-1H-1,2,4-triazole-3-carboxylate | c |
| 305 | 1-(5-[(2-methoxyphenyl)methyl]amino-3-(pyridin-3-yl)-1H-1,2,4-triazol-1-yl)-2-methylpropan-1-one | c |
| 306 | 1-(5-[(4-chlorophenyl)methyl]amino-3-(pyridin-3-yl)-1H-1,2,4-triazol-1-yl)-2-methylpropan-1-one | a |
| 307 | 1-(5-[(4-chlorophenyl)methyl]amino-3-(pyridin-3-yl)-1H-1,2,4-triazol-1-yl)ethan-1-one | a |
| 308 | 1-(5-[(4-chlorophenyl)methyl]amino-3-(pyridin-3-yl)-1H-1,2,4-triazol-1-yl)propan-1-one | a |
| 309 | 1-(5-[(4-fluorophenyl)methyl]amino-3-(furan-2-yl)-1H-1,2,4-triazol-1-yl)-2,2-dimethylpropan-1-one | a |
| 310 | 1-(5-[(4-fluorophenyl)methyl]amino-3-(furan-2-yl)-1H-1,2,4-triazol-1-yl)-2-methylpropan-1-one | a |
| 311 | 1-(5-[(4-fluorophenyl)methyl]amino-3-(pyridin-3-yl)-1H-1,2,4-triazol-1-yl)-2-methoxyethan-1-one | c |

TABLE C-continued

| Cmpd No | IUPAC name | Thrombin Activity |
|---|---|---|
| 312 | 1-(5-[(4-fluorophenyl)methyl]amino-3-(pyridin-3-yl)-1H-1,2,4-triazol-1-yl)-2-methylpropan-1-one | a |
| 313 | 1-(5-[(4-fluorophenyl)methyl]amino-3-(pyridin-3-yl)-1H-1,2,4-triazol-1-yl)-2-phenylethan-1-one | a |
| 314 | 1-(5-[(4-fluorophenyl)methyl]amino-3-(pyridin-3-yl)-1H-1,2,4-triazol-1-yl)-3-methylbutan-1-one | a |
| 315 | 1-(5-[(4-fluorophenyl)methyl]amino-3-(pyridin-3-yl)-1H-1,2,4-triazol-1-yl)-3-phenylpropan-1-one | a |
| 316 | 1-(5-[(4-fluorophenyl)methyl]amino-3-(pyridin-3-yl)-1H-1,2,4-triazol-1-yl)butan-1-one | a |
| 317 | 1-(5-[(4-fluorophenyl)methyl]amino-3-(pyridin-3-yl)-1H-1,2,4-triazol-1-yl)ethan-1-one | a |
| 318 | 1-(5-[(4-methoxyphenyl)methyl]amino-3-(pyridin-3-yl)-1H-1,2,4-triazol-1-yl)-2-methylpropan-1-one | a |
| 319 | 1-(5-[(4-methoxyphenyl)methyl]amino-3-(pyridin-3-yl)-1H-1,2,4-triazol-1-yl)-2-phenylethan-1-one | a |
| 320 | 1-(5-[(4-methoxyphenyl)methyl]amino-3-(pyridin-3-yl)-1H-1,2,4-triazol-1-yl)-3-methylbutan-1-one | a |
| 321 | 1-(5-[(4-methoxyphenyl)methyl]amino-3-(pyridin-3-yl)-1H-1,2,4-triazol-1-yl)-3-phenylpropan-1-one | b |
| 322 | 1-(5-[(4-methoxyphenyl)methyl]amino-3-(pyridin-3-yl)-1H-1,2,4-triazol-1-yl)butan-1-one | a |
| 323 | 1-(5-[(4-methoxyphenyl)methyl]amino-3-(pyridin-3-yl)-1H-1,2,4-triazol-1-yl)ethan-1-one | b |
| 324 | 1-(5-[(4-methoxyphenyl)methyl]amino-3-(pyridin-3-yl)-1H-1,2,4-triazol-1-yl)propan-1-one | b |
| 325 | 1-(5-[(4-methylphenyl)methyl]amino-3-(pyridin-3-yl)-1H-1,2,4-triazol-1-yl)ethan-1-one | a |
| 326 | 1-(benzenesulfonyl)-3-(pyridin-3-yl)-1H-1,2,4-triazol-5-amine | c |
| 327 | 1-(benzenesulfonyl)-3-(pyridin-3-yl)-N-(thiophen-2-ylmethyl)-1H-1,2,4-triazol-5-amine | c |
| 328 | 1-(benzenesulfonyl)-3-[(morpholin-4-yl)carbonyl]-1H-1,2,4-triazol-5-amine | c |
| 329 | 1-(ethanesulfonyl)-3-[(morpholin-4-yl)carbonyl]-1H-1,2,4-triazol-5-amine | c |
| 330 | 1-[(2-chlorophenyl)carbonyl]-3-(furan-2-yl)-5-(methylsulfanyl)-1H-1,2,4-triazole | a |
| 331 | 1-[(2-chlorophenyl)carbonyl]-N-[(4-fluorophenyl)methyl]-3-(furan-2-yl)-1H-1,2,4-triazol-5-amine | a |
| 332 | 1-[(2-chlorophenyl)carbonyl]-N-[(4-fluorophenyl)methyl]-3-(pyridin-3-yl)-1H-1,2,4-triazol-5-amine | a |
| 333 | 1-[(2-methoxyphenyl)carbonyl]-3-(pyridin-3-yl)-1H-1,2,4-triazol-5-amine | b |
| 334 | 1-[(2-methoxyphenyl)carbonyl]-3-phenyl-1H-1,2,4-triazol-5-amine | c |
| 335 | 1-[(2-methoxyphenyl)carbonyl]-3-phenyl-N-(thiophen-2-ylmethyl)-1H-1,2,4-triazol-5-amine | a |
| 336 | 1-[(4-chlorobenzene)sulfonyl]-3-(pyridin-3-yl)-N-(thiophen-2-ylmethyl)-1H-1,2,4-triazol-5-amine | c |
| 337 | 1-[(4-chlorobenzene)sulfonyl]-3-[(morpholin-4-yl)carbonyl]-1H-1,2,4-triazol-5-amine | c |
| 338 | 1-[(4-chlorophenyl)carbonyl]-N-[(4-fluorophenyl)methyl]-3-(pyridin-3-yl)-1H-1,2,4-triazol-5-amine | a |
| 339 | 1-[(4-methylphenyl)carbonyl]-3-(pyridin-3-yl)-1H-1,2,4-triazol-5-amine | b |
| 340 | 1-[(furan-2-yl)carbonyl]-N-[(4-methoxyphenyl)methyl]-3-(pyridin-3-yl)-1H-1,2,4-triazol-5-amine | b |
| 341 | 1-[3-(furan-2-yl)-5-(methylsulfanyl)-1H-1,2,4-triazol-1-yl]propan-1-one | c |
| 342 | 1-[3-(pyridin-3-yl)-5-[(thiophen-2-ylmethyl)amino]-1H-1,2,4-triazol-1-yl]butan-1-one | a |
| 343 | 1-[3-(pyridin-3-yl)-5-[(thiophen-2-ylmethyl)amino]-1H-1,2,4-triazol-1-yl]ethan-1-one | a |
| 344 | 1-[3-(pyridin-3-yl)-5-[(thiophen-2-ylmethyl)amino]-1H-1,2,4-triazol-1-yl]propan-1-one | a |
| 345 | 1-[5-(benzylamino)-3-(4-fluorophenyl)-1H-1,2,4-triazol-1-yl]propan-1-one | c |
| 346 | 1-[5-(benzylamino)-3-(furan-2-yl)-1H-1,2,4-triazol-1-yl]-2-phenylethan-1-one | a |
| 347 | 1-[5-(benzylamino)-3-(furan-2-yl)-1H-1,2,4-triazol-1-yl]-3-phenylpropan-1-one | a |
| 348 | 1-[5-(benzylamino)-3-(furan-2-yl)-1H-1,2,4-triazol-1-yl]propan-1-one | a |
| 349 | 1-[5-(benzylamino)-3-(pyridin-3-yl)-1H-1,2,4-triazol-1-yl]-2-methylpropan-1-one | a |
| 350 | 1-[5-(benzylamino)-3-(pyridin-3-yl)-1H-1,2,4-triazol-1-yl]-3-methylbutan-1-one | a |
| 351 | 1-[5-(benzylamino)-3-(pyridin-3-yl)-1H-1,2,4-triazol-1-yl]propan-1-one | a |
| 352 | 1-[5-(benzylamino)-3-(thiophen-2-yl)-1H-1,2,4-triazol-1-yl]propan-1-one | a |
| 353 | 1-[5-(benzylamino)-3-phenyl-1H-1,2,4-triazol-1-yl]-2-phenylethan-1-one | a |
| 354 | 1-[5-(benzylamino)-3-phenyl-1H-1,2,4-triazol-1-yl]-3-phenylpropan-1-one | c |
| 355 | 1-[5-(benzylamino)-3-phenyl-1H-1,2,4-triazol-1-yl]propan-1-one | b |
| 356 | 1-benzoyl-N-[(4-fluorophenyl)methyl]-3-(pyridin-3-yl)-1H-1,2,4-triazol-5-amine | a |
| 357 | 1-benzoyl-N-[(4-methoxyphenyl)methyl]-3-(pyridin-3-yl)-1H-1,2,4-triazol-5-amine | b |

TABLE C-continued

| Cmpd No | IUPAC name | Thrombin Activity |
|---|---|---|
| 358 | 1-benzoyl-N-benzyl-3-(furan-2-yl)-1H-1,2,4-triazol-5-amine | a |
| 359 | 1-benzoyl-N-benzyl-3-phenyl-1H-1,2,4-triazol-5-amine | a |
| 360 | 1-methanesulfonyl-3-[(morpholin-4-yl)carbonyl]-1H-1,2,4-triazol-5-amine | c |
| 361 | 1-5-[(furan-2-ylmethyl)amino]-3-(pyridin-3-yl)-1H-1,2,4-triazol-1-yl-2-methylpropan-1-one | a |
| 362 | 1-5-[(furan-2-ylmethyl)amino]-3-(pyridin-3-yl)-1H-1,2,4-triazol-1-ylbutan-1-one | a |
| 363 | 1-5-[(furan-2-ylmethyl)amino]-3-(pyridin-3-yl)-1H-1,2,4-triazol-1-ylethan-1-one | a |
| 364 | 1-5-[(furan-2-ylmethyl)amino]-3-(pyridin-3-yl)-1H-1,2,4-triazol-1-ylpropan-1-one | b |
| 365 | 2-fluoro-N-[5-(furan-2-yl)-1H-1,2,4-triazol-3-yl]benzamide | c |
| 366 | 2-methyl-1-(5-[(4-methylphenyl)methyl]amino-3-(pyridin-3-yl)-1H-1,2,4-triazol-1-yl)propan-1-one | a |
| 367 | 3-(furan-2-yl)-1-[(2-methoxyphenyl)carbonyl]-5-(methylsulfanyl)-1H-1,2,4-triazole | a |
| 368 | 3-(furan-2-yl)-1-[(pyridin-3-yl)carbonyl]-N-(thiophen-2-ylmethyl)-1H-1,2,4-triazol-5-amine | a |
| 369 | 3-(furan-2-yl)-1-methanesulfonyl-N-(thiophen-2-ylmethyl)-1H-1,2,4-triazol-5-amine | c |
| 370 | 3-(furan-2-yl)-N-[(2-methoxyphenyl)methyl]-1-[(4-methylphenyl)carbonyl]-1H-1,2,4-triazol-5-amine | b |
| 371 | 3-(furan-2-yl)-N-[(4-methoxyphenyl)methyl]-1-[(4-methylphenyl)carbonyl]-1H-1,2,4-triazol-5-amine | b |
| 372 | 3-(pyridin-3-yl)-1-[(pyridin-3-yl)carbonyl]-N-(thiophen-2-ylmethyl)-1H-1,2,4-triazol-5-amine | b |
| 373 | 3-(thiophen-2-yl)-1H-1,2,4-triazol-5-amine | c |
| 374 | 3-methyl-1-(5-[(4-methylphenyl)methyl]amino-3-(pyridin-3-yl)-1H-1,2,4-triazol-1-yl)butan-1-one | a |
| 375 | 3-methyl-1-[3-(pyridin-3-yl)-5-[(thiophen-2-ylmethyl)amino]-1H-1,2,4-triazol-1-yl]butan-1-one | a |
| 376 | ethyl 5-amino-3-(4-chlorophenyl)-1H-pyrazole-1-carboxylate | c |
| 377 | methyl 3-[(2,4-dichlorobenzene)amido]-1H-1,2,4-triazole-5-carboxylate | c |
| 378 | methyl 5-(2,2-dimethylpropanamido)-1H-1,2,4-triazole-3-carboxylate | c |
| 379 | methyl 5-(2-methylfuran-3-amido)-1H-1,2,4-triazole-3-carboxylate | c |
| 380 | methyl 5-[(2-methylbenzene)amido]-1H-1,2,4-triazole-3-carboxylate | c |
| 381 | methyl 5-[(3,4,5,6-tetrahydro-2H-azepin-7-yl)amino]-1H-1,2,4-triazole-3-carboxylate | c |
| 382 | methyl 5-[(3-methylbenzene)amido]-1H-1,2,4-triazole-3-carboxylate | c |
| 383 | methyl 5-[(4-bromobenzene)amido]-1H-1,2,4-triazole-3-carboxylate | c |
| 384 | methyl 5-[(4-chlorobenzene)amido]-1H-1,2,4-triazole-3-carboxylate | c |
| 385 | methyl 5-[(4-fluorobenzene)amido]-4H-1,2,4-triazole-3-carboxylate | b |
| 386 | methyl 5-[(4-tert-butylbenzene)amido]-1H-1,2,4-triazole-3-carboxylate | b |
| 387 | methyl 5-[(pyridin-3-ylmethylidene)amino]-1H-1,2,4-triazole-3-carboxylate | c |
| 388 | methyl 5-[3-(4-methylphenyl)propanamido]-1H-1,2,4-triazole-3-carboxylate | c |
| 389 | methyl 5-amino-1H-1,2,4-triazole-3-carboxylate | c |
| 390 | N-(2,4-dichlorophenyl)-5-(1H-1,2,4-triazol-1-ylmethyl)-4H-1,2,4-triazole-3-carboxamide | c |
| 391 | N-(2-chlorophenyl)-3-(4H-1,2,4-triazol-4-yl)-1H-1,2,4-triazole-5-carboxamide | c |
| 392 | N-(4-bromophenyl)-3-(4H-1,2,4-triazol-4-yl)-1H-1,2,4-triazole-5-carboxamide | c |
| 393 | N-(4-ethoxyphenyl)-3-(4H-1,2,4-triazol-4-yl)-1H-1,2,4-triazole-5-carboxamide | c |
| 394 | N-(furan-2-ylmethyl)-1-[(2-methoxyphenyl)carbonyl]-3-phenyl-1H-1,2,4-triazol-5-amine | a |
| 395 | N-(furan-2-ylmethyl)-1-methanesulfonyl-3-(pyridin-3-yl)-1H-1,2,4-triazol-5-amine | c |
| 396 | N-(furan-2-ylmethyl)-3-(pyridin-3-yl)-1-[(pyridin-3-yl)carbonyl]-1H-1,2,4-triazol-5-amine | c |
| 397 | N-[(2-chlorophenyl)methyl]-3-(furan-2-yl)-1-[(pyridin-3-yl)carbonyl]-1H-1,2,4-triazol-5-amine | b |
| 398 | N-[(2-methoxyphenyl)methyl]-3-(pyridin-3-yl)-1-[(pyridin-3-yl)carbonyl]-1H-1,2,4-triazol-5-amine | c |
| 399 | N-[(4-fluorophenyl)methyl]-1-[(2-methoxyphenyl)carbonyl]-3-(pyridin-3-yl)-1H-1,2,4-triazol-5-amine | a |
| 400 | N-[(4-fluorophenyl)methyl]-1-[(2-methoxyphenyl)carbonyl]-3-phenyl-1H-1,2,4-triazol-5-amine | a |
| 401 | N-[(4-fluorophenyl)methyl]-1-[(4-methylphenyl)carbonyl]-3-(pyridin-3-yl)-1H-1,2,4-triazol-5-amine | a |
| 402 | N-[(4-fluorophenyl)methyl]-1-[(furan-2-yl)carbonyl]-3-(pyridin-3-yl)-1H-1,2,4-triazol-5-amine | a |
| 403 | N-[(4-fluorophenyl)methyl]-3-(pyridin-3-yl)-1-[(thiophen-2-yl)carbonyl]-1H-1,2,4-triazol-5-amine | a |
| 404 | N-[(4-methoxyphenyl)methyl]-1-[(4-methylphenyl)carbonyl]-3-(pyridin-3-yl)-1H-1,2,4-triazol-5-amine | b |
| 405 | N-[(4-methoxyphenyl)methyl]-3-(pyridin-3-yl)-1-[(thiophen-2-yl)carbonyl]-1H-1,2,4-triazol-5-amine | c |

TABLE C-continued

| Cmpd No | IUPAC name | Thrombin Activity |
|---|---|---|
| 406 | N-[5-(benzylamino)-1H-1,2,4-triazol-3-yl]acetamide | c |
| 407 | N-[5-(furan-2-yl)-1H-1,2,4-triazol-3-yl]benzamide | c |
| 408 | N-benzyl-1-[(2-chlorophenyl)carbonyl]-3-(furan-2-yl)-1H-1,2,4-triazol-5-amine | a |
| 409 | N-benzyl-1-[(2-chlorophenyl)carbonyl]-3-(thiophen-2-yl)-1H-1,2,4-triazol-5-amine | a |
| 410 | N-benzyl-1-[(2-methoxyphenyl)carbonyl]-3-(pyridin-3-yl)-1H-1,2,4-triazol-5-amine | A |
| 411 | N-benzyl-1-[(4-methylphenyl)carbonyl]-3-(pyridin-3-yl)-1H-1,2,4-triazol-5-amine | A |
| 412 | N-benzyl-3-(thiophen-2-yl)-1-[(thiophen-2-yl)carbonyl]-1H-1,2,4-triazol-5-amine | C |

In some embodiments, the disease or disorder is a thrombotic disease or disorder. In some embodiments, the thrombotic disease or disorder is acute coronary syndrome, venous thromboembolism, arterial thromboembolism or cardiogenic thromboembolism. In some embodiments, the thrombotic disease or disorder is acute coronary syndrome. In some embodiments, the thrombotic disease or disorder is venous thromboembolism. In some embodiments, the thrombotic disease or disorder is arterial thromboembolism. In some embodiments, the thrombotic disease or disorder is cardiogenic thromboembolism.

In some embodiments, the disease or disorder is fibrosis, Alzheimer's Disease, multiple sclerosis, pain, or cancer. In some embodiments, the disease or disorder is Alzheimer's Disease. In some embodiments, the disease or disorder is multiple sclerosis.

In some embodiments, the disease or disorder is fibrosis. In some embodiments contemplating fibrosis, the method is directed to treating chronic liver injury. In some embodiments, the disease or disorder is ischemia reperfusion injury. In some embodiments, the disease or disorder is pulmonary fibrosis.

In some embodiments, the disease or disorder is pain. In some embodiments, the pain is neuropathic pain.

In some embodiments, the disease or disorder is cancer. In some embodiments, the cancer is limited small cell lung cancer. In some embodiments, the cancer is a glioma. In some embodiments, the cancer is malignant breast cancer. In some embodiments, the cancer is a micrometastasis. In some embodiments, the micrometastasis is of the blood or liver. In some embodiments, the cancer is a lung metastasis. In some embodiments, the cancer is prostatic cancer.

In another aspect, there is provided a method for preventing a disease or disorder in a subject. The method includes administering a compound of any of Formulae (Ia), (Ib), (IIa), (IIb), (IIIa), (IIIb), (IV) or (V) as disclosed herein, compound as set forth in any of Tables A, B or C herein, pharmaceutically acceptable salt, ester, solvate, or prodrug thereof, or pharmaceutical composition thereof, to a subject in need thereof in an amount effective to prevent the disease or disorder.

In some embodiments, the disease or disorder is a thrombotic disorder. In some embodiments, the thrombotic disorder is acute coronary syndrome, venous thromboembolism, arterial thromboembolism or cardiogenic thromboembolism. In some embodiments, the thrombotic disease or disorder is disseminated intravascular coagulation. In some embodiments, the thrombotic disorder involves the presence or the potential formation of a blood clot thrombus.

Yet further to this aspect, in some embodiments, the disease or disorder is fibrosis, Alzheimer's Disease, multiple sclerosis, pain, or cancer. In some embodiments, the disease or disorder is fibrosis. In some embodiments, the disease or disorder is Alzheimer's Disease. In some embodiments, the disease or disorder is multiple sclerosis. In some embodiments, the disease or disorder is pain. In some embodiments, the disease or disorder is cancer.

V. ASSAYS

Compounds described herein can be assayed, by a variety of methods known in the art and described herein, for inhibition of biological activity, e.g., protease activity, of a variety of proteins, e.g., thrombin. For example, the protease activity of such proteins, e.g., thrombin, can be monitored using a chromophoric substrate, e.g., a p-nitroanilide peptide substrate, which upon hydrolysis releases p-nitroanilide, which in turn gives rise to a color change which can be determined spectrophotometrically. See e.g., Lottenberg, R, et al, 1983, *Biochemica et Biophysica Acta*, 752:539-557. Accordingly, the change in color can be monitored with a spectrophotometer at e.g., 405 nm to provide a signal which is directly proportional to the proteolytic activity of the enzyme.

The thrombin activity reported herein (e.g., Table A) was obtained as follows. Human thrombin was obtained from Haematologic Technologies Inc. The chromogenic substrate S-2238 was obtained from DiaPharma. Thrombin was assayed in buffer containing 0.05 M Tris (pH 7.4), 0.015 M NaCl and 0.01% PEG-8000. The final concentration of enzyme used was 3 nM thrombin. The final concentration of substrate used was 125 µM S-2238 for thrombin. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

VI. PHARMACEUTICAL COMPOSITIONS

In another aspect, there is provided a pharmaceutical composition comprising a compound disclosed herein and a pharmaceutically acceptable excipient. The compound is a compound of any of Formulae (Ia), (Ib), (IIa), (IIb), (IIIa), (IIIb), (IV) or (V) as disclosed herein, a compound as set forth in any of Tables A, B or C herein, or pharmaceutically acceptable salt, ester, solvate, or prodrug thereof. In some embodiments, the compound is set forth in Table A herein. In some embodiments, the compound is set forth in Table B herein. In some embodiments, the compound is set forth in Table C herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds disclosed herein contain both basic and acidic functionalities that allow the compounds to be converted into either base or acid addition salts.

Compounds disclosed herein may exist as salts, such as with pharmaceutically acceptable acids. Accordingly, the compounds contemplated herein includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutically acceptable salts of the compounds above, where a basic or acidic group is present in the structure, are also included within the scope of compounds contemplated herein. When an acidic substituent is present, such as —$NHSO_3H$, —COOH and —$P(O)(OH)_2$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the embodiments in which R—COOH is present, pharmaceutically acceptable esters can be employed, e.g., methyl, ethyl, tert-butyl, pivaloyloxymethyl, and the like, and those esters known in the art for modifying solubility or hydrolysis characteristics for use as sustained release or prodrug formulations.

A. Formulations

The compounds disclosed herein can be prepared and administered in a wide variety of oral, parenteral, and topical dosage forms. Thus, the compounds can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds disclosed herein can be administered transdermally. It is also envisioned that multiple routes of administration (e.g., intramuscular, oral, transdermal) can be used to administer the compounds disclosed herein. In some embodiments, the compounds disclosed herein may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In some embodiments, tablets contain the acting ingredient in admixture with non-toxic pharmaceutically acceptable excipients that are suitable for the manufacture of tablets. These excipients may be, for example, (1) inert diluents, such as calcium carbonate, lactose, calcium phosphate, carboxymethylcellulose, or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

A compound disclosed herein, in the form of a free compound or a pharmaceutically-acceptable pro-drug, metabolite, analogue, derivative, solvate or salt, can be administered, for in vivo application, parenterally by injection or by gradual perfusion over time. Administration may be intravenously, intraperitoneally, intramuscularly, subcutaneously, intracavity, or transdermally. For in vitro studies the compounds may be added or dissolved in an appropriate biologically acceptable buffer and added to a cell or tissue.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use in the pharmaceuticals compositions and methods disclosed herein include those described, for example, in PHARMACEUTICAL SCIENCES (17th Ed., Mack Pub. Co., Easton, Pa.) and WO 96/05309, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

By the present, there are provided methods for ameliorating wound healing and for mediating tissue repair (including but not limited to treatment of peripheral and coronary vascular disease). According to these methods, a subject having a wound or in need of tissue repair, is treated at the site of the wound or damaged tissue or treated systemically, with a compound disclosed herein in the form of a free compound or a pharmaceutically-acceptable prodrug, metabolite, analogue, derivative, solvate or salt.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or disorder or sign or symptom thereof, and/or may be therapeutic in terms of a partial or complete cure for a disorder and/or adverse effect attributable to it. "Treating" as used herein covers any treatment of, or prevention of a disease or disorder in a vertebrate, a mammal, particularly a human, and includes: (a) preventing the disease or disorder from occurring in a subject that may be predisposed to the disease or disorder, but has not yet been diagnosed as having it; (b) inhibiting the disease or disorder, i.e., arresting its development; or (c) relieving or ameliorating the disease or disorder, i.e., cause regression of the disease or disorder.

There are provided various pharmaceutical compositions useful for ameliorating diseases and disorders, including thrombosis. In some embodiments, the disease or disorder is a thrombotic disorder. In some embodiments, the disease or disorder is acute coronary syndrome, venous thromboembolism, arterial thromboembolism or cardiogenic thromboembolism. In some embodiments, the disease or disorder is fibrosis. In some embodiments, the disease or disorder is Alzheimer's Disease. In some embodiments, the disease or disorder is multiple sclerosis. In some embodiments, the disease or disorder is pain. In some embodiments, the disease or disorder is cancer. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV, 14th ed. Washington: American Pharmaceutical Association (1975), the contents of which are hereby incorporated by reference. The pH and exact concentration of the various components of the pharmaceutical composition are adjusted according to routine skills in the art. See e.g., Goodman and Gilman (eds.), 1990, THE PHARMACOLOGICAL BASIS FOR THERAPEUTICS (7th ed.).

The pharmaceutical compositions are preferably prepared and administered in dose units. Solid dose units are tablets, capsules and suppositories. For treatment of a subject, depending on activity of the compound, manner of administration, nature and severity of the disease or disorder, age and body weight of the subject, different daily doses can be used.

Under certain circumstances, however, higher or lower daily doses may be appropriate. The administration of the daily dose can be carried out both by single administration in the form of an individual dose unit or else several smaller dose units and also by multiple administrations of subdivided doses at specific intervals.

The pharmaceutical compositions contemplated herein may be administered locally or systemically in a therapeutically effective dose. Amounts effective for this use will, of course, depend on the severity of the disease or disorder and the weight and general state of the subject. Typically, dosages used in vitro may provide useful guidance in the amounts useful for in situ administration of the pharmaceutical composition, and animal models may be used to determine effective dosages for treatment of particular disorders.

Various considerations are described, e.g., in Langer, 1990, Science, 249: 1527; Goodman and Gilman's (eds.), 1990, Id., each of which is herein incorporated by reference and for all purposes. Dosages for parenteral administration of active pharmaceutical agents can be converted into corresponding dosages for oral administration by multiplying parenteral dosages by appropriate conversion factors. As to general applications, the parenteral dosage in mg/m2 times 1.8=the corresponding oral dosage in milligrams ("mg"). As to oncology applications, the parenteral dosage in mg/m2 times 1.6=the corresponding oral dosage in mg. An average adult weighs about 70 kg. See e.g., Miller-Keane, 1992, ENCYCLOPEDIA & DICTIONARY OF MEDICINE, NURSING & ALLIED HEALTH, 5th Ed., (W. B. Saunders Co.), pp. 1708 and 1651.

The method by which the compound disclosed herein may be administered for oral use would be, for example, in a hard gelatin capsule wherein the active ingredient is mixed with an inert solid diluent, or soft gelatin capsule, wherein the active ingredient is mixed with a co-solvent mixture, such as PEG 400 containing Tween-20. A compound disclosed herein may also be administered in the form of a sterile injectable aqueous or oleaginous solution or suspension. The compound can generally be administered intravenously or as an oral dose of 0.1 ug to 20 mg/kg given, for example, every 3-12 hours.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents that have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

A compound disclosed herein may also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

The compounds disclosed herein as used in the methods disclosed herein may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds disclosed herein, are employed.

In addition, some of the compounds disclosed herein may form solvates with water or common organic solvents. Such solvates are encompassed within the scope of the methods contemplated herein.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat thrombosis, such compositions will contain an amount of active ingredient effective to achieve the desired result (e.g. decreasing the extent of the thrombosis).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to inhibition of thrombin); presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from a variety of techniques known in the art, e.g., biochemical characterization of inhibition of thrombin, cell culture assays, and the like. Target concentrations will be those concentrations of active compound(s) that are capable of decreasing thrombin enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring thrombin inhibition and adjusting the dosage upwards or downwards, as described above.

Dosages may be varied depending upon the requirements of the patient and the compound being employed. The dose administered to a patient, in the context of the methods disclosed herein, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments of a method disclosed herein, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Accordingly, in some embodiments, dosage levels of the compounds disclosed herein as used in the present methods are of the order of e.g., about 0.1 mg to about 1 mg, about 1 mg to about 10 mg, about 0.5 mg to about 20 mg per kilogram body weight, an average adult weighing 70 kilograms, with a preferred dosage range between about 0.1 mg to about 20 mg per kilogram body weight per day (from about 7.0 mg to about 1.4 gm per patient per day). The amount of the compound disclosed herein that may be combined with the carrier materials to produce a single dosage will vary depending upon the host treated and the particular mode of administration. For example, a formulation intended for oral administration to humans may contain about 5 ug to 1 g of a compound disclosed herein with an appropriate and convenient amount of carrier material that may vary from about 5 to 95 percent of the total composition. Dosage unit forms will generally contain between from about 0.1 mg to 500 mg of a compound disclosed herein.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

VII. EXAMPLES

The examples below are meant to illustrate certain embodiments of the invention and not to limit the scope of the invention. Abbreviations used herein have their conventional meaning in the art, unless indicated otherwise. Specific abbreviations include the following: Å=Ångström; Ac$_2$O=acetic anhydride; AcOH=acetic acid; aq=aqueous; Bt=benzotriazole; BOC=N-tert-butoxycarbonyl; br=broad; t-BuOH=tert-butanol; ° C.=degree Celsius; d=doublet; DABCO=1,4-diazabicyclo[2.2.2]octane; DCE=1,2-dichloroethane; DCM=dichloromethane; dd=doublet of doublets; DIEA=diethylisopropylamine; DMAP=4-dimethylaminopyridine; DMF=N,N-dimethylformamide; DMSO=dimethylsulfoxide; δ=chemical shift (given in ppm, unless otherwise indicated); EDCI=1-ethyl-3-(3-dimethylaminopropyl)carbodiimide; eq=equivalent; Et$_2$O=diethyl ether; Et$_3$N=triethylamine; EtOAc=ethyl acetate; EtOH=ethanol; g=gram; h (or hr)=hour; HOBt=hydroxybenzotriazole; HPLC=high performance liquid chromatography; Hz=Hertz; IC$_{50}$=inhibitory concentration at 50% inhibition; J=coupling constant (given in Hz, unless otherwise indicated); LC=liquid chromatography; LHMDS=lithium hexamethyldisilazide; m=multiplet; M=molar; [M+H]$^+$=parent mass spectrum peak plus H$^+$; MS=mass spectrum; ms=molecular sieves; MP=melting point; Me$_2$NH=dimethylamine; MeOH=methanol; mg=milligram; mL=milliliter; mM=millimolar; mmol=millimole; min=minute; gL=microliter; gM=micromolar; ng=nanogram; nM=nanomolar; NMR=nuclear magnetic resonance; ppm=parts per million; q=quartet; R$_f$=retention factor; RT=room temperature; s=singlet; t=triplet; TFA=trifluoroacetic acid; THF=tetrahydrofuran; TLC=thin layer chromatography.

Example 1

Preparation of Cmpd 1

General Scheme I. A synthetic scheme useful for synthesis of compounds described herein is disclosed in General Scheme I following, wherein the term "Ar" in General Scheme I refers to substituted or unsubstituted aryl, or substituted or unsubstituted heteroaryl, and the terms "R$^1$" and "R$^2$" are as defined above.

General Scheme I

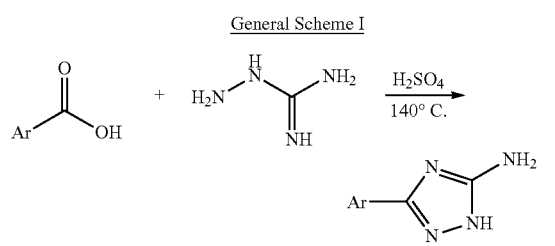

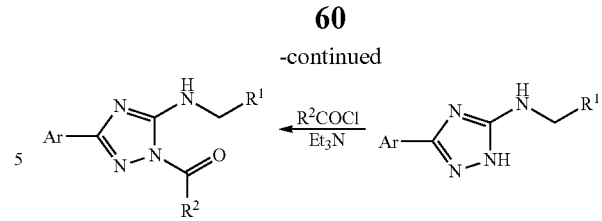

The synthesis of Cmpd 1 followed General Procedure 1 following.

General Procedure 1

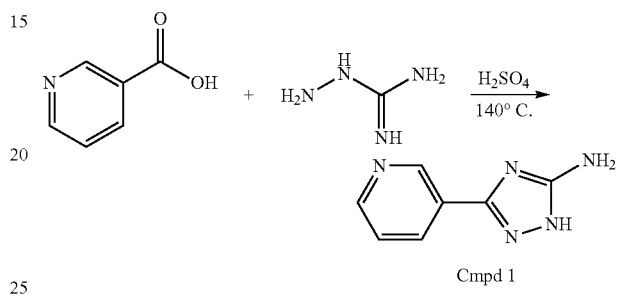

Cmpd 1

A solution of nicotinic acid (9.9 g, 80.9 mmol) in water (30 mL) was added slowly portion-wise to a previously stirred mixture of aminoguanidine sulfate (10 g, 73.5 mmol) in concentrated H$_2$SO$_4$ (8.8 mL, 162 mmol), and the reaction mixture was stirred at 140° C. for 72 h. The reaction mixture was diluted with water (50 mL) and neutralized with saturated aqueous K$_2$CO$_3$ (30 mL), and the resultant solid was filtered. The residue was washed with water (2×30 mL), Et$_2$O (2×30 mL) and dried under vacuum to afford Cmpd 1 (4.6 g, 39%) as an off-white solid. $^1$H NMR: (DMSO-d$_6$) δ 12.23 (s, 1H), 9.05 (s, 1H), 8.54 (d, J=2.8 Hz, 1H), 8.17 (d, J=7.4 Hz, 1H), 7.42-7.52 (m, 1H), 6.19 (s, 2H); MS: 162 [M+H]$^+$; MP: 234-236° C.; TLC: 20% MeOH/NH$_3$ in CHCl$_3$: R$_f$: 0.40.

Example 2

Preparation of Cmpd 2

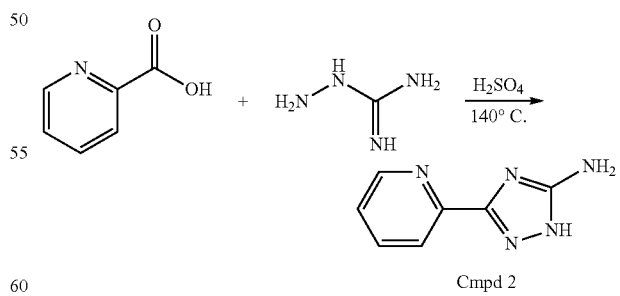

Cmpd 2

General Procedure 1 was followed to obtain Cmpd 2 (8.5 g, 46%). $^1$H NMR: (DMSO-d$_6$) δ 8.60 (d, J=4.4 Hz, 1H), 7.86-7.91 (m, 2H), 7.37 (br s, 1H), 5.79 (br s, 2H); MS: 162 [M+H]$^+$; MP: 218-220° C.; TLC: 20% MeOH/NH$_3$ in CHCl$_3$: R$_f$: 0.40.

Example 3

Preparation of Cmpd 3

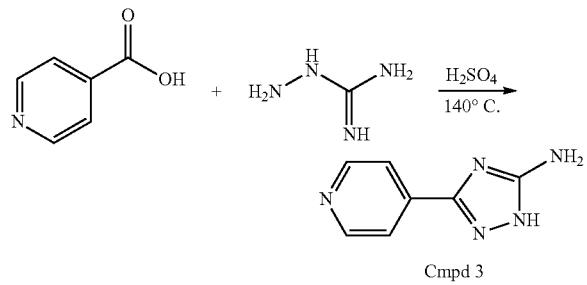

General Procedure 1 was followed to obtain Cmpd 3 (12 g, 67%). $^1$H NMR: (DMSO-$d_6$) δ 12.35 (br s, 1H), 8.59 (d, J=5.5 Hz, 2H), 7.76-7.78 (m, 2H), 6.23 (s, 2H); MS: 162 [M+H]$^+$; TLC: 20% MeOH/NH$_3$ in CHCl$_3$: $R_f$: 0.40.

Example 4

Preparation of Cmpd 4

The synthesis of Cmpd 4 followed the procedure of General Procedure 2 following.
General Procedure 2

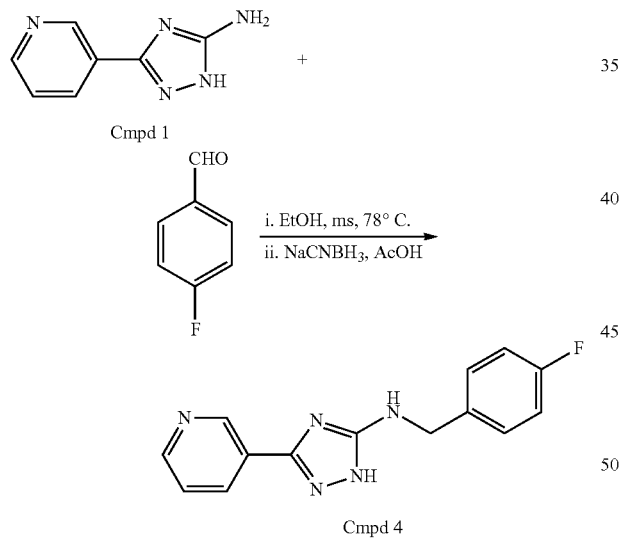

4-Fluorobenzaldehyde (3.1 g, 24.8 mmol, 2 eq) and molecular sieves (4 Å powder) were added to a solution of Cmpd 1 (2 g, 12.4 mmol) in EtOH (20 mL) at RT and refluxed for 8 h. Then was added a catalytic quantity of AcOH, NaCNBH$_3$ (1.6 g, 24.8 mmol, 2 eq) at 0° C. and with stirring for 15 h at RT. The solvent was distilled off, and the residue was dissolved in EtOAc (200 mL) and filtered through a Celite® pad to remove inorganic materials. The filtrate was washed with saturated aqueous NaHCO$_3$ (2×20 mL), water (20 mL), brine (20 mL), dried over Na$_2$SO$_4$, filtered and concentrated in vacuo. The resultant compound was purified by column chromatography over silica gel (100-200 mesh) by using a solvent gradient of 0-10% MeOH—CHCl$_3$ as the eluent to afford Cmpd 4 (1.7 g, 51%). $^1$H NMR: (DMSO-$d_6$) δ 12.50 (s, 1H), 9.06 (d, J=1.4 Hz, 1H), 8.53-8.55 (m, 1H), 8.17-8.20 (m, 1H), 7.33-7.45 (m, 4H), 7.12-7.19 (m, 2H), 4.40 (d, J=6.4 Hz, 2H); MS: 270 [M+H]$^+$; MP: 185-186° C.; TLC: 10% MeOH in CHCl$_3$: $R_f$: 0.25.

Example 5

Preparation of Intermediate 1

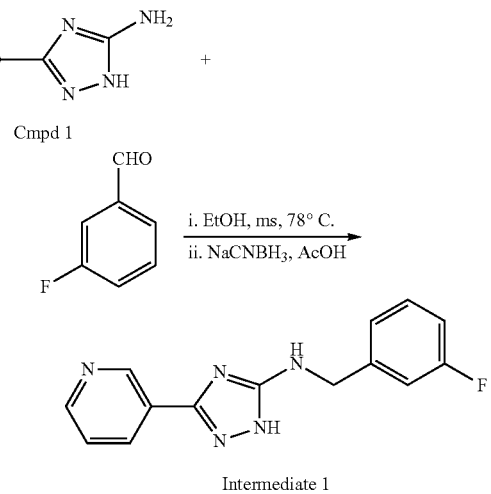

General Procedure 2 was followed to obtain Intermediate 1 (80 mg). $^1$H NMR: (DMSO-$d_6$) δ 12.53 (s, 1H), 9.05 (d, J=1.3 Hz, 1H), 8.50-8.54 (m, 1H), 8.18-8.20 (m, 1H), 7.01-7.62 (m, 6H), 4.44 (d, J=6.2 Hz, 2H); TLC: 10% MeOH in CHCl$_3$: $R_f$: 0.25.

Example 6

Preparation of Intermediate 2

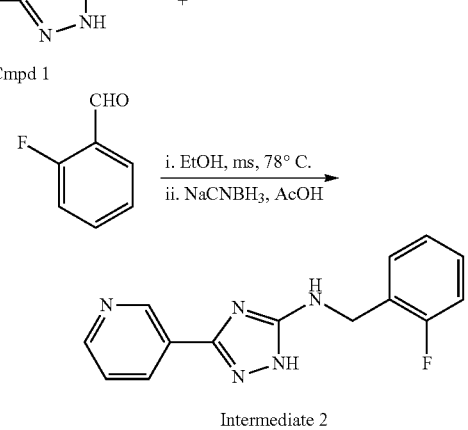

General Procedure 2 was followed to obtain Intermediate 2 (75 mg). $^1$H NMR: (DMSO-$d_6$) δ 12.51 (s, 1H), 9.06 (d, J=1.8 Hz, 1H), 8.54-8.55 (m, 1H), 8.17-8.20 (m, 1H), 7.15-7.45 (m, 6H), 4.49 (d, J=6.2 Hz, 2H); TLC: 10% MeOH in CHCl$_3$: R$_f$: 0.25.

Example 7

Preparation of Intermediate 3

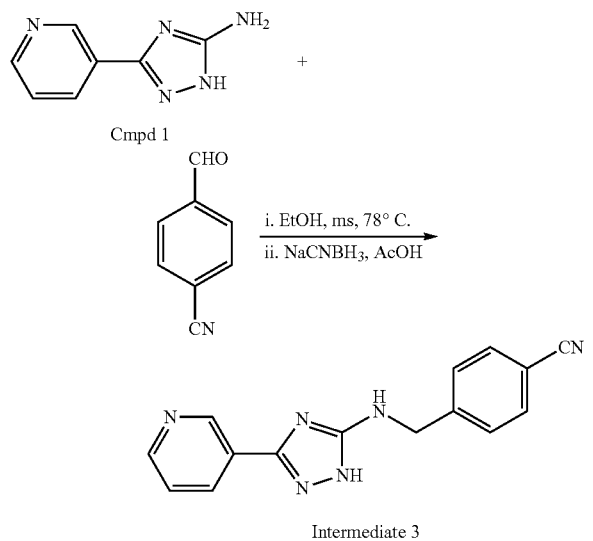

Intermediate 3

General Procedure 2 was followed to obtain Intermediate 3 (180 mg). $^1$H NMR: (DMSO-d$_6$) δ 12.57 (s, 1H), 9.05 (s, 1H), 8.54-8.55 (m, 1H), 8.16-8.18 (m, 1H), 7.41-7.95 (m, 6H), 4.52 (d, J=6.6 Hz, 2H); TLC: 10% MeOH in CHCl$_3$: R$_f$: 0.25.

Example 8

Preparation of Cmpd 5

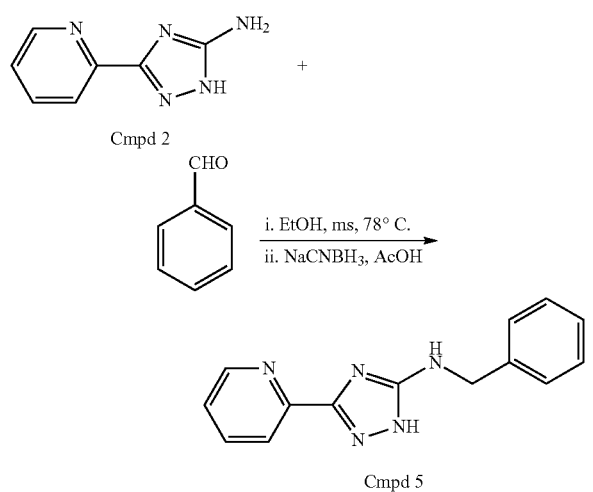

Cmpd 5

General Procedure 2 was followed to obtain Cmpd 5 (2.8 g, 60%). MS: 252 [M+H]$^+$; MP: 226-228° C.; TLC: 10% MeOH in CHCl$_3$: R$_f$: 0.30.

Example 9

Preparation of Cmpd 6

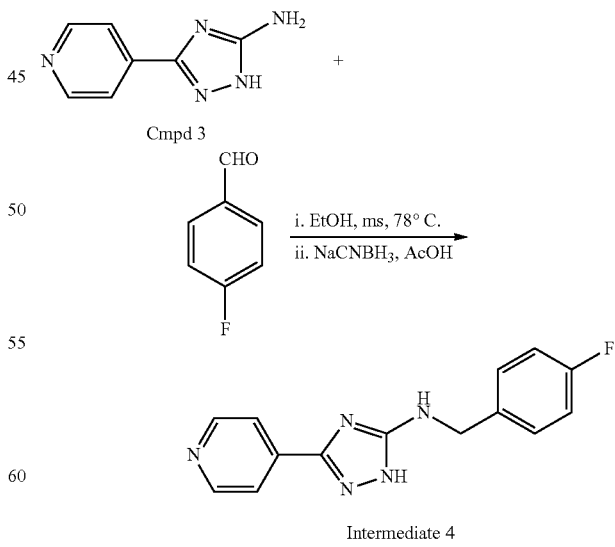

Cmpd 6

General Procedure 2 was followed to obtain Cmpd 6 (1.6 g, 48%). $^1$H NMR: (DMSO-d$_6$) δ 13.15 (br s, 1H), 8.60 (d, J=4.0 Hz, 1H), 7.86-7.93 (m, 2H), 7.30-7.42 (m, 3H), 7.02-7.15 (m, 2H), 6.84 (br s, 1H), 4.37 (d, J=6.2 Hz, 2H); MS: 270 [M+H]$^+$; MP: 219-220° C.; TLC: 10% MeOH in CHCl$_3$: R$_f$: 0.25.

Example 10

Preparation of Intermediate 4

Intermediate 4

General Procedure 2 was followed to obtain Intermediate 4 (1.4 g, 42%). MS: 270 [M+H]$^+$; TLC: 10% MeOH in CHCl$_3$: R$_f$: 0.25.

Example 11

Preparation of Intermediate 5

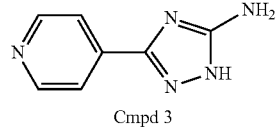

Cmpd 3

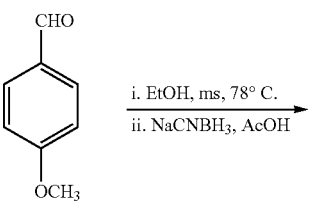

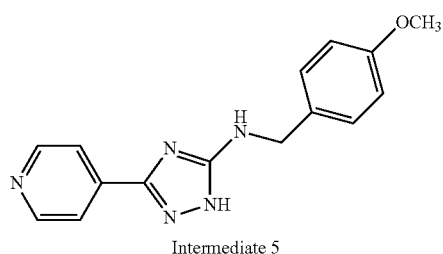

Intermediate 5

General Procedure 2 was followed to obtain Intermediate 5 (1.3 g, 38%). MS: 282 [M+H]⁺; TLC: 10% MeOH in CHCl₃: R_f: 0.30.

Example 12

Preparation of Cmpd 7

The synthesis of Cmpd 7 followed General Procedure 3 following.
General Procedure 3

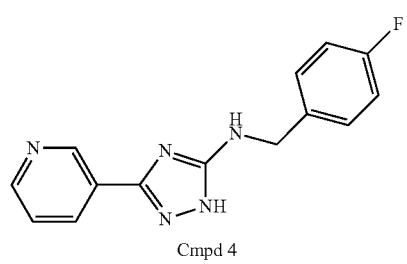

Cmpd 4

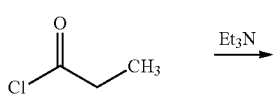

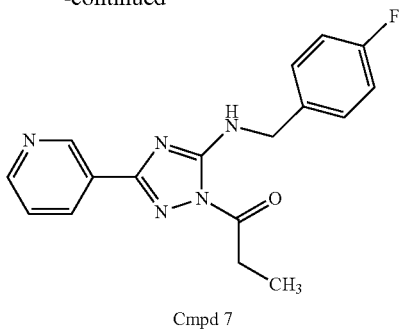

Cmpd 7

Propionyl chloride (39 µL, 0.44 mmol, 1.2 eq) was added to a solution of Cmpd 4 (100 mg, 0.37 mmol) in triethylamine (3 mL) at RT and stirred for 5 h. The reaction mixture was diluted with water (5 mL) and extracted with EtOAc (20 mL). The organic layer washed with water (2×5 mL), saturated aqueous NaHCO₃ (5 mL), brine (5 mL), dried over Na₂SO₄, filtered and concentrated in vacuo. The crude compound was purified by column chromatography over silica gel (100-200 mesh) by using a gradient mixture of 0-30% EtOAc-hexane as the eluent to afford Cmpd 7 (40 mg, 33%). ¹H NMR: (DMSO-d₆) δ 9.14 (d, J=1.8 Hz, 1H), 8.66-8.67 (m, 1H), 8.28-8.34 (m, 2H), 7.47-7.53 (m, 3H), 7.13-7.17 (m, 2H), 4.63 (d, J=6.2 Hz, 2H), 3.05 (q, J=7.5 Hz, 2H), 1.16 (t, J=7.5 Hz, 3H); MS: 326 [M+H]⁺; TLC: 50% EtOAc in hexane: R_f: 0.60.

Example 13

Preparation of Cmpd 8

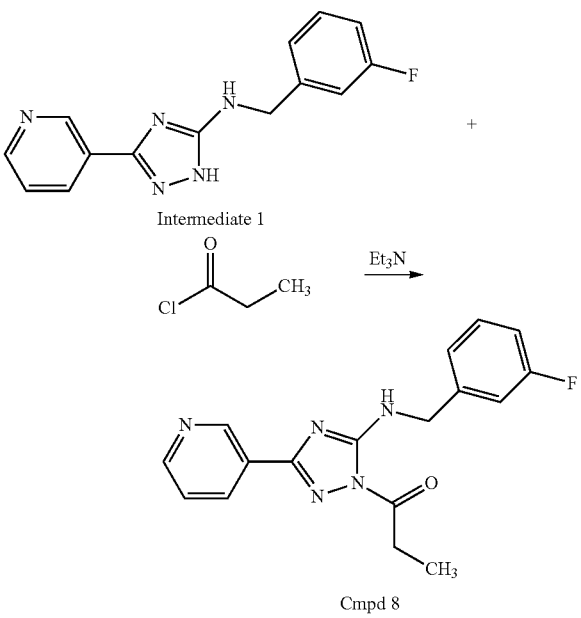

General Procedure 3 was followed to obtain Cmpd 8 (50 mg, 51%). ¹H NMR: (DMSO-d₆) δ 9.13 (d, J=1.8 Hz, 1H), 8.65-8.67 (m, 1H), 8.42 (t, J=6.4 Hz, 1H), 8.27-8.29 (m, 1H), 7.50-7.53 (m, 1H), 7.24-7.41 (m, 3H), 7.06-7.10 (m, 1H), 4.67 (d, J=6.6 Hz, 2H), 3.06 (q, J=7.3 Hz, 2H), 1.16 (t, J=7.3 Hz, 3H); MS: 326 [M+H]⁺; MP: 140-142° C.; TLC: 50% EtOAc in hexane: $R_f$: 0.60.

Example 14

Preparation of Cmpd 9

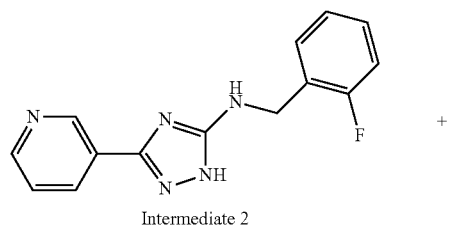
Intermediate 2

+

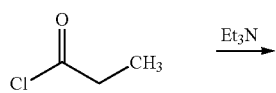

→ Et₃N

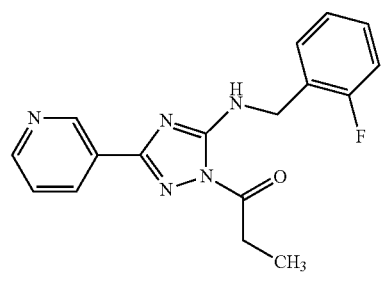
Cmpd 9

General Procedure 3 was followed to obtain Cmpd 9 (35 mg, 38%). ¹H NMR: (DMSO-d₆) δ 9.12 (d, J=1.3 Hz, 1H), 8.65-8.67 (m, 1H), 8.26-8.32 (m, 2H), 7.45-7.52 (m, 2H), 7.15-7.33 (m, 3H), 4.73 (d, J=6.2 Hz, 2H), 3.07 (q, J=7.5 Hz, 2H), 1.16 (t, J=7.3 Hz, 3H); MS: 326 [M+H]⁺; MP: 142-144° C.; TLC: 50% EtOAc in hexane: $R_f$: 0.60.

Example 15

Preparation of Cmpd 10

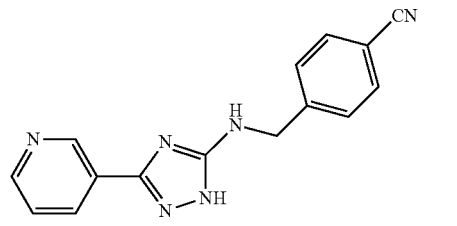
Intermediate 3

+

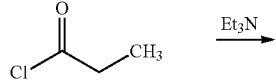

→ Et₃N

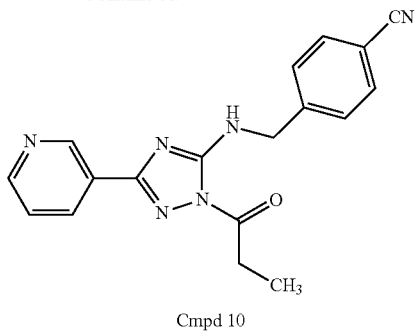
Cmpd 10

General Procedure 3 was followed to obtain Cmpd 10 (25 mg, 20%). ¹H NMR: (DMSO-d₆) δ 9.11 (s, 1H), 8.50-8.67 (m, 2H), 8.26 (d, J=7.8 Hz, 1H), 7.81 (d, J=7.8 Hz, 2H), 7.49-7.62 (m, 3H), 4.73 (d, J=6.3 Hz, 2H), 3.06 (q, J=7.1 Hz, 2H), 1.16 (t, J=7.3 Hz, 3H); MS: 333 [M+H]⁺; MP: 143-145° C.; TLC: 50% EtOAc in hexane: $R_f$: 0.65.

Example 16

Preparation of Cmpd 11

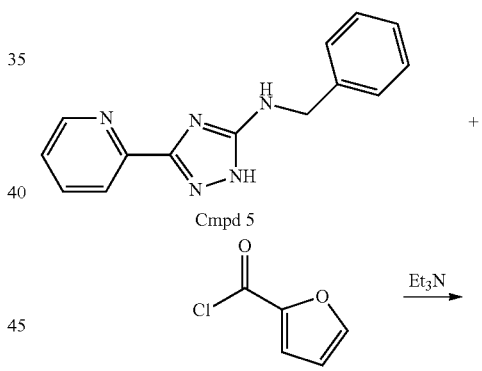
Cmpd 5

→ Et₃N

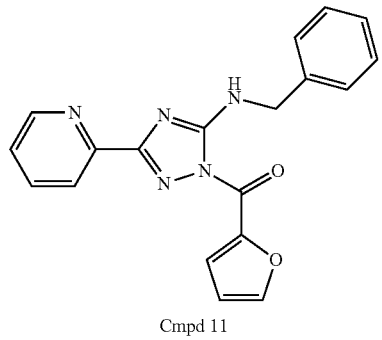
Cmpd 11

General Procedure 3 was followed to obtain Cmpd 11 (48 mg, 35%). ¹H NMR: (DMSO-d₆) δ 8.71 (d, J=4.0 Hz, 1H), 8.46 (br s, 1H), 8.13-8.23 (m, 3H), 7.92-7.96 (m, 1H), 7.24-7.52 (m, 6H), 6.88-6.89 (m, 1H), 4.74 (d, J=6.2 Hz, 2H); MS: 346 [M+H]⁺; MP: 143-145° C.; TLC: 50% EtOAc in hexane: $R_f$: 0.60.

Example 17

Preparation of Cmpd 12

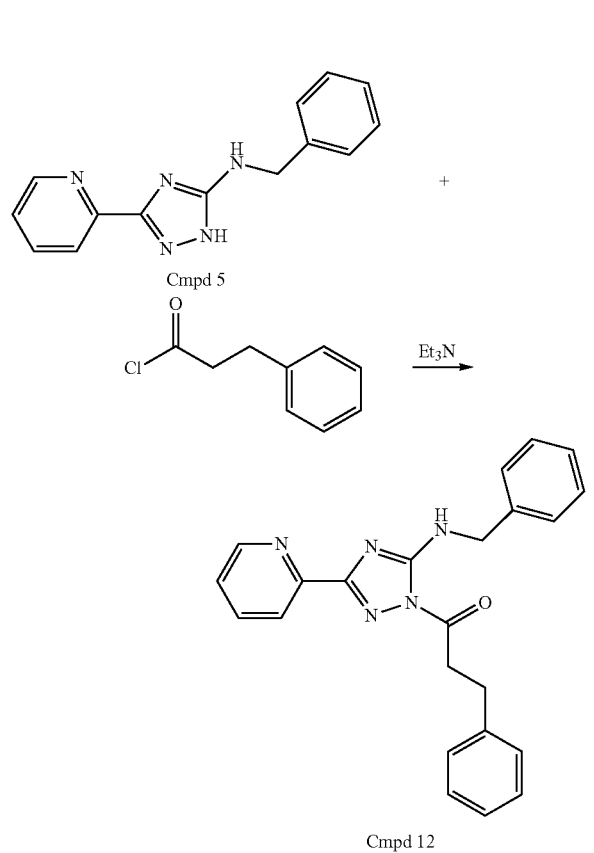

General Procedure 3 was followed to obtain Cmpd 12 (25 mg, 16%). $^1$H NMR: (DMSO-$d_6$) δ 8.65 (d, J=4.0 Hz, 1H), 8.26 (br s, 1H), 8.03 (d, J=8.1 Hz, 1H), 7.90 (t, J=7.7 Hz, 1H), 7.19-7.48 (m, 11H), 4.67 (d, J=6.0 Hz, 2H), 3.30-3.41 (m, 2H), 2.99-3.03 (m, 2H); MS: 384 [M+H]$^+$; MP: 118-120° C.; TLC: 50% EtOAc in hexane: $R_f$: 0.40.

Example 18

Preparation of Cmpd

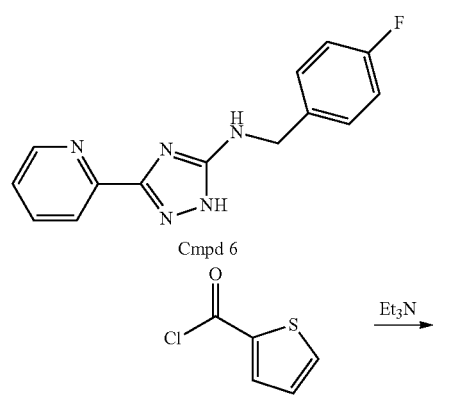

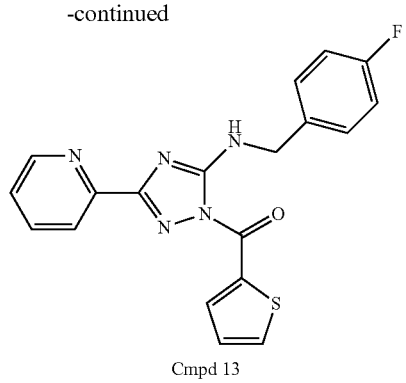

General Procedure 3 was followed to obtain Cmpd 13 (40 mg, 28%). $^1$H NMR: (DMSO-$d_6$) δ 8.72 (d, J=4.6 Hz, 1H), 8.47-8.54 (m, 2H), 8.12-8.23 (m, 2H), 7.94-7.98 (m, 1H), 7.48-7.52 (m, 3H), 7.34-7.36 (m, 1H), 7.16 (t, J=9.0 Hz, 2H), 4.71 (d, J=6.1 Hz, 2H); MS: 380 [M+H]$^+$; MP: 159-160° C.; TLC: 50% EtOAc in hexane: $R_f$: 0.60.

Example 19

Preparation of Cmpd 14

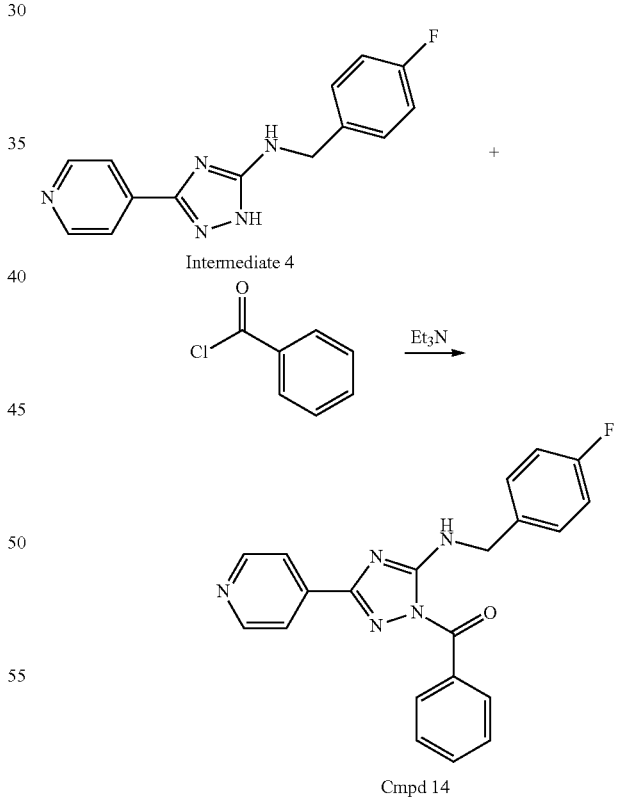

General Procedure 3 was followed to obtain Cmpd 14 (48 mg, 46%). $^1$H NMR: (DMSO-$d_6$) δ 8.68-8.70 (m, 3H), 8.14-8.16 (m, 2H), 7.85-7.87 (m, 2H), 7.53-7.73 (m, 5H), 7.18 (t, J=8.9 Hz, 2H), 4.70 (d, J=6.2 Hz, 2H); MS: 374 [M+H]$^+$; MP: 174-178° C.; TLC: 50% EtOAc in hexane: $R_f$: 0.50.

Example 20

Preparation of Cmpd 15

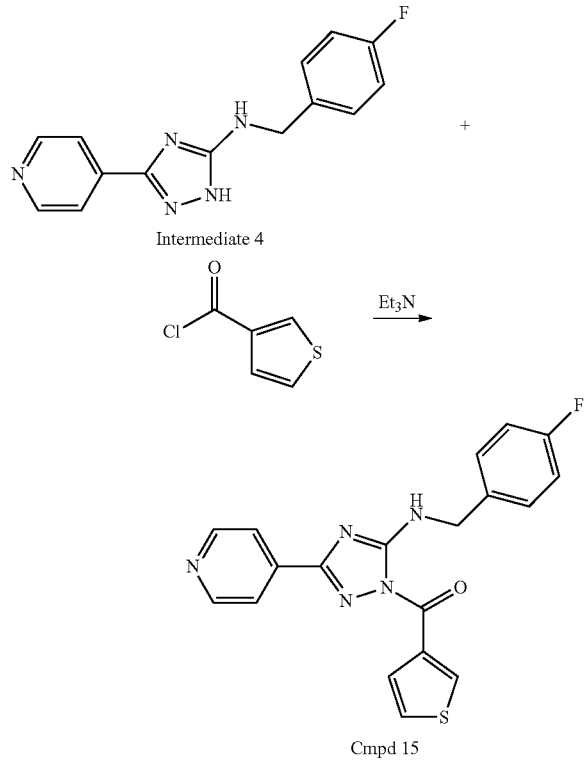

General Procedure 3 was followed to obtain Cmpd 15 (20 mg, 14%). $^1$H NMR: (DMSO-d$_6$) δ 9.19 (d, J=1.3 Hz, 1H), 8.63-8.73 (m, 3H), 8.00 (d, J=5.7 Hz, 2H), 7.72-7.88 (m, 2H), 7.50-7.54 (m, 2H), 7.17 (t, J=8.8 Hz, 2H), 4.70 (d, J=6.2 Hz, 2H); MS: 380 [M+H]$^+$; MP: 187-188° C.; TLC: 50% EtOAc in hexane: R$_f$: 0.60.

Example 21

Preparation of Cmpd 16

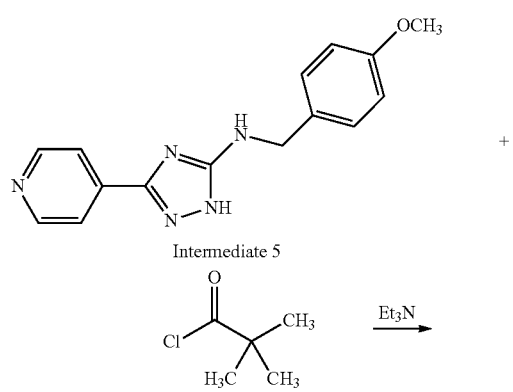

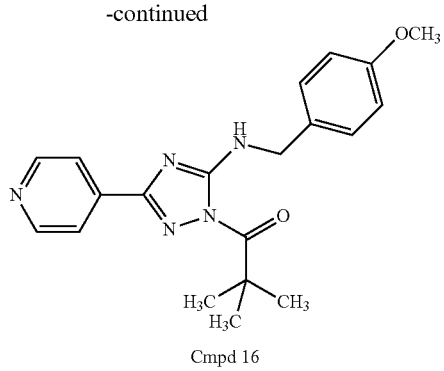

General Procedure 3 was followed to obtain Cmpd 16 (35 mg, 36%). $^1$H NMR: (DMSO-d$_6$) δ 8.71 (d, J=6.2 Hz, 2H), 8.38 (t, J=6.2 Hz, 1H), 7.90 (d, J=5.7 Hz, 2H), 7.38 (d, J=8.3 Hz, 2H), 6.90 (d, J=8.8 Hz, 2H), 4.58 (d, J=6.2 Hz, 2H), 3.72 (s, 3H), 1.46 (s, 9H); MS: 366 [M+H]$^+$; MP: 143-146° C.; TLC: 50% EtOAc in hexane: R$_f$: 0.60.

Example 22

Preparation of Cmpd 17

The synthesis of Cmpd 17 followed General Procedure 4 following.

General Procedure 4

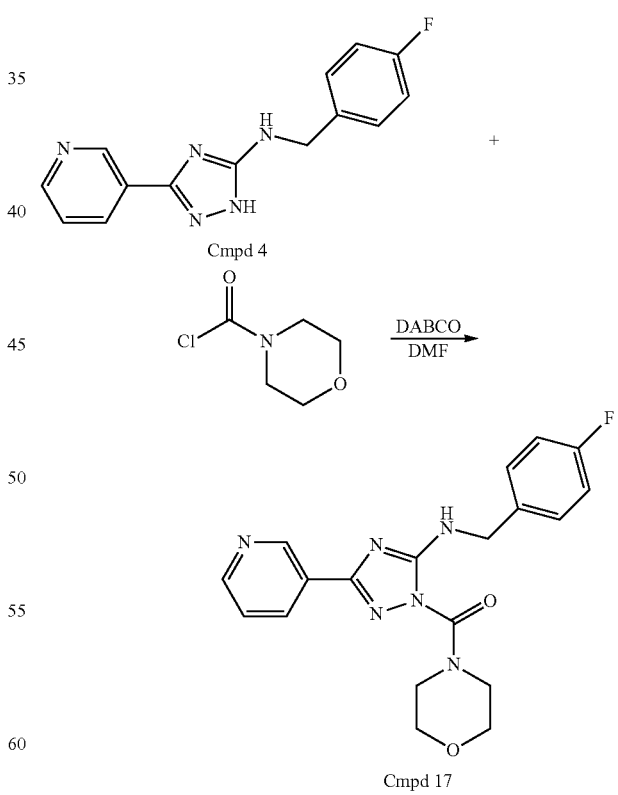

A solution of Cmpd 4 (100 mg, 0.37 mmol) in dry DMF (2 mL) was added to a solution of morpholinecarbonyl chloride (86 μL, 0.74 mmol, 2 eq), DABCO (124 mg, 1.11 mmol, 3 eq) in DMF (3 mL) at RT and stirred for 2 h. The reaction mixture was diluted with water (10 mL) and extracted with EtOAc (30 mL). The organic layer washed with water (2×5 mL), saturated aqueous NaHCO$_3$ (2×5 mL), brine (10 mL), dried over Na$_2$SO$_4$, filtered and concentrated in vacuo to get a crude residue. The crude compound was purified by column chromatography over silica gel (100-200 mesh) by using a gradient mixture of 0-50% EtOAc-hexane as the eluent to afford Cmpd 17 (33 mg, 23%). $^1$H NMR: (DMSO-d$_6$) δ 9.11 (s, 1H), 8.64 (d, J=4.8 Hz, 1H), 8.25 (d, J=7.9 Hz, 1H), 7.90 (s, 1H), 7.46-7.52 (m, 3H), 7.16 (t, J=8.8, 2H), 4.59 (d, J=6.2 Hz, 2H), 3.70-3.99 (m, 8H); MS: 383 [M+H]$^+$; TLC: 50% EtOAc in hexane: R$_f$: 0.40.

Example 23

Preparation of Cmpd 18 [General Procedure 5]

The synthesis of Cmpd 18 followed General Procedure 5 following.
General Procedure 5

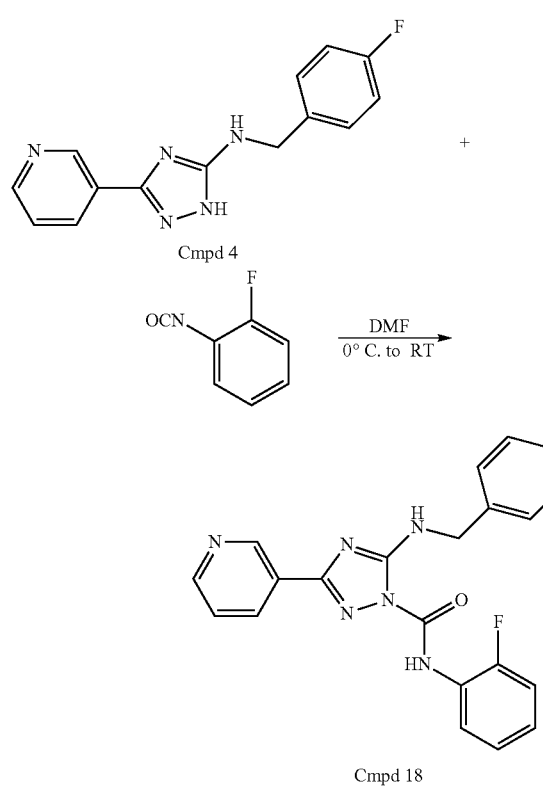

2-Fluorophenyl isocyanate (29 μL, 0.26 mmol, 0.7 eq) was added to a solution of Cmpd 4 (100 mg, 0.37 mmol) in DMF (5 mL) at 0° C. and stirred at RT for 6 h. The reaction mixture was diluted with water (10 mL) and extracted with EtOAc (30 mL). The organic layer washed with water (2×5 mL), saturated aqueous NaHCO$_3$ (2×5 mL), brine (10 mL), dried over Na$_2$SO$_4$, filtered and concentrated in vacuo to get crude a residue. The crude compound was purified by column chromatography over silica gel (100-200 mesh) by using a gradient mixture of 0-30% EtOAc-hexane as the eluent to afford Cmpd 18 (60 mg, 39%). $^1$H NMR: (DMSO-d$_6$) δ 9.94 (s, 1H), 9.23 (s, 1H), 8.68 (d, J=4.4 Hz, 1H), 8.34-8.36 (m, 1H), 8.11-8.14 (m, 1H), 7.48-7.67 (m, 4H), 7.14-7.38 (m, 5H), 4.64 (d, J=5.7 Hz, 2H); MS: 407 [M+H]$^+$; MP: 157-159° C.; TLC: 40% EtOAc in hexane: R$_f$: 0.50.

Example 24

Preparation of Cmpd 19

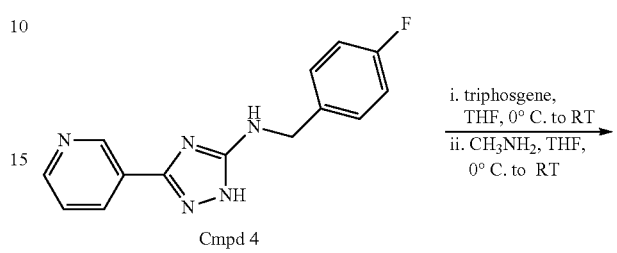

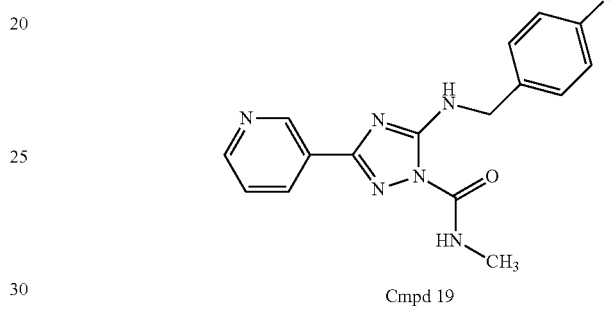

A solution of Cmpd 4 (200 mg, 0.74 mmol) in dry THF (5 mL) was added to a solution of triphosgene (100 mg, 0.37 mmol, 0.5 eq) in THF (3 mL) at 0° C. and stirred at RT for 1 h. The reaction re-cooled to 0° C., added methylamine (2.47 mL, 3M solution in THF, 7.43 mmol, 10 eq), sealed the reaction vessel, and stirred at RT for 16 h. The reaction mixture was diluted with water (30 mL) and extracted with EtOAc (2×30 mL). The combined organic layer was washed with water (2×30 mL), saturated aqueous NaHCO$_3$ (20 mL), brine (10 mL), dried over Na$_2$SO$_4$, filtered and concentrated in vacuo. The crude compound was purified by column chromatography over silica gel (100-200 mesh) by using a gradient mixture of 0-50% EtOAc-hexane as eluent to afford Cmpd 19 (70 mg, 34%). $^1$H NMR: (DMSO-d$_6$) δ 9.16 (d, J=1.3 Hz, 1H), 8.64-8.66 (m, 1H), 8.24-8.29 (m, 2H), 8.01 (t, J=6.2 Hz, 1H), 7.46-7.54 (m, 3H), 7.16 (t, J=9.0 Hz, 2H), 4.61 (d, J=6.2 Hz, 2H), 2.81 (d, J=4.4 Hz, 3H); MS: 327 [M+H]$^+$; MP: 154-158° C.; TLC: 50% EtOAc in hexane: R$_f$: 0.50.

Example 25

Preparation of Cmpd 20

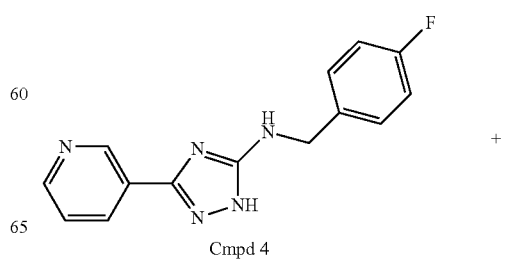

75

-continued

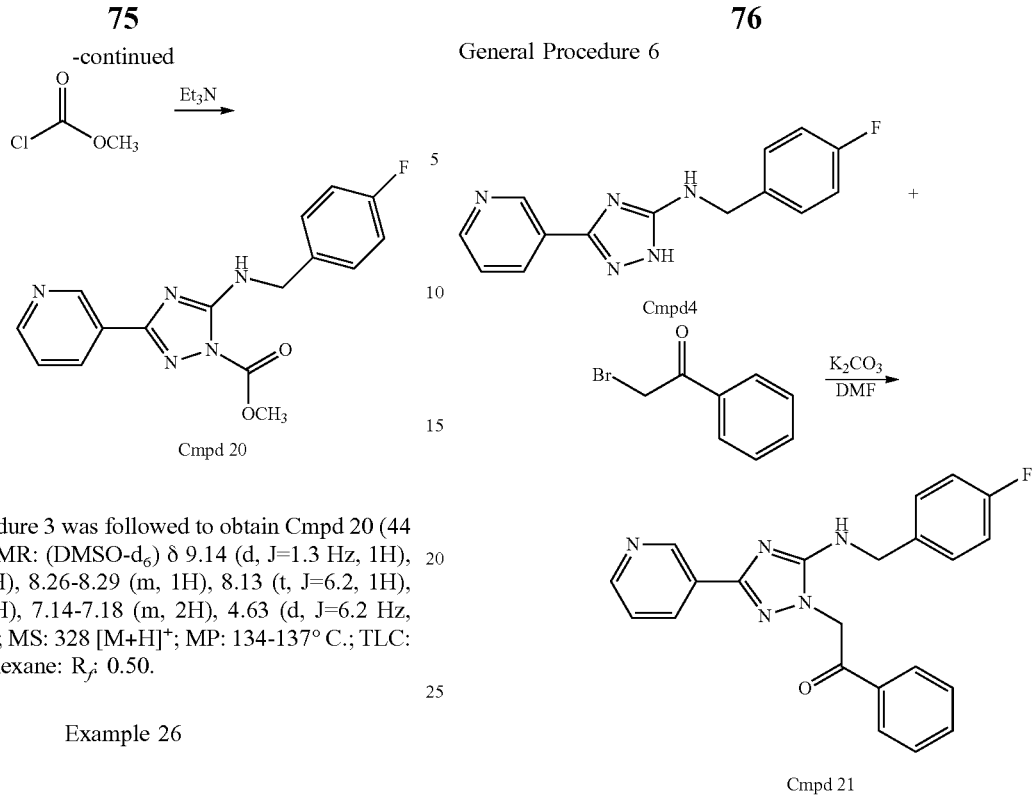

Cmpd 20

General Procedure 3 was followed to obtain Cmpd 20 (44 mg, 40%). $^1$H NMR: (DMSO-$d_6$) δ 9.14 (d, J=1.3 Hz, 1H), 8.65-8.67 (m, 1H), 8.26-8.29 (m, 1H), 8.13 (t, J=6.2, 1H), 7.47-7.52 (m, 3H), 7.14-7.18 (m, 2H), 4.63 (d, J=6.2 Hz, 2H), 3.99 (s, 3H); MS: 328 [M+H]$^+$; MP: 134-137° C.; TLC: 60% EtOAc in hexane: $R_f$: 0.50.

Example 26

Preparation of Cmpd 21

General Scheme II. A synthetic scheme useful for synthesis of compounds described herein is disclosed in General Scheme II following, wherein the term "X" in General Scheme II refers to halogen, e.g., Cl, Br, "base" is a base known in the art, e.g., $K_2CO_3$, $Et_3N$, and the like, and "R" is a substituent as disclosed herein, e.g., substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

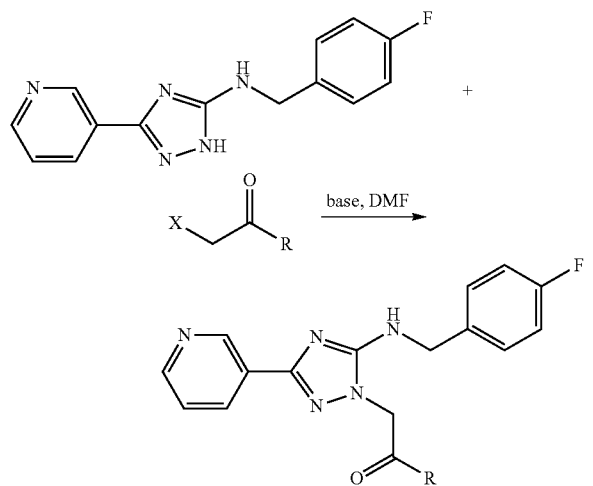

X = Cl, Br
base = $K_2CO_3$ or $Et_3N$

Synthesis of Cmpd 21 followed General Procedure 6 following.

76

General Procedure 6

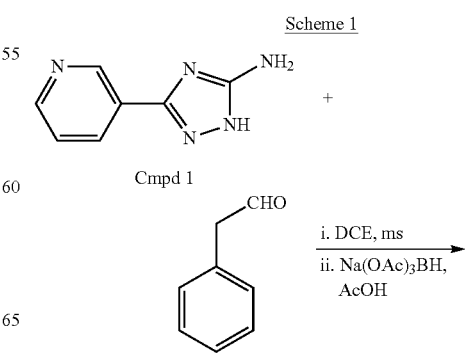

Cmpd 21

2-Bromoacetophenone (44 mg, 0.22 mmol) was added to a solution of Cmpd 4 (100 mg, 0.37 mmol), $K_2CO_3$ (102 mg, 0.74 mmol) in DMF (4 mL) at RT and stirred for 5 h. The reaction mixture was diluted with water (10 mL), and extracted with EtOAc (30 mL). The organic layer washed with water (2×5 mL), saturated aqueous $NaHCO_3$ (5 mL), brine (5 mL), dried over $Na_2SO_4$, filtered and concentrated in vacuo. The crude compound was purified by column chromatography over silica gel (100-200 mesh) by using a gradient mixture of 0-5% MeOH/$CHCl_3$ as the eluent to afford Cmpd 21 (25 mg, 17%). $^1$H NMR: (DMSO-$d_6$) δ 9.06 (d, J=1.3 Hz, 1H), 8.55-8.57 (m, 1H), 8.19 (d, J=7.9 Hz, 1H), 8.06 (d, J=7.0, 2H), 7.59-7.75 (m, 3H), 7.41-7.46 (m, 3H), 7.15-7.29 (m, 3H), 5.74 (s, 2H), 4.52 (d, J=5.7, 2H); MS: 388 [M+H]$^+$; TLC: 10% MeOH in $CHCl_3$: $R_f$: 0.50.

Example 27

Preparation of Cmpd 22

A useful scheme for the preparation of compounds of the type of Cmpd 22 is provided in Scheme 1 following.

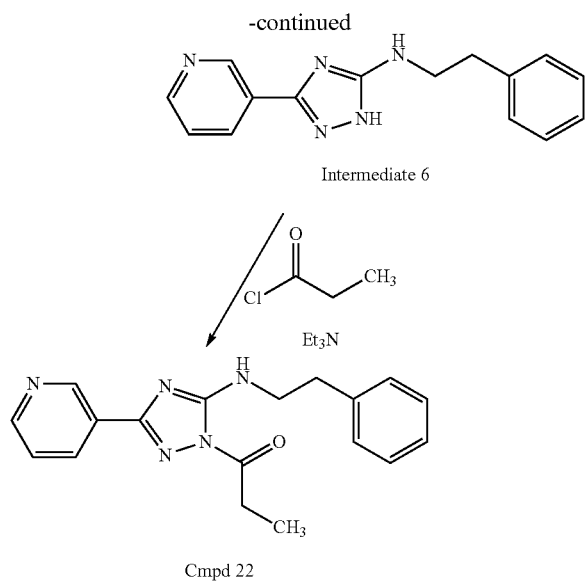

Intermediate 6

Cmpd 22

A detailed description of the preparation of Intermediate 6 and Cmpd 22 follows.

Preparation of Intermediate 6

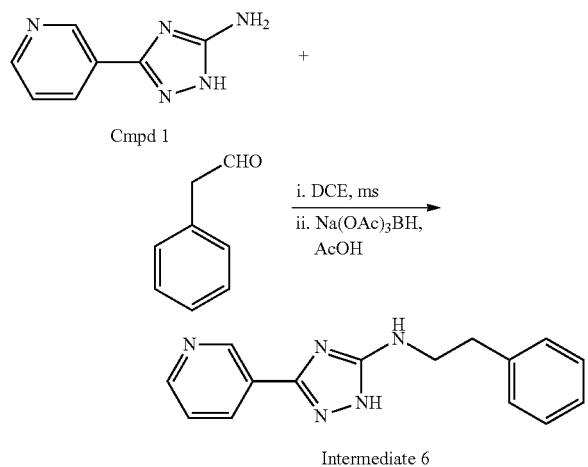

Intermediate 6

Phenylacetaldehyde (0.29 mL, 2.48 mmol, 2 eq), molecular sieves (4 Å powder), AcOH (0.1 mL, 2.48 mmol, 2 eq), and Na(OAc)$_3$BH (655 mg, 7.71 mmol, 6.2 eq) at 0° C. were added to a solution of Cmpd 1 (200 mg, 1.24 mmol) in DCE (10 mL) and stirred at RT for 18 h. The solvent was distilled-off and the residue was diluted with EtOAc (150 mL). The organic layer was washed with saturated aqueous NaHCO$_3$ (50 mL), brine (30 mL), dried over Na$_2$SO$_4$, filtered and concentrated in vacuo to obtain crude Intermediate 6 (220 mg) which was used without additional purification. TLC: 10% MeOH in CHCl$_3$: R$_f$: 0.40.

Preparation of Cmpd 22

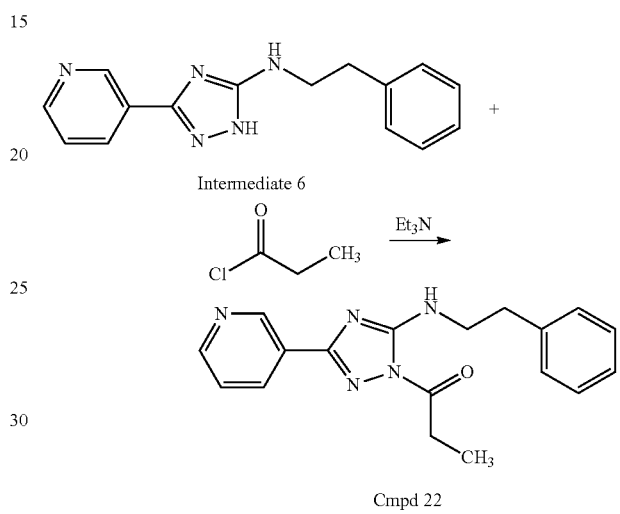

Intermediate 6

Cmpd 22

General Procedure 3 was followed to obtain Cmpd 22 (13 mg, 5%). $^1$H NMR: (DMSO-d$_6$) δ 9.17 (s, 1H), 8.68 (d, J=4.4 Hz, 1H), 8.33 (d, J=7.9 Hz, 1H), 7.83 (t, J=5.7 Hz, 1H), 7.52-7.55 (m, 1H), 7.21-7.34 (m, 5H), 3.70 (q, J=6.6 Hz, 2H), 2.95-3.07 (m, 4H), 1.14 (t, J=7.3 Hz, 3H); MS: 322 [M+H]$^+$; MP: 98-100° C.; TLC: 60% EtOAc in hexane: R$_f$: 0.60.

Example 28

Preparation of Cmpd 23

A useful scheme for the preparation of compounds of the type of Cmpd 23 is provided in Scheme 2 following.

Scheme 2

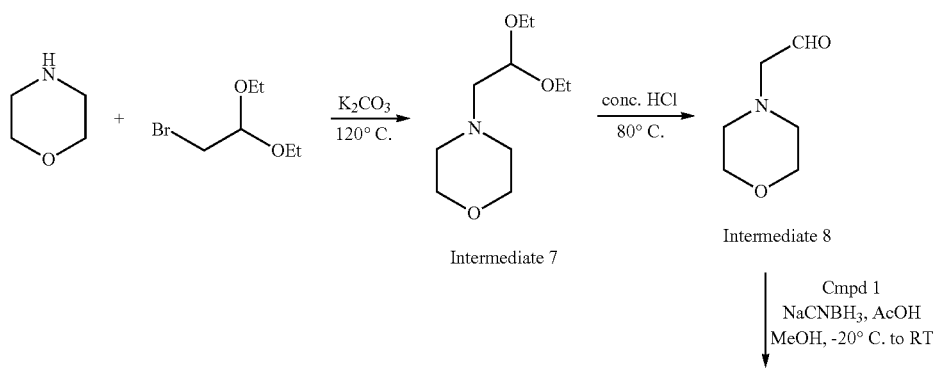

Intermediate 7

Intermediate 8

Cmpd 1
NaCNBH$_3$, AcOH
MeOH, -20° C. to RT

-continued

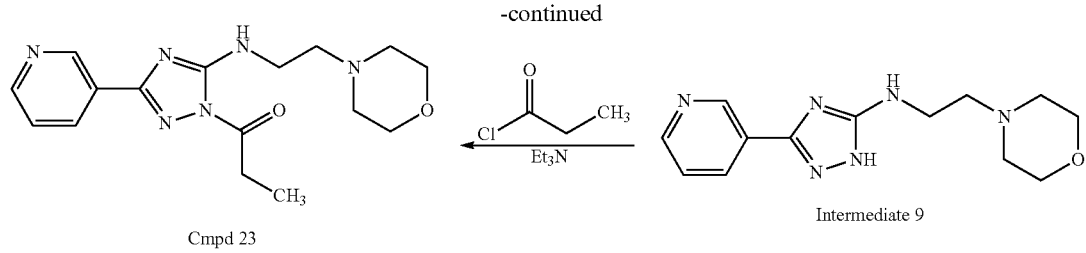

Cmpd 23 → Intermediate 9

A detailed description of the preparation of Intermediates 7-9 and Cmpd 23 follows.

Preparation of Intermediate 7

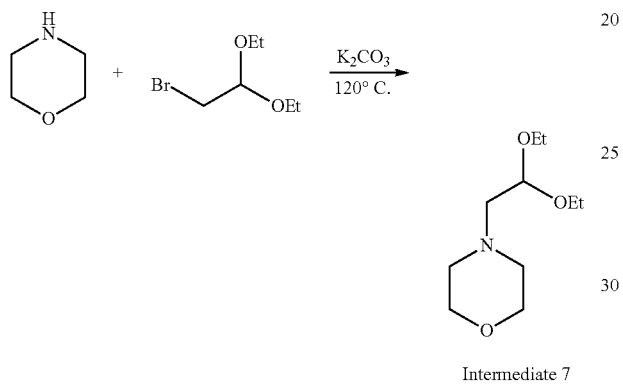

Intermediate 7

A mixture of 2-bromoacetaldehyde diethyl acetal (4.5 g, 22.9 mmol), morpholine (2.0 g, 22.9 mmol) and $K_2CO_3$ (6.34 g, 45.9 mmol, 2 eq) was stirred at 120° C. for 16 h. The reaction mixture was cooled to RT, diluted with water (50 mL) and extracted with DCM (3×50 mL). The organic layer was washed with saturated aqueous $NaHCO_3$ (50 mL), brine (50 mL), dried over $Na_2SO_4$, filtered and concentrated to get crude a residue. The crude compound was purified by column chromatography over silica gel (100-200 mesh) by using a gradient mixture of 0-50% EtOAc-hexane as the eluent to afford Intermediate 7 (2.6 g, 56%) as a pale yellow liquid. $^1$H NMR: ($CDCl_3$) δ 4.64 (t, J=5.3 Hz, 1H), 3.63-3.70 (m, 6H), 3.50-3.58 (m, 2H), 2.52-2.55 (m, 6H), 1.20 (t, J=7.0 Hz, 6H); TLC: 60% EtOAc in hexane: $R_f$: 0.50.

Preparation of Intermediate 8

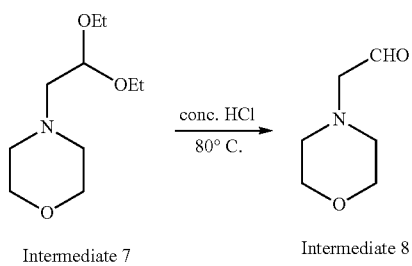 [SMILES: CCOC(CN1CCOCC1)OCC ; O=CCN1CCOCC1]

A solution of Intermediate 7 (600 mg, 2.95 mmol) dissolved in concentrated aqueous HCl (4 mL) was stirred at 80° C. for 2 h. The reaction mixture was cooled to RT, made alkaline (pH ~10) with saturated aqueous $NaHCO_3$ (20 mL) and the resulting solution was extracted with DCM (3×50 mL). The combined organic layers were washed with water (50 mL), brine (30 mL), dried over $Na_2SO_4$, filtered and concentrated in vacuo to obtain crude Intermediate 8 (340 mg) as a colorless oil which was used without additional purification. TLC: 60% EtOAc in hexane: $R_f$: 0.30.

Preparation of Intermediate 9

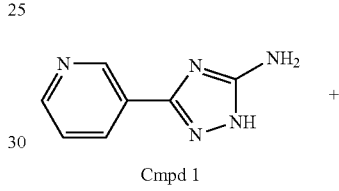

Cmpd 1

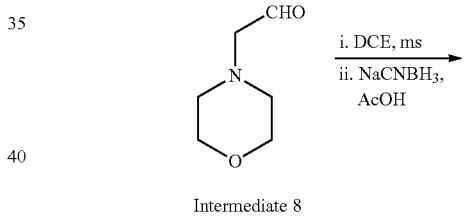

Intermediate 8

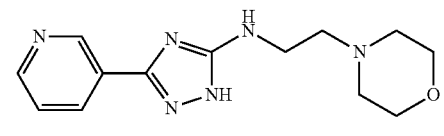

Intermediate 9

Intermediate 8 (320 mg, 2.48 mmol, 2 eq) and molecular sieves (4 Å powder) were added to a solution of Cmpd 1 (200 mg, 1.24 mmol) in MeOH (10 mL) at −20° C. and the resulting solution was stirred at RT. After 16 h, added AcOH (1 mL) and $NaCNBH_3$ (156 mg, 2.48 mmol, 2 eq) at 0° C. and the reaction mixture was stirred for 3 h at RT. The solvent was evaporated and the residue was dissolved in EtOAc (75 mL) and filtered through a Celite pad to remove inorganic materials. The filtrate was washed with saturated aqueous $NaHCO_3$ (2×10 mL), brine (20 mL), dried over $Na_2SO_4$, filtered and concentrated. The crude compound was purified by column chromatography over silica gel (100-200 mesh) by using a solvent gradient of 0-80% EtOAc-hexane as the eluent to afford Intermediate 9 (210 mg). TLC: 10% MeOH in $CHCl_3$: $R_f$: 0.40.

Preparation of Cmpd 23

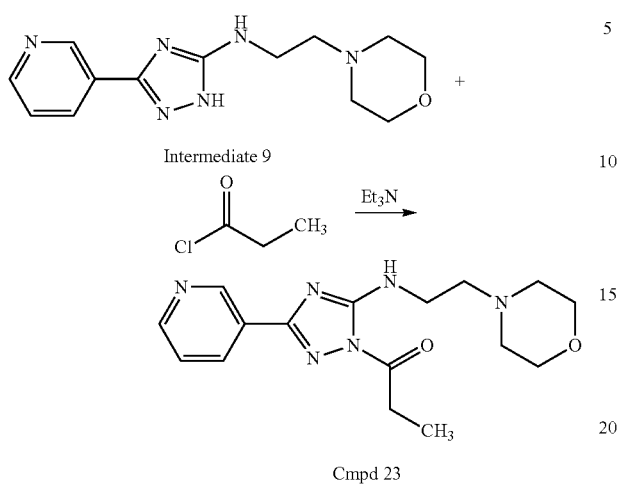

Cmpd 23

General Procedure 3 was followed to obtain Cmpd 23 (10 mg, 4%). $^1$H NMR: (DMSO-$d_6$) δ 9.15 (s, 1H), 8.67 (d, J=4.8 Hz, 1H), 8.30 (d, J=7.9 Hz, 1H), 7.83 (br s, 1H), 7.51-7.54 (m, 1H), 3.58 (d, J=4.4 Hz, 6H), 3.02-3.08 (m, 2H), 2.44-2.59 (m, 6H), 1.15 (t, J=7.3 Hz, 3H); MS: 331 [M+H]$^+$; TLC: 50% EtOAc in hexane: $R_f$: 0.50.

Example 29

Preparation of Cmpd 24

A useful scheme for the preparation of compounds of the type of Cmpd 24 is provided in Scheme 3 following.

A detailed description of the preparation of Intermediates 10-13 and Cmpd 24 follows.

Preparation of Intermediate 10

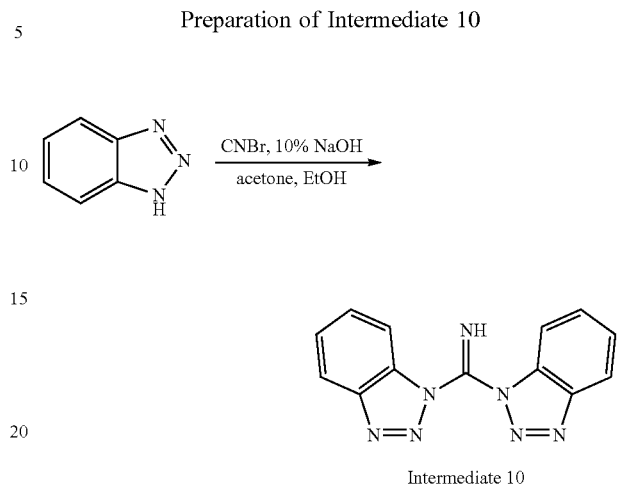

Intermediate 10

A solution of cyanogen bromide (1.3 g, 12.6 mmol) in acetone (5 mL) was added portion-wise slowly to a mixture of benzotriazole (3 g, 25.2 mmol, 2 eq) in EtOH (50 mL) followed by 10% aqueous NaOH (6 mL, 12.6 mmol, 1 eq) at 0° C. The reaction mixture was then stirred at RT for 30 min. Solid formation was observed. The solid was filtered and washed with cold EtOH. The resulting material was recrystallized from benzene to afford Intermediate (2.2 g, 33%) as a white solid. $^1$H NMR: (DMSO-$d_6$) δ 11.76 (s, 1H), 8.29-8.39 (m, 2H), 7.86-8.09 (m, 2H), 7.44-7.72 (m, 4H), MS: 264 [M+H]$^+$; TLC: 30% EtOAc in hexane: $R_f$: 0.50.

Scheme 3

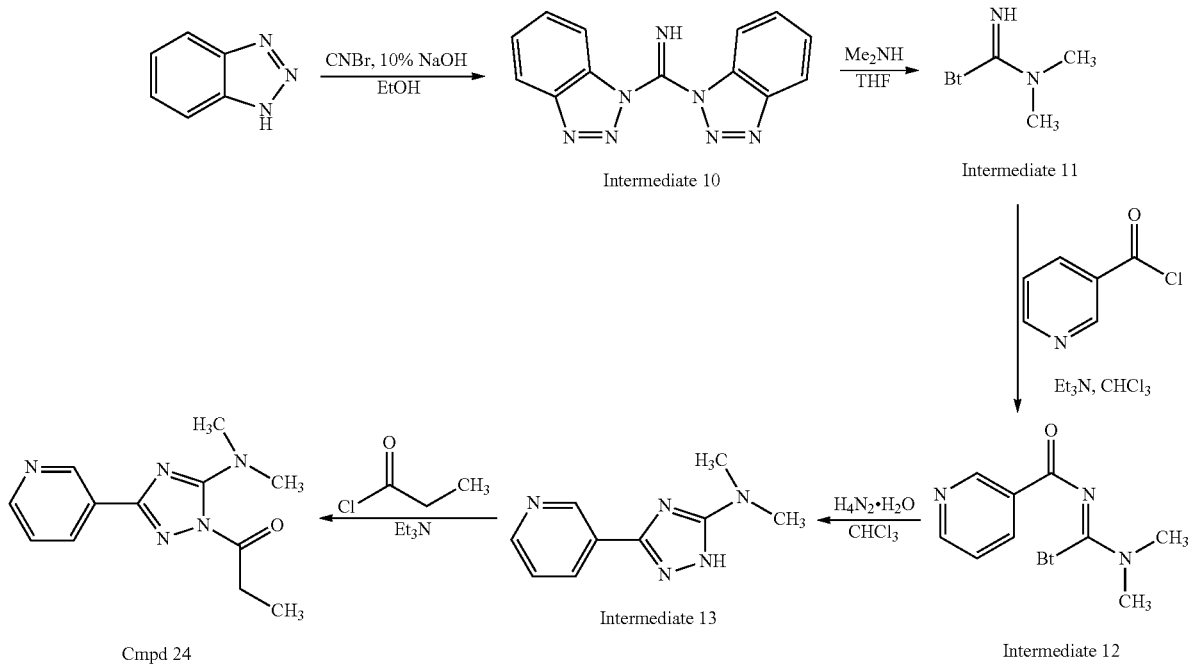

Preparation of Intermediate 11

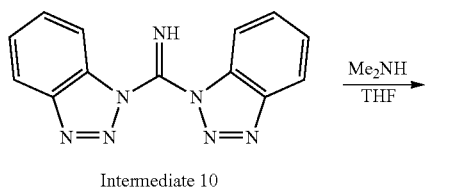

Intermediate 10

Intermediate 11

Dimethylamine (1.59 mL, 7.60 mmol, 1 eq) was added to Intermediate 10 (2 g, 7.60 mmol) in THF (30 mL) at RT and the resulting mixture was allowed to stir for 24 h. The solvent was evaporated and the residue was dissolved in DCM (100 mL). The organic layer was washed with 10% $Na_2CO_3$ (3×5 mL), brine (10 mL), dried over $Na_2SO_4$, filtered and concentrated in vacuo to afford Intermediate 11 (1.2 g, 71%) as a light yellow liquid which was used without additional purification. $^1$H NMR: (DMSO-$d_6$) δ 8.17 (d, J=8.4 Hz, 1H), 7.65-7.80 (m, 3H), 7.49-7.53 (m, 1H), 2.87 (s, 6H); MS: 190 [M+H]$^+$; TLC: 30% EtOAc in hexane: $R_f$: 0.30.

Preparation of Intermediate 12

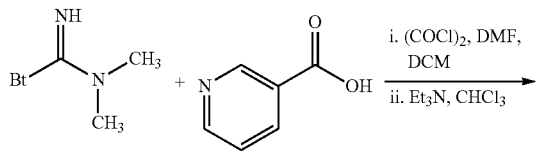

Intermediate 11

Intermediate 12

Oxalyl chloride (2 mL, 23.3 mmol, 1.4 eq) was added to a solution of nicotinic acid (2 g, 16.3 mmol) in DCM followed by catalytic amount of DMF (0.5 mL) at 0° C. and stirred for 5 h at RT. The solvent was then evaporated to afford nicotinic acid chloride as a yellow solid. Nicotinic acid chloride (1.1 g, 7.93 mmol, 1.5 eq) was then added to a solution of Intermediate 11 (1 g, 5.29 mmol) in CHCl$_3$ (30 mL) followed by Et$_3$N (0.7 mL, 5.29 mmol, 1 eq) at 0° C. The reaction mixture was allowed to warm to RT for stir for 18 h. The mixture was then diluted with CHCl$_3$ (20 mL). The organic layer was washed with water (10 mL), brine (10 mL), dried over Na$_2$SO$_4$, filtered and concentrated in vacuo. The resulting compound was purified by column chromatography over silica gel (100-200 mesh) by using a gradient mixture of 0-50% EtOAc-hexane as the eluent to afford Intermediate 12 (900 mg, 60%) as a white solid. MS: 295 [M+H]$^+$; TLC: 50% EtOAc in DCM: $R_f$: 0.40.

Preparation of Intermediate 13

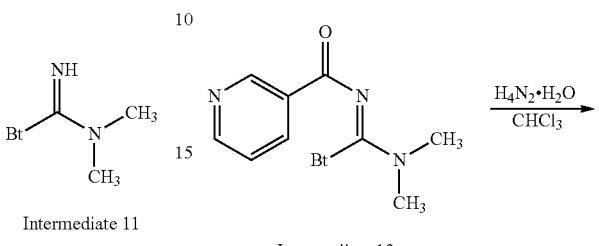

Intermediate 12

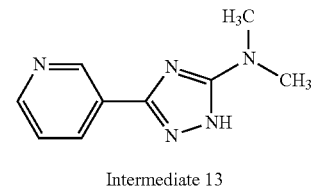

Intermediate 13

Hydrazine hydrate (5 mL) was added solution of Intermediate 12 (900 mg, 25.2 mmol) in chloroform (20 mL) at RT and the resulting mixture was allowed to stir for 24 h. The mixture was diluted with excess CHCl$_3$ (20 mL). The organic layer was then washed with water (15 mL), brine (10 mL), dried over Na$_2$SO$_4$, filtered and concentrated in vacuo. The crude residue was partially purified by column chromatography over silica gel (100-200 mesh) by using a gradient mixture of 0-50% EtOAc-hexane as the eluent to afford Intermediate 13 (150 mg) as a thick brown mass. MS: 190 [M+H]$^+$; TLC: 10% MeOH in CHCl$_3$: $R_f$: 0.30.

Preparation of Cmpd 24

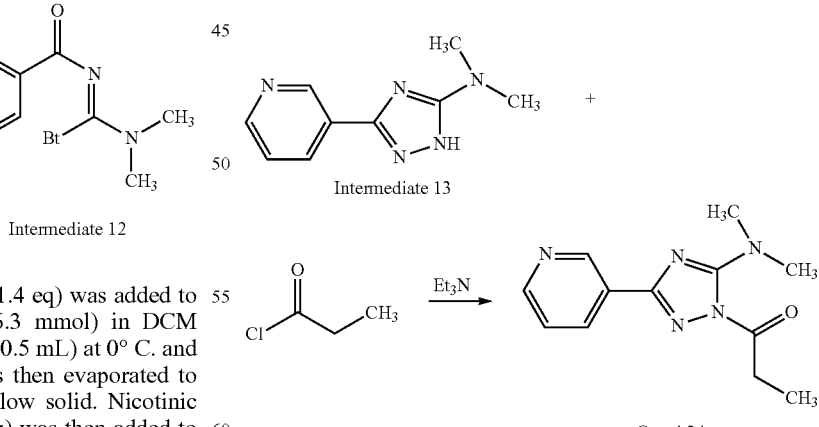

Cmpd 24

General Procedure 3 was followed to obtain Cmpd 24 (13 mg, 6%). $^1$H NMR: (DMSO-$d_6$) δ 9.15 (s, 1H), 8.68 (d, J=3.5 Hz, 1H), 8.31 (d, J=7.9 Hz, 1H), 7.53 (dd, J=7.9, 4.8 Hz, 1H), 3.04-3.14 (m, 8H), 1.15 (t, J=7.3 Hz, 3H); MS: 246 [M+H]$^+$; TLC: 50% EtOAc in DCM: $R_f$: 0.50.

Example 30

Triazolyl Ring Formation

A general chemical scheme which includes the formation of the triazolyl ring is provided in General Scheme III following, wherein "Ar," "R" and "R²" are as defined in Example 1.

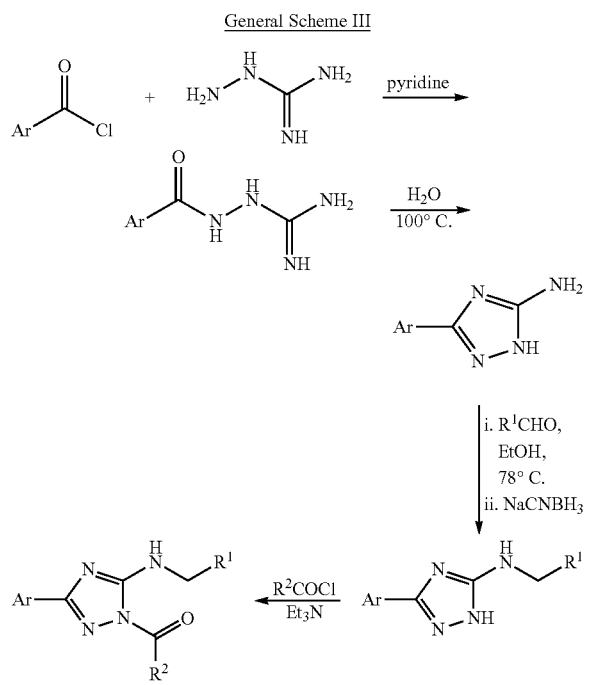

General Scheme III

Example 31

Preparation of Cmpd 25

Synthesis of Cmpd 25 followed General Procedure 7 following.
General Procedure 7

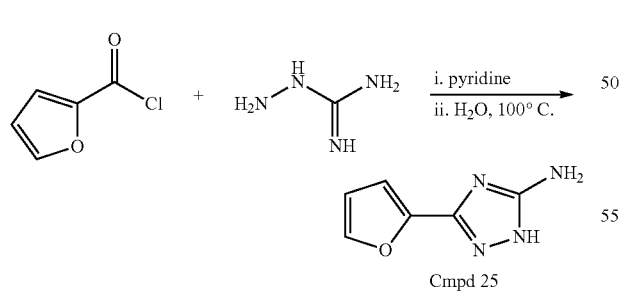

Cmpd 25

2-Furoyl chloride (7.9 mL, 75.2 mmol) was added to a solution of aminoguanidine sulfate (10 g, 75.2 mmol, 1 eq) in pyridine (50 mL) at 0° C. The reaction mixture was then allowed to stir at RT for 14 h before being neutralized with saturated aqueous NaHCO$_3$ (20 mL), extracted with t-BuOH (3×100 mL), dried over Na$_2$SO$_4$, filtered and concentrated in vacuo. The crude residue was then dissolved in water (150 mL) and stirred at 100° C. for 6 h. The reaction mixture was cooled to 0° C. and extracted with EtOAc (5×100 mL), dried over Na$_2$SO$_4$, filtered and concentrated to afford Cmpd 25 (3.5 g, 31%) as an off-white solid. $^1$H NMR: (DMSO-d$_6$) δ 12.17 (br s, 1H), 7.69 (s, 1H), 6.69 (d, J=2.5 Hz, 1H), 6.55 (dd, J=2.9, 1.8 Hz, 1H), 6.05 (br s, 2H); MS: 151 [M+H]$^+$; MP: 202-204° C.; TLC: 20% MeOH/NH$_3$ in CHCl$_3$: R$_f$: 0.40.

Example 32

Preparation of Intermediate 14

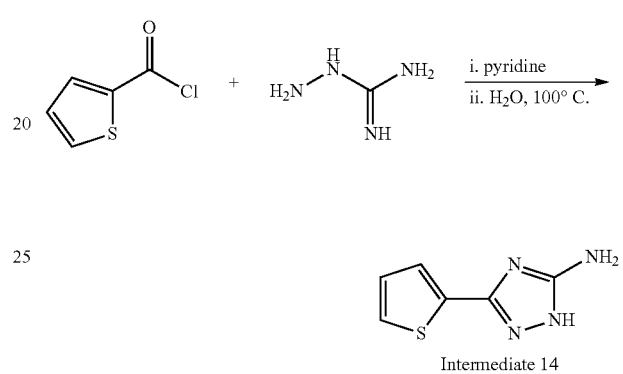

Intermediate 14

General Procedure 7 was followed to obtain crude Intermediate 14 (2.2 g). $^1$H NMR: (DMSO-d$_6$) δ 12.07 (br s, 1H), 7.39-7.46 (m, 2H), 7.07 (s, 1H), 6.09 (br s, 2H); MS: 167 [M+H]$^+$; MP: 206-208° C.; TLC: 20% MeOH/NH$_3$ in CHCl$_3$: R$_f$: 0.40.

Example 33

Preparation of Intermediate 15

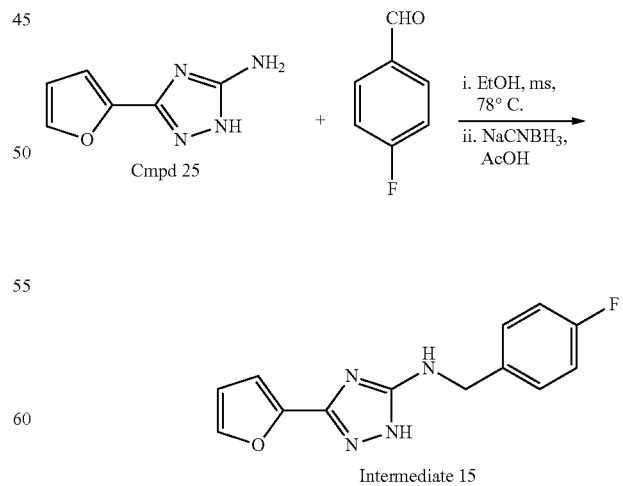

Intermediate 15

General Procedure 2 was followed to obtain Intermediate 15 (350 mg, 25%). MS: 259 [M+H]$^+$; TLC: 10% MeOH in CHCl$_3$: R$_f$: 0.25.

Example 34

Preparation of Intermediate 16

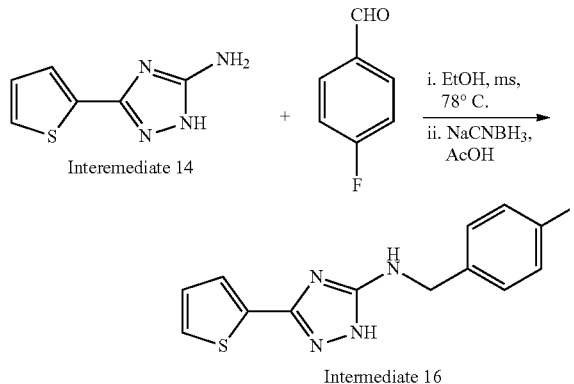

General Procedure 2 was followed to obtain Intermediate 16 (500 mg, 38%). $^1$H NMR: (DMSO-d$_6$) δ 12.27 (s, 1H), 7.38-7.47 (m, 4H), 7.07-22 (m, 4H), 4.37 (d, J=6.2 Hz, 2H); MS: 275 [M+H]$^+$; TLC: 10% MeOH in CHCl$_3$: R$_f$: 0.25.

Example 35

Preparation of Cmpd 26

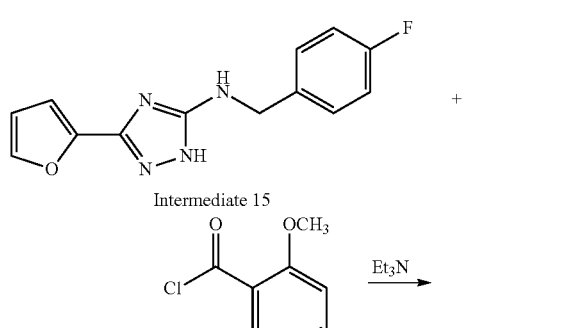

Cmpd 26

General Procedure 3 was followed to obtain Cmpd 26 (20 mg, 17%). $^1$H NMR: (DMSO-d$_6$) δ 8.51 (t, J=6.2 Hz, 1H), 7.76 (s, 1H), 7.49-7.57 (m, 4H), 7.06-7.21 (m, 4H), 6.94 (d, J=3.5 Hz, 1H), 6.59 (m, 1H), 4.64 (d, J=6.2 Hz, 2H), 3.77 (s, 3H); MS: 393 [M+H]$^+$; MP: 150-152° C.; TLC: 50% EtOAc in hexane: R$_f$: 0.60.

Example 36

Preparation of Cmpd 27

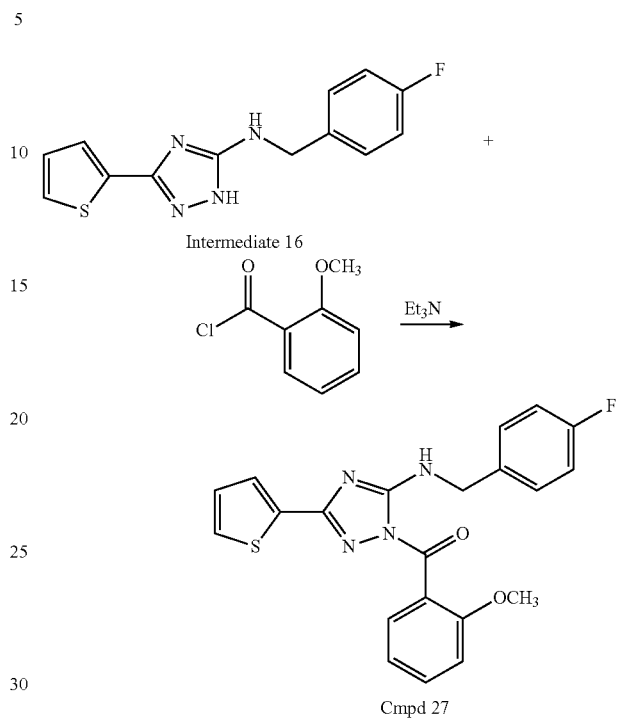

Cmpd 27

General Procedure 3 was followed to obtain Cmpd 27 (25 mg, 21%). $^1$H NMR: (DMSO-d$_6$) δ 8.47 (t, J=6.2 Hz, 1H), 7.50-7.63 (m, 6H), 7.06-7.22 (m, 5H), 4.65 (d, J=6.2 Hz, 2H), 3.77 (s, 3H); MS: 409 [M+H]$^+$; MP: 151-152° C.; TLC: 50% EtOAc in hexane: R$_f$: 0.60.

Example 37

Preparation of Cmpd 28

A general chemical scheme for the formation of compounds of the type of Cmpd 28 is provided in General Scheme IV following, wherein "Ar," "R" and "R$^2$" are as defined in Example 1.

General Scheme IV

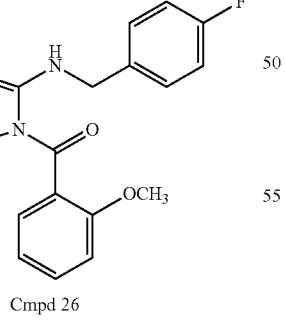

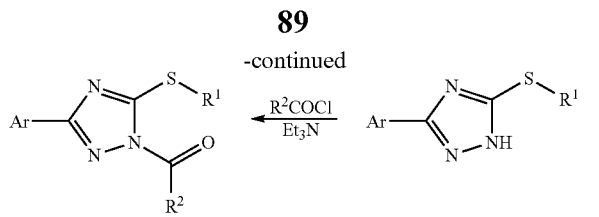

A detailed description of the preparation of Intermediates 17, 18 and Cmpd 28 follows.

Preparation of Intermediate 17

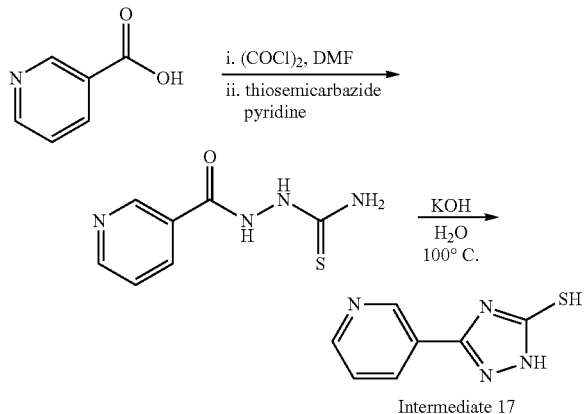

Intermediate 17

Oxalyl chloride (5.4 mL, 61.0 mmol, 1.5 eq) and DMF (3 mL) was added sequentially to a solution of nicotinic acid (5 g, 40.7 mmol) in dry DCM (300 mL) at RT. The reaction mixture was allowed to stir at RT for 2 h. The solvent was removed and co- distilled with dry toluene (2×50 mL) and to afford 5 g of crude nicotinic acid chloride (5 g, 35.5 mmol). This material was added slowly portion-wise to a solution of thiosemicarbazide (5 g, 54.9 mmol, 1.5 eq) in pyridine (50 mL) at 0.degree. C. over a period of 1 h and then allowed to stir at RT for 14 h. The reaction mixture was neutralized with saturated aqueous NaHCO.sub.3 (30 mL) and extracted with t-BuOH (3.times.100 mL) and dried over Na.sub.2SO.sub.4, filtered and concentrated in vacuo. The crude residue was dissolved in water (20 mL) along with 10% aqueous KOH (50 mL) and the resulting mixture was allowed to stir at 100.degree. C. for 3 h. The reaction mixture was then cooled to 0.degree. C. and neutralized with 10% aqueous AcOH (60 mL), extracted with EtOAc (2.times.150 mL), dried over Na.sub.2SO.sub.4 filtered and concentrated in vacuo to afford crude Intermediate 17 (1.2 g) as an off-white solid. MS: 179 [M+H].sup.+; TLC: 20% MeOH/ NH.sub.3 in CHCl.sub.3: R.sub.f: 0.30.

Preparation of Intermediate 18

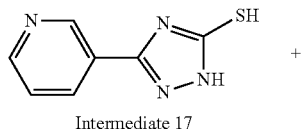

Intermediate 17

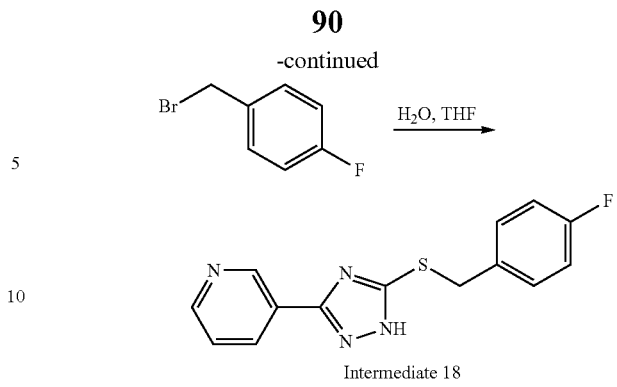

Intermediate 18

4-Fluorobenzyl bromide (0.12 mL, 1.01 mmol, 0.6 eq) was added to a solution of Intermediate 17 (300 mg, 1.68 mmol) in water (5 mL) and THF (15 mL) at −10° C. and the reaction mixture was allowed to stir at −10° C. for 8 h. The solvent was removed and the residue was diluted with water (10 mL) and extracted with EtOAc (50 mL). The organic layer was washed with water (15 mL), saturated aqueous NaHCO$_3$ (10 mL), brine, dried over Na$_2$SO$_4$, filtered and concentrated in vacuo. The crude compound was purified by column chromatography over silica gel (100-200 mesh) by using a solvent gradient mixture of 0-10% MeOH—CHCl$_3$ as the eluent to afford Intermediate 18 (110 mg, 23%) as an off-white solid. MS: 287 [M+H]$^+$; TLC: EtOAc: R$_f$: 0.40.

Preparation of Cmpd 28

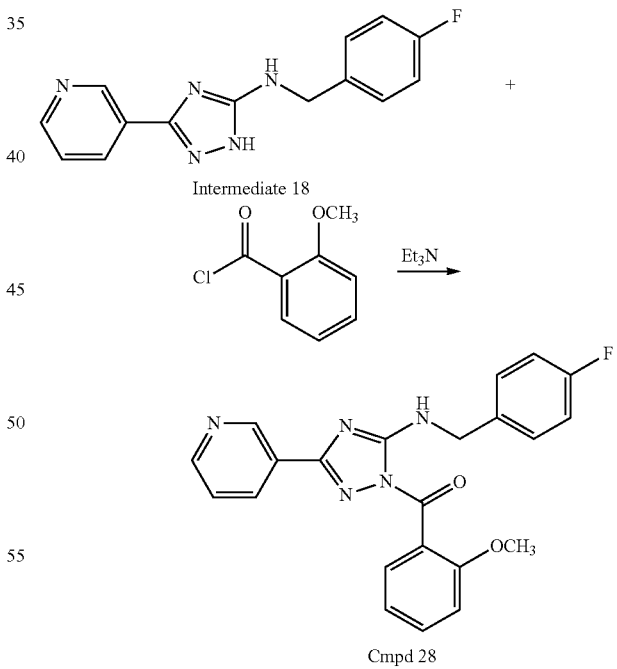

Cmpd 28

General Procedure 3 was followed to obtain Cmpd 28 (20 mg, 30%). $^1$H NMR: (DMSO-d$_6$) δ 9.13 (s, 1H), 8.71 (d, J=4.0 Hz, 1H), 8.26 (d, J=7.9 Hz, 1H), 7.53-7.67 (m, 5H), 7.09-7.25 (m, 4H), 4.64 (s, 2H), 3.75 (s, 3H); MS: 421 [M+H]$^+$; MP: 108-112° C.; TLC: 30% EtOAc in hexane: R$_f$: 0.40.

Example 38

Preparation of Intermediate 19

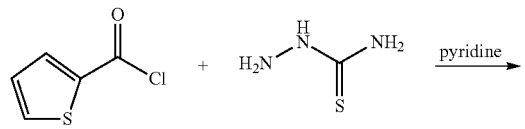

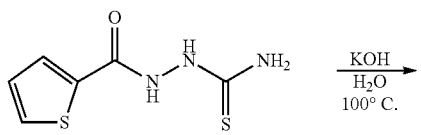

2-Thiophene carboxylic acid chloride (6.5 mL, 60.4 mmol) was added slowly portion-wise to a solution of thiosemicarbazide (5 g, 54.9 mmol, 1.1 eq) in pyridine (50 mL) at 0° C. over a period of 1 h and then allowed to stir at RT for 14 h. The reaction mixture was neutralized with saturated aqueous $NaHCO_3$ (50 mL) and extracted with t-BuOH (3×100 mL) and dried over $Na_2SO_4$, filtered and concentrated in vacuo. The crude residue was dissolved in water (30 mL) along with 10% aqueous KOH (60 mL) and the resulting mixture was allowed to stir at 100° C. for 3 h. The reaction mixture was then cooled to 0° C. and neutralized with 10% aqueous AcOH, extracted with EtOAc (2×150 mL), dried over $Na_2SO_4$, filtered and concentrated in vacuo to afford crude Intermediate 19 (1.2 g) as an off-white solid. MS: 184 $[M+H]^+$; TLC: 10% $MeOH/NH_3$ in $CHCl_3$: $R_f$: 0.60.

Example 39

Preparation of Intermediate 20

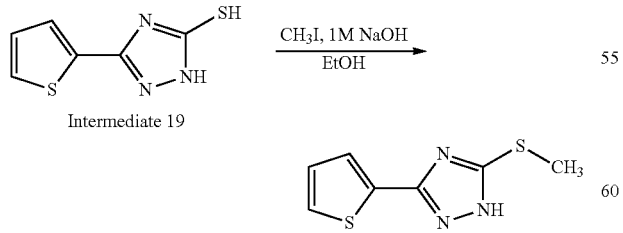

A solution of methyl iodide (65 μL, 1.04 mmol, 1.6 eq) in EtOH (2 mL) was added to a solution of Intermediate 19 (120 mg, 0.66 mmol) in 1M aqueous NaOH (3 mL) at RT and the resulting mixture was allowed to stir for 3 h. The reaction mixture was then neutralized with 10% aqueous AcOH (5 mL) and extracted with EtOAc (30 mL). The organic layer was washed with water (10 mL), saturated aqueous $NaHCO_3$ (5 mL), brine, dried over $Na_2SO_4$, filtered and concentrated in vacuo. The crude compound was purified by column chromatography over silica gel (100-200 mesh) by using a solvent gradient mixture of 0-10% $MeOH$—$CHCl_3$ as the eluent to afford Intermediate 20 (90 mg, 70%) as an off-white solid. $^1H$ NMR: (DMSO-$d_6$) δ 14.19 (br s, 1H), 7.62-7.67 (m, 2H), 7.16-7.18 (m, 1H), 2.60 (s, 3H); MS: 198 $[M+H]^+$; TLC: 50% EtOAc in hexane: $R_f$: 0.50.

Example 40

Preparation of Cmpd 29

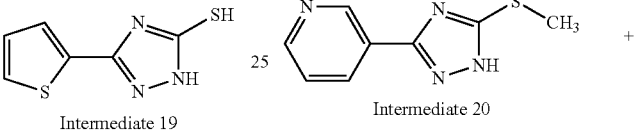

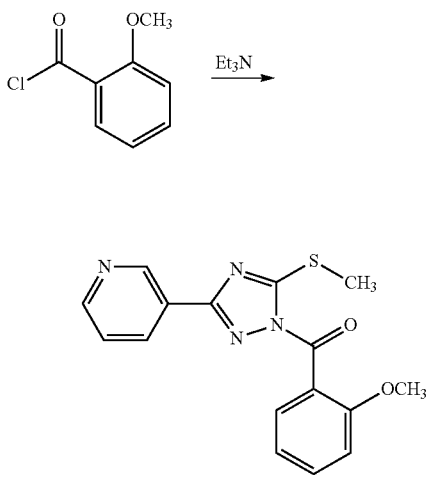

General Procedure 3 was followed to obtain Cmpd 29 (30 mg, 29%). $^1H$ NMR: (DMSO-$d_6$) δ 7.72 (d, J=4.8 Hz, 1H), 7.56-7.65 (m, 3H), 7.25 (d, J=8.8 Hz, 1H), 7.09-7.24 (m, 2H), 3.77 (s, 3H), 2.73 (s, 3H); MS: 332 $[M+H]^+$; MP: 165-167° C.; TLC: 30% EtOAc in hexane: $R_f$: 0.40.

Example 41

Preparation of Cmpd 30

A general chemical scheme for the formation of compounds of the type of Cmpd 30 is provided in General Scheme V following, wherein "$R^1$" and "$R^2$" are as defined in Example 1.

General Scheme V

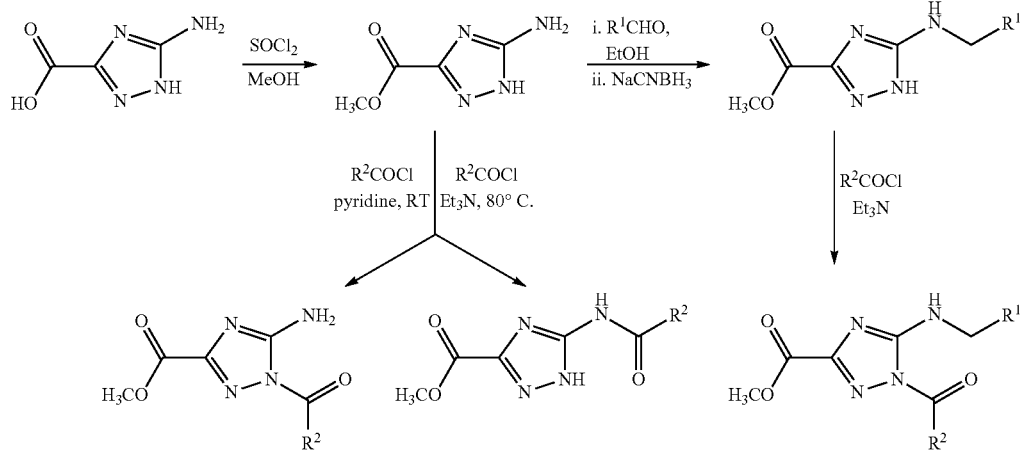

A detailed description of the preparation of Intermediates 21, 22 and Cmpd 30 follows.

Preparation of Intermediate 21

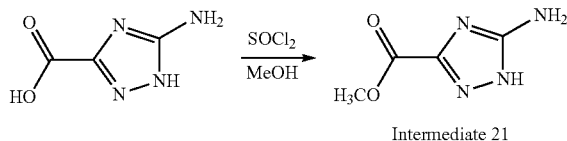

Thionyl chloride (5.43 mL, 74.9 mmol, 3.2 eq) was added to a cold solution of 5-amino-[1,2,4]triazole-3-carboxylic acid (3 g, 23.4 mmol) in MeOH (21 mL) at RT and the resulting mixture was allowed to stir for 24 h. The solvent was then removed and the crude residue was recrystallized from a mixture of MeOH-Et$_2$O to afford Intermediate 21 (3.5 g, 98%) as an HCl salt. $^1$H NMR: (DMSO-d$_6$) δ 12.62 (s, 1H), 6.23 (s, 2H), 3.76 (s, 3H); MS: 143 [M+H]$^+$; MP: 240-241° C.; TLC: 15% MeOH in CHCl$_3$: R$_f$: 0.50.

Preparation of Intermediate 22

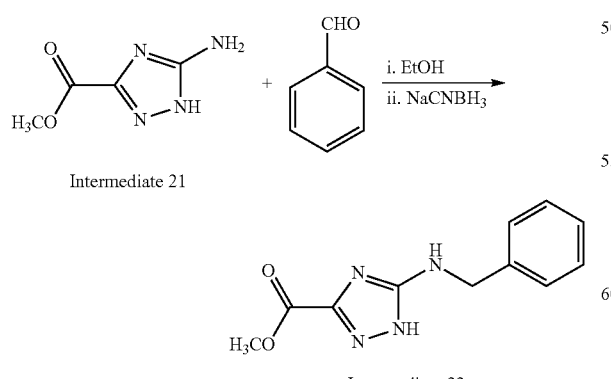

Benzaldehyde (0.7 mL, 6.74 mmol, 2 eq) was added to a solution of Intermediate 21 (600 mg, 3.37 mmol) in EtOH (10 mL) and the resulting solution was allowed to stir for 6 h at 75° C. NaCNBH$_3$ (424 mg, 6.74 mmol, 2 eq) was then added and the mixture was allowed to stir for 16 h at RT. The reaction mixture was then diluted with water (20 mL) and extracted with EtOAc (2×100 mL). The combined organic layer was washed with brine (20 mL), dried over Na$_2$SO$_4$, filtered and concentrated in vacuo. The crude residue was purified by column chromatography over silica (100-200 mesh) using a gradient mixture of 10-40% of EtOAc-hexane as the eluent to afford Intermediate 22 (120 mg, 15%) as a yellow solid. $^1$H NMR: (DMSO-d$_6$) δ 12.87 (s, 1H), 7.23-7.38 (m, 7H), 4.39 (d, J=6.6 Hz, 2H), 3.76 (s, 3H), 3.08-3.10 (m, 1H); MS: 233 [M+H]$^+$; TLC: EtOAc: R$_f$: 0.70.

Preparation of Cmpd 30

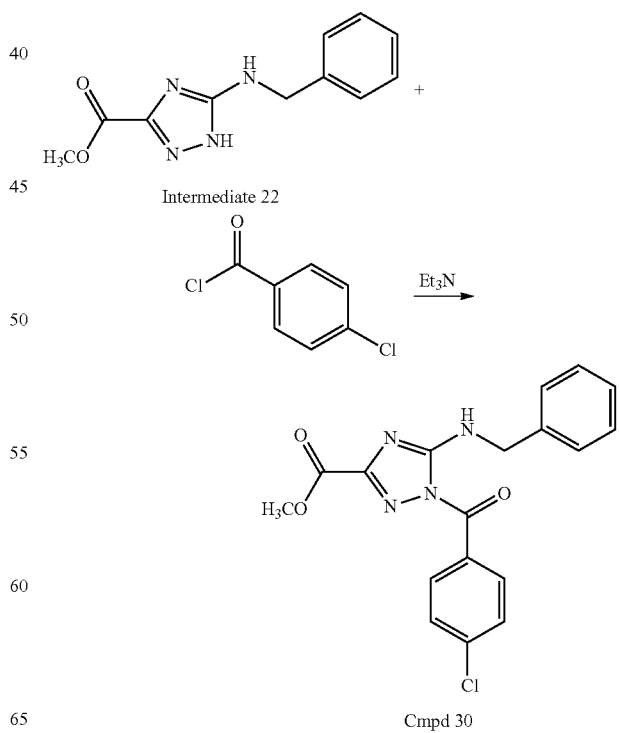

General Procedure 3 was followed to obtain Cmpd 30 (25 mg, 47%). $^1$H NMR: (DMSO-d$_6$) δ 8.56 (t, J=6.4 Hz, 1H), 8.06 (d, J=8.3 Hz, 2H), 7.67 (d, J=8.8 Hz, 2H), 7.24-7.41 (m, 5H), 4.67 (d, J=6.2 Hz, 2H), 3.82 (s, 3H); MS: 371 [M+H]$^+$; TLC: 20% EtOAc in hexane: R$_f$: 0.50.

Example 42

Preparation of Cmpd 31

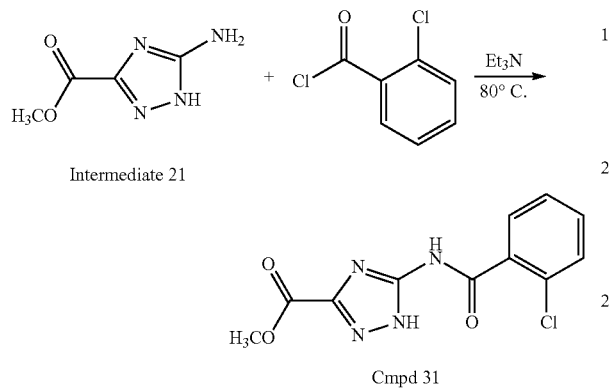

Intermediate 21

Cmpd 31

2-Chlorobenzoyl chloride (0.33 mL, 2.46 mmol, 1.1 eq) was added to a solution of Intermediate 21 (400 mg, 2.24 mmol) in Et$_3$N (6 mL) at 0° C. The resulting mixture was heated to 80° C. and allowed to stir for 4 h. The reaction mixture was diluted with saturated aqueous NaHCO$_3$ and extracted with DCM (3×40 mL). The combined organic layers were washed with water (40 mL), brine (30 mL), dried over Na$_2$SO$_4$, filtered and concentrated in vacuo. The crude residue was purified by column chromatography over silica gel (100-200 mesh) using a gradient mixture of 0-6% MeOH—CHCl$_3$ as the eluent to afford Cmpd 31 (80 mg, 12%). $^1$H NMR: (DMSO-d$_6$) δ 14.36 (s, 1H), 12.37 (s, 1H), 7.46-7.67 (m, 4H), 3.84 (s, 3H); MS: 281 [M+H]$^+$; MP: 100-101° C.; TLC: 10% MeOH in CHCl$_3$: R$_f$: 0.60.

Example 43

Preparation of Cmpd 32

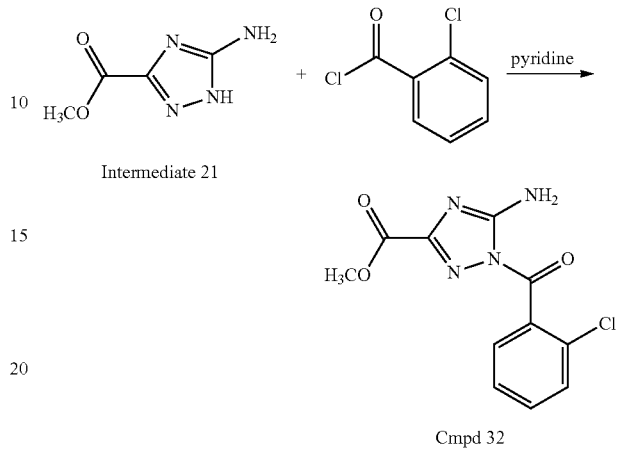

Intermediate 21

Cmpd 32

2-Chlorobenzoyl chloride (0.24 mL, 1.80 mmol, 1.1 eq) was added to a solution of Intermediate 21 (300 mg, 1.68 mmol) in pyridine (6 mL) at 0° C. The resulting solution was warmed to RT and allowed to stir for 2 h. The reaction mixture was diluted with saturated aqueous NaHCO$_3$ and extracted with CHCl$_3$ (3×40 mL). The combined organic layers were washed with water (40 mL), brine (30 mL), dried over Na$_2$SO$_4$, filtered and concentrated in vacuo. The crude residue was purified by column chromatography over silica gel (100-200 mesh) using a gradient mixture of 0-6% MeOH—CHCl$_3$ as the eluent to afford Cmpd 32 (99 mg, 21%). $^1$H NMR: (DMSO-d$_6$) δ 8.00 (s, 2H), 7.73 (d, J=7.5 Hz, 1H), 7.49-7.64 (m, 3H), 3.77 (s, 3H); MS: 281 [M+H]$^+$; TLC: 10% MeOH in CHCl$_3$: R$_f$: 0.60.

Example 44

Preparation of Cmpd 33

General Scheme VI. A synthetic scheme useful for synthesis of compounds described herein including Cmpd 33 is disclosed in General Scheme VI following, wherein the terms "Ar," "R$^1$" and "R$^2$" are as defined in Example 1.

General Scheme VI

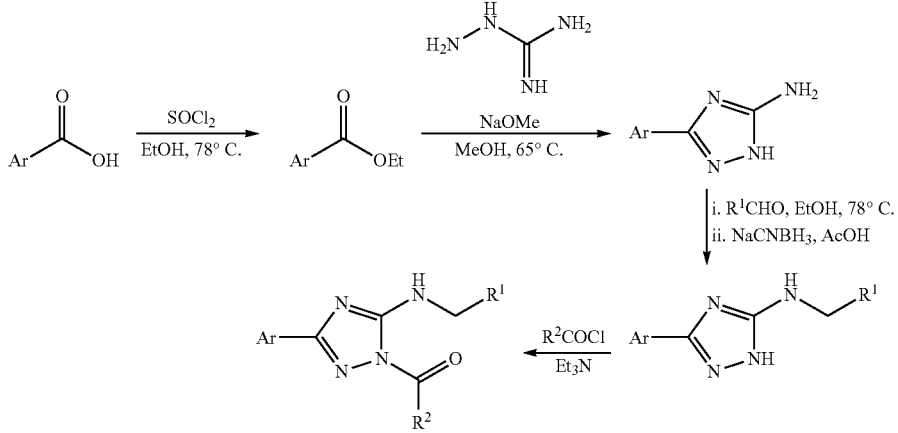

A description of the synthesis of Intermediates 23-28 and Cmpd 33 follows. Synthesis of Intermediate 23 followed General Procedure 8 following.

Preparation of Intermediate 23 [General Procedure 8]

General procedure 8 was followed in the preparation of Intermediate 23.
General Procedure 8

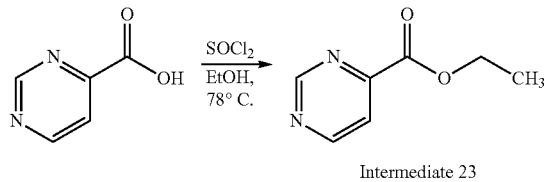

Intermediate 23

Thionyl chloride (3.55 mL, 48.4 mmol, 3 eq) was added drop-wise to a solution of pyrimidine-4-carboxylic acid (2 g, 16.1 mmol) in EtOH (15 mL) and the resulting mixture was heated to reflux for 14 h. The mixture was then cooled to RT and made alkaline with saturated aqueous NaHCO$_3$ to pH 8. The basic solution was then extracted with EtOAc (4×50 mL). The combined organic layers were washed with brine (30 mL), dried over Na$_2$SO$_4$, filtered and concentrated in vacuo to afford Intermediate 23 (1.7 g, 77%). $^1$H NMR: (DMSO-d$_6$) δ 9.40 (d, J=1.0 Hz, 1H), 9.10 (d, J=5.1 Hz, 1H), 8.05 (dd, J=5.1, 1.3 Hz, 1H), 4.39 (q, J=7.1 Hz, 2H), 1.35 (t, J=7.1 Hz, 3H); MS: 153 [M+H]$^+$; TLC: 40% hexane in EtOAc: R$_f$: 0.40.

Preparation of Intermediate 24

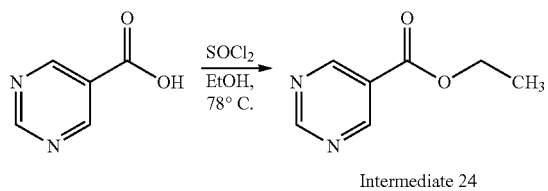

Intermediate 24

General Procedure 8 was followed to obtain crude Intermediate 24 (950 mg, 86%). $^1$H NMR: (DMSO-d$_6$) δ 9.43 (s, 1H), 9.26 (s, 2H), 4.39 (q, J=7.1 Hz, 2H), 1.35 (t, J=7.1 Hz, 3H); TLC: 40% EtOAc in hexane: R$_f$: 0.50.

Preparation of Intermediate 25 [General Procedure 9]

General Procedure 9 was followed in the preparation of Intermediate 25.
General Procedure 9

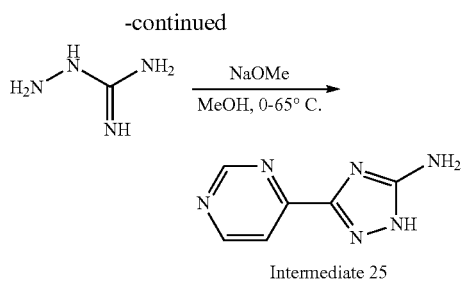

Intermediate 25

Intermediate 23 (1.6 g, 10.5 mmol) was added drop-wise to a vigorously stirring mixture of aminoguanidine sulfate (10.3 g, 42.1 mmol, 4 eq) in freshly prepared NaOMe (using 968 mg, 42.1 mmol of Na in 28 mL of dry MeOH) at 0° C. The resulting mixture was heated to reflux for 20 h. The mixture was then cooled to RT, carefully poured over ice cold water (20 mL) and concentrated in vacuo. The crude residue was purified over neutral alumina using 4-10% MeOH—CHCl$_3$ as the eluent to give Intermediate 25 (500 mg, 26%). MS: 163 [M+H]$^+$; TLC: 20% MeOH in CHCl$_3$: R$_f$: 0.20.

Preparation of Intermediate 26

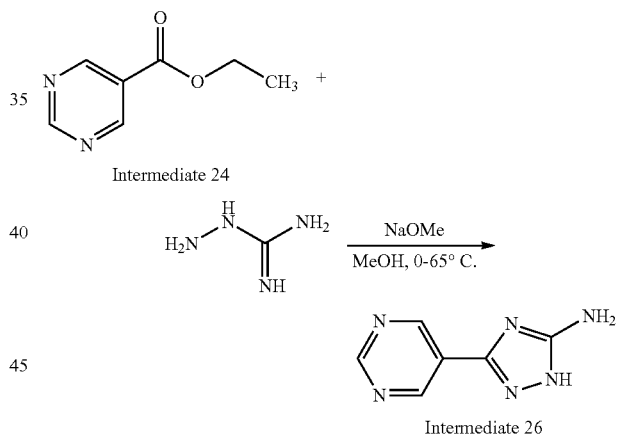

Intermediate 26

General Procedure 9 was followed to obtain Intermediate 26 (500 mg, 45%). $^1$H NMR: (DMSO-d$_6$) δ 12.44 (br s, 1H), 9.17-9.18 (m, 3H), 6.32 (s, 2H); TLC: 20% MeOH in CHCl$_3$: R$_f$: 0.20.

Preparation of Intermediate 27

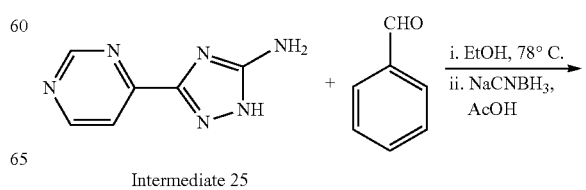

Intermediate 25

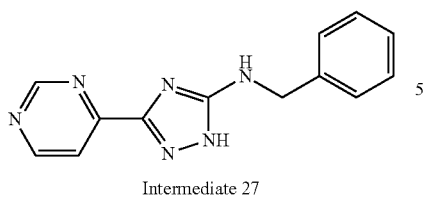

Intermediate 27

General Procedure 2 was followed to obtain Intermediate 27 (210 mg, 34%). $^1$H NMR: (DMSO-$d_6$) δ 12.80 (s, 1H), 9.18 (s, 1H), 8.83 (s, 1H), 7.92 (d, J=4.4 Hz, 1H), 7.25-7.40 (m, 5H), 4.44 (d, J=5.7 Hz, 2H); TLC: EtOAc: $R_f$: 0.30.

Preparation of Intermediate 28

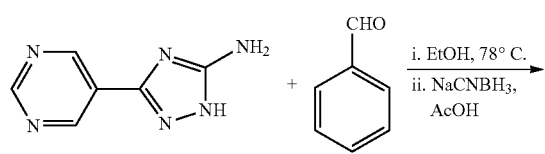

Intermediate 26

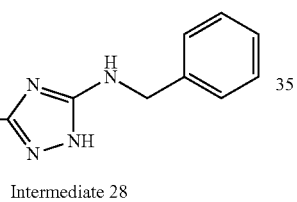

Intermediate 28

General Procedure 2 was followed to obtain Intermediate 28 (160 mg, 20%). MS: 253 [M+H]$^+$; TLC: EtOAc: $R_f$: 0.30.

Preparation of Cmpd 33 [General Procedure 10]

General Procedure 10 was followed in the preparation of Cmpd 33.

General Procedure 10

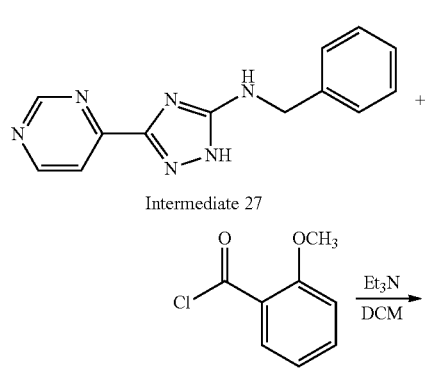

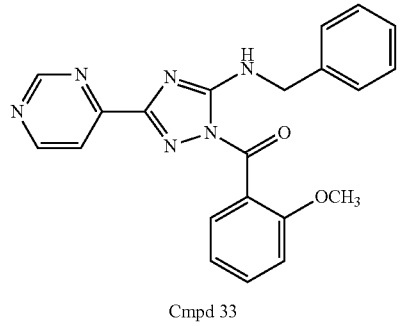

Cmpd 33

2-Methoxybenzoyl chloride (72 μL, 0.54 mmol, 2 eq) was added to a solution of Intermediate 27 (70 mg, 0.27 mmol) in Et$_3$N (0.18 mL, 1.35 mmol) and DCM (3 mL) at 0° C. The resulting mixture was allowed to stir at RT for 2 h. The reaction mixture was then diluted with water (5 mL) and extracted with DCM (3×15 mL). The combined organic layers were washed with saturated aqueous NaHCO$_3$ (10 mL), water (2×5 mL), brine (15 mL), dried over Na$_2$SO$_4$, filtered and concentrated in vacuo. The crude material was purified by column chromatography over silica gel (100-200 mesh) using a gradient mixture of 0-70% EtOAc-hexane as the eluent to afford Cmpd 33 (45 mg, 29%). $^1$H NMR: (DMSO-$d_6$) δ 9.21 (s, 1H), 8.90 (d, J=5.1 Hz, 1H), 8.59 (t, J=6.0 Hz, 1H), 7.93 (d, J=5.1 Hz, 1H), 7.08-7.60 (m, 10H), 4.72 (d, J=5.7 Hz, 2H), 3.77 (s, 3H); MS: 387 [M+H]$^+$; MP: 192-195° C.; TLC: 40% hexane in EtOAc: $R_f$: 0.30.

Example 45

Preparation of Cmpd 34

Cmpd 34

General Procedure 10 was followed by preparative HPLC purification to obtain Cmpd 34 (30 mg, 16%). $^1$H NMR:

(DMSO-d$_6$) δ 9.26 (s, 1H), 9.11 (s, 2H), 8.64 (t, J=6.3 Hz, 1H), 7.07-7.60 (m, 9H), 4.71 (d, J=6.3 Hz, 2H), 3.78 (s, 3H); MS: 387 [M+H]$^+$; MP: 154-157° C.; TLC: 40% EtOAc in hexane: R$_f$: 0.20.

Example 46

Preparation of Cmpd 35

General Scheme VII.

A synthetic scheme useful for synthesis of compounds described herein including Cmpd 35 is disclosed in General Scheme VII following, wherein the terms "Ar," "R$^1$" and "R$^2$" are as defined in Example 1.

General Scheme VII

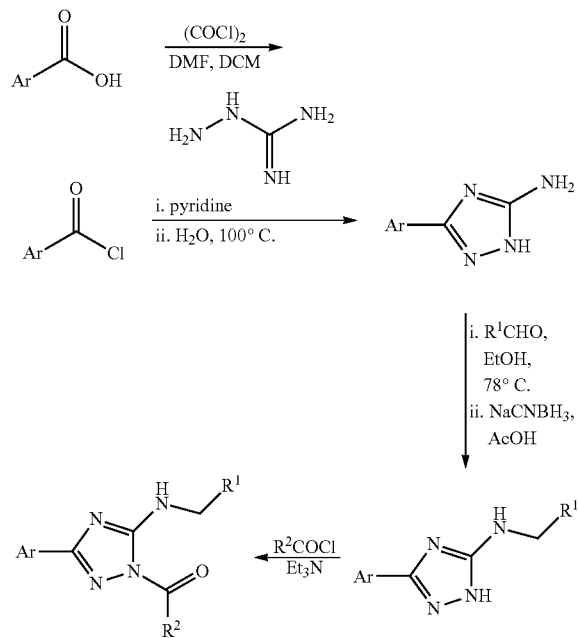

A description of the synthesis of Intermediates 29, 30 and Cmpd 35 follows.

Preparation of Intermediate 29

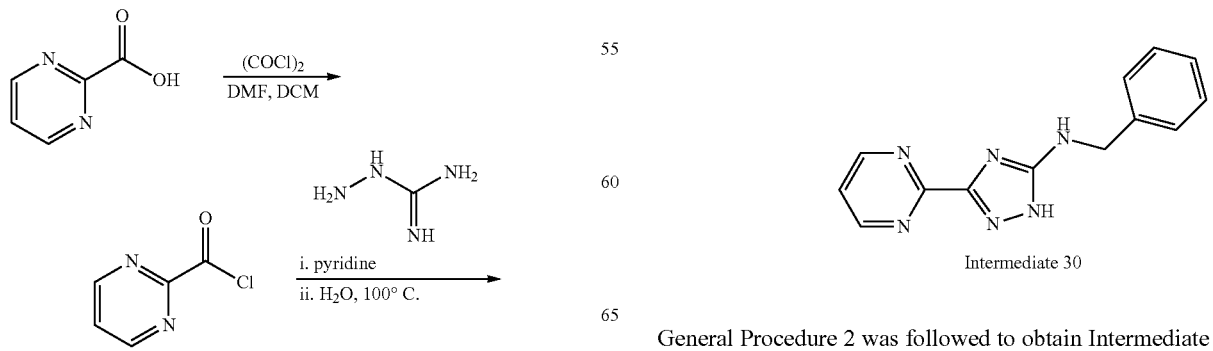

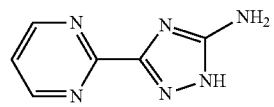

Intermediate 29

Oxalyl chloride (2.36 mL, 24.2 mmol, 1.5 eq) and a catalytic quantity of DMF were added to a solution of pyrimidine-2-carboxylic acid (2 g, 16.1 mmol) in dry DCM (30 mL) at 0° C. The resulting mixture was allowed to warm to RT and stir for 3 h. The volatiles were removed in vacuo and the residue was thoroughly dried to afford pyrimidine-2-carboxylic acid chloride (2.1 g, 14.8 mmol) as a black solid. The crude material was added portion-wise to a solution of aminoguanidine sulfate (5.5 g, 22.2 mmol, 1.5 eq) in pyridine (20 mL) at 0° C. The resulting mixture was allowed to warm to RT and stir for 14 h. The mixture was then neutralized with saturated aqueous NaHCO$_3$, extracted with t-BuOH (5×50 mL), dried over Na$_2$SO$_4$, filtered and concentrated in vacuo. The crude material was dissolved in water (45 mL) and the resulting solution was heated to 100° C. for 24 h. The reaction mixture was then cooled to RT, extracted with t-BuOH (5×30 mL), dried over Na$_2$SO$_4$, filtered and concentrated in vacuo to afford Intermediate 29 (650 mg, 25%) as off-white solid. TLC: 30% MeOH in CHCl$_3$: R$_f$: 0.20.

Preparation of Intermediate 30

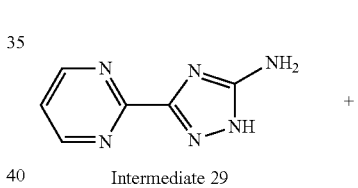

Intermediate 29

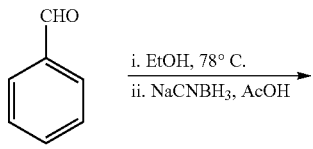

Intermediate 30

General Procedure 2 was followed to obtain Intermediate 30 (120 mg, 17%). MS: 253 [M+H]$^+$; TLC: EtOAc: R$_f$: 0.30.

Preparation of Cmpd 35

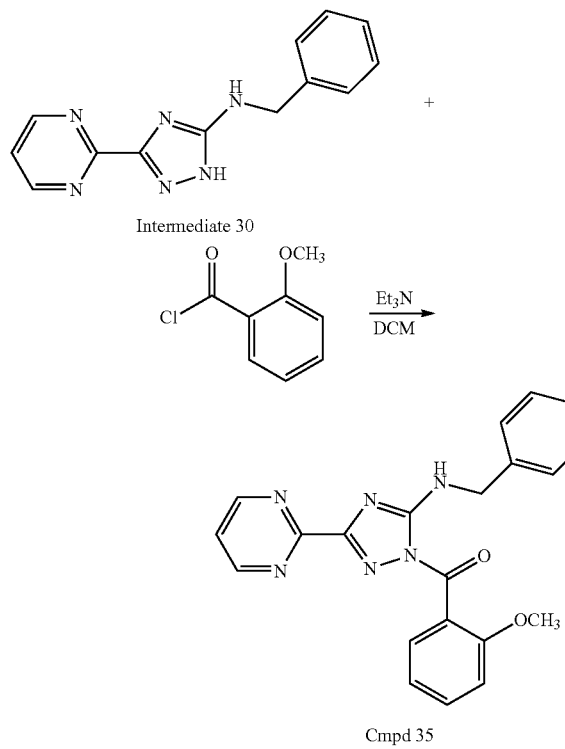

General Procedure 10 was followed to obtain Cmpd 35 (32 mg, 21%). $^1$H NMR: (DMSO-$d_6$) δ 8.86 (d, J=5.1 Hz, 2H), 8.44 (t, J=6.0 Hz, 1H), 7.08-7.59 (m, 10H), 4.73 (d, J=6.3 Hz, 2H), 3.77 (s, 3H); MS: 387 [M+H]$^+$; MP: 203-205° C.; TLC: 40% hexane in EtOAc: $R_f$: 0.40.

Example 47

Preparation of Cmpd 36

General Scheme VIII.

A synthetic scheme useful for synthesis of compounds described herein including Cmpd 36 is disclosed in General Scheme VII following, wherein the terms "Ar," "R$^1$" and "R$^2$" are as defined in Example 1.

General Scheme VIII.

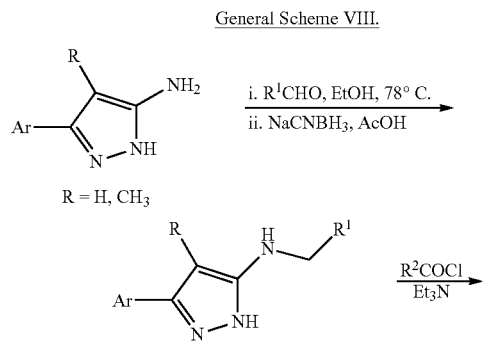

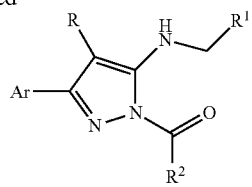

Preparation of Intermediate 31

General Procedure 11 was followed in the preparation of Intermediate 31.
General Procedure 11

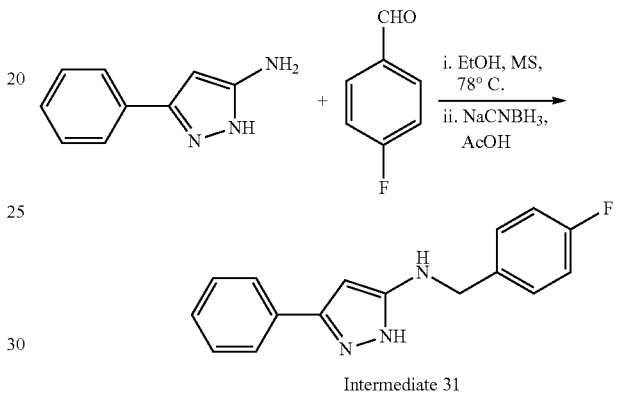

4-Fluorobenzaldehyde (0.54 mL, 5.03 mmol, 2 eq) and molecular sieves (4 Å powder) were added to a solution of 3-amino-5-phenylpyrazole (400 mg, 2.51 mmol) in EtOH (20 mL) at RT and the resulting mixture was heated to reflux. After 8 h, the reaction mixture was cooled to 0° C. and AcOH (0.4 mL) and NaCNBH$_3$ (316 mg, 5.03 mmol, 2 eq) were added. The mixture was then allowed to warm to RT and stir for 15 h. The solvent was evaporated and the residue was dissolved in EtOAc (100 mL) and filtered through a Celite pad to remove inorganic materials. The filtrate was then washed with saturated aqueous NaHCO$_3$ (2×20 mL), water (20 mL), brine (20 mL), dried over Na$_2$SO$_4$, filtered and concentrated in vacuo. The crude material was purified by column chromatography over silica gel (100-200 mesh) by using a solvent gradient of 0-50% EtOAc-petroleum ether as the eluent to afford Intermediate 31 (240 mg, 36%) as an off white solid. MS: 268 [M+H]$^+$; TLC: EtOAc: $R_f$: 0.60.

Preparation of Cmpd 36

General Procedure 12 was followed in the preparation of Cmpd 36.
General Procedure 12

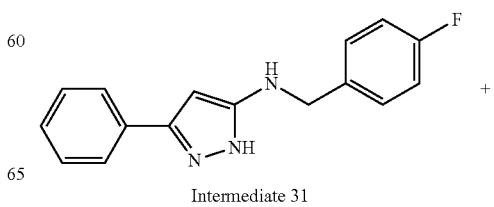

Intermediate 31

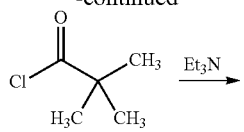

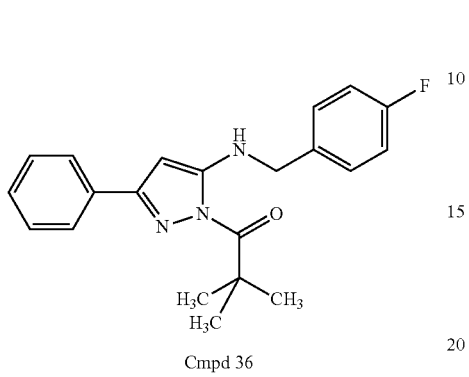

Cmpd 36

Pivaloyl chloride (32 μL, 0.26 mmol, 1.2 eq) was added to a solution of Intermediate 31 (60 mg, 0.22 mmol) in triethylamine (3 mL) at RT and stirred for 3 h. The reaction mixture was diluted with water (5 mL) and extracted with EtOAc (20 mL). The organic layer was washed with water (2×5 mL), saturated aqueous NaHCO$_3$ (5 mL), brine (5 mL), dried over Na$_2$SO$_4$, filtered and concentrated in vacuo. The crude compound was purified by column chromatography over silica gel (100-200 mesh) by using a gradient mixture of 0-10% EtOAc-hexane as the eluent to afford Cmpd 36 (23 mg, 29%). $^1$H NMR: (DMSO-d$_6$) δ 7.79-7.84 (m, 3H), 7.37-7.49 (m, 5H), 7.17 (t, J=8.8 Hz, 2H), 5.89 (s, 1H), 4.38 (d, J=6.2 Hz, 2H), 1.49 (s, 9H); MS: 352 [M+H]$^+$; TLC: 20% EtOAc in hexane: R$_f$: 0.60.

Example 48

Preparation of Intermediate 32

General Procedure 11 was followed to afford Intermediate 32 (200 mg, 24%). MS 269 [M+H]$^+$; TLC: EtOAc: R$_f$: 0.40.

Example 49

Preparation of Cmpd 37

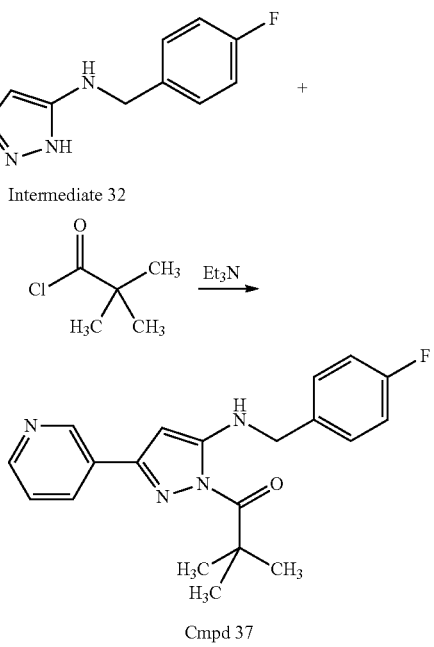

Cmpd 37

General Procedure 12 was followed to afford Cmpd 37 (10 mg, 15%). $^1$H NMR: (DMSO-d$_6$) δ 8.99 (d, J=1.5 Hz, 1H), 8.58 (dd, J=4.9, 1.3 Hz, 1H), 8.14-8.16 (m, 1H), 7.83 (t, J=6.4 Hz, 1H), 7.45-7.48 (m, 3H), 7.16 (t, J=8.7 Hz, 2H), 6.01 (s, 1H), 4.38 (d, J=6.1 Hz, 2H), 1.49 (s, 9H); MS: 353 [M+H]$^+$; TLC: 30% EtOAc in hexane: R$_f$: 0.60.

Example 50

Preparation of Intermediate 33

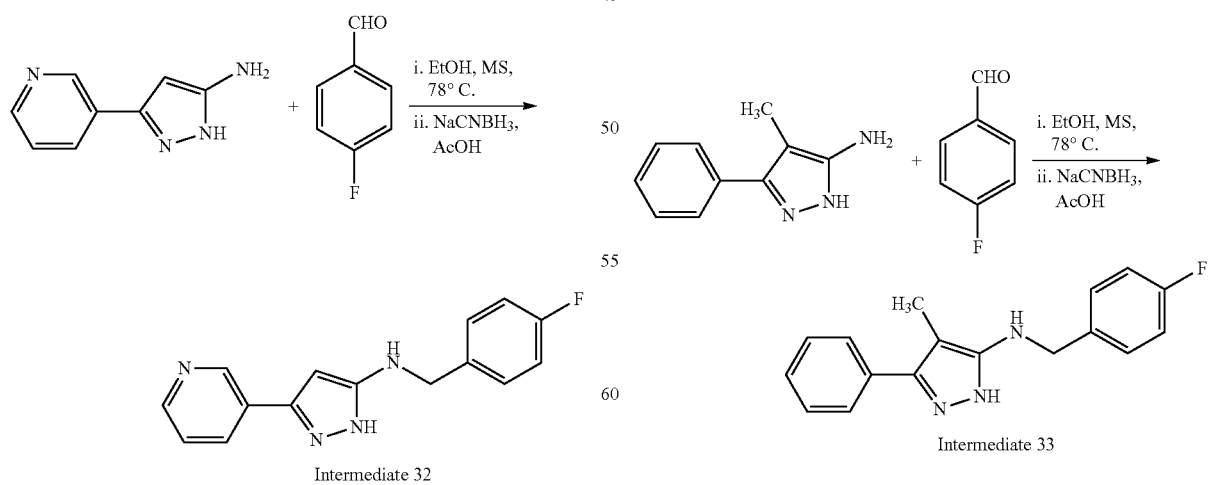

Intermediate 33

General Procedure 11 was followed to afford Intermediate 33 (35 mg, 44%). MS: 282 [M+H]$^+$; TLC: 50% EtOAc in hexane: R$_f$: 0.50.

Example 51

Preparation of Cmpd 38

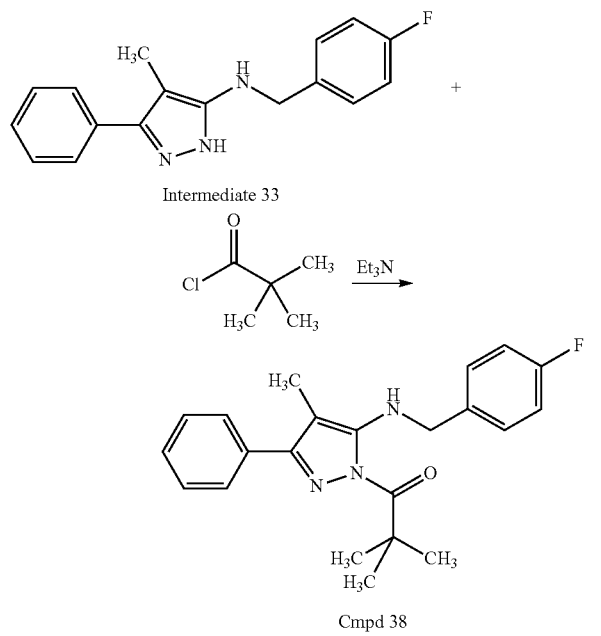

Intermediate 33

Cmpd 38

General Procedure 12 was followed to afford Cmpd 38 (6 mg, 7%). $^1$H NMR: (DMSO-$d_6$) δ 7.56-7.59 (m, 2H), 7.34-7.49 (m, 6H), 7.18 (t, J=9.0 Hz, 2H), 4.52 (d, J=6.8 Hz, 2H), 2.04 (s, 3H), 1.43 (s, 9H); MS: 366 [M+H]$^+$; TLC: 20% EtOAc in hexane: $R_f$: 0.70.

Example 52

Preparation of Cmpd 39

General Scheme IX.

A synthetic scheme useful for synthesis of compounds described herein including Cmpd 39 is disclosed in General Scheme IX following, wherein the terms "Ar," "R$^1$" and "R$^2$" are as defined in Example 1.

General Scheme IX

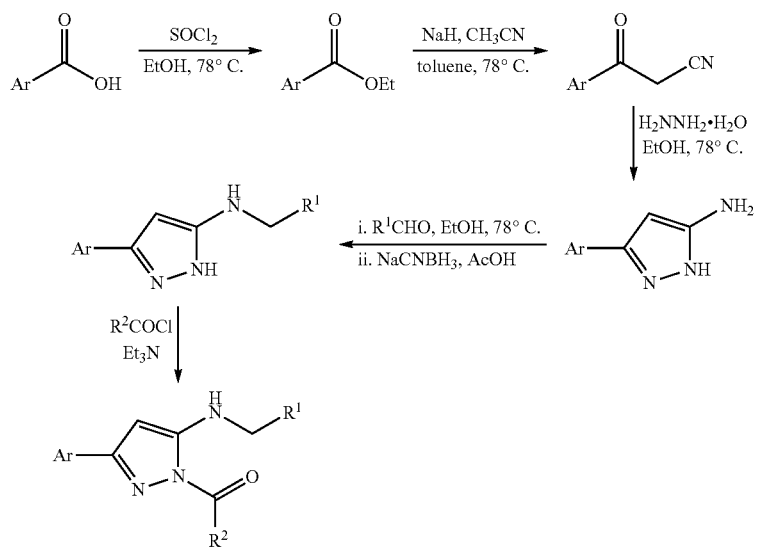

A description of the syntheses of Intermediates 34-37 and Cmpd 39 follows.

Preparation of Intermediate 34 [General Procedure 13]

General Procedure 13 was followed in the preparation of Intermediate 34.

General Procedure 13

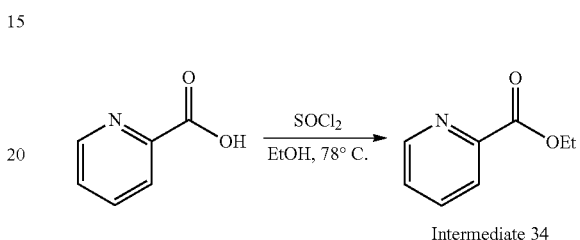

Intermediate 34

Thionyl chloride (5.4 mL, 73.2 mmol, 3 eq) was added to a solution of picolinic acid (3 g, 24.4 mmol) in EtOH (50 mL) at 0° C. The resulting mixture was heated to reflux and allowed to stir for 2 h. The mixture was then cooled and the solvent was evaporated. The resulting residue was poured into saturated aqueous NaHCO$_3$ and extracted with EtOAc (2×50 mL). The combined organic layers were dried over Na$_2$SO$_4$, filtered and concentrated in vacuo. The crude material was purified by column chromatography over silica gel (100-200 mesh) by using DCM as the eluent to afford Intermediate 34 (3 g, 81%) as a colorless liquid. MS: 152 [M+H]$^+$; TLC: 10% MeOH/NH$_3$ in CHCl$_3$: $R_f$: 0.70.

Preparation of Intermediate 35 [General Procedure 14]

General Procedure 14 was followed in the preparation of Intermediate 35.

General Procedure 14

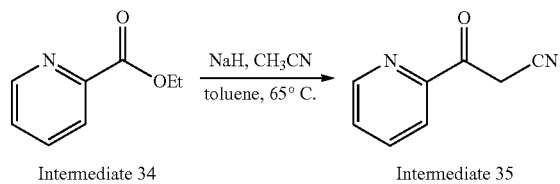

Intermediate 34          Intermediate 35

A solution of Intermediate 34 (3 g, 19.6 mmol) and CH₃CN (0.8 mL, 19.6 mmol, 1 eq) in dry toluene (10 mL) was slowly added to a mixture of NaH (784 mg, 19.6 mmol, 1 eq, 60% in mineral oil) in toluene (50 mL) at 65° C. The resulting mixture was allowed to stir at 65° C. for 16 h. The reaction mixture was then cooled to RT and quenched with ice cold water (20 mL). The resulting solid was filtered to afford Intermediate 35 (1.5 g, 53%) as a brown solid. $^1$H NMR: (CDCl₃) δ 8.70 (d, J=4.8 Hz, 1H), 8.12 (d, J=7.5 Hz, 1H), 7.90-7.94 (m, 1H), 7.56-7.60 (m, 1H), 4.41 (s, 2H); MS: 147 [M+H]$^+$; TLC: EtOAc: R$_f$: 0.40.

Preparation of Intermediate 36 [General Procedure 15]

General Procedure 15 was followed in the preparation of Intermediate 36.

General Procedure 15

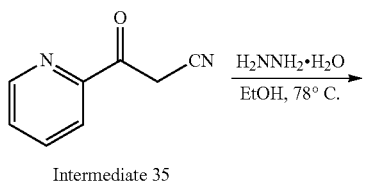

Intermediate 35

Intermediate 36

Hydrazine hydrate (0.34 mL, 6.8 mmol, 1 eq) was added to a solution of Intermediate (1 g, 6.8 mmol) in EtOH (30 mL) at RT. The mixture was then heated to reflux and allowed to stir for 20 h. The solvent was then evaporated. The resulting crude material was triturated with Et₂O (2×20 mL) and dried under vacuum to afford Intermediate 36 (700 mg, 64%) as a brown liquid. $^1$H NMR: (DMSO-d₆) δ 8.53 (d, J=4.4 Hz, 1H), 7.78 (d, J=4.4 Hz, 2H), 7.23-7.26 (m, 1H), 5.95 (s, 1H), 4.84 (br s, 2H); MS: 161 [M+H]$^+$; TLC: EtOAc: R$_f$: 0.20.

Preparation of Intermediate 37

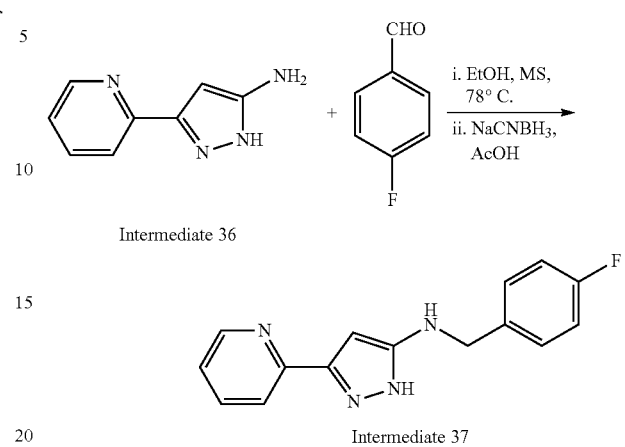

Intermediate 36

Intermediate 37

General Procedure 11 was followed to afford Intermediate 37 (450 mg). MS: 269 [M+H]$^+$; TLC: EtOAc: R$_f$: 0.40.

Preparation of Cmpd 39

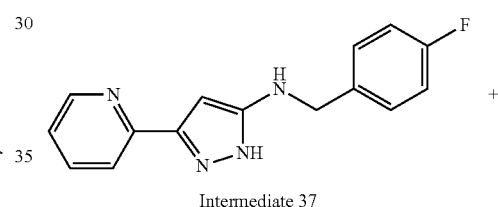

Intermediate 37

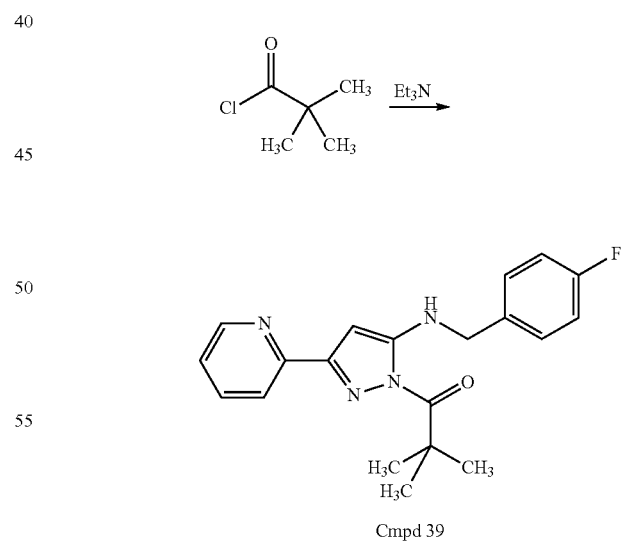

Cmpd 39

General Procedure 12 was followed to afford Cmpd 39 (40 mg, 30%). $^1$H NMR: (DMSO-d₆) δ 8.58 (d, J=4.4 Hz, 1H), 7.86-7.98 (m, 3H), 7.38-7.46 (m, 3H), 7.18 (t, J=8.8 Hz, 2H), 5.84 (s, 1H), 4.40 (d, J=6.2 Hz, 2H), 1.50 (s, 9H); MS: 353 [M+H]; MP: 102-103° C.; TLC: 20% EtOAc in hexane: R$_f$: 0.60.

Example 53

Preparation of Cmpd 40

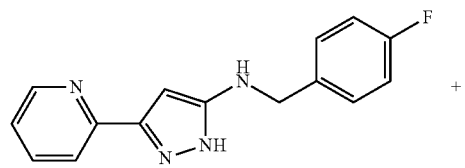

Intermediate 37

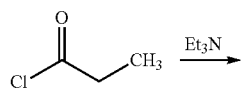

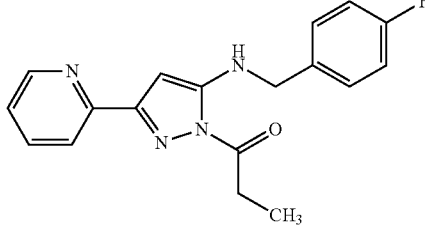

Cmpd 40

General Procedure 12 was followed to afford Cmpd 40 (38 mg, 29%). $^1$H NMR: (DMSO-$d_6$) δ 8.58 (d, J=4.4 Hz, 1H), 7.97 (d, J=7.9 Hz, 1H), 7.79-7.88 (m, 2H), 7.37-7.46 (m, 3H), 7.17 (t, J=8.8 Hz, 2H), 5.87 (s, 1H), 4.42 (d, J=6.2 Hz, 2H), 3.13 (q, J=7.3 Hz, 2H), 1.17 (t, J=7.3 Hz, 3H); MS: 325 [M+H]$^+$; MP: 106-108° C.; TLC: 20% EtOAc in hexane: $R_f$: 0.50.

Example 54

Preparation of Cmpd 41

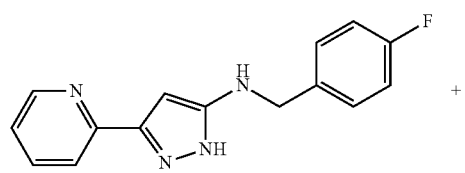

Intermediate 37

-continued

Cmpd 41

General Procedure 12 was followed to afford Cmpd 41 (30 mg, 20%). $^1$H NMR: (DMSO-$d_6$) δ 8.55 (d, J=4.4 Hz, 1H), 7.97 (t, J=5.9 Hz, 1H), 7.71-7.78 (m, 2H), 7.49-7.63 (m, 6H), 7.34-7.37 (m, 1H), 7.20 (t, J=8.8 Hz, 2H), 5.94 (s, 1H), 4.49 (d, J=6.2 Hz, 2H); MS: 407 [M+H], 409 [M+2+H]; MP: 137-136° C.; TLC: 20% EtOAc in hexane: $R_f$: 0.30.

Example 55

General Scheme X

A synthetic scheme useful for synthesis of compounds described herein is disclosed in General Scheme X following, wherein the term "R" is each occurrence is independently "$R^1$" and "$R^2$" as defined in Example 1, and "$Ar^1$" and "$Ar^2$" are defined as "Ar" in Example 1.

General Scheme X

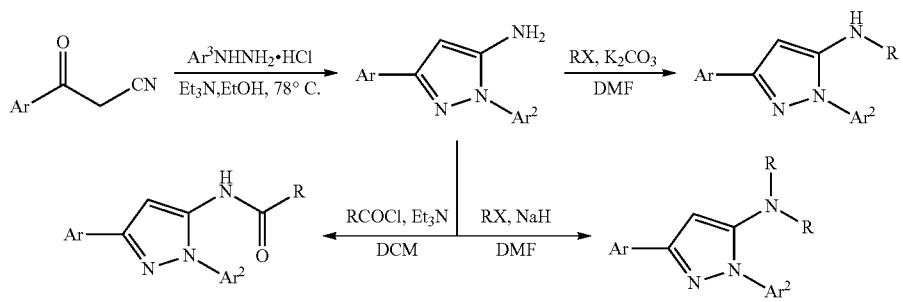

Example 56

Preparation of Cmpd 42 [General Procedure 16]

General Procedure 16 was followed in the preparation of Cmpd 42.

General Procedure 16

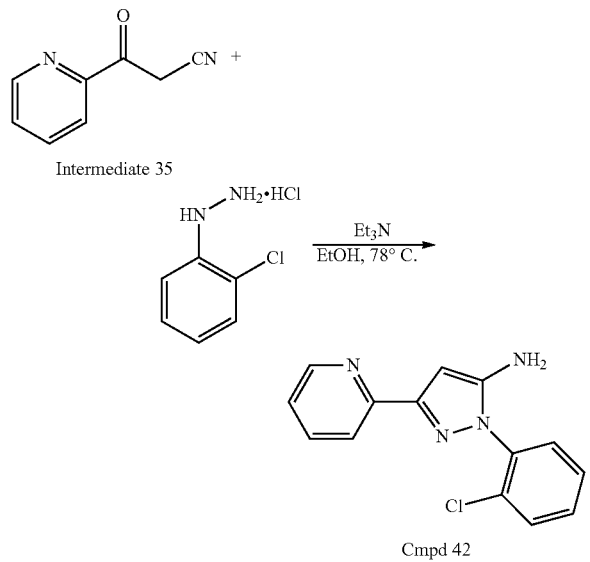

2-Chlorophenylhydrazine hydrochloride (122 mg, 0.68 mmol, 1 eq) and Et$_3$N (95 μL, 0.68 mmol, 1 eq) was added to a solution of Intermediate 35 (100 mg, 0.68 mmol) in EtOH (3 mL). The resulting solution was heated to reflux and allowed to stir for 2 h. The solvent was then evaporated. The crude material was purified by column chromatography over silica gel (100-200 mesh) by using a gradient mixture of 0-70% EtOAc-hexane as the eluent to afford Cmpd 42 (70 mg, 37%). $^1$H NMR: (DMSO-d$_6$) δ 8.56 (d, J=4.4 Hz, 1H), 7.64-7.84 (m, 3H), 7.28-7.29 (m, 1H), 6.00 (s, 1H), 5.31 (s, 2H); MS: 271 [M+H]$^+$, 273 [M+2+H]$^+$; MP: 134-137° C.; TLC: EtOAc: R$_f$: 0.20.

Example 57

Preparation of Cmpd 43 [General Procedure 17]

General Procedure 17 was followed in the preparation of Cmpd 43.

General Procedure 17

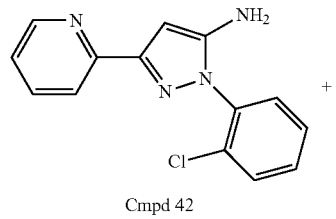

Cmpd 42

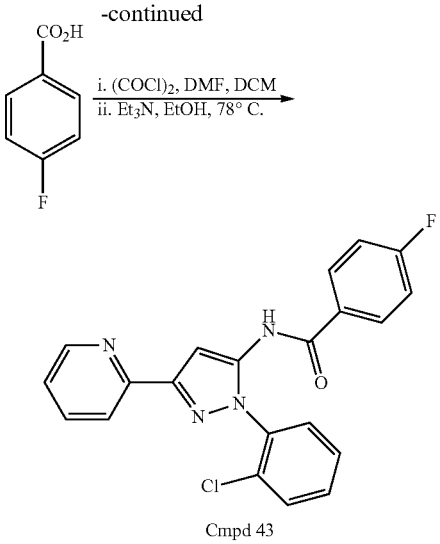

Cmpd 43

Oxalyl chloride (7.2 mL, 5.37 mmol, 1.5 eq) and DMF (0.5 mL) was added to a solution of 4-fluorobenzoic acid in DCM (20 mL) at 0° C. The resulting mixture was allowed to warm to RT and stir for 1 h. The volatiles were evaporated and the mixture was co-distilled with toluene (30 mL). The resulting material was dried under vacuum to afford crude 4-fluorobenzoyl chloride (500 mg) as a colorless liquid, which was used without additional purification. 4-Fluorobenzoyl chloride (49 mg, 0.31 mmol, 1.2 eq) and Et$_3$N (0.36 mL, 2.59 mmol, 10 eq) were added to a solution of Cmpd 42 (70 mg, 0.26 mmol) in DCM (4 mL) at RT and the resulting mixture was allowed to stir for 3 h. The mixture was diluted with water (10 mL) and extracted into EtOAc (30 mL). The organic layer washed with water (2×5 mL), saturated aqueous NaHCO$_3$ (2×5 mL) brine (10 mL), dried over Na$_2$SO$_4$, filtered and concentrated in vacuo. The crude material was purified by column chromatography over silica gel (100-200 mesh) by using a gradient mixture of 0-60% EtOAc-hexane as the eluent to afford Cmpd 43 (25 mg, 25%). $^1$H NMR: (DMSO-d$_6$) δ 10.57 (s, 1H), 8.64 (d, J=4.4 Hz, 1H), 7.97 (d, J=7.9 Hz, 1H), 7.82-7.88 (m, 3H), 7.49-7.68 (m, 4H), 7.31-7.39 (m, 3H), 7.06 (s, 1H); MS: 393 [M+H]$^+$, 395 [M+2+H]$^+$; MP: 186-188° C.; TLC: EtOAc: R$_f$: 0.40.

Example 58

Preparation of Cmpd 44 [General Procedure 18]

General Procedure 18 was followed in the preparation of Cmpd 44.

General Procedure 18

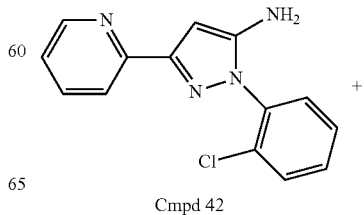

Cmpd 42

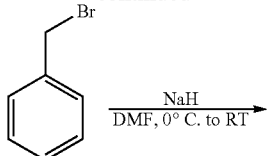

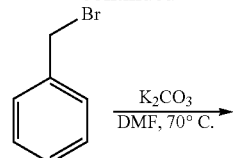

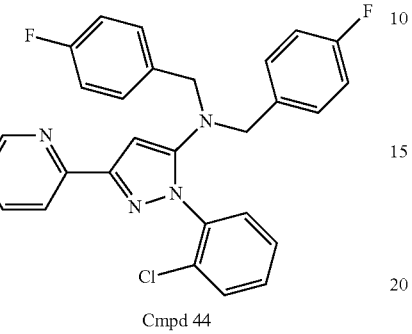

Cmpd 44

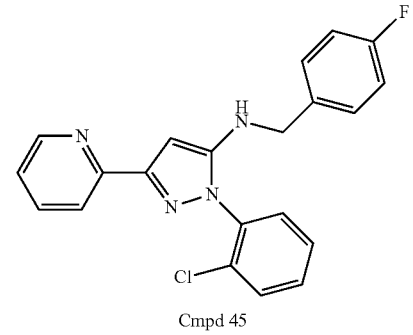

Cmpd 45

Sodium hydride (17.7 mg, 0.37 mmol, 1 eq, 60% in mineral oil) was added to a solution of Cmpd 42 (100 mg, 0.37 mmol) and 4-fluorobenzyl bromide (30 μL, 0.22 mmol, 0.6 eq) in DMF (4 mL) at 0° C. The resulting mixture was allowed to warm to RT and stir for 1 h. The mixture was diluted with water (10 mL) and extracted into EtOAc (30 mL). The organic layer washed with water (2×5 mL), saturated aqueous NaHCO$_3$ (2×5 mL) brine (10 mL), dried over Na$_2$SO$_4$, filtered and concentrated in vacuo. The crude material was purified by column chromatography over silica gel (100-200 mesh) by using a gradient mixture of 0-20% EtOAc-hexane as the eluent to afford Cmpd 44 (25 mg, 13%). $^1$H NMR: (DMSO-d$_6$) δ 8.57 (d, J=4.4 Hz, 1H), 7.73-7.88 (m, 3H), 7.49-7.62 (m, 3H), 7.30-7.33 (m, 1H), 7.06-7.15 (m, 8H), 6.63 (s, 1H), 3.96 (s, 4H); MS: 487 [M+H]$^+$, 489 [M+2+H]$^+$; MP: 113-117° C.; TLC: EtOAc: R$_f$: 0.60.

Example 59

Preparation of Cmpd 45 [General Procedure 19]

General Procedure 19 was followed in the preparation of Cmpd 45.

General Procedure 19

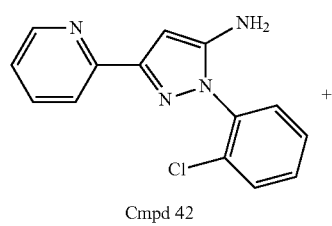

Cmpd 42

4-Fluorobenzyl bromide (126 mg, 0.67 mmol, 0.6 eq) and K$_2$CO$_3$ (310 mg, 2.24 mmol, 2 eq) were added to a solution of Cmpd 42 (300 mg, 1.11 mmol) in DMF (8 mL) at RT. The resulting mixture was heated to 70° C. and allowed to stir for 8 h. The mixture was diluted with water (10 mL) and extracted with EtOAc (30 mL). The organic layer was washed with water (2×5 mL), saturated aqueous NaHCO$_3$ (2×5 mL) brine (10 mL), dried over Na$_2$SO$_4$, filtered and concentrated in vacuo. The crude material was partially purified by preparative-TLC using 40% EtOAc-hexane and subsequently by preparative-HPLC to afford Cmpd 45 (16 mg, 4%) as an off-white solid. $^1$H NMR: (DMSO-d$_6$) δ 8.51 (d, J=4.4 Hz, 1H), 7.70-7.83 (m, 3H), 7.54-7.60 (m, 3H), 7.40-7.43 (m, 2H), 7.12-7.27 (m, 3H), 6.13 (t, J=5.7 Hz, 1H), 5.87 (s, 1H), 4.24 (d, J=5.7 Hz, 2H); MS: 379 [M+H]$^+$, 381 [M+2+H]$^+$; MP: 159-162° C.; TLC: EtOAc: R$_f$: 0.30.

Example 60

General Scheme XI

A synthetic scheme useful for synthesis of compounds described herein is disclosed in General Scheme XI following, wherein the terms "Ar," "R$^1$" and "R$^2$" are as defined in Example 1.

General Scheme XI

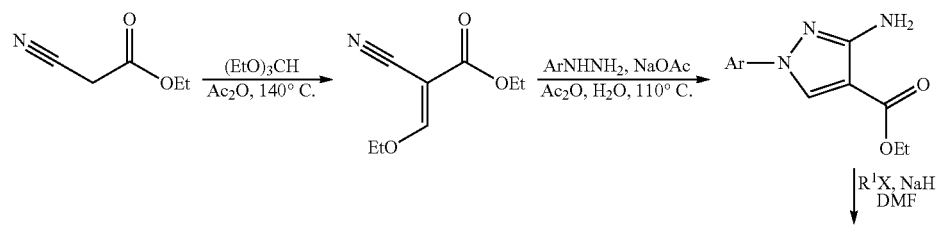

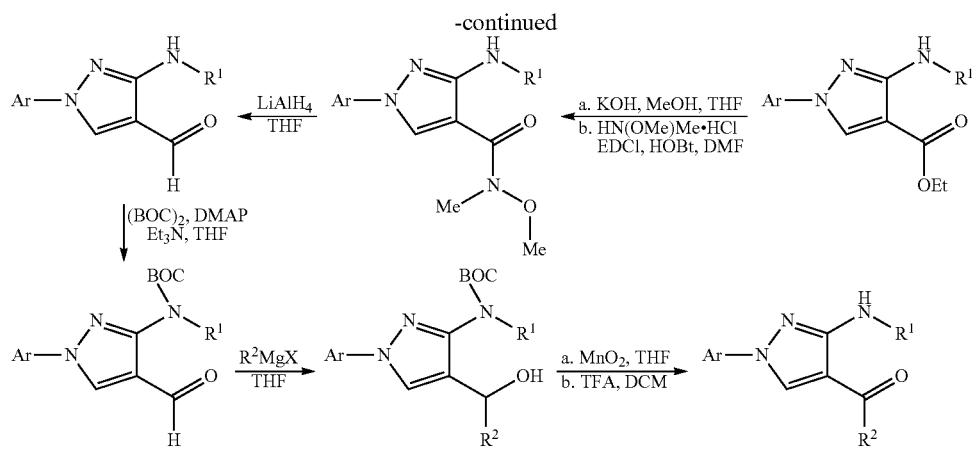

Example 61

Preparation of Intermediate 38

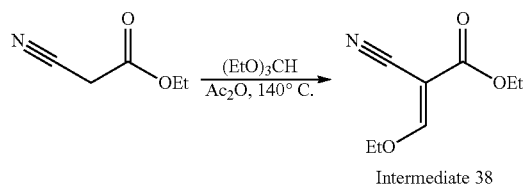 [SMILES: "(EtO)3CH" ; CCOC(=O)CC#N ; "Ac2O, 140° C." ; CCO/C=C(\C#N)C(=O)OCC]

Intermediate 38

A solution of ethyl cyanoacetate (20 g, 176.8 mmol) and triethyl orthoformate (29.4 mL, 176.8 mmol) in acetic anhydride (100 mL) was heated to 140° C. and allowed to stir for 5 h. The solvent was then evaporated to afford crude Intermediate 38 (23 g, 76%) as low melting solid. MS: 170 [M+H]$^+$; TLC: 30% EtOAc in hexane: R$_f$: 0.40.

Example 62

Preparation of Intermediate 39

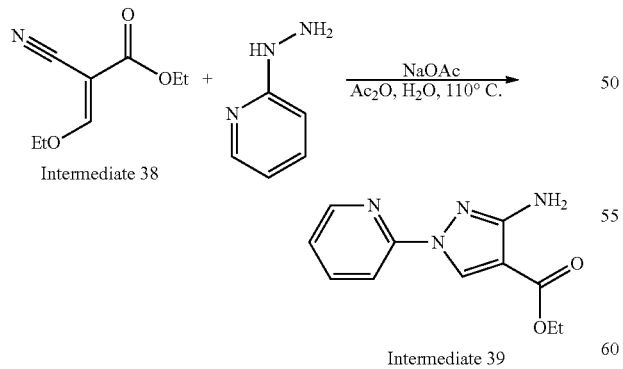

Sodium acetate (8.2 g, 100 mmol, 2 eq) was added to a solution of Intermediate 38 (8.45 g, 50.0 mmol) and 2-hydrazinopyridine (5 g, 45.5 mmol, 0.9 eq) in AcOH (100 mL) and water (20 mL). The resulting mixture was heated at 110° C. and allowed to stir for 16 h. The mixture was then allowed to cool and ice-cold water was added. The precipitate was collected by filtration and washed with Et$_2$O and dried under vacuum to afford Intermediate 39 (4 g, 38%) as a pale yellow solid. $^1$H NMR: (DMSO-d$_6$) δ 8.48-8.49 (m, 1H), 8.00-8.04 (m, 1H), 7.87 (d, J=8.3 Hz, 1H), 7.79 (s, 1H), 7.65 (br s, 2H), 7.33-7.36 (m, 1H), 4.22 (q, J=7.0 Hz, 2H), 1.28 (t, J=7.0 Hz, 3H); MS: 233 [M+H]$^+$; TLC: 15% EtOAc in hexane: R$_f$: 0.50.

Example 63

Preparation of Cmpd 46

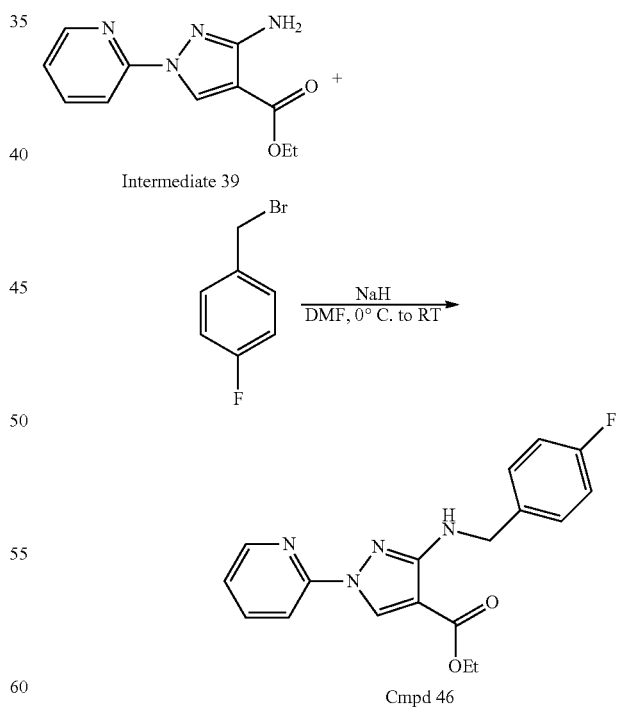

Sodium hydride (603 mg, 15.1 mmol, 1 eq, 60% in mineral oil) was added to a solution of Intermediate 39 (3.5 g, 15.1 mmol) in DMF (300 mL) at 0° C. After 30 minutes, a solution of 4-fluorobenzyl bromide (2.85 g, 15.1 mmol, 1 eq) in DMF (50 mL) was added and the resulting mixture was allowed to warm to RT. After 5 h, the reaction mixture was diluted with water (100 mL) and extracted with EtOAc (3×100 mL). The combined organic layers were washed with water (5×50 mL), brine (50 mL), dried over Na$_2$SO$_4$, filtered and concentrated in vacuo. The crude material was purified by column chromatography over silica gel (100-200 mesh) by using a gradient mixture of 0-5% EtOAc-hexane as the eluent to afford a partially pure product. The material was then recrystallized from Et$_2$O and pentane to afford Cmpd 46 (2.8 g, 55%) as a pale yellow solid. $^1$H NMR: (DMSO-d$_6$) δ 9.50 (t, J=6.6 Hz, 1H), 8.45-8.46 (m, 1H), 8.00-8.05 (m, 1H), 7.82-7.89 (m, 2H), 7.24-7.38 (m, 3H), 7.11 (t, J=8.8 Hz, 2H), 4.88 (d, J=6.6 Hz, 2H), 4.17 (q, J=7.0 Hz, 2H), 1.24 (t, J=7.0 Hz, 3H); MS: 341 [M+H]$^+$; MP: 99-100° C.; TLC: 15% EtOAc in hexane: R$_f$: 0.40.

Example 64

Preparation of Cmpd 47

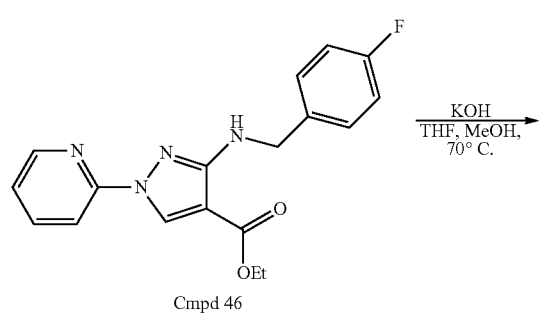

Cmpd 46

Potassium hydroxide (922 mg, 16.5 mmol) was added to a solution of Cmpd 46 (2.8 g, 8.23 mmol) in THF (10 mL) and MeOH (10 mL). The resulting mixture was heated to 70° C. and allowed to stir for 16 h. The reaction mixture was then neutralized with aqueous HCl (2N) and the resulting precipitate was collected by filtration, washed with water (50 mL) and dried thoroughly to afford Cmpd 47 (2.1 g, 84%) as an off-white solid. MS: 313 [M+H]$^+$; TLC: 50% EtOAc in hexane: R$_f$: 0.30.

Example 65

Preparation of Cmpd 48 [General Procedure 20]

General Procedure 20 was followed in the preparation of Cmpd 48.
General Procedure 20

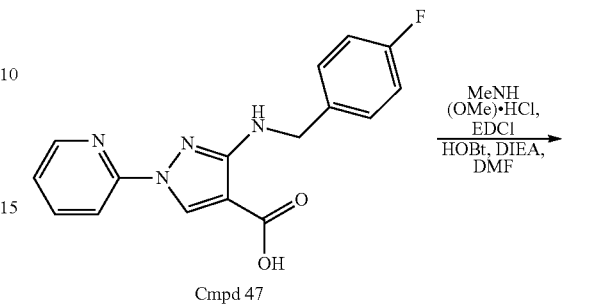

N,O-Dimethylhydroxylamine hydrochloride (979 mg, 10.1 mmol, 1.5 eq) was added to a mixture of EDCI (2.0 g, 10.1 mmol, 1.5 eq), HOBt (3.1 g, 21.2 mmol, 3.2 eq), DIEA (3.5 mL, 20.2 mmol, 3 eq) and Cmpd 47 (2.1 g, 6.73 mmol) in DMF (30 mL). The resulting mixture was allowed to stir at RT for 16 h. The mixture was then diluted with water (50 mL) and extracted with EtOAc (100 mL). The organic layer was washed with water (2×50 mL), saturated aqueous NaHCO$_3$ (50 mL), brine (50 mL), dried over Na$_2$SO$_4$, filtered and concentrated in vacuo. The crude material was purified by column chromatography over silica gel (100-200 mesh) by using a gradient mixture of 0-30% EtOAc-hexane as the eluent to afford Cmpd 48 (1.5 g, 65%). $^1$H NMR: (DMSO-d$_6$) δ 9.29 (t, J=6.6 Hz, 1H), 8.49 (d, J=4.9 Hz, 1H), 7.98-8.04 (m, 1H), 7.82-7.85 (m, 1H), 7.69 (s, 1H), 7.34-7.38 (m, 1H), 7.06-7.19 (m, 4H), 4.54 (d, J=7.0 Hz, 2H), 3.28 (s, 3H), 3.14 (s, 3H); MS: 356 [M+H]$^+$; MP: 88-99° C.; TLC: 50% EtOAc in hexane: R$_f$: 0.30.

Example 66

Preparation of Cmpd 49

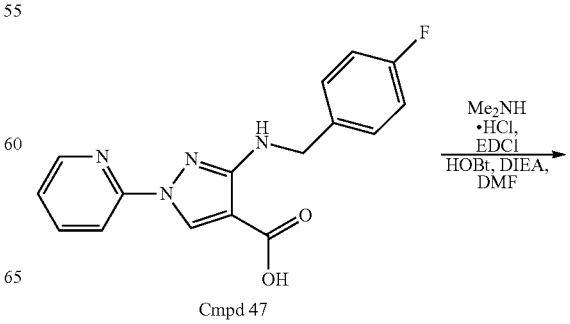

Cmpd 47

-continued

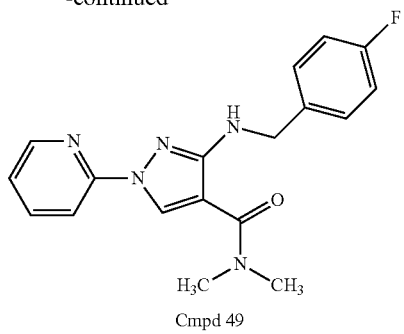

Cmpd 49

General Procedure 20 was followed to afford Cmpd 49 (31 mg, 32%). $^1$H NMR: (DMSO-d$_6$) δ 9.23 (t, J=6.6 Hz, 1H), 8.48 (d, J=3.5 Hz, 1H), 7.99-8.03 (m, 1H), 7.88-7.91 (m, 1H), 7.49 (s, 1H), 7.32-7.35 (m, 1H), 7.09-7.20 (m, 4H), 4.50 (d, J=6.6 Hz, 2H), 2.57-2.89 (m, 6H); MS: 340 [M+H]$^+$; MP: 107-109° C.; TLC: 50% EtOAc in hexane: R$_f$: 0.30.

Example 67

Preparation of Intermediate 40

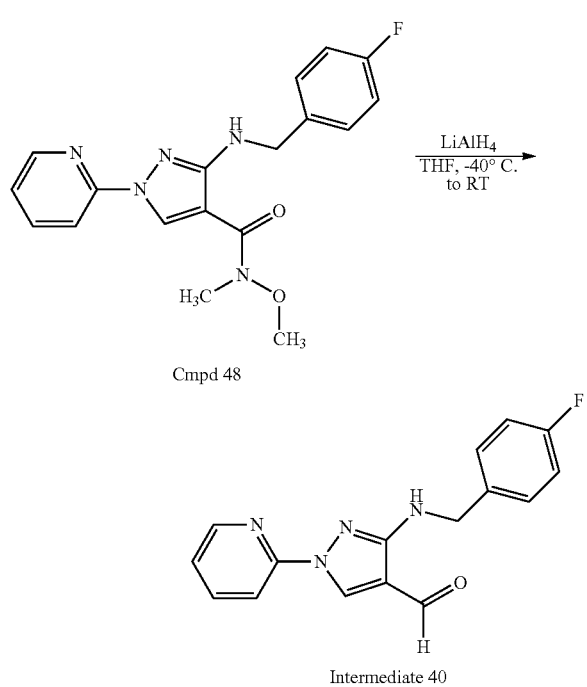

Lithium aluminum hydride (642 mg, 16.9 mmol) was added to a solution of Cmpd 48 (1.5 g, 4.22 mmol) in THF (20 mL) at −40° C. The resulting mixture was allowed to warm to 0° C. and stir for 5 h. The mixture was then quenched with saturated aqueous NH$_4$Cl (20 mL) and extracted with EtOAc (30 mL). The organic layer washed with water (2×50 mL), saturated aqueous NaHCO$_3$ (10 mL), brine (10 mL), dried over Na$_2$SO$_4$, filtered and concentrated in vacuo. The crude material was purified by column chromatography over silica gel (100-200 mesh) by using a gradient mixture of 0-10% EtOAc-hexane as the eluent to afford Intermediate (1 g, 80%). $^1$H NMR: (DMSO-d$_6$) δ 10.09 (s, 1H), 9.53 (s, 1H), 8.47 (d, J=5.1 Hz, 1H), 8.05 (t, J=7.9 Hz, 1H), 7.99 (s, 1H), 7.92 (d, J=8.2 Hz, 1H), 7.34-7.37 (m, 3H), 7.15-7.20 (m, 2H), 4.96 (d, J=6.3 Hz, 2H); MS: 297 [M+H]$^+$; TLC: 20% EtOAc in hexane: R$_f$: 0.30.

Example 68

Preparation of Intermediate 41

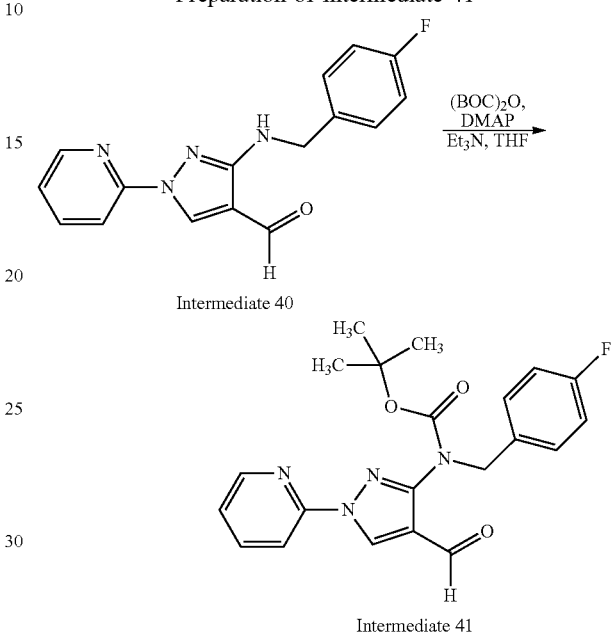

Triethylamine (4.6 mL, 33.7 mmol, 10 eq), DMAP (410 mg, 3.36 mmol, 1 eq) and (BOC)$_2$O (5 mL, 20.5 mmol, 6.1 eq) was added to a solution of Intermediate 40 (1 g, 3.36 mmol) in THF (3 mL). The resulting mixture was allowed to stir at RT for 16 h. The mixture was then diluted with water (75 mL) and extracted with EtOAc (150 mL). The organic layer was washed with water (2×75 mL), brine (75 mL), dried over Na$_2$SO$_4$, filtered and concentrated in vacuo. The crude material was purified by column chromatography over silica gel (100-200 mesh) by using a gradient mixture of 0-15% EtOAc-hexane as the eluent to afford Intermediate 41 (1 g, 76%) as a pale yellow liquid. MS: 397 [M+H]$^+$; TLC: 30% EtOAc in hexane: R$_f$: 0.50.

Example 69

Preparation of Intermediate 42

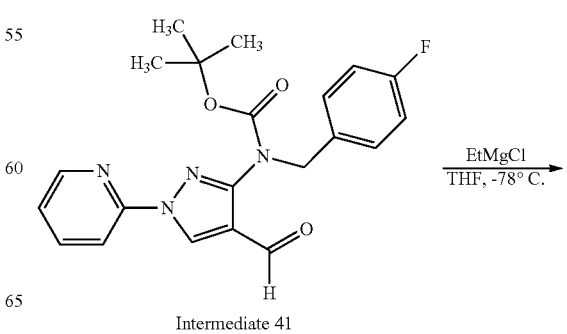

Intermediate 41

-continued

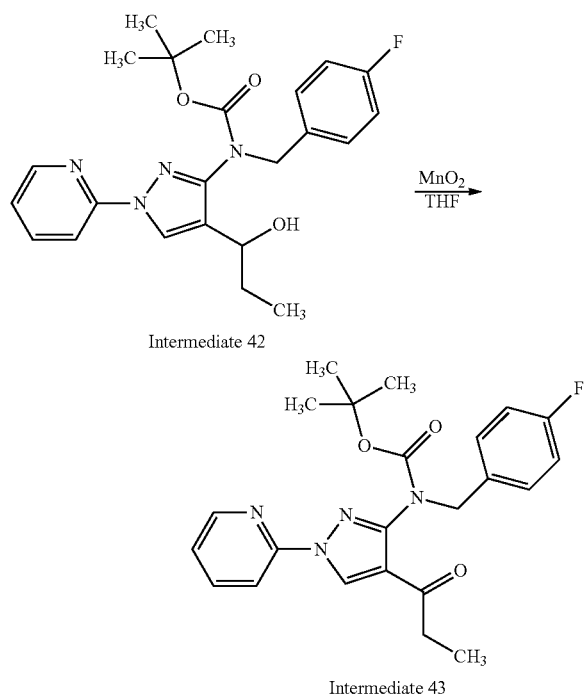

Intermediate 42

Ethyl magnesium chloride (0.75 mL, 1.5 mmol, 3 eq, 2M in THF) was added to a solution of Intermediate 41 (200 mg, 0.50 mmol) in THF (10 mL) at −78° C. The resulting mixture was warmed to 0° C. and allowed to stir for 4 h. The reaction was then quenched with saturated aqueous NH$_4$Cl (20 mL) and extracted with EtOAc (30 mL). The organic layer washed with water (10 mL), saturated aqueous NaHCO$_3$ (10 mL), brine (10 mL), dried over Na$_2$SO$_4$, filtered and concentrated in vacuo. The crude material was purified by column chromatography over silica gel (100-200 mesh) by using a gradient mixture of 0-30% EtOAc-hexane as the eluent to afford Intermediate 42 (140 mg, 65%) as a yellow solid. MS: 427 [M+H]$^+$; TLC: 50% EtOAc in hexane: R$_f$: 0.50.

Example 70

Preparation of Intermediate 43

Intermediate 42

Intermediate 43

Manganese dioxide (245 mg, 2.81 mmol) was added to a solution of Intermediate 42 (120 mg, 0.28 mmol) in THF (10 mL) and the resulting mixture was allowed to stir at RT for 48 h. The mixture was then filtered through Celite and washed with EtOAc (20 mL). The organic phase was washed with water (10 mL), saturated aqueous NaHCO$_3$ (10 mL), brine (10 mL), dried over Na$_2$SO$_4$, filtered and concentrated in vacuo. The crude material was purified by column chromatography over silica gel (100-200 mesh) by using a gradient mixture of 0-30% EtOAc-hexane as the eluent to afford Intermediate 43 (90 mg, 75%). MS: 425 [M+H]$^+$; TLC: 40% EtOAc in hexane: R$_f$: 0.50.

Example 71

Preparation of Cmpd 50

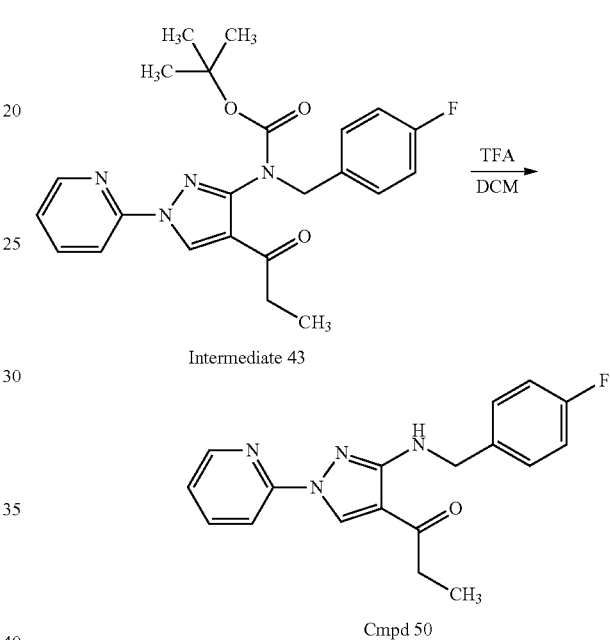

Intermediate 43

Cmpd 50

Trifluoroacetic acid (2 mL) was added to a solution of Intermediate 43 (90 mg, 0.21 mmol) in DCM (2 mL) at 0° C. The resulting mixture was allowed to warm to RT and stir for 2 h. The reaction mixture was then neutralized with saturated aqueous NaHCO$_3$ and extracted with EtOAc (30 mL). The organic layer was washed with water (10 mL), brine (10 mL), dried over Na$_2$SO$_4$, filtered and concentrated in vacuo. The crude material was purified by column chromatography over silica gel (100-200 mesh) by using a gradient mixture of 0-20% EtOAc-hexane as the eluent to afford Cmpd 50 (50 mg, 73%). $^1$H NMR: (DMSO-d$_6$) δ 9.40-9.43 (m, 1H), 8.46 (d, J=3.2 Hz, 1H), 7.97-8.08 (m, 2H), 7.79 (d, J=8.2 Hz, 1H), 7.35-7.38 (m, 1H), 7.03-7.14 (m, 4H), 4.72 (d, J=6.7 Hz, 2H), 2.70 (q, J=7.3 Hz, 2H), 1.00 (t, J=7.5 Hz, 3H); MS: 325 [M+H]$^+$; MP: 108-110° C.; TLC: 50% EtOAc in hexane: R$_f$: 0.40.

Example 72

General Scheme XII

A synthetic scheme useful for synthesis of compounds described herein is disclosed in General Scheme XII following, wherein the terms "Ar," "R$^1$" and "R$^2$" are as defined in Example 1, and the term "X" refers to halogen, e.g., Cl, Br.

General Scheme XII

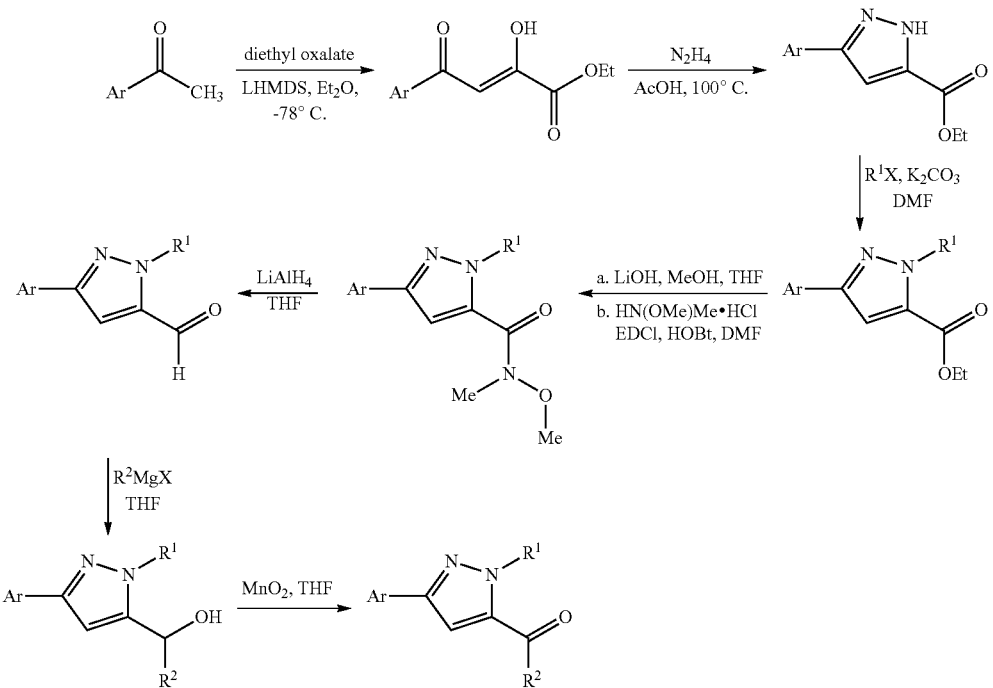

Example 73

Preparation of Intermediate 44

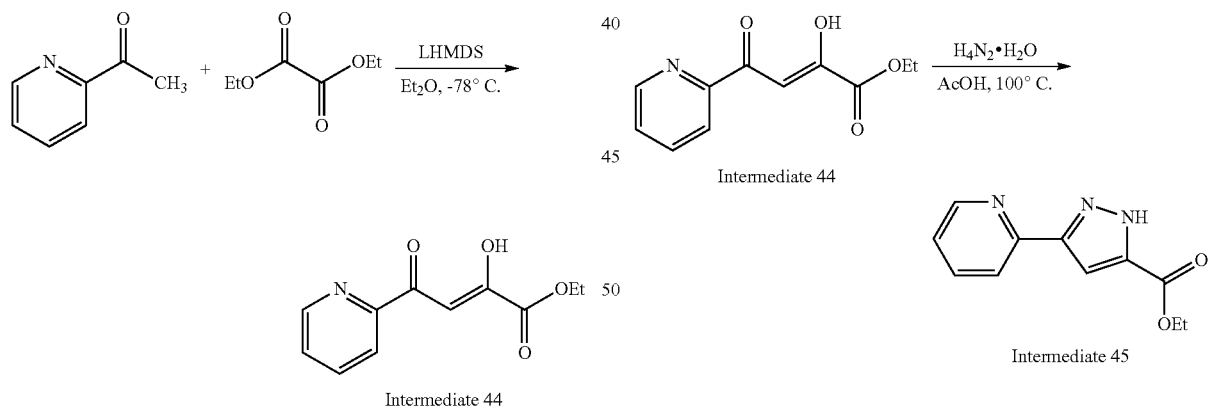

Lithium hexamethyldisilazide (24.8 mL, 24.8 mmol, 1 eq, 1M in THF) was diluted with anhydrous Et$_2$O (100 mL) and cooled to −78° C. under an argon atmosphere. After 15 min, 2-acetylpyridine (3 g, 24.8 mmol) in Et$_2$O (20 mL) was added to the cold mixture. After 30 min at −78° C., diethyl oxalate (3.61 g, 24.8 mmol, 1 eq) in Et$_2$O (25 mL) was added in a single portion and the resulting mixture was allowed to warm to RT and stir for 20 h. The resulting precipitate was collected by filtration and dried to afford Intermediate 44 (4 g, 74%) as the lithium salt. MS: 222 [M+H]$^+$; TLC: EtOAc: R$_f$: 0.10.

Example 74

Preparation of Intermediate 45

Hydrazine hydrate (602 mg, 13.3 mmol, 15 eq) was added to a solution of Intermediate 44 (200 mg, 0.90 mmol) in AcOH (5 mL). The resulting mixture was heated to 100° C. and allowed to stir for 12 h. The reaction mixture was then neutralized with saturated aqueous NaHCO$_3$ (20 mL) and extracted with EtOAc (40 mL). The organic layer was washed with saturated aqueous NaHCO$_3$ (2×10 mL), water (20 mL), brine (20 mL), dried over Na$_2$SO$_4$, filtered and concentrated in vacuo. The crude material was washed with pentane (2×10 mL) and dried under vacuum to afford Intermediate 45 (120 mg, 66%) as a viscous liquid. MS: 218 [M+H]$^+$; TLC: EtOAc: R$_f$: 0.40.

Example 75

Preparation of Cmpd 51

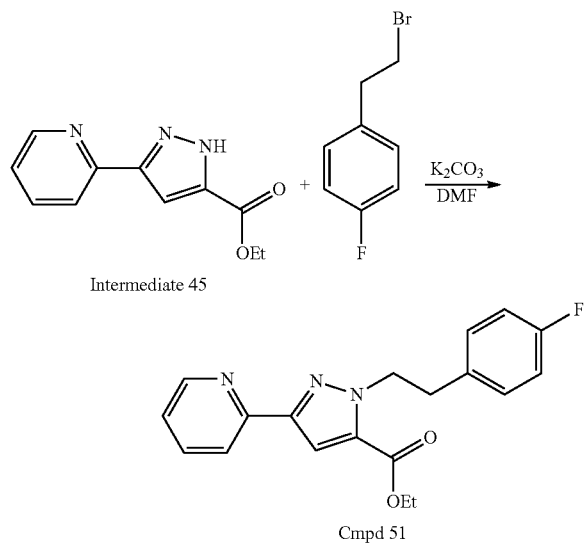

Anhydrous K₂CO₃ (1.27 g, 9.21 mmol, 2.5 eq) and 4-fluorophenethyl bromide (1 g, 4.61 mmol, 1.25 eq) was added to a solution of Intermediate 45 (744 mg, 3.68 mmol) in DMF (30 mL) and the resulting mixture was allowed to stir at RT for 8 h. The mixture was then diluted with water (30 mL) and extracted with EtOAc (100 mL). The organic layer was washed with water (2×10 mL), saturated aqueous NaHCO₃ (2×15 mL), brine (20 mL), dried over Na₂SO₄, filtered and concentrated in vacuo. The crude material was purified by column chromatography over silica gel (100-200 mesh) by using a gradient mixture of 0-10% EtOAc-hexane as the eluent to afford Cmpd 51 (700 mg, 58%). $^1$H NMR: (DMSO-$d_6$) δ 8.61 (d, J=4.3 Hz, 1H), 7.85-7.96 (m, 2H), 7.31-7.38 (m, 2H), 7.07-7.19 (m, 4H), 4.78 (t, J=7.2 Hz, 2H), 4.27 (q, J=7.2 Hz, 2H), 3.12 (t, J=7.2 Hz, 2H), 1.29 (t, J=7.0 Hz, 3H); MS: 340 [M+H]⁺; MP: 94-95° C.; TLC: 30% EtOAc in hexane: $R_f$: 0.40.

Example 76

Preparation of Cmpd 52 [General Procedure 21]

General Procedure 21 was followed in the preparation of Cmpd 52.

General Procedure 21

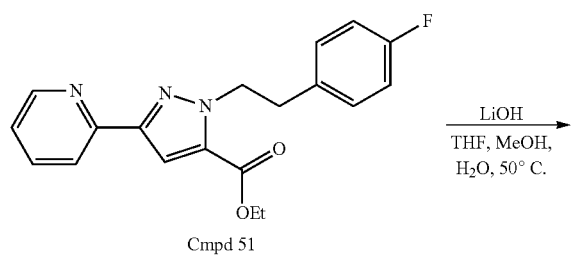

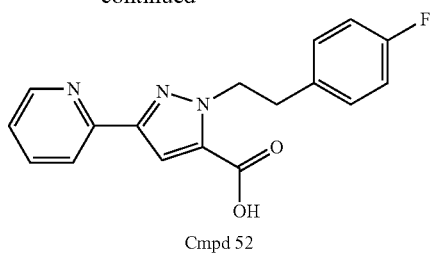

To a solution of Cmpd 51 (300 mg, 0.88 mmol) in THF (3 mL) was added LiOH.H₂O (185 mg, 4.42 mmol, 5 eq) in water (3 mL) and MeOH (3 mL). The mixture was heated to 50° C. and allowed to stir for 3 h. The reaction mixture was then neutralized with aqueous HCl (2N) and the precipitate was collected by filtration, washed with water (20 mL) and dried thoroughly to afford Cmpd 52 (220 mg, 83%) as a pale pink solid. $^1$H NMR: (DMSO-$d_6$) δ 8.74 (d, J=4.5 Hz, 1H), 8.29-8.33 (m, 2H), 7.72 (br s, 2H), 7.08-7.19 (m, 4H), 4.84 (t, J=6.7 Hz, 2H), 3.16 (t, J=7.0 Hz, 2H); MS: 312 [M+H]⁺; MP: 256-258° C.; TLC: EtOAc: $R_f$: 0.10.

Example 77

Preparation of Cmpd 53

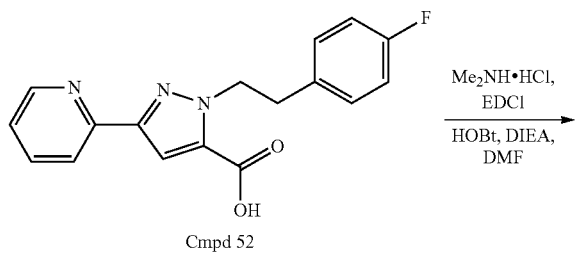

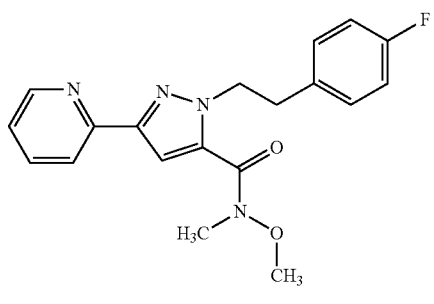

General Procedure 20 was followed to afford Cmpd 53 (190 mg, 55%). $^1$H NMR: (DMSO-$d_6$) δ 8.60 (d, J=4.4 Hz, 1H), 7.95 (d, J=7.9 Hz, 1H), 7.86-7.88 (m, 1H), 7.34-7.37 (m, 1H), 7.07-7.21 (m, 5H), 4.67 (t, J=7.1 Hz, 2H), 3.57 (s, 3H), 3.25 (s, 3H), 3.12 (t, J=7.1 Hz, 2H); MS: 355 [M+H]⁺; MP: 110-111° C.; TLC: 50% EtOAc in hexane: $R_f$: 0.30.

Example 78

Preparation of Cmpd 54

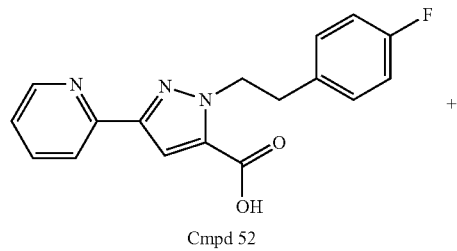

Cmpd 52

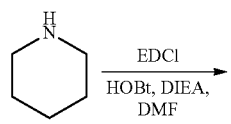

EDCl
HOBt, DIEA,
DMF

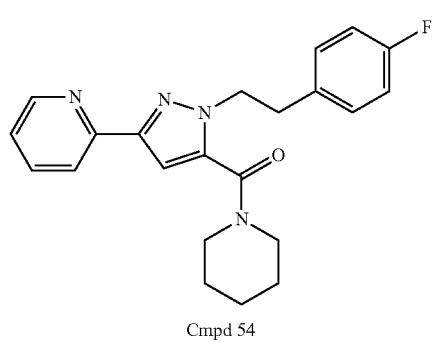

Cmpd 54

General Procedure 20 was followed to afford Cmpd 54 (25 mg, 21%). $^1$H NMR: (DMSO-$d_6$) δ 8.57 (d, J=4.4 Hz, 1H), 7.82-7.94 (m, 2H), 7.31-7.34 (m, 1H), 7.04-7.14 (m, 4H), 6.84 (s, 1H), 4.56 (t, J=7.0 Hz, 2H), 3.52 (br s, 2H), 3.25 (br s, 2H), 3.10 (t, J=7.0 Hz, 2H), 1.41-1.58 (m, 6H); MS: 379 [M+H]$^+$; MP: 88-90° C.; TLC: EtOAc: $R_f$: 0.50.

Example 79

Preparation of Intermediate 46

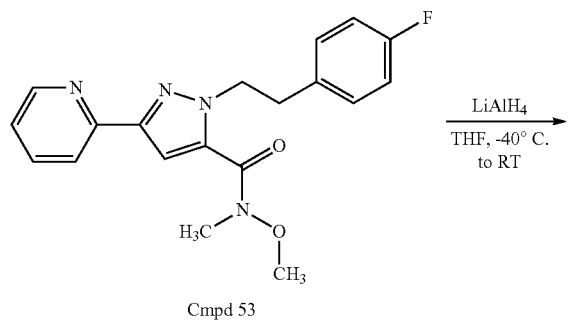

Cmpd 53

LiAlH$_4$
THF, -40° C.
to RT

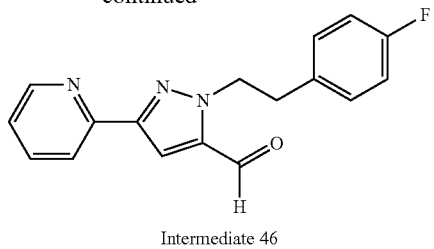

Intermediate 46

Lithium aluminum hydride (11 mg, 0.28 mmol) was added to a solution of Cmpd 53 (100 mg, 0.28 mmol) in THF (4 mL) at -40° C. The resulting mixture was allowed to slowly warm to 0° C. and stir for 2 h. The mixture was then quenched with saturated aqueous NH$_4$Cl (20 mL) and extracted with EtOAc (30 mL). The organic layer washed with water (10 mL), saturated aqueous NaHCO$_3$ (10 mL), brine (10 mL), dried over Na$_2$SO$_4$, filtered and concentrated in vacuo. The crude material was washed with pentane (2×5 mL) and dried under vacuum to afford Intermediate 46 (65 mg, 79%). $^1$H NMR: (DMSO-$d_6$) δ 9.82 (s, 1H), 8.63 (d, J=3.5 Hz, 1H), 7.86-7.97 (m, 2H), 7.54 (s, 1H), 7.36-7.39 (m, 1H), 7.07-7.19 (m, 4H), 4.75-4.78 (m, 2H), 3.11-3.14 (m, 2H); TLC: 30% EtOAc in hexane: $R_f$: 0.50.

Example 80

Preparation of Cmpd 55

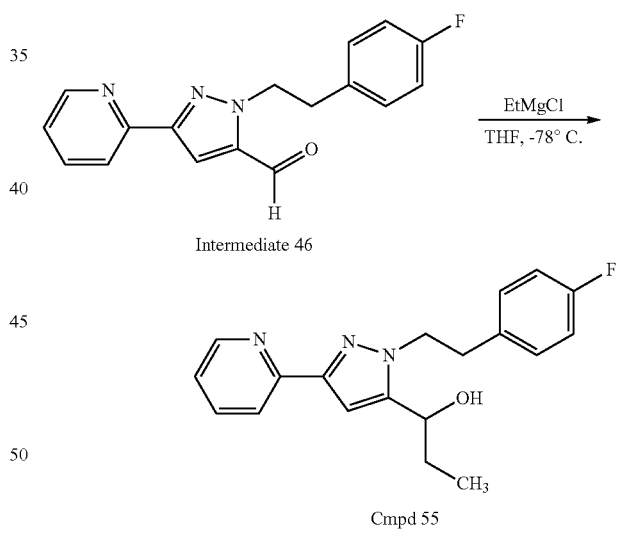

Ethyl magnesium chloride (0.33 mL, 0.66 mmol, 3 eq, 2M in THF) was added to a solution of Intermediate 46 (65 mg, 0.22 mmol) in THF (4 mL) at -78° C. The resulting mixture was warmed to 0° C. and allowed to stir for 4 h. The reaction was then quenched with saturated aqueous NH$_4$Cl (20 mL) and extracted with EtOAc (30 mL). The organic layer washed with water (10 mL), saturated aqueous NaHCO$_3$ (10 mL), brine (10 mL), dried over Na$_2$SO$_4$, filtered and concentrated in vacuo. The crude material was purified by column chromatography over silica gel (100-200 mesh) by using a gradient mixture of 0-30% EtOAc-hexane as the eluent to afford Cmpd 55 (60 mg, 84%) as an off-white solid. $^1$H NMR: (DMSO-$d_6$) δ 8.55 (d, J=3.8 Hz, 1H), 7.79-7.93

(m, 2H), 7.10-7.30 (m, 5H), 6.65 (s, 1H), 5.31 (d, J=6.0 Hz, 1H), 4.25-4.39 (m, 3H), 3.14-3.16 (m, 2H), 1.58-1.69 (m, 2H), 0.81 (t, J=7.3 Hz, 3H); MS: 326 [M+H]$^+$; MP: 91-96° C.; TLC: 50% EtOAc in hexane: $R_f$: 0.20.

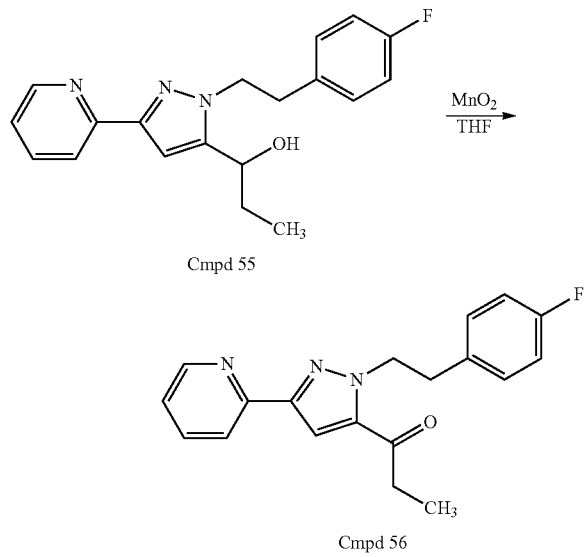

Example 81

Preparation of Cmpd 56

Manganese dioxide (83 mg, 0.96 mmol, 3 eq) was added to a solution of Cmpd 55 (100 mg, 0.32 mmol) in THF (4 mL) and the resulting mixture was allowed to stir at RT for 14 h. The mixture was then filtered through Celite and washed with EtOAc (20 mL). The organic phase was washed with water (10 mL), saturated aqueous NaHCO$_3$ (10 mL), brine (10 mL), dried over Na$_2$SO$_4$, filtered and concentrated in vacuo. The crude material was purified by column chromatography over silica gel (100-200 mesh) by using a gradient mixture of 0-30% EtOAc-hexane as the eluent to afford Cmpd 56 (22 mg, 21%). $^1$H NMR: (DMSO-d$_6$) δ 8.61 (d, J=5.1 Hz, 1H), 7.85-7.95 (m, 2H), 7.60 (s, 1H), 7.35-7.38 (m, 1H), 7.08-7.21 (m, 4H), 4.74 (t, J=7.6 Hz, 2H), 3.06 (t, J=7.3 Hz, 2H), 2.94 (q, J=7.2 Hz, 2H), 1.03 (t, J=7.3 Hz, 3H); MS: 324 [M+H]$^+$; MP: 129-130° C.; TLC: 50% EtOAc in hexane: $R_f$: 0.50.

Example 82

General Scheme XIII

A synthetic scheme useful for synthesis of compounds described herein is disclosed in General Scheme XII following, wherein the terms "Ar," "R$^1$" and "R$^2$" are as defined in Example 1.

General Scheme XIII

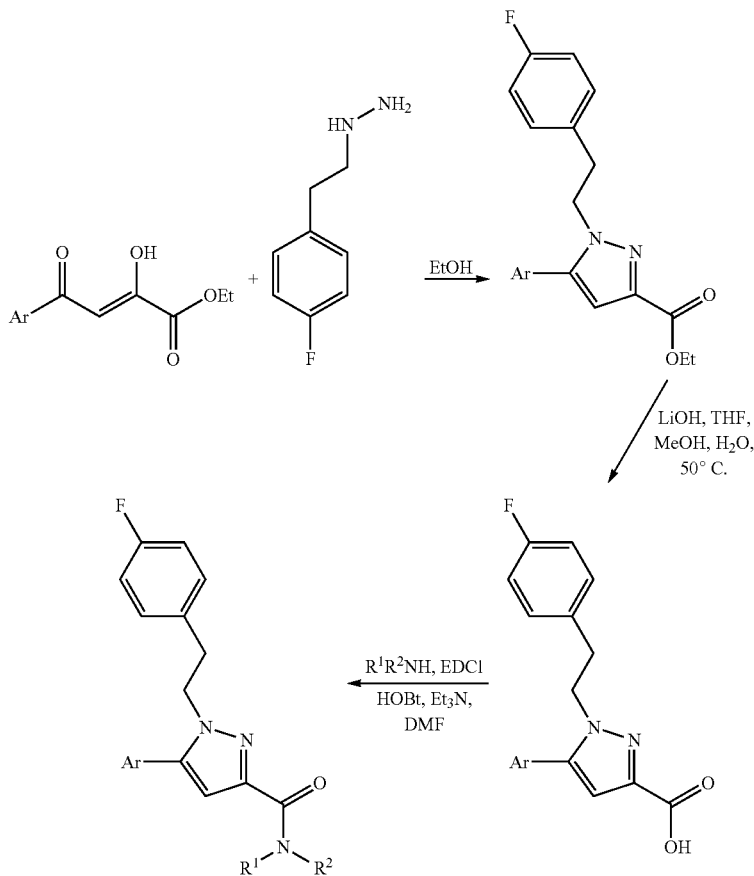

Example 83

Preparation of Cmpd 57

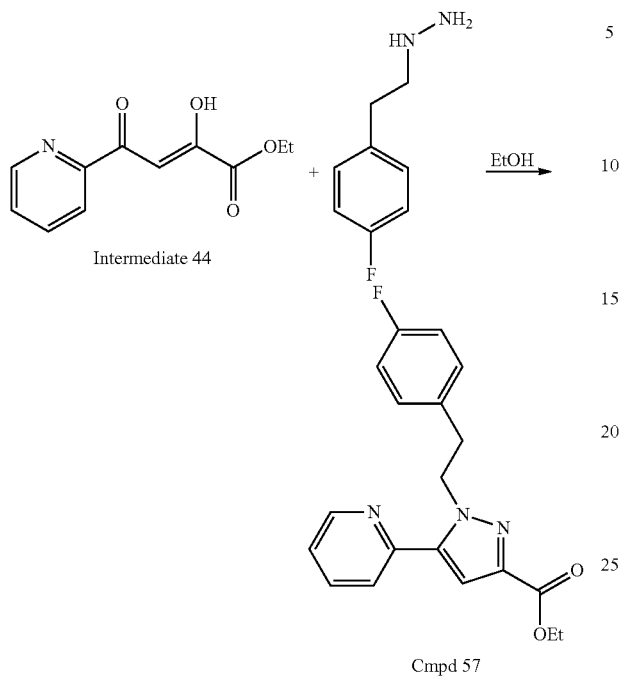

[2-(4-Fluorophenyl)-ethyl]-hydrazine (348 mg, 2.26 mmol, 2 eq) was added to a solution of Intermediate 44 (500 mg, 2.26 mmol) in EtOH (30 mL) and the resulting mixture was allowed to stir for 12 h. The solvent was evaporated and the residue was dissolved in EtOAc (100 mL) and filtered through Celite to remove any residual inorganic material. The filtrate was washed with saturated aqueous NaHCO$_3$ (2×10 mL), water (20 mL), brine (20 mL), dried over Na$_2$SO$_4$, filtered and concentrated in vacuo. The crude material was purified by column chromatography over silica gel (100-200 mesh) by using a solvent gradient of 0-15% EtOAc-hexane as the eluent to afford Cmpd 57 (400 mg, 52%). $^1$H NMR: (DMSO-d$_6$) δ 8.72-8.73 (m, 1H), 7.87-7.91 (m, 1H), 7.75-7.77 (m, 1H), 7.41-7.44 (m, 1H), 7.29 (s, 1H), 6.99-7.15 (m, 4H), 4.91 (t, J=7.6 Hz, 2H), 4.31 (q, J=7.1 Hz, 2H), 3.06 (t, J=7.6 Hz, 2H), 1.3 (t, J=7.0 Hz, 3H); MS: 340 [M+H]$^+$; MP: 91-92° C.; TLC: 30% EtOAc in hexane: R$_f$: 0.30.

Example 84

Preparation of Cmpd 58

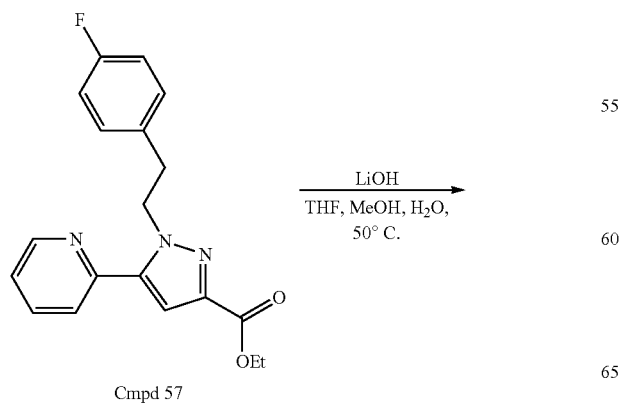

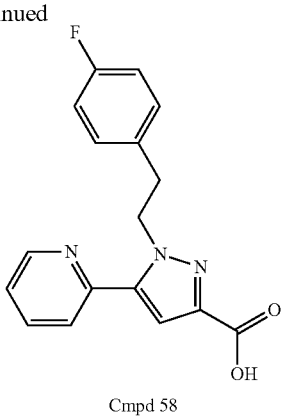

General Procedure 21 was followed to afford Cmpd 58 (230 mg, 84%) as an off-white solid. $^1$H NMR: (DMSO-d$_6$) δ 12.84 (s, 1H), 8.71 (d, J=4.4 Hz, 1H), 7.73-7.90 (m, 2H), 7.40-7.43 (m, 1H), 6.99-7.22 (m, 5H), 4.88 (t, J=7.3 Hz, 2H), 3.06 (t, J=7.6 Hz, 2H); MS: 312 [M+H]$^+$; MP: 132-134° C.; TLC: EtOAc: R$_f$: 0.10.

Example 85

Preparation of Cmpd 59

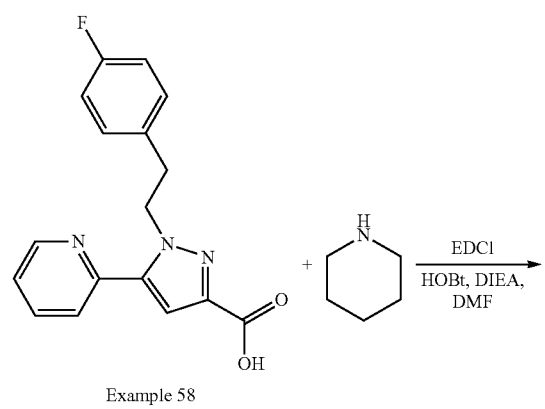

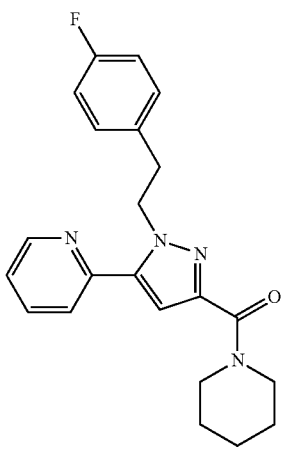

General Procedure 20 was followed to afford Cmpd 59 (25 mg, 21%). $^1$H NMR: (DMSO-d$_6$) δ 8.69 (d, J=4.4 Hz, 1H), 7.85-7.89 (m, 1H), 7.73 (d, J=7.6 Hz, 1H), 7.38-7.41 (m, 1H), 6.95-7.06 (m, 5H), 4.86 (t, J=7.0 Hz, 2H), 3.54-3.95 (m, 4H), 3.01 (t, J=7.0 Hz, 2H), 1.42-1.60 (m, 6H); MS: 379 [M+H]$^+$; TLC: EtOAc: R$_f$: 0.50.

The contents of all references, patents, and published applications cited herein are hereby incorporated by reference in their entirety and for all purposes.

While the invention has been described in detail with reference to certain preferred embodiments thereof, it will be understood that modifications and variations are within the spirit and scope of that which is described and claimed.

What is claimed is:

1. A compound with structure of the following formula:

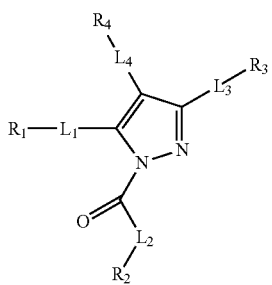

or pharmaceutically acceptable salt, ester, solvate, or prodrug thereof;
wherein:
L$^1$ is —NR$^5$—;
L$^2$ is a bond;
L$^3$ is a bond, substituted or unsubstituted alkylene, substituted or unsubstituted heteroalkylene, —S—, —SO—, —SO$_2$—, —O—, —NHSO$_2$—, or —NR$^5$—;
L$^4$ is a bond, substituted or unsubstituted alkylene, substituted or unsubstituted heteroalkylene, —S—, —SO—, —SO$_2$—, —O—, —NHSO$_2$—, or —NR$^5$—;
R$^1$ is substituted alkyl, wherein the substituted alkyl has one or more substituent group selected from the group consisting of —OH, —NH$_2$, —SH, —CN, —CF$_3$, —NO$_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is substituted or unsubstituted cycloalkyl, substituted or unsubstituted cycloalkenyl, substituted or unsubstituted heterocycloalkyl, substituted or unsubstituted heterocycloalkenyl, substituted or unsubstituted fused ring aryl, or substituted or unsubstituted heteroaryl, wherein the substituted cycloalkyl, substituted cycloalkenyl, substituted heterocycloalkyl, substituted heterocycloalkenyl, substituted fused ring aryl, or substituted heteroaryl has one or more substituent group selected from the group consisting of oxo, —OH, —NH$_2$, —SH, —CN, —CF$_3$, —NO$_2$, halogen, —COOH, substituted or unsubstituted alkyl, substituted or unsubstituted heteroalkyl, substituted or unsubstituted cycloalkyl, or substituted or unsubstituted heterocycloalkyl;
R$^3$ is substituted alkyl, substituted or unsubstituted heteroalkyl, substituted or unsubstituted cycloalkyl, substituted or unsubstituted cycloalkenyl, substituted or unsubstituted aryl, or substituted or unsubstituted heteroaryl, wherein the substituted heteroaryl group has one or more substituent group selected from the group consisting of —OH, —NH$_2$, —SH, —CN, —CF$_3$, —NO$_2$, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^4$ is hydrogen, substituted or unsubstituted alkyl, substituted or unsubstituted heteroalkyl, substituted or unsubstituted cycloalkyl, substituted or unsubstituted heterocycloalkyl, substituted aryl, or substituted or unsubstituted heteroaryl; and
R$^5$ is hydrogen, or substituted or unsubstituted alkyl.

2. The compound according to claim 1, wherein L$^3$ is a bond, substituted or unsubstituted alkylene, or substituted or unsubstituted heteroalkylene, and R$^3$ is substituted or unsubstituted aryl, or substituted or unsubstituted heteroaryl.

3. The compound according to claim 1, wherein L$^3$ is a bond, —NH—, —NHCH$_2$— or —NH(CH$_2$)$_2$—.

4. The compound according to claim 1, wherein L$^4$ is a bond; and R$^4$ is hydrogen, substituted or unsubstituted alkyl, or substituted or unsubstituted heteroalkyl.

5. A compound with structure of the following formula:

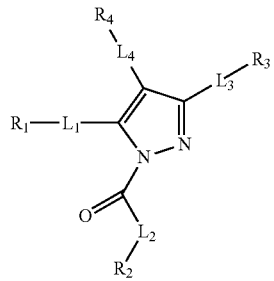

or pharmaceutically acceptable salt, ester, solvate, or prodrug thereof;
wherein:
L$^1$ is a bond, substituted or unsubstituted alkylene, substituted or unsubstituted heteroalkylene, —S—, —SO—, —SO$_2$—, —NHSO$_2$—, or —NR$^5$—;
L$^2$ is a bond;
L$^3$ is a bond, substituted or unsubstituted alkylene, substituted or unsubstituted heteroalkylene, —S—, —SO—, —SO$_2$—, —O—, —NHSO$_2$—, or —NR$^5$—;
L$^4$ is a bond;
R$^1$ is substituted or unsubstituted alkyl, substituted or unsubstituted heteroalkyl having at least one heteroatom selected from the group consisting of N, P, Si, and S, substituted or unsubstituted cycloalkyl, substituted or unsubstituted heterocycloalkyl, substituted or unsubstituted aryl, or substituted or unsubstituted heteroaryl, wherein the substituted alkyl, substituted heteroalkyl, substituted cycloalkyl, substituted heterocycloalkyl, substituted aryl, or substituted heteroaryl has one or more substituent group selected from the group consisting of —OH, —NH$_2$, —SH, —CN, —CF$_3$, —NO$_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is substituted or unsubstituted cycloalkyl, substituted or unsubstituted cycloalkenyl, substituted or unsubstituted heterocycloalkyl, substituted or unsubstituted heterocycloalkenyl, substituted or unsubstituted fused ring aryl, or substituted or unsubstituted heteroaryl, wherein the substituted cycloalkyl, substituted cycloalkenyl, substituted heterocycloalkyl, substituted heterocycloalkenyl, substituted fused ring aryl, or substituted heteroaryl has one or more substituent group selected from the group consisting of oxo, —OH, —$NH_2$, —SH, —CN, —$CF_3$, —$NO_2$, halogen, —COOH, substituted or unsubstituted alkyl, substituted or unsubstituted heteroalkyl, substituted or unsubstituted cycloalkyl, or substituted or unsubstituted heterocycloalkyl;

$R^3$ is substituted alkyl, substituted or unsubstituted heteroalkyl, substituted or unsubstituted cycloalkyl, substituted or unsubstituted cycloalkenyl, substituted or unsubstituted aryl, or substituted or unsubstituted heteroaryl, wherein the substituted heteroaryl group has one or more substituent selected from the group consisting of —OH, —$NH_2$, —SH, —CN, —$CF_3$, —$NO_2$, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is unsubstituted alkyl; and $R^5$ is hydrogen, or substituted or unsubstituted alkyl;

provided that:

$L^1$ is a bond, $R^1$ is substituted or unsubstituted heteroalkyl, substituted or unsubstituted cycloalkyl, substituted or unsubstituted heterocycloalkyl, when $L^1$ is a substituted or unsubstituted alkylene, $R^1$ is substituted or unsubstituted heteroalkyl, substituted or unsubstituted cycloalkyl, unsubstituted heterocycloalkyl, substituted or unsubstituted aryl, or substituted or unsubstituted heteroaryl; and when $L^1$ is —S— or substituted or unsubstituted heteroalkylene wherein the heteroatom is S, $R^1$ is substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

6. A pharmaceutical composition comprising a compound according to claim 1, and a pharmaceutically acceptable excipient.

7. A compound with structure of the following formula:

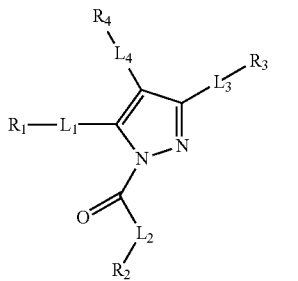

or pharmaceutically acceptable salt, ester, solvate, or prodrug thereof;

wherein:

$L^1$ is a bond, substituted or unsubstituted alkylene, substituted or unsubstituted heteroalkylene, —S—, —SO—, —$SO_2$—, —$NHSO_2$—, or —$NR^5$—;

$L^2$ is a bond;

$L^3$ is a bond, substituted or unsubstituted alkylene, substituted or unsubstituted heteroalkylene, —S—, —SO—, —$SO_2$—, —O—, —$NHSO_2$—, or —$NR^5$—;

$L^4$ is a bond; substituted or unsubstituted alkylene, substituted or unsubstituted heteroalkylene, —S—, —SO—, —$SO_2$—, —O—, —$NHSO_2$—, or —$NR^5$—;

$R^1$ is substituted or unsubstituted alkyl, substituted or unsubstituted heteroalkyl having at least one heteroatom selected from the group consisting of N, P, Si, and S, substituted or unsubstituted cycloalkyl, substituted or unsubstituted heterocycloalkyl, substituted or unsubstituted aryl, or substituted or unsubstituted heteroaryl, wherein the substituted alkyl, substituted heteroalkyl, substituted cycloalkyl, substituted heterocycloalkyl, substituted aryl, or substituted heteroaryl has one or more substituent group selected from the group consisting of —OH, —$NH_2$, —SH, —CN, —$CF_3$, —$NO_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is substituted or unsubstituted cycloalkyl, substituted or unsubstituted cycloalkenyl, substituted or unsubstituted heterocycloalkyl, substituted or unsubstituted heterocycloalkenyl, substituted or unsubstituted fused ring aryl, or substituted or unsubstituted heteroaryl, wherein the substituted cycloalkyl, substituted cycloalkenyl, substituted heterocycloalkyl, substituted heterocycloalkenyl, substituted fused ring aryl, or substituted heteroaryl has one or more substituent group selected from the group consisting of oxo, —OH, —$NH_2$, —SH, —CN, —$CF_3$, —$NO_2$, halogen, —COOH, substituted or unsubstituted alkyl, substituted or unsubstituted heteroalkyl, substituted or unsubstituted cycloalkyl, or substituted or unsubstituted heterocycloalkyl;

$R^3$ is substituted or unsubstituted heteroaryl, wherein the substituted heteroaryl group has one or more substituent selected from the group consisting of —OH, —$NH_2$, —SH, —CN, —$CF_3$, —$NO_2$, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, substituted or unsubstituted alkyl, substituted or unsubstituted heteroalkyl, substituted or unsubstituted cycloalkyl, substituted or unsubstituted heterocycloalkyl, substituted aryl, or substituted or unsubstituted heteroaryl; and $R^5$ is hydrogen, or substituted or unsubstituted alkyl;

provided that:

$L^1$ is a bond, $R^1$ is substituted or unsubstituted heteroalkyl, substituted or unsubstituted cycloalkyl, or substituted or unsubstituted heterocycloalkyl, when $L^1$ is a substituted or unsubstituted alkylene, $R^1$ is substituted or unsubstituted heteroalkyl, substituted or unsubstituted cycloalkyl, unsubstituted heterocycloalkyl, or substituted or unsubstituted aryl, or substituted or unsubstituted heteroaryl; and when L¹ is —S— or substituted or unsubstituted heteroalkylene wherein the heteroatom is S, R¹ is substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

8. The compound according to claim 7, wherein said $R^3$ substituted or unsubstituted heteroaryl contains nitrogen as a heteroatom.

9. The compound according to claim 8, wherein $R^3$ is substituted or unsubstituted pyrrolyl, substituted or unsubstituted pyrazolyl, substitute or unsubstituted pyridyl, substituted or unsubstituted pyrimidinyl, substituted or unsubstituted imidazolyl, substituted or unsubstituted pyrazinyl, substituted or unsubstituted pyridazinyl, substituted or unsubstituted purinyl, substituted or unsubstituted indolyl, substituted or unsubstituted quinolinyl, substituted or unsubstituted isoquinolinyl, substituted or unsubstituted triazolyl, or substituted or unsubstituted tetrazolyl.

10. The compound according to claim 1, wherein said $R^1$ substituted alkyl group is substituted with one or more aryl or heteroaryl groups.

11. The compound according to claim 10, wherein said $R^1$ substituted alkyl group is substituted with one or more aryl or heteroaryl groups substituted with one or more halogens.

12. The compound according to claim 1, wherein $L^3$ is a bond, or substituted or unsubstituted alkylene, and $R^3$ is substituted or unsubstituted aryl or substituted or unsubstituted heteroaryl.

13. A compound with structure of the following formula:

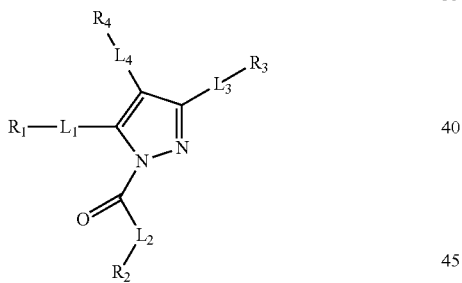

or pharmaceutically acceptable salt, ester, solvate, or prodrug thereof;
wherein:
L¹ is a bond, substituted or unsubstituted alkylene, substituted or unsubstituted heteroalkylene, —S—, —SO—, —SO₂—, —NHSO₂—, or —NR⁵—;
L² is a bond;
L³ is —C(O)O—;
L⁴ is a bond, substituted or unsubstituted alkylene, substituted or unsubstituted heteroalkylene, —S—, —SO—, —SO₂—, —O—, —NHSO₂—, or —NR⁵—;
R¹ is substituted or unsubstituted alkyl, substituted or unsubstituted heteroalkyl having at least one heteroatom selected from the group consisting of N, P, Si, and S, substituted or unsubstituted cycloalkyl, substituted or unsubstituted heterocycloalkyl, substituted or unsubstituted aryl, or substituted or unsubstituted heteroaryl, wherein the substituted alkyl, substituted heteroalkyl, substituted cycloalkyl, substituted heterocycloalkyl, substituted aryl, or substituted heteroaryl has one or more substituent group selected from the group consisting of —OH, —NH₂, —SH, —CN, —CF₃, —NO₂, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is substituted or unsubstituted cycloalkyl, substituted or unsubstituted cycloalkenyl, substituted or unsubstituted heterocycloalkyl, substituted or unsubstituted heterocycloalkenyl, substituted or unsubstituted fused ring aryl, or substituted or unsubstituted heteroaryl, wherein the substituted cycloalkyl, substituted cycloalkenyl, substituted heterocycloalkyl, substituted heterocycloalkenyl, substituted fused ring aryl, or substituted heteroaryl has one or more substituent group selected from the group consisting of oxo, —OH, —NH₂, —SH, —CN, —CF₃, —NO₂, halogen, —COOH, substituted or unsubstituted alkyl, substituted or unsubstituted heteroalkyl, substituted or unsubstituted cycloalkyl, or substituted or unsubstituted heterocycloalkyl;

R³ is substituted or unsubstituted alkyl;

R⁴ is hydrogen, substituted or unsubstituted alkyl, substituted or unsubstituted heteroalkyl, substituted or unsubstituted cycloalkyl, substituted or unsubstituted heterocycloalkyl, substituted aryl, or substituted or unsubstituted heteroaryl; and R⁵ is hydrogen, or substituted or unsubstituted alkyl;

provided that:

L¹ is a bond, R¹ is substituted or unsubstituted heteroalkyl, substituted or unsubstituted cycloalkyl, or substituted or unsubstituted heterocycloalkyl, when L¹ is a substituted or unsubstituted alkylene, R¹ is substituted or unsubstituted heteroalkyl, substituted or unsubstituted cycloalkyl, unsubstituted heterocycloalkyl, or substituted or unsubstituted aryl, or substituted or unsubstituted heteroaryl; and when L¹ is —S— or substituted or unsubstituted heteroalkylene wherein the heteroatom is S, R¹ is substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

14. A compound with structure of the following formula:

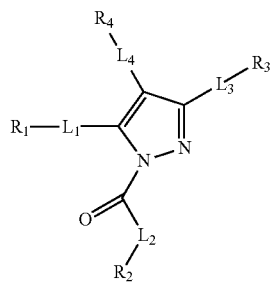

or pharmaceutically acceptable salt, ester, solvate, or prodrug thereof;

wherein:
L¹ is a bond, substituted or unsubstituted alkylene, substituted or unsubstituted heteroalkylene, —S—, —SO—, —SO₂—, —NHSO₂—, or —NR⁵—;
L² is a bond;
L³ —C(O)NR⁶, where R⁶ is hydrogen or akyl;
L⁴ is a bond; substituted or unsubstituted alkylene, substituted or unsubstituted heteroalkylene, —S—, —SO—, —SO₂—, —O—, —NHSO₂—, or —NR⁵—;
R¹ is substituted or unsubstituted alkyl, substituted or unsubstituted heteroalkyl having at least one heteroatom selected from the group consisting of N, P, Si, and S, substituted or unsubstituted cycloalkyl, substituted or unsubstituted heterocycloalkyl, substituted or unsubstituted aryl, or substituted or unsubstituted heteroaryl, wherein the substituted alkyl, substituted heteroalkyl, substituted cycloalkyl, substituted heterocycloalkyl, substituted aryl, or substituted heteroaryl has one or more substituent group selected from the group consisting of —OH, —NH₂, —SH, —CN, —CF₃, —NO₂, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R² is substituted or unsubstituted cycloalkyl, substituted or unsubstituted cycloalkenyl, substituted or unsubstituted heterocycloalkyl, substituted or unsubstituted heterocycloalkenyl, substituted or unsubstituted fused ring aryl, or substituted or unsubstituted heteroaryl, wherein the substituted cycloalkyl, substituted cycloalkenyl, substituted heterocycloalkyl, substituted heterocycloalkenyl, substituted fused ring aryl, or substituted heteroaryl has one or more substituent group selected from the group consisting of oxo, —OH, —NH₂, —SH, —CN, —CF₃, —NO₂, halogen, —COOH, substituted or unsubstituted alkyl, substituted or unsubstituted heteroalkyl, substituted or unsubstituted cycloalkyl, or substituted or unsubstituted heterocycloalkyl;
R³ is substituted or unsubstituted alkyl, or substituted or unsubstituted aryl;
R⁴ is hydrogen, substituted or unsubstituted alkyl, substituted or unsubstituted heteroalkyl, substituted or unsubstituted cycloalkyl, substituted or unsubstituted heterocycloalkyl, substituted aryl, or substituted or unsubstituted heteroaryl; and
R⁵ is hydrogen, or substituted or unsubstituted alkyl;
provided that:
L¹ is a bond, R¹ is substituted or unsubstituted heteroalkyl, substituted or unsubstituted cycloalkyl, or substituted or unsubstituted heterocycloalkyl,
when L¹ is a substituted or unsubstituted alkylene, R¹ is substituted or unsubstituted heteroalkyl, substituted or unsubstituted cycloalkyl, unsubstituted heterocycloalkyl, or substituted or unsubstituted aryl, or substituted or unsubstituted heteroaryl; and
when L¹ is —S—or substituted or unsubstituted heteroalkylene wherein the heteroatom is S, R¹ is substituted alkyl, substituted or unsubstituted cycloalkyl, substituted or unsubstituted heterocycloalkyl, substituted or unsubstituted aryl, or substituted or unsubstituted heteroaryl.

15. The compound according to claim 1, wherein R³ is substituted or unsubstituted phenyl or substituted or unsubstituted pyridyl.
16. The compound according to claim 7, wherein L¹ is —S—, —NR⁵, substituted or unsubstituted alkylene, or substituted or unsubstituted heteroalkylene, and R¹ is substituted or unsubstituted aryl, substituted or unsubstituted heteroaryl, or unsubstituted heterocycloalkyl.
17. The compound according to claim 1, wherein R² is substituted or unsubstituted cycloalkyl, substituted or unsubstituted cycloalkenyl, substituted or unsubstituted heterocycloalkyl, or substituted or unsubstituted heterocycloalkenyl.
18. The compound according to claim 1, wherein R² is substituted or unsubstituted heteroaryl.
19. The compound according to claim 18, wherein R² is substituted or unsubstituted furyl, substituted or unsubstituted thienyl, or substituted or unsubstituted pyridyl.
20. A compound with structure of the following formula:

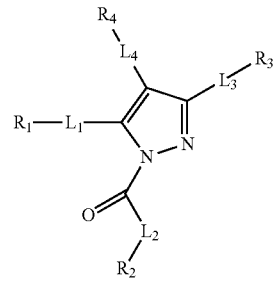

or pharmaceutically acceptable salt, ester, solvate, or prodrug thereof;
wherein:
L¹ is a bond, substituted or unsubstituted alkylene, substituted or unsubstituted heteroalkylene, —S—, —SO—, —SO₂—, —NHSO₂—, or —NR⁵—;
L² is a bond;
L³ is a bond, substituted or unsubstituted alkylene, substituted or unsubstituted heteroalkylene, —S—, —SO—, —SO₂—, —O—, —NHSO₂—, or —NR⁵—;
L⁴ is a bond; substituted or unsubstituted alkylene, substituted or unsubstituted heteroalkylene, —S—, —SO—, —SO₂—, —O—, —NHSO₂—, or —NR⁵—;
R¹ is substituted or unsubstituted alkyl, substituted or unsubstituted heteroalkyl having at least one heteroatom selected from the group consisting of N, P, Si, and S, substituted or unsubstituted cycloalkyl, substituted or unsubstituted heterocycloalkyl, substituted or unsubstituted aryl, or substituted or unsubstituted heteroaryl, wherein the substituted alkyl, substituted heteroalkyl, substituted cycloalkyl, substituted heterocycloalkyl, substituted aryl, or substituted heteroaryl has one or more substituent group selected from the group consisting of —OH, —NH₂, —SH, —CN, —CF₃, —NO₂, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R² is substituted or unsubstituted fused ring aryl;
R³ is substituted alkyl, substituted or unsubstituted heteroalkyl, substituted or unsubstituted cycloalkyl, substituted or unsubstituted cycloalkenyl, substituted or unsubstituted aryl, or substituted or unsubstituted heteroaryl, wherein the substituted heteroaryl group has one or more substituent selected from the group consisting of —OH, —NH$_2$, —SH, —CN, —CF$_3$, —NO$_2$, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, substituted or unsubstituted alkyl, substituted or unsubstituted heteroalkyl, substituted or unsubstituted cycloalkyl, substituted or unsubstituted heterocycloalkyl, substituted aryl, or substituted or unsubstituted heteroaryl; and R$^5$ is hydrogen, or substituted or unsubstituted alkyl; provided that:

L$^1$ is a bond, R$^1$ is substituted or unsubstituted heteroalkyl, substituted or unsubstituted cycloalkyl, or substituted or unsubstituted heterocycloalkyl, when L$^1$ is a substituted or unsubstituted alkylene, R$^1$ is substituted or unsubstituted heteroalkyl, substituted or unsubstituted cycloalkyl, unsubstituted heterocycloalkyl, or substituted or unsubstituted aryl, or substituted or unsubstituted heteroaryl; and when L$^1$ is —S—or substituted or unsubstituted heteroalkylene wherein the heteroatom is S, R$^1$ is substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

21. The compound according to claim 20, wherein R$^2$ is substituted or unsubstituted naphthyl.

22. The compound according to claim 1, wherein said compound is selected from the group consisting of:

Compound 41, 1-[(2-chlorophenyl)carbonyl]-N-[(4-fluorophenyl)methyl]-3-(pyridin-2-yl)-1H-pyrazol-5-amine;

Compound 103, 1-[(2-amino-4-methoxyphenyl)carbonyl]-N-benzyl-3-(2-fluorophenyl)-1H-pyrazol-5-amine;

Compound 105, 1-[(2-amino-4-methoxyphenyl)carbonyl]-N-benzyl-3-(pyridin-2-yl)-1H-pyrazol-5-amine;

Compound 106, 1-[(2-amino-4-methylphenyl)carbonyl]-N-benzyl-3-(2-fluorophenyl)-1H-pyrazol-5-amine;

Compound 108, 1-[(2-amino-4-methylphenyl)carbonyl]-N-benzyl-3-(pyridin-2-yl)-1H-pyrazol-5-amine;

Compound 114, 1-[(2-chlorophenyl)carbonyl]-N-[(4-fluorophenyl)methyl]-3-phenyl-1H-pyrazol-5-amine;

Compound 116, 1-[(2-methoxyphenyl)carbonyl]-3-(pyridin-2-yl)-N-(thiophen-2-ylmethyl)-1H-pyrazol-5-amine;

Compound 118, 1-[(2-methoxyphenyl)carbonyl]-3-(pyridin-2-yl)-N-(thiophen-3-ylmethyl)-1H-pyrazol-5-amine;

Compound 201, N-(furan-2-ylmethyl)-1-[(2-methoxyphenyl)carbonyl]-3-(pyridin-2-yl)-1H-pyrazol-5-amine;

Compound 202, N-(furan-3-ylmethyl)-1-[(2-methoxyphenyl)carbonyl]-3-(pyridin-2-yl)-1H-pyrazol-5-amine;

Compound 208, N-[(4-fluorophenyl)methyl]-1-[(2-methoxyphenyl)carbonyl]-3-phenyl-1H-pyrazol-5-amine;

Compound 234, N-benzyl-1-[(2,4-dimethoxyphenyl)carbonyl]-3-(2-fluorophenyl)-1H-pyrazol-5-amine;

Compound 236, N-benzyl-1-[(2,4-dimethoxyphenyl)carbonyl]-3-(pyridin-2-yl)-1H-pyrazol-5-amine;

Compound 241, N-benzyl-1-[(2-bromophenyl)carbonyl]-3-(pyridin-2-yl)-1H-pyrazol-5-amine;

Compound 242, N-benzyl-1-[(2-chlorophenyl)carbonyl]-3-(2-fluorophenyl)-1H-pyrazol-5-amine;

Compound 244, N-benzyl-1-[(2-chlorophenyl)carbonyl]-3-(pyridin-2-yl)-1H-pyrazol-5-amine;

Compound 247, N-benzyl-1-[(2-ethylphenyl)carbonyl]-3-(pyridin-2-yl)-1H-pyrazol-5-amine;

Compound 251, N-benzyl-1-[(2-fluorophenyl)carbonyl]-3-(pyridin-2-yl)-1H-pyrazol-5-amine;

Compound 256, N-benzyl-1-[(2-methoxyphenyl)carbonyl]-3-(pyridin-2-yl)-1H-pyrazol-5-amine;

Compound 260, N-benzyl-1-[(2-methylphenyl)carbonyl]-3-(pyridin-2-yl)-1H-pyrazol-5-amine;

Compound 270, N-benzyl-1-[(naphthalen-1-yl)carbonyl]-3-(pyridin-2-yl)-1H-pyrazol-5-amine;

Compound 272, N-benzyl-1-[(naphthalen-2-yl)carbonyl]-3-(pyridin-2-yl)-1H-pyrazol-5-amine;

Compound 276, N-benzyl-1-[2-(propan-2-yl)phenyl]carbonyl-3-(pyridin-2-yl)-1H-pyrazol-5-amine;

Compound 277, N-benzyl-3-(2-fluorophenyl)-1-[(2-fluorophenyl)carbonyl]-1H-pyrazol-5-amine;

Compound 278, N-benzyl-3-(2-fluorophenyl)-1-[(2-methoxyphenyl)carbonyl]-1H-pyrazol-5-amine;

Compound 279 N-benzyl-3-(2-fluorophenyl)-1-[(thiophen-3-yl)carbonyl]-1H-pyrazol-5-amine;

Compound 284, N-benzyl-3-(pyridin-2-yl)-1-[(thiophen-3-yl)carbonyl]-1H-pyrazol-5-amine;

Compound 609, 2-[5-(benzylamino)-3-(pyridin-3-yl)-1H-pyrazol-1-yl]carbonylbenzonitrile;

Compound 613, 2-[5-(benzylamino)-3-phenyl-1H-pyrazol-1-yl]carbonylbenzonitrile;

Compound 625, 3-[5-(benzylamino)-3-(pyridin-3-yl)-1H-pyrazol-1-yl]carbonylbenzonitrile;

Compound 629, 3-[5-(benzylamino)-3-phenyl-1H-pyrazol-1-yl]carbonylbenzonitrile;

Compound 641, 4-[5-(benzylamino)-3-(pyridin-3-yl)-1H-pyrazol-1-yl]carbonylbenzonitrile;

Compound 645, 4-[5-(benzylamino)-3-phenyl-1H-pyrazol-1-yl]carbonylbenzonitrile;

Compound 648, N-benzyl-1-[(2-chlorophenyl)carbonyl]-3-(pyridin-3-yl)-1H-pyrazol-5-amine;

Compound 650, N-benzyl-1-[(2-chlorophenyl)carbonyl]-3-phenyl-1H-pyrazol-5-amine;

Compound 652, N-benzyl-1-[(2-fluorophenyl)carbonyl]-3-(pyridin-3-yl)-1H-pyrazol-5-amine;

Compound 655, N-benzyl-1-[(2-fluorophenyl)carbonyl]-3-phenyl-1H-pyrazol-5-amine;

Compound 656, N-benzyl-1-[(2-methoxyphenyl)carbonyl]-3-(pyridin-3-yl)-1H-pyrazol-5-amine;

Compound 657, N-benzyl-1-[(2-methoxyphenyl)carbonyl]-3-phenyl-1H-pyrazol-5-amine;

Compound 658, N-benzyl-1-[(2-methylphenyl)carbonyl]-3-(pyridin-3-yl)-1H-pyrazol-5-amine;

Compound 662, N-benzyl-1-[(2-methylphenyl)carbonyl]-3-phenyl-1H-pyrazol-5-amine;

Compound 664, N-benzyl-1-[(3-chlorophenyl)carbonyl]-3-(pyridin-3-yl)-1H-pyrazol-5-amine;

Compound 668, N-benzyl-1-[(3-chlorophenyl)carbonyl]-3-phenyl-1H-pyrazol-5-amine;

Compound 670, N-benzyl-1-[(3-fluorophenyl)carbonyl]-3-(pyridin-3-yl)-1H-pyrazol-5-amine;

Compound 673, N-benzyl-1-[(3-fluorophenyl)carbonyl]-3-phenyl-1H-pyrazol-5-amine;
Compound 674, N-benzyl-1-[(3-methoxyphenyl)carbonyl]-3-(pyridin-3-yl)-1H-pyrazol-5-amine;
Compound 678, N-benzyl-1-[(3-methoxyphenyl)carbonyl]-3-phenyl-1H-pyrazol-5-amine;
Compound 680, N-benzyl-1-[(3-methylphenyl)carbonyl]-3-(pyridin-3-yl)-1H-pyrazol-5-amine;
Compound 684, N-benzyl-1-[(3-methylphenyl)carbonyl]-3-phenyl-1H-pyrazol-5-amine;
Compound 686, N-benzyl-1-[(4-chlorophenyl)carbonyl]-3-(pyridin-3-yl)-1H-pyrazol-5-amine;
Compound 689, N-benzyl-1-[(4-chlorophenyl)carbonyl]-3-phenyl-1H-pyrazol-5-amine;
Compound 690, N-benzyl-1-[(4-fluorophenyl)carbonyl]-3-(pyridin-3-yl)-1H-pyrazol-5-amine;
Compound 692, N-benzyl-1-[(4-fluorophenyl)carbonyl]-3-phenyl-1H-pyrazol-5-amine;
Compound 693, N-benzyl-1-[(4-methoxyphenyl)carbonyl]-3-(pyridin-3-yl)-1H-pyrazol-5-amine;
Compound 697, N-benzyl-1-[(4-methoxyphenyl)carbonyl]-3-phenyl-1H-pyrazol-5-amine;
Compound 699, N-benzyl-1-[(4-methylphenyl)carbonyl]-3-(pyridin-3-yl)-1H-pyrazol-5-amine;
Compound 702, N-benzyl-1-[(4-methylphenyl)carbonyl]-3-phenyl-1H-pyrazol-5-amine;
Compound 704, N-benzyl-1-[(furan-2-yl)carbonyl]-3-phenyl-1H-pyrazol-5-amine;
Compound 706, N-benzyl-1-[(pyridin-2-yl)carbonyl]-3-(pyridin-3-yl)-1H-pyrazol-5-amine;
Compound 714, N-benzyl-1-[2-(dimethylamino)phenyl]carbonyl-3-(pyridin-3-yl)-1H-pyrazol-5-amine;
Compound 718, N-benzyl-1-[2-(dimethylamino)phenyl]carbonyl-3-phenyl-1H-pyrazol-5-amine;
Compound 722, N-benzyl-1-[3-(dimethylamino)phenyl]carbonyl-3-(pyridin-3-yl)-1H-pyrazol-5-amine;
Compound 726, N-benzyl-1-[3-(dimethylamino)phenyl]carbonyl-3-phenyl-1H-pyrazol-5-amine;
Compound 730, N-benzyl-1-[4-(dimethylamino)phenyl]carbonyl-3-(pyridin-3-yl)-1H-pyrazol-5-amine;
Compound 734, N-benzyl-1-[4-(dimethylamino)phenyl]carbonyl-3-phenyl-1H-pyrazol-5-amine;
Compound 744, N-benzyl-3-(pyridin-3-yl)-1-[(pyridin-3-yl)carbonyl]-1H-pyrazol-5-amine;
Compound 746, N-benzyl-3-(pyridin-3-yl)-1-[(pyridin-4-yl)carbonyl]-1H-pyrazol-5-amine;
Compound 747, N-benzyl-3-(pyridin-3-yl)-1-[(thiophen-2-yl)carbonyl]-1H-pyrazol-5-amine;
Compound 750, N-benzyl-3-phenyl-1-[(pyridin-2-yl)carbonyl]-1H-pyrazol-5-amine;
Compound 752, N-benzyl-3-phenyl-1-[(pyridin-3-yl)carbonyl]-1H-pyrazol-5-amine;
Compound 754, N-benzyl-3-phenyl-1-[(pyridin-4-yl)carbonyl]-1H-pyrazol-5-amine; and
Compound 755, N-benzyl-3-phenyl-1-[(thiophen-2-yl)carbonyl]-1H-pyrazol-5-amine.

\* \* \* \* \*

UNITED STATES PATENT AND TRADEMARK OFFICE
CERTIFICATE OF CORRECTION

PATENT NO.         : 9,533,967 B2
APPLICATION NO.    : 13/630201
DATED              : January 3, 2017
INVENTOR(S)        : Kevin Michael Short et al.

It is certified that error appears in the above-identified patent and that said Letters Patent is hereby corrected as shown below:

In the Claims

At Claim 22, Column 143, Lines 38-66, delete:
"Compound 41, 1-[(2-chlorophenyl)carbonyl]-N-[(4-fluorophenyl)methyl]-3-(pyridin-2-yl)-1H-pyrazol-5-amine; Compound 103, 1-[(2-amino-4-methoxyphenyl)carbonyl]-N-benzyl-3-(2-fluorophenyl)-1H-pyrazol-5-amine; Compound 105, 1-[(2-amino-4-methoxyphenyl)carbonyl]-N-benzyl-3-(pyridin-2-yl)-1H-pyrazol-5-amine; Compound 106, 1-[(2-amino-4-methylphenyl)carbonyl]-N-benzyl-3-(2-fluorophenyl)-1H-pyrazol-5-amine; Compound 108, 1-[(2-amino-4-methylphenyl)carbonyl]-N-benzyl-3-(pyridin-2-yl)-1H-pyrazol-5-amine; Compound 114, 1-[(2-chlorophenyl)carbonyl]-N-[(4-fluorophenyl)methyl]-3-phenyl-1H-pyrazol-5-amine; Compound 116, 1-[(2-methoxyphenyl)carbonyl]-3-(pyridin-2-yl)-N-(thiophen-2-ylmethyl)-1H-pyrazol-5-amine; Compound 118, 1-[(2-methoxyphenyl)carbonyl]-3-(pyridin-2-yl)-N-(thiophen-3-ylmethyl)-1H-pyrazol-5-amine; Compound 201, N-(furan-2-ylmethyl)-1-[(2-methoxyphenyl)carbonyl]-3-(pyridin-2-yl)-1H-pyrazol-5-amine; Compound 202, N-(furan-3-ylmethyl)-1-[(2-methoxyphenyl)carbonyl]-3-(pyridin-2-yl)-1H-pyrazol-5-amine; Compound 208, N-[(4-fluorophenyl)methyl]-1-[(2-methoxyphenyl)carbonyl]-3-phenyl-1H-pyrazol-5-amine;"

At Claim 22, Column 144, Lines 1-18, delete:
"Compound 234, N-benzyl-1-[(2,4-dimethoxyphenyl)carbonyl]-3-(2-fluorophenyl)-1H-pyrazol-5-amine; Compound 236, N-benzyl-1-[(2,4-dimethoxyphenyl)carbonyl]-3-(pyridin-2-yl)-1H-pyrazol-5-amine; Compound 241, N-benzyl-1-[(2-bromophenyl)carbonyl]-3-(pyridin-2-yl)-1H-pyrazol-5-amine; Compound 242, N-benzyl-1-[(2-chlorophenyl)carbonyl]-3-(2-fluorophenyl)-1H-pyrazol-5-amine; Compound 244, N-benzyl-1-[(2-chlorophenyl)carbonyl]-3-(pyridin-2-yl)-1H-pyrazol-5-amine; Compound 247, N-benzyl-1-[(2-ethylphenyl)carbonyl]-3-(pyridin-2-yl)-1H-pyrazol-5-amine; Compound 251, N-benzyl-1-[(2-fluorophenyl)carbonyl]-3-(pyridin-2-yl)-1H-pyrazol-5-amine; Compound 256, N-benzyl-1-[(2-methoxyphenyl)carbonyl]-3-(pyridin-2-yl)-1H-pyrazol-5-amine; Compound 260, N-benzyl-1-[(2-methylphenyl)carbonyl]-3-(pyridin-2-yl)-1H-pyrazol-5-amine;"

Signed and Sealed this
Second Day of April, 2019

Andrei Iancu
*Director of the United States Patent and Trademark Office*

CERTIFICATE OF CORRECTION (continued)
U.S. Pat. No. 9,533,967 B2

At Claim 22, Column 144, Lines 23-28, delete:
"Compound 276, N-benzyl-1-[2-(propan-2-yl)phenyl]carbonyl-3-(pyridin-2-yl)-1H-pyrazol-5-amine; Compound 277, N-benzyl-3-(2-fluorophenyl)-1-[(2-fluorophenyl)carbonyl]-1H-pyrazol-5-amine; Compound 278, N-benzyl-3-(2-fluorophenyl)-1-[(2-methoxyphenyl)carbonyl]-1H-pyrazol-5-amine;"

At Claim 22, Column 144, Lines 33-66, delete:
"Compound 609, 2-[5-(benzylamino)-3-(pyridin-3-yl)-1H-pyrazol-1-yl]carbonylbenzonitrile; Compound 613, 2-[5-(benzylamino)-3-phenyl-1H-pyrazol-1-yl]carbonylbenzonitrile; Compound 625, 3-[5-(benzylamino)-3-(pyridin-3-yl)-1H-pyrazol-1-yl]carbonylbenzonitrile; Compound 629, 3-[5-(benzylamino)-3-phenyl-1H-pyrazol-1-yl]carbonylbenzonitrile; Compound 641, 4-[5-(benzylamino)-3-(pyridin-3-yl)-1H-pyrazol-1-yl]carbonylbenzonitrile; Compound 645, 4-[5-(benzylamino)-3-phenyl-1H-pyrazol-1-yl]carbonylbenzonitrile; Compound 648, N-benzyl-1-[(2-chlorophenyl)carbonyl]-3-(pyridin-3-yl)-1H-pyrazol-5-amine; Compound 650, N-benzyl-1-[(2-chlorophenyl)carbonyl]-3-phenyl-1H-pyrazol-5-amine; Compound 652, N-benzyl-1-[(2-fluorophenyl)carbonyl]-3-(pyridin-3-yl)-1H-pyrazol-5-amine; Compound 655, N-benzyl-1-[(2-fluorophenyl)carbonyl]-3-phenyl-1H-pyrazol-5-amine; Compound 656, N-benzyl-1-[(2-methoxyphenyl)carbonyl]-3-(pyridin-3-yl)-1H-pyrazol-5-amine; Compound 657, N-benzyl-1-[(2-methoxyphenyl)carbonyl]-3-phenyl-1H-pyrazol-5-amine; Compound 658, N-benzyl-1-[(2-methylphenyl)carbonyl]-3-(pyridin-3-yl)-1H-pyrazol-5-amine; Compound 662, N-benzyl-1-[(2-methylphenyl)carbonyl]-3-phenyl-1H-pyrazol-5-amine; Compound 664, N-benzyl-1-[(3-chlorophenyl)carbonyl]-3-(pyridin-3-yl)-1H-pyrazol-5-amine; Compound 668, N-benzyl-1-[(3-chlorophenyl)carbonyl]-3-phenyl-1H-pyrazol-5-amine; Compound 670, N-benzyl-1-[(3-fluorophenyl)carbonyl]-3-(pyridin-3-yl)-1H-pyrazol-5-amine;"

At Claim 22, Column 145, Lines 1-26, delete:
"Compound 673, N-benzyl-1-[(3-fluorophenyl)carbonyl]-3-phenyl-1H-pyrazol-5-amine; Compound 674, N-benzyl-1-[(3-methoxyphenyl)carbonyl]-3-(pyridin-3-yl)-1H-pyrazol-5-amine; Compound 678, N-benzyl-1-[(3-methoxyphenyl)carbonyl]-3-phenyl-1H-pyrazol-5-amine; Compound 680, N-benzyl-1-[(3-methylphenyl)carbonyl]-3-(pyridin-3-yl)-1H-pyrazol-5-amine; Compound 684, N-benzyl-1-[(3-methylphenyl)carbonyl]-3-phenyl-1H-pyrazol-5-amine; Compound 686, N-benzyl-1-[(4-chlorophenyl)carbonyl]-3-(pyridin-3-yl)-1H-pyrazol-5-amine; Compound 689, N-benzyl-1-[(4-chlorophenyl)carbonyl]-3-phenyl-1H-pyrazol-5-amine; Compound 690, N-benzyl-1-[(4-fluorophenyl)carbonyl]-3-(pyridin-3-yl)-1H-pyrazol-5-amine; Compound 692, N-benzyl-1-[(4-fluorophenyl)carbonyl]-3-phenyl-1H-pyrazol-5-amine; Compound 693, N-benzyl-1-[(4-methoxyphenyl)carbonyl]-3-(pyridin-3-yl)-1H-pyrazol-5-amine; Compound 697, N-benzyl-1-[(4-methoxyphenyl)carbonyl]-3-phenyl-1H-pyrazol-5-amine; Compound 699, N-benzyl-1-[(4-methylphenyl)carbonyl]-3-(pyridin-3-yl)-1H-pyrazol-5-amine; Compound 702, N-benzyl-1-[(4-methylphenyl)carbonyl]-3-phenyl-1H-pyrazol-5-amine;"

At Claim 22, Column 146, Lines 3-14, delete:

"Compound 714, N-benzyl-1-[2-(dimethylamino)phenyl]carbonyl-3-(pyridin-3-yl)-1H-pyrazol-5-amine; Compound 718, N-benzyl-1-[2-(dimethylamino)phenyl]carbonyl-3-phenyl-1H-pyrazol-5-amine; Compound 722, N-benzyl-1-[3-(dimethylamino)phenyl]carbonyl-3-(pyridin-3-yl)-1H-pyrazol-5-amine; Compound 726, N-benzyl-1-[3-(dimethylamino)phenyl]carbonyl-3-phenyl-1H-pyrazol-5-amine; Compound 730, N-benzyl-1-[4-(dimethylamino)phenyl]carbonyl-3-(pyridin-3-yl)-1H-pyrazol-5-amine; Compound 734, N-benzyl-1-[4-(dimethylamino)phenyl]carbonyl-3-phenyl-1H-pyrazol-5-amine;"